(12) United States Patent
Foo

(10) Patent No.: US 8,993,631 B2
(45) Date of Patent: Mar. 31, 2015

(54) METHOD OF TREATING CONTRAST-INDUCED NEPHROPATHY

(75) Inventor: Shi Yin Foo, Brookline, MA (US)

(73) Assignee: Novartis AG, Basel (CH)

( * ) Notice: Subject to any disclaimer, the term of this patent is extended or adjusted under 35 U.S.C. 154(b) by 164 days.

(21) Appl. No.: 13/294,295

(22) Filed: Nov. 11, 2011

(65) Prior Publication Data

US 2012/0122844 A1 May 17, 2012

Related U.S. Application Data

(60) Provisional application No. 61/414,174, filed on Nov. 16, 2010.

(51) Int. Cl.

| | | |
|---|---|---|
| A61K 31/16 | (2006.01) | |
| A61K 31/04 | (2006.01) | |
| A61K 31/5375 | (2006.01) | |
| A61K 31/192 | (2006.01) | |
| A61K 31/194 | (2006.01) | |
| A61K 31/198 | (2006.01) | |
| A61K 31/216 | (2006.01) | |
| A61K 31/235 | (2006.01) | |
| A61K 31/335 | (2006.01) | |
| A61K 31/34 | (2006.01) | |
| A61K 31/341 | (2006.01) | |
| A61K 31/343 | (2006.01) | |
| A61K 31/35 | (2006.01) | |
| A61K 31/357 | (2006.01) | |
| A61K 31/381 | (2006.01) | |

(Continued)

(52) U.S. Cl.
CPC ........... *A61K 31/5375* (2013.01); *A61K 31/192* (2013.01); *A61K 31/194* (2013.01); *A61K 31/198* (2013.01); *A61K 31/216* (2013.01); *A61K 31/235* (2013.01); *A61K 31/335* (2013.01); *A61K 31/34* (2013.01); *A61K 31/341* (2013.01); *A61K 31/343* (2013.01); *A61K 31/35* (2013.01); *A61K 31/357* (2013.01); *A61K 31/381* (2013.01); *A61K 31/40* (2013.01); *A61K 31/4045* (2013.01); *A61K 31/41* (2013.01); *A61K 31/415* (2013.01); *A61K 31/4164* (2013.01); *A61K 31/4184* (2013.01); *A61K 31/4196* (2013.01); *A61K 31/42* (2013.01); *A61K 31/421* (2013.01); *A61K 31/4245* (2013.01); *A61K 31/44* (2013.01); *A61K 31/4402* (2013.01); *A61K 31/445* (2013.01); *A61K 31/505* (2013.01); *A61K 31/513* (2013.01); *A61K 45/06* (2013.01); *A61K 31/197* (2013.01); *C07C 235/06* (2013.01); *C07C 235/74* (2013.01); *C07C 235/82* (2013.01); *C07C 275/24* (2013.01); *C07D 207/16* (2013.01); *C07D 213/56* (2013.01); *C07D 213/76* (2013.01); *C07D 231/14* (2013.01); *C07D 231/20* (2013.01); *C07D 235/16* (2013.01); *C07D 239/28* (2013.01); *C07D 239/34* (2013.01); *C07D 249/12* (2013.01); *C07D 257/04* (2013.01); *C07D 261/18* (2013.01); *C07D 263/34* (2013.01); *C07D 271/113* (2013.01); *C07D 307/68* (2013.01); *C07D 317/40* (2013.01)
USPC .......................................... 514/613; 514/740

(58) Field of Classification Search
USPC .................................. 514/613, 740
See application file for complete search history.

(56) References Cited

U.S. PATENT DOCUMENTS

| | | |
|---|---|---|
| 4,610,816 A | 9/1986 | Berger et al. |
| 5,208,255 A | 5/1993 | Duhamel et al. |

(Continued)

FOREIGN PATENT DOCUMENTS

| | | |
|---|---|---|
| EP | 0342850 A1 | 11/1989 |
| WO | 98/33780 A1 | 8/1998 |

(Continued)

OTHER PUBLICATIONS

Kitajima et al. "Recent issues in contrast-induced nephropathy". International Journal of Urology (2011) 18, 686-690.*

(Continued)

*Primary Examiner* — Renee Claytor
(74) *Attorney, Agent, or Firm* — Sophie Binet Cross

(57) ABSTRACT

The present invention provides the use of a neutral endopeptidase inhibitor, in the manufacture of a medicament for the treatment, amelioration and/or prevention of contrast-induced nephropathy. The invention also relates to the use of a compound of Formula I:

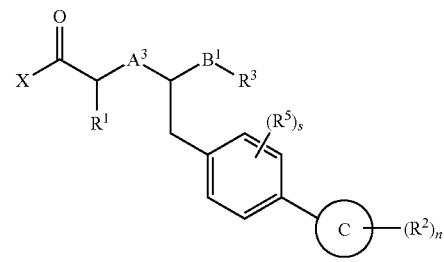

wherein $R^1$, $R^2$, $R^3$, $R^5$, X, $A^3$, $B^1$, s and n are defined herein, for the treatment, amelioration and/or prevention of contrast-induced nephropathy. The present invention further provides a combination of pharmacologically active agents for use in the treatment, amelioration and/or prevention of contrast-induced nephropathy.

5 Claims, No Drawings

(51) Int. Cl.

| | | |
|---|---|---|
| A61K 31/40 | (2006.01) | |
| A61K 31/4045 | (2006.01) | |
| A61K 31/41 | (2006.01) | |
| A61K 31/415 | (2006.01) | |
| A61K 31/4164 | (2006.01) | |
| A61K 31/4184 | (2006.01) | |
| A61K 31/4196 | (2006.01) | |
| A61K 31/42 | (2006.01) | |
| A61K 31/421 | (2006.01) | |
| A61K 31/4245 | (2006.01) | |
| A61K 31/44 | (2006.01) | |
| A61K 31/4402 | (2006.01) | |
| A61K 31/445 | (2006.01) | |
| A61K 31/505 | (2006.01) | |
| A61K 31/513 | (2006.01) | |
| A61K 45/06 | (2006.01) | |
| A61K 31/197 | (2006.01) | |
| C07C 235/06 | (2006.01) | |
| C07C 235/74 | (2006.01) | |
| C07C 235/82 | (2006.01) | |
| C07C 275/24 | (2006.01) | |
| C07D 207/16 | (2006.01) | |
| C07D 213/56 | (2006.01) | |
| C07D 213/76 | (2006.01) | |
| C07D 231/14 | (2006.01) | |
| C07D 231/20 | (2006.01) | |
| C07D 235/16 | (2006.01) | |
| C07D 239/28 | (2006.01) | |
| C07D 239/34 | (2006.01) | |
| C07D 249/12 | (2006.01) | |
| C07D 257/04 | (2006.01) | |
| C07D 261/18 | (2006.01) | |
| C07D 263/34 | (2006.01) | |
| C07D 271/113 | (2006.01) | |
| C07D 307/68 | (2006.01) | |
| C07D 317/40 | (2006.01) | |

(56) References Cited

U.S. PATENT DOCUMENTS

| | | |
|---|---|---|
| 5,217,996 A | 6/1993 | Ksander et al. |
| 5,514,696 A | 5/1996 | Murugesan et al. |
| 5,599,951 A | 2/1997 | Plaquevent et al. |
| 5,612,359 A | 3/1997 | Murugesan |
| 5,780,473 A | 7/1998 | Murugesan et al. |
| 5,846,985 A | 12/1998 | Murugesan |
| 8,222,286 B2 * | 7/2012 | Iwaki et al. ............ 514/381 |
| 8,394,853 B2 * | 3/2013 | Coppola et al. ............ 514/533 |
| 2004/0106611 A1 | 6/2004 | Challenger et al. |
| 2006/0205625 A1 | 9/2006 | Straub et al. |

FOREIGN PATENT DOCUMENTS

| | | |
|---|---|---|
| WO | 02/083130 A1 | 10/2002 |
| WO | 2006/087371 A1 | 8/2006 |
| WO | 2007/109456 A2 | 9/2007 |
| WO | 2010/136474 A2 | 12/2010 |
| WO | 2010/136493 A1 | 12/2010 |
| WO | 2011/061271 A1 | 5/2011 |

OTHER PUBLICATIONS

Morikawa et al., "Renal Protective Effects and the Prevention of Contrast Induced Nephropathy by Atrial Natriuretic Peptide," Journal of the American College of Cardiology 53(12):1040-1046 (Mar. 24, 2009).
Kuroda et al., "Study of the Mechanism of Diuretic and Natriuretic Effects of Neutral Endopeptidase 24.11 Inhibitor," Sapporo Igaku Zasshi—Sapporo Medical Journal 63(1):11-21 (1994).
Capasso et al., "inhibition of neutral endopeptidase potentiates the effects of atrial natriuretic peptide on acute cyclosporin-induced nephrotoxicity," Nephron 86(3):298-305 (Nov. 2000).
Roques et al., "Neutral Endopeptidase 24.11: Structure, Inhibition, and Experimental and Clinical Pharmacology," Pharmacological Reviews 45(1):87-146 (1993).
Burrell et al., "Inhibition of neurtral endopeptidase, the degradative enzyme for natriuretic peptides, in rat kidney after oral SCH 42495," Clinical Science 93(1):43-50 (1997).
Ksander et al., "Dicarboxylic Acid Dipeptide Neutral Endopeptidase Inhibitors," Journal of Medicinal Chemistry 38(10):1689-1700 (Jan. 1, 1995).
Ruilope et al., "Blood pressure reduction with LCZ696, a novel dual-acting inhibitor of the anbiotensin II receptor and neprilysin: a randomised, double-blind, placebo-controlled, active comparator study," The Lancet 375(9722):1255-1266 (Oct. 4, 2010).
Kanno et al., "Synthesis and evaluation of 2-(biphenylmethyl) glutaric acid amide derivatives as neutral endopeptidase inhibitors," Bioorganic & Medicinal Chemistry Letters 6(13):1487-1490 (Sep. 7, 1996).
Kanno et al., "Potent inhibitors of neutral endopeptidase, 2-biphenyl-methylglutaric acid amide derivatives," Bioorganic & Medicinal Chemistry Letters 6(1):65-70 (Jan. 9, 1996).
Miller et al., "Contrast-Media Induced Nephropathy and Diagnostic CT," 5(2):1-4(Feb. 2007).
Perazella, Mark, "Drug-Induced Nephropathy: an update," Expert Opin. Drug Saf. 4(4):689-706 (2005).
Shepperson et al., "Inhibition of Neutral Endopeptidase leads to an Atrial Natriuretic Factor-Mediated Natriuretic, Diuretic and Antihypertensive Response in Rodents," Clinical Science 80:265-269 (1991).

* cited by examiner

METHOD OF TREATING CONTRAST-INDUCED NEPHROPATHY

This application claims benefit under 35 U.S.C. §119(e) of U.S. Provisional Application No. 61/414,174, filed Nov. 16, 2010, the content of which is incorporated herein by reference in its entirety.

BACKGROUND OF THE INVENTION

Contrast-induced nephropathy (CIN) is a form of acute renal failure that occurs after the exposure to iodinated intravenous contrast, such as is used in cardiac catheterization procedures or CT scans. Individuals with baseline renal disease, diabetes, ongoing hypotension/heart failure/acute myocardial infarction, use of nephrotoxic drugs, or who are exposed to large amounts of contrast dye are at increased risk of this renal failure.

The natural history of Contrast-induced nephropathy is usually a transient decrease in renal function. In patients with severe baseline renal dysfunction however, the risk of proceeding to endstage renal disease (i.e requiring dialysis can be as high as 30%). Despite the usually transient nature of the Contrast-induced nephropathy episode itself, Contrast-induced nephropathy has been associated with increased longer term (1-2 year) morbidity and mortality. In addition, Contrast-induced nephropathy is also tightly associated with increased hospital stays and more acute cardiac events (such as pulmonary edema) during the index hospitalization.

The mechanism of contrast-induced kidney damage has been postulated to be a function of two separate processes: the first is a direct toxic effect of the dye to the tubular cells of the nephron unit. The second is a vasoconstrictive effect on the blood vessels of the renal medullary bed. In large part, the prior interventions attempted for the amelioration of CIN have focused on vasodilation in the renal beds—this included N-acetylcysteine, fenoldapam, theophylline, adenosine-receptor antagonists, calcium channel blockers and iloprost. None of these interventions has been definitively shown to decrease the incidence of CIN. N-Acetylcysteine (NAC) is nevertheless commonly used as it is generic, cheap and lacks toxicity. The current standard of care for those at risk of Contrast-induced nephropathy is to institute IV hydration 8-16 hours prior to exposure to the dyes.

Therefore, there is a clear need for improved therapy for the treatment and prevention of contrast-induced Nephropathy.

SUMMARY OF THE INVENTION

The aim of the present invention is to provide a novel method of treating, preventing or ameliorating contrast-induced nephropathy in a subject comprising, administering to the subject a neutral endopeptidase (NEP) inhibitor.

The invention pertains to a method of treating, preventing or ameliorating contrast-induced nephropathy in a subject, comprising administering to the subject a neutral endopeptidase (NEP) inhibitor selected from the group consisting of: Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxypropionylamino)-2-methyl-pentanoic acid ethyl ester or a pharmaceutically acceptable salt thereof.

In one embodiment, the invention pertains to the method of the invention using Candoxatril or Candoxatrilat, or a compound of the European patent Number EP0342850, which is herein incorporated by reference, or a pharmaceutically acceptable salt thereof. Candoxatril is the orally active pro-drug of Candoxatrilat, a potent NEP inhibitor having the following structure:

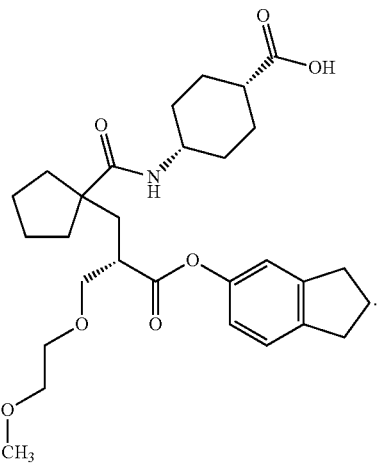 [SMILES: COCCOC[C@H](CC1(C(=O)N[C@H]2CC[C@@H](C(=O)O)CC2)CCCC1)C(=O)Oc1ccc2c(c1)CCC2]

In another embodiment, the invention pertains to the method of the invention wherein the NEP inhibitor is Racecadotril (RS), Dexecadotril (R) or Ecadotril (S) or a compound of European patent Numbers, EP0318377 or EP0501870, each of which is incorporated by reference, or a pharmaceutically acceptable salt thereof. Ecadotril is the (S)-enantiomer of N-[2-[(Acetylthio)methyl]-1-oxo-3-phenylpropyl]-glycine phenylmethyl ester and Dexecadotril is the (R)-enantiomer of N-[2-[(Acetylthio)methyl]-1-oxo-3-phenylpropyl]-glycine phenylmethyl ester as depicted below. Racecadotril is the racemic mixture:

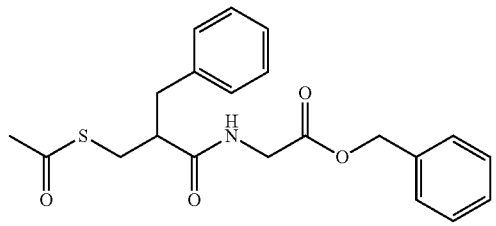

Racecadotril

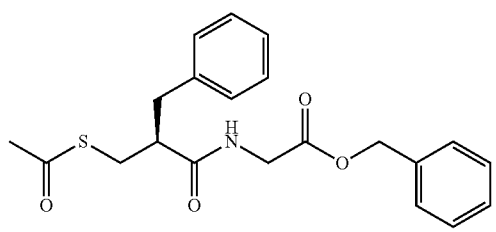

(S): Ecadotril

-continued

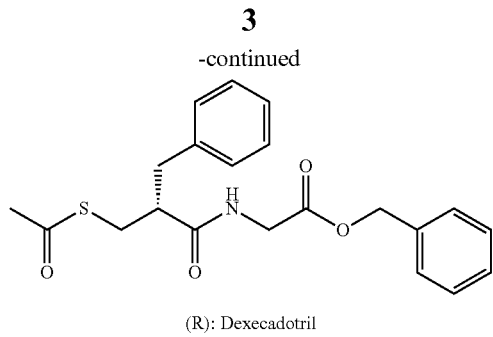

(R): Dexecadotril

In one embodiment, the invention pertains to method of the invention wherein the NEP inhibitor is Sampatrilat, or a compound of the European patent EP0358398, which is herein incorporated by reference, or a pharmaceutically acceptable salt thereof. Sampatrilat is a dual ACE/NEP inhibitor of the following formula:

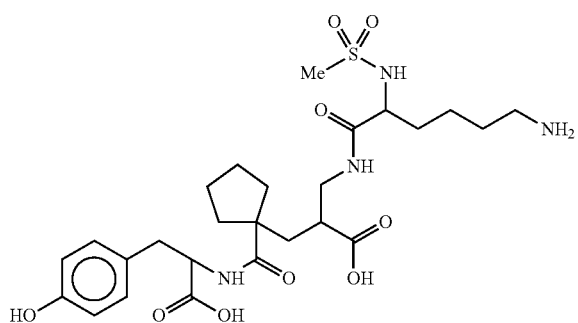

In one embodiment, the invention pertains to method of the invention wherein the NEP inhibitor is Fasidotril, or a compound of the European patent EP0419327 which is herein incorporated by reference, or a pharmaceutically acceptable salt thereof. Fasidotril is a dual ACE/NEP inhibitor of the following formula:

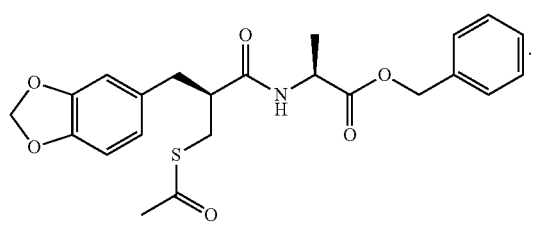 [SMILES: CC(=O)SC[C@@H](Cc1ccc2c(c1)OCO2)C(=O)N[C@@H](C)C(=O)OCc1ccccc1]

In one embodiment, the invention pertains to method of the invention wherein the NEP inhibitor is Omapatrilat, or a compound of the European patent EP0629627 which is herein incorporated by reference, or a pharmaceutically acceptable salt thereof. Omapatrilat is a dual ACE/NEP inhibitor of the following formula:

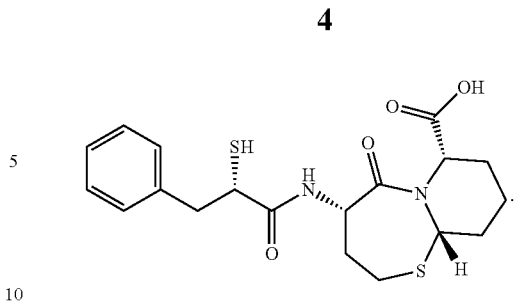

In one embodiment, the invention pertains to method of the invention wherein the NEP inhibitor is Gemopatrilat, or a compound of the European patent EP0599444 which is herein incorporated by reference, or a pharmaceutically acceptable salt thereof. Gemopatrilat is a dual ACE/NEP inhibitor of the following formula:

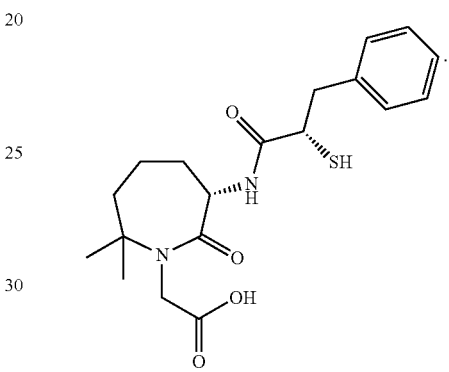

In one embodiment, the invention pertains to method of the invention wherein the NEP inhibitor is Daglutril, or a compound of the European patent EP0733642 which is herein incorporated by reference, or a pharmaceutically acceptable salt thereof. Daglutril is a dual ECE/NEP inhibitor of the following formula:

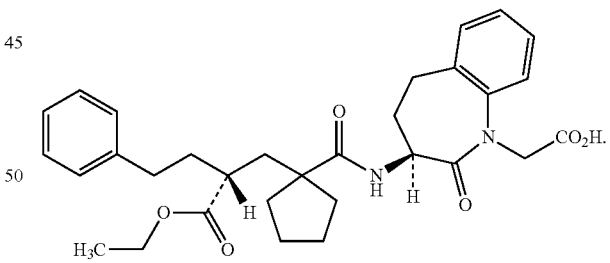

In one embodiment, the invention pertains to method of the invention wherein the NEP inhibitor is UK-447841, or a compound of the PCT application WO 2002/079143, which is herein incorporated by reference, or a pharmaceutically acceptable salt thereof. UK-447841 is an NEP inhibitor of the following formula:

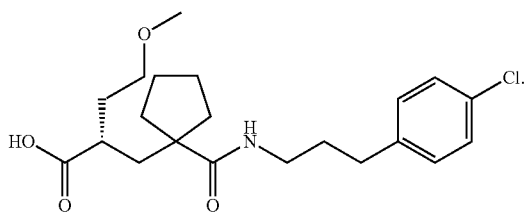
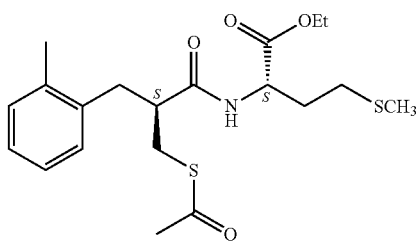

In one embodiment, the invention pertains to method of the invention wherein the NEP inhibitor is (2R,4S)-5-Biphenyl-4-yl-4-(3-carboxy-propionylamino)-2-methyl-pentanoic acid ethyl ester or a compound of U.S. Pat. No. 5,217,996, which is herein incorporated by reference, or a pharmaceutically acceptable salt thereof. (2R,4S)-5-Biphenyl-4-yl-4-(3-carboxy-propionylamino)-2-methyl-pentanoic acid ethyl ester is a NEP inhibitor of the following Formula:

In one embodiment, the invention pertains to method of the invention wherein the NEP inhibitor is SCH-32615 or a compound disclosed in U.S. Pat. No. 4,640,816 or European patent number EP0254032, each of which are incorporated by reference herein, or a pharmaceutically acceptable salt thereof. SCH-32615 is B-Alanine, [N-(1-carboxy-2-phenyl-ethyl)-L-phenylalanyl]-, (S)- which has the following chemical structure:

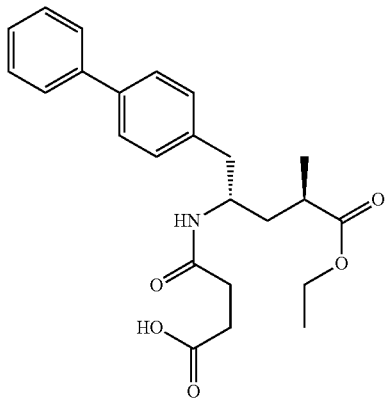 [SMILES: CCOC(=O)[C@H](C)C[C@@H](Cc1ccc(-c2ccccc2)cc1)NC(=O)CCC(=O)O]

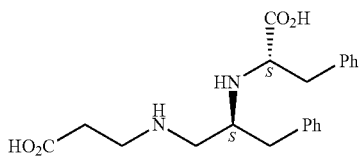

In one embodiment, the invention pertains to method of the invention wherein the NEP inhibitor is AVE-0848 or a compound of PCT application WO 2002/083671, which is incorporated by reference herein, or a pharmaceutically acceptable salt thereof. AVE-0848 is a dual ACE/NEP inhibitor with the chemical name of (4S,7S,12bR)-7-[3-Methyl-2(S)-sulfanyl-butyramido]-6-oxo-1,2,3,4,6,7,8,12b-octahydropyrido[2,1-a][2]benzazepine-4-carboxylic acid, which has the following chemical structure:

In one embodiment, the invention pertains to method of the invention wherein the NEP inhibitor is PL-37 (DEBIO 0827) or a compound disclosed in PCT application WO 2007/048787, which is incorporated by reference, or a pharmaceutically acceptable salt thereof. PL 27 is 14-amino-3-methyl-5,8-dioxo-9-(phenylmethyl)-, ethyl ester, (9S,14S) which has the following structure:

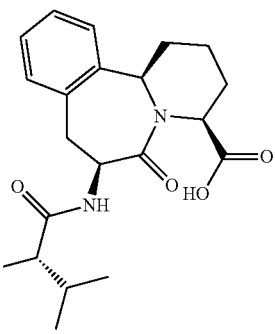

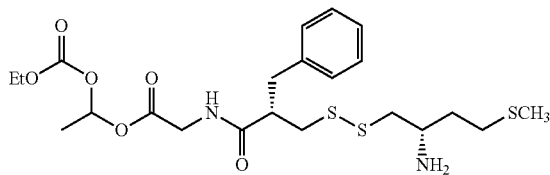 [SMILES: CCOC(=O)OC(C)OC(=O)CNC(=O)[C@@H](CSSC[C@@H](N)CCSC)Cc1ccccc1]

In one embodiment, the invention pertains to method of the invention wherein the NEP inhibitor is SCH-42495 or a compound disclosed in U.S. Pat. No. 4,929,641, which is incorporated by reference, or a pharmaceutically salt thereof. SCH-42495 is L-Methionine, N-[2-[(acetylthio)methyl]-3-(2-methylphenyl)1-oxopropyl]-ethyl ester, (S) which has the following chemical structure:

In one embodiment, the invention pertains to method of the invention wherein the NEP inhibitor is a Phosphono/biaryl substituted dipeptide derivative, as disclosed in U.S. Pat. No. 5,155,100, which is herein incorporated by reference.

In one embodiment, the invention pertains to method of the invention wherein the NEP inhibitor is a N-mercaptoacyl phenylalanine derivative as disclosed in PCT application Number WO 2003/104200, which is herein incorporated by reference.

In one embodiment, the invention pertains to method of the invention wherein the NEP inhibitor is a dual-acting antihypertensive agent as disclosed in PCT application Numbers WO 2008/133896, WO 2009/035543 or WO 2009/134741, each which is herein incorporated by reference.

The invention also provides a method of treating, ameliorating or preventing contrast-induced nephropathy in a subject, comprising administering to the subject a therapeutically effective amount of a compound of formula I:

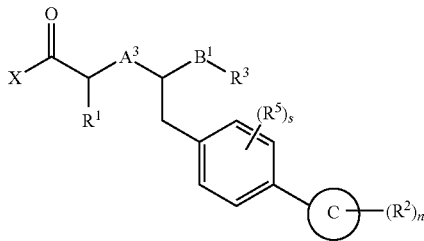

or a pharmaceutically acceptable salt thereof, wherein:
$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy, $C_{3-7}$cycloalkyl or $C_{1-6}$ alkoxy;
$R^2$ for each occurrence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^bR^c$, $C_{6-10}$aryl, heteroaryl or heterocyclyl;
$R^3$ is $A^1$-C(O)$X^1$ or $A^2$-$R^4$;
$R^4$ is $C_{6-10}$aryl, $C_{3-7}$cycloalkyl, or a heteroaryl, which can be monocyclic or bicyclic, each of which can be optionally substituted with one or more substituents independently selected from the group consisting of hydroxy, hydroxy$C_{1-7}$alkyl, nitro, —$NR^bR^c$, —C(O)$C_{1-7}$alkyl, C(O)—O—$C_{1-7}$alkyl, $C_{1-7}$alkoxy, halo, $C_{1-7}$alkyl, halo-$C_{1-7}$alkyl, $C_{2-7}$alkenyl, $C_{6-10}$aryl, heteroaryl, —$NHSO_2$—$C_{1-7}$alkyl, $S(O)_2$—$C_{1-7}$alkyl, C(O)—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —$NHSO_2$—$C_{1-7}$alkyl and benzyl;
$R^5$ is H, halo, hydroxy, $C_{1-7}$alkoxy, halo, $C_{1-7}$alkyl or halo-$C_{1-7}$alkyl; and
X and $X^1$ are independently OH, —O—$C_{1-7}$alkyl, —$NR^bR^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of $C_{6-10}$aryl, heteroaryl, heterocyclyl, C(O)NH$_2$, C(O)NH—$C_{1-6}$alkyl, and C(O)N($C_{1-6}$alkyl)$_2$;
$B^1$ is —C(O)$NR^d$— or —$NR^d$C(O)—;
$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or
$A^1$ is a linear or branched $C_{1-7}$alkenylene; or
$A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which
$R^a$ for each occurrence, is independently H, $C_{1-7}$alkyl, —C(O)—O—$C_{1-7}$alkyl or —CH$_2$C(O)OH; or
$A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^bR^c$, —$OCH_2CO_2H$, and —$OCH_2C(O)NH_2$; or
$A^1$ is a $C_{3-7}$cycloalkyl or heterocyclyl;
$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and
$A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl;
$A^3$ is $CH_2$, O, $NR^e$ or is absent; and when $A^3$ is O or $NR^e$ then $B^1$ is C(O)$NR^d$;
$R^b$ and $R^c$ for each occurrence are independently H, $C_{6-10}$aryl or $C_{1-7}$alkyl;
$R^d$ and $R^e$ are independently H or $C_{1-7}$alkyl;
Ring C is a phenyl or a monocyclic heteroaryl;
n is 0, 1, 2, 3, 4 or 5;
s is 0, 1, 2, 3 or 4; and
when $B^1$ is C(O)$NR^d$ and $R^3$ is $A^2$-$R^4$, then $R^d$ and $A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-4}$alkyl, halo, halo$C_{1-6}$alkyl, $C_{1-6}$alkoxy, hydroxy, $CO_2H$ and $CO_2C_{1-6}$alkyl;
wherein each heteroaryl is a monocyclic or bicyclic aromatic ring comprising 5-10 ring atoms selected from carbon atoms and 1 to 5 heteroatoms unless otherwise specified, and
each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

The compounds of the invention, by inhibiting the neutral endopeptidase EC.3.4.24.11, can increase the levels of atrial natriuretic peptide (ANP) and are therefore useful for the treatment and prevention of contrast-induced nephropathy.

In another embodiment, the invention pertains to a method for treating, ameliorating and/or preventing contrast-induced nephropathy in a subject in need of such treatment, comprising: administering to the subject an effective amount of a compound according to anyone of Formulae I, II, II-A to II-S, III, III-A to IV and IV-A to IV-D, or a pharmaceutically acceptable salt thereof.

In another embodiment, the invention pertains to the use of a compound according to anyone of Formulae I, II, II-A to II-S, III, III-A to III-T, IV and IV-A to IV-D, or a pharmaceutically acceptable salt thereof, in the manufacture of a medicament, for the treatment, amelioration and/or prevention of contrast-induced nephropathy, in a subject in need of such treatment.

In another embodiment, the invention pertains to the use of a neutral endopeptidase EC. 3.4. 24.11. inhibitor, in the manufacture of a medicament, for the treatment, amelioration and/or prevention of contrast-induced nephropathy, in a subject in need of such treatment.

In another embodiment, the invention pertains to the use of a neutral endopeptidase EC. 3.4. 24.11. inhibitor, selected from the group consisting of Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester, in the manufacture of a medicament, for the treatment, amelioration and/or prevention of contrast-induced nephropathy, in a subject in need of such treatment.

In another embodiment, the invention pertains to the use of a neutral endopeptidase EC. 3.4. 24.11. inhibitor, wherein the NEP inhibitor is a Phosphono/biaryl substituted dipeptide derivative, as disclosed in U.S. Pat. No. 5,155,100, which is herein incorporated by reference, in the manufacture of a medicament, for the treatment, amelioration and/or prevention of contrast-induced nephropathy, in a subject in need of such treatment.

In one embodiment, the invention pertains to the use of a neutral endopeptidase EC. 3.4. 24.11. inhibitor, wherein the NEP inhibitor is a N-mercaptoacyl phenylalanine derivative as disclosed in PCT application Number WO 2003/104200, which is herein incorporated by reference, in the manufacture of a medicament, for the treatment, amelioration and/or prevention of contrast-induced nephropathy, in a subject in need of such treatment.

In one embodiment, the invention pertains to the use of a neutral endopeptidase EC. 3.4. 24.11. inhibitor, wherein the NEP inhibitor is a dual-acting antihypertensive agent as disclosed in PCT application Numbers WO 2008/133896, WO 2009/035543 or WO 2009/134741, each which is herein incorporated by reference, in the manufacture of a medicament, for the treatment, amelioration and/or prevention of contrast-induced nephropathy, in a subject in need of such treatment.

In still another embodiment, the invention pertains to combinations including, a neutral endopeptidase EC. 3.4 24.11. inhibitor, or a pharmaceutically acceptable salt thereof, and pharmaceutical combinations of one or more therapeutically active agents, for the treatment, amelioration and/or prevention of contrast-induced nephropathy, in a subject in need of such treatment.

In still another embodiment, the invention pertains to combinations including, a compound according to anyone of Formulae I, II, II-A to II-S, III, III-A to III-T, IV and IV-A to IVD, or a pharmaceutically acceptable salt thereof, and pharmaceutical combinations of one or more therapeutically active agents, for the treatment, amelioration and/or prevention of contrast-induced nephropathy, in a subject in need of such treatment.

In a particular aspect of this embodiment, the second agent is an adenosine-receptor antagonist, a calcium channel blockers, an antioxidant, an anti-apoptotic agent, a MAP kinase inhibitor, a prostacyclin or prostacyclin analogue, an endothelin receptor antagonist and a dopamine receptor agonist.

DETAILED DESCRIPTION OF THE INVENTION

Definition:

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 6 carbon atoms, and more preferably 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-6}$alkyl" refers to a hydrocarbon having from one to six carbon atoms. The term "alkylene" refers to a divalent alkyl radical, wherein alkyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-6}$alkyl" refers to a hydrocarbon having one to six carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

As used herein, the term "cycloalkyl" refers to saturated or partially unsaturated monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$cycloakyl" refers to a cyclic hydrocarbon groups having 3 to 7 carbon atoms.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindol, indanyl or tetrahydronaphthyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-$CH_2CH_2$—. The term "$C_{6-10}$aryl-$C_{1-6}$alkyl" refers to a hydrocarbon having one to six carbon atoms, which hydrocarbon is substituted with an aryl having 6 to 10 carbon atoms.

The term "Heteroaryl" includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3, 4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl rings, where the radical or point of attachment is on the heteroaromatic ring or on the fused aryl ring. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl. When a heteroaryl moiety is substituted with hydroxy, the invention also pertains to its oxo tautomeric. For example, an oxadiazole substituted with hydroxy also includes oxo-oxadiazole also known as oxadiazolone. The tautomerisation is represented as follow:

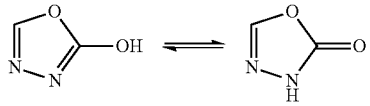 [SMILES: Oc1nnco1 ; O=c1[nH]nco1]

As used herein, the term "heterocyclyl" or "heterocyclo" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "halogen" or "halo" includes fluoro, bromo, chloro and iodo. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment the heteroatoms is selected from N, O and S.

Compounds for the Method of the Invention:

Various embodiments of the invention are described herein. It will be recognized that features specified in each embodiment may be combined with other specified features to provide further embodiments.

In one embodiment, the invention pertains to a method of treating and/or preventing CIN in a subject, comprising administering to the subject a therapeutically effective amount of a compound of Formula II:

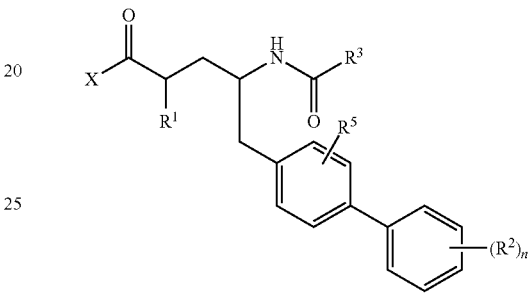

Formula II or a pharmaceutically acceptable salt thereof, wherein:
$R^1$ is $C_{1-7}$alkyl; for each occurrence, $R^2$ is independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl; wherein $R^b$ and $R^c$ for each occurrence, are independently H or $C_{1-7}$alkyl;
$R^3$ is $A^1C(O)X^1$ or $A^2$-$R^4$;
$R^4$ is $C_{6-10}$aryl or a heteroaryl, which can be monocyclic or bicyclic and which can be optionally substituted with one or more substituents independently selected from hydroxy, hydroxy-$C_{1-7}$alkyl, $NR^bR^c$, nitro, $C_{1-7}$alkoxy, halo, $C_{1-7}$alkyl, halo-$C_{1-7}$alkyl, $C_{2-7}$alkenyl, $C_{6-10}$aryl, heteroaryl, —C(O)$C_{1-7}$alkyl, —NHS(O)$_2$—$C_{1-7}$alkyl, —SO$_2$$C_{1-7}$alkyl and benzyl;
$R^5$ is H, halo, hydroxy, $C_{1-7}$alkoxy, halo, $C_{1-7}$alkyl or halo-$C_{1-7}$alkyl; and
X and $X^1$ are independently OH, —O—$C_{1-7}$alkyl, —$NR^bR^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of aryl, heteroaryl, heterocyclyl, —C(O)NH$_2$, —C(O)NH—$C_{1-6}$alkyl, and —C(O)N($C_{1-6}$alkyl)$_2$;
$A^1$ is a bond or a linear $C_{1-4}$alkylene substituted with one or more substituents independently selected from the group consisting of halo, O-acetate, $C_{1-7}$ alkyl and $C_{3-7}$cycloalkyl; in which two geminal alkyl can optionally combine to form a $C_{3-7}$cycloalkyl; or
$A^1$ is a linear or branched $C_{2-6}$alkenylene; or
$A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, $C_{1-7}$alkyl or $CH_2C(O)OH$; or
$A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$, and $OCH_2C(O)NH_2$; or $A^1$ is —$C_{1-4}$alkylene-$C_{6-10}$-aryl-, —$C_{1-4}$alkylene-heteroaryl- or —$C_{1-7}$alkylene-heterocyclyl-, wherein $A^1$ may be in either direction; and $A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

In another embodiment, the invention pertains to the use of a compound according to Formula II, or a pharmaceutically acceptable salt thereof, for the treatment, amelioration and/or prevention of contrast-induced nephropathy, in a subject in need of such treatment; wherein $R^1$, $R^2$, $R^3$, $R^4$, $R^5$, X, $X^1$, $A^1$, $A^2$ and n are as defined supra.

In a further embodiment, the invention pertains to the method of treating, ameliorating or preventing contrast-induced nephropathy in a subject, comprising administering to the subject a therapeutically useful amount of a compound according to anyone of the following formulae II-A to II-S:

Formula II-A

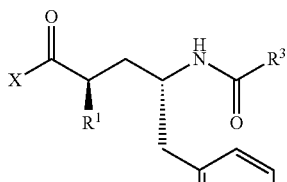

Formula II-B

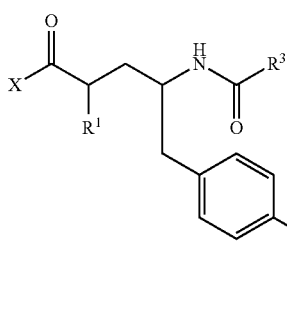

Formula II-C

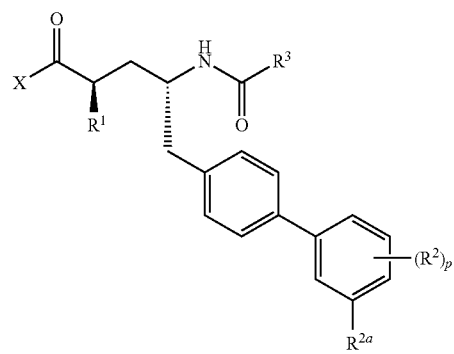

Formula II-D

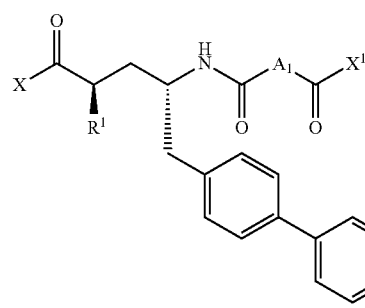

Formula II-E

Formula II-F

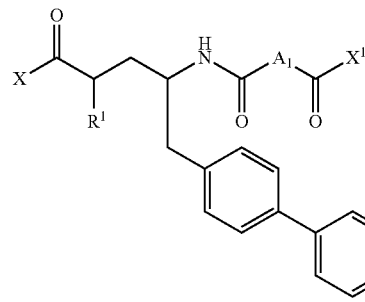

Formula II-G
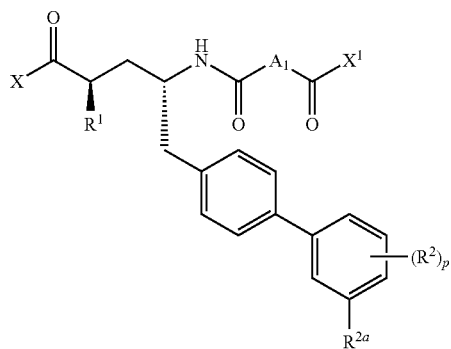
Formula II-H
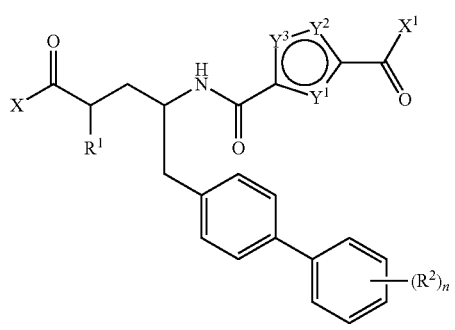
Formula II-I
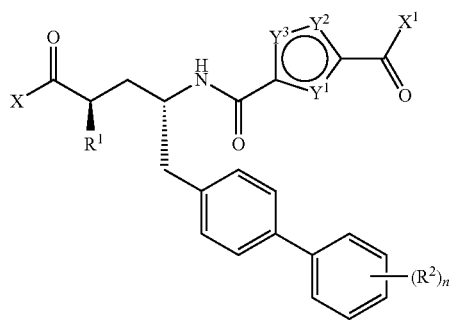
Formula II-J
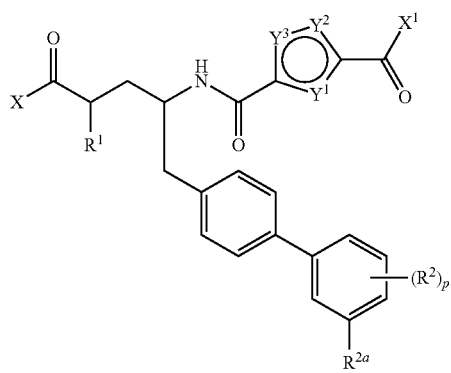
Formula II-K
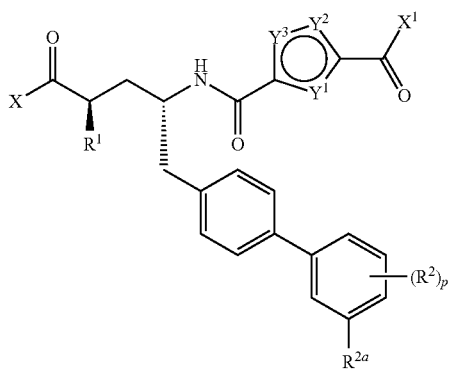
Formula II-L
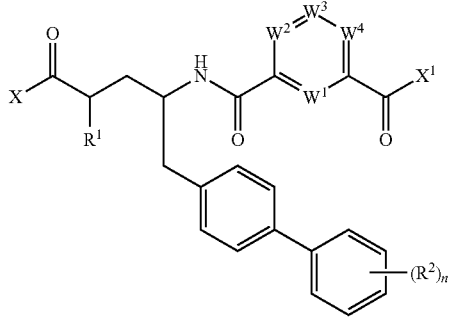
Formula II-M
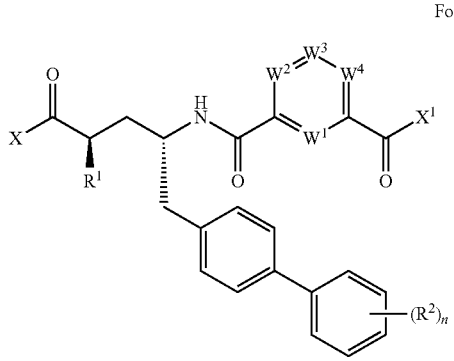
Formula II-N
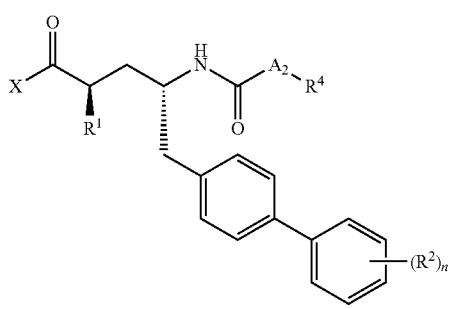

-continued

Formula II-O

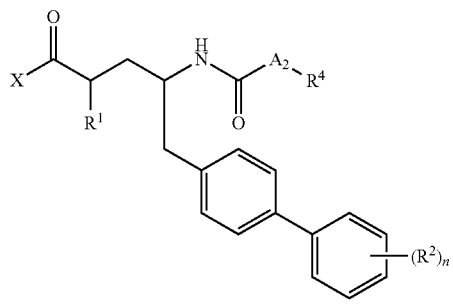

Formula II-P

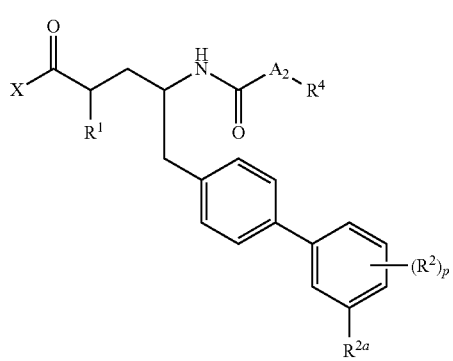

Formula II-Q

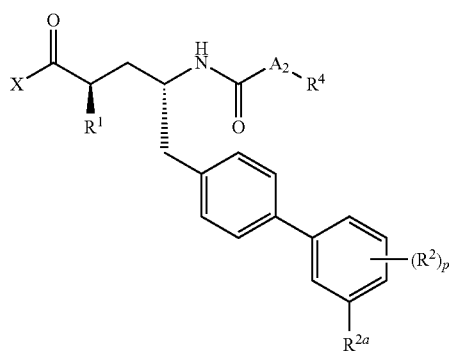

Formula II-R

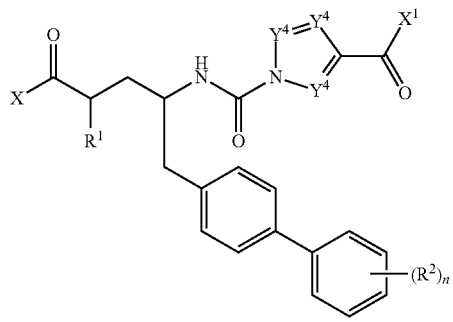

Formula II-S

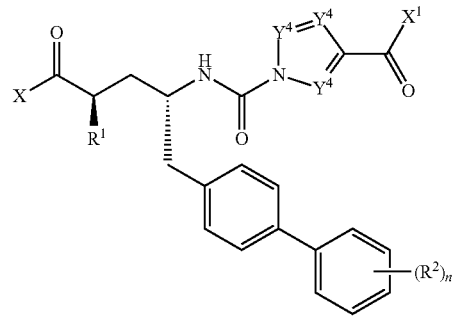

or a pharmaceutically acceptable salt thereof, wherein X, $X^1$, $A^1$, $A^2$, $R^1$, $R^2$, $R^4$ and n have the definitions of Formula II, supra; p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; $R^b$ and $R^c$ for each occurrence, are independently H or $C_{1-7}$alkyl; and $Y^1$, $Y^2$ and $Y^3$ are independently N, NH, S, O or CH and form together with the ring atoms to which they are attached a 5-membered heteroaryl ring, and each $Y^4$ is independently N, S, O or CH.

In another embodiment, the invention pertains to the use of a compound according to anyone of the formulae II-A to II-S, or a pharmaceutically acceptable salt thereof, in the manufacture of a medicament for the treatment, amelioration and/or prevention of contrast-induced nephropathy, in a subject in need of such treatment, wherein X, $X^1$, $A^1$, $A^2$, $R^1$, $R^2$, $R^4$ and n have the definitions of Formula II, supra; p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; and $Y^1$, $Y^2$ and $Y^3$ are independently N, NH, S, O or CH and form together with the ring atoms to which they are attached a 5-membered heteroaryl ring, and each $Y^4$ is independently N, S, O or CH.

In another embodiment, the invention pertains to a method of treating and/or preventing CIN in a subject, comprising administering to the subject a therapeutically effective amount of a compound of Formula III:

Formula III

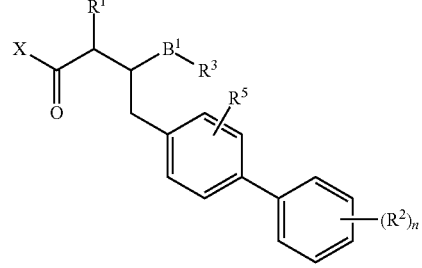

or a pharmaceutically acceptable salt thereof, wherein:
$R^1$ is H, $C_{1-7}$alkyl, hydroxy, $C_{1-7}$alkoxy, halogen, —SH, —S—$C_{1-7}$alkyl or $NR^bR^c$;
$R^2$ for each occurrence, is independently $C_{1-7}$alkyl, halogen, $NO_2$, CN, $C_{1-7}$alkanoylamino, $C_{3-7}$cycloalkyl, hydroxy, $C_{1-7}$alkoxy, halo$C_{1-7}$alkyl, —$NR^bR^c$, $C_{6-10}$aryl, heteroaryl or heterocyclyl; wherein $R^b$ and $R^c$ for each occurrence are independently H or $C_{1-7}$alkyl;

$R^3$ is $A^1$-C(O)$X^1$ or $A^2$-$R^4$;

$R^4$ is $C_{6-10}$aryl or a heteroaryl, which can be monocyclic or bicyclic, and which can be optionally substituted with one or more substituents independently selected from the group consisting of hydroxy, hydroxy$C_{1-7}$alkyl, nitro, —$NR^bR^c$, —C(O)$C_{1-7}$alkyl, C(O)—O—$C_{1-7}$alkyl, $C_{1-7}$alkoxy, halo, $C_{1-7}$alkyl, halo-$C_{1-7}$alkyl, $C_{2-7}$alkenyl, $C_{6-10}$aryl, heteroaryl, —$NHSO_2$—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —$NHSO_2$—$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, —$NR^bR^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of $C_{6-10}$aryl, heteroaryl, heterocyclyl, C(O)$NH_2$, C(O)NH—$C_{1-6}$alkyl, and C(O)N($C_{1-6}$alkyl)$_2$;

$B^1$ is —C(O)NH— or —NHC(O)—;

$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a linear or branched $C_{1-7}$alkenylene; or $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, $C_{1-7}$alkyl, —C(O)—O—$C_{1-7}$alkyl or —$CH_2$C(O)OH; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^bR^c$, —$OCH_2CO_2H$, and —$OCH_2C(O)NH_2$; or $A^1$ is a $C_{3-7}$cycloalkyl;

$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$alkylene; which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

In another embodiment, the invention pertains to the use of a compound according to Formula III, or a pharmaceutically acceptable salt thereof, in the manufacture of a medicament for the treatment, amelioration and/or prevention of contrast-induced nephropathy, in a subject in need of such treatment, wherein $R^1$, $R^2R^3$, $R^4$, $R^5$, X, $X^1$, $B^1$, $A^1$, $A^2$ and n are as defined supra.

In a further embodiment, the invention pertains to the method of treating, ameliorating or preventing contrast-induced nephropathy in a subject, comprising administering to the subject a therapeutically useful amount of a compound according to anyone of the following formulae III-A to III-T:

Formula III-A

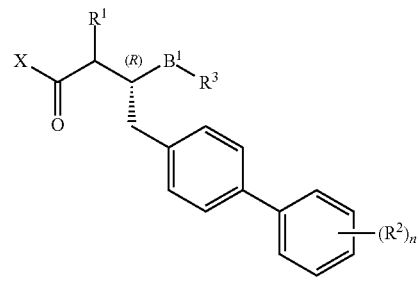

Formula III-B

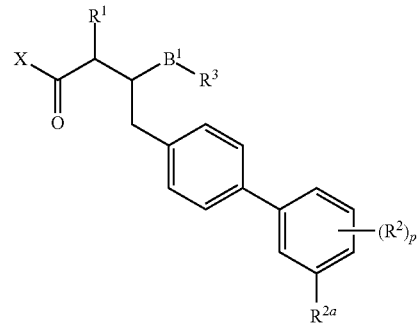

Formula III-C

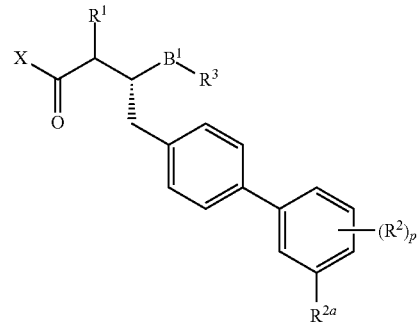

Formula III-D

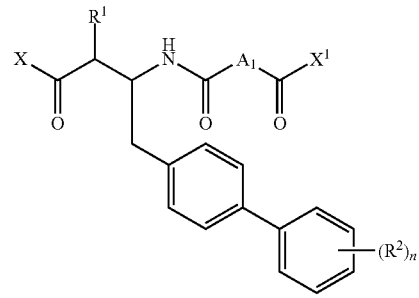

Formula III-E
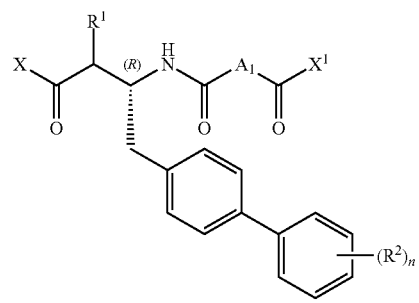
Formula III-F
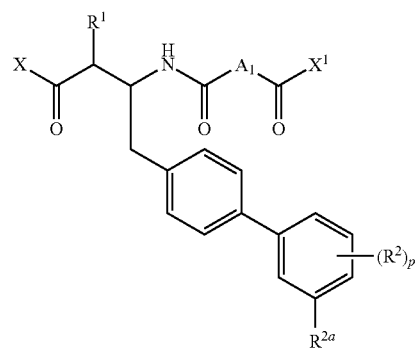
Formula III-G
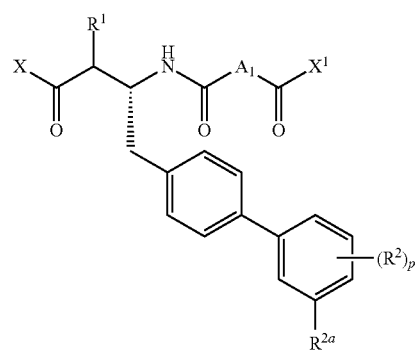
Formula III-H
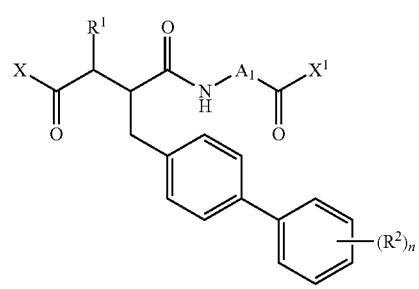
Formula III-I
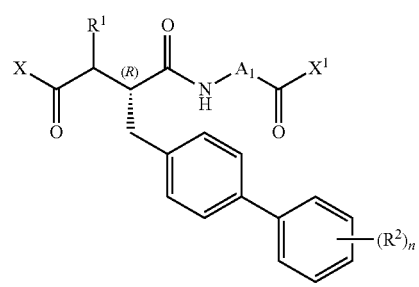
Formula III-J
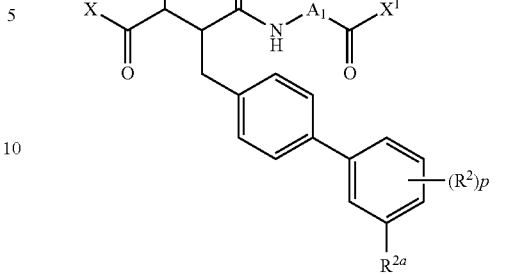
Formula III-K
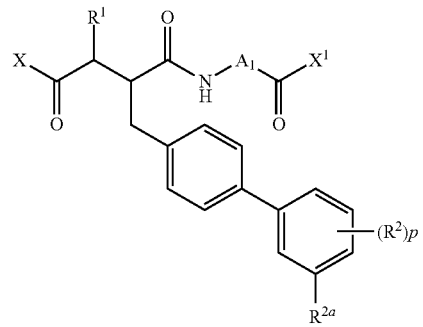
Formula III-L
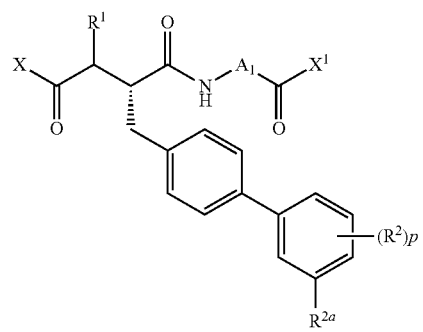
Formula III-M
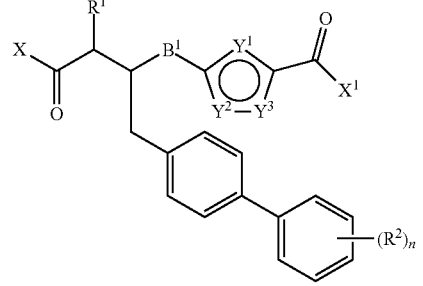
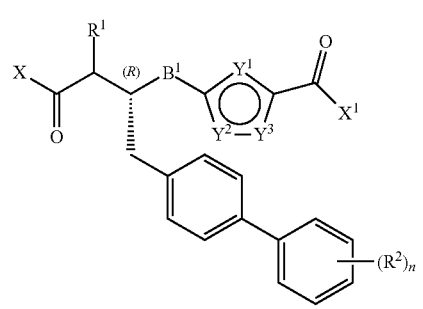

Formula III-N

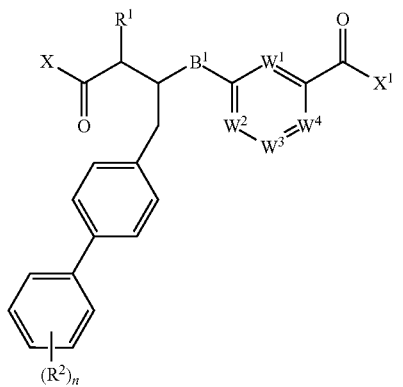

Formula III-O

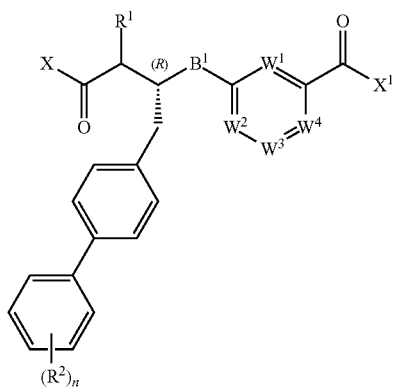

Formula III-P

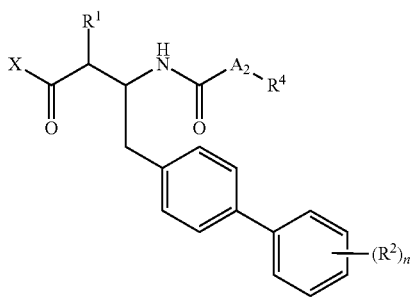

Formula III-Q

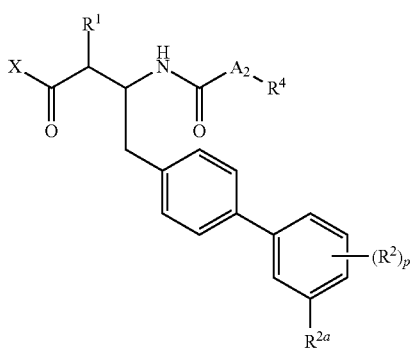

Formula III-R

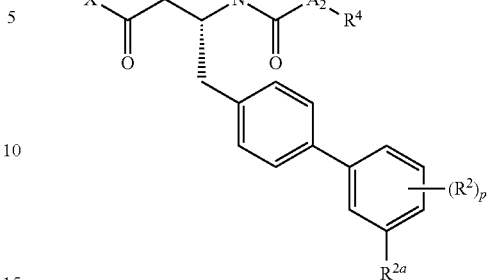

Formula III-S

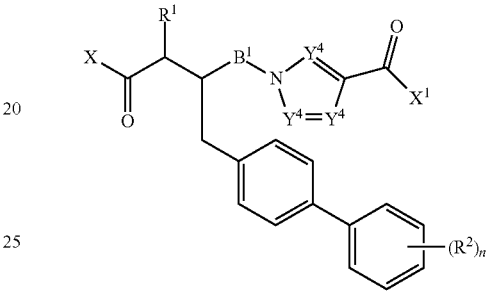

Formula III-T

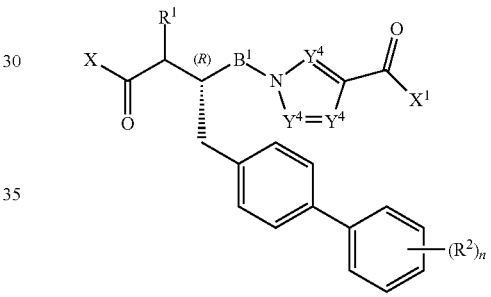

or a pharmaceutically acceptable salt thereof, wherein X, $A^2$, $A^1$, $R^1$, $B^1$, $R^2$, $X^1$ and n have the definitions of Formula III, supra; p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; and $Y^1$, $Y^2$ and $Y^3$ are independently N, NH, S, O or CH and form together with the ring atoms to which they are attached a 5-membered heteroaryl ring, and each $Y^4$ is independently N, S, O or CH and $Y^4$.

In another embodiment, the invention pertains to the use of a compound according to anyone of Formulae III-A to III-T, or a pharmaceutically acceptable salt thereof, in the manufacture of a medicament for the treatment, amelioration and/or prevention of contrast-induced nephropathy, in a subject in need of such treatment, wherein X, $A^2$, $A^1$, $R^1$, $B^1$, $R^2$, $X^1$ and n have the definitions of Formula II, supra; p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; and $Y^1$, $Y^2$ and $Y^3$ are independently N, NH, S, O or CH and form together with the ring atoms to which they are attached a 5-membered heteroaryl ring, and each $Y^4$ is independently N, S, O or CH.

In another embodiment the invention provides method of the invention using a compound according to anyone of formulae III-D to III-G, or a pharmaceutically acceptable salt or solvate thereof, wherein $A^1$ is a linear $C_{1-7}$alkylene, which is optionally substituted with one or more substituents independently selected from the group consisting of halo, $C_{1-7}$alkoxy, hydroxy, O-acetate and $C_{3-7}$cycloalkyl; in which two geminal alkyl can optionally combine to form a $C_{3-7}$cycloalkyl.

A further embodiment includes method of the invention using compounds according to anyone of Formulae III-D to III-G, or a pharmaceutically acceptable salt thereof, wherein $A^1$ is —$CH_2$—, —$CH_2CH_2$—, —$CH_2CH_2CH_2$. A further embodiment includes method of the invention using compounds according to Formula III-F or III-G, or a pharmaceutically acceptable salt thereof, wherein $A^1$ is —$CH_2$—, —$CH_2CH_2$—, —$CH_2CH_2CH_2$.

In one embodiment the invention provides method of the invention using compounds according to any one of Formulae III-A to III-T or a pharmaceutically acceptable salt thereof, wherein $R^1$ is H.

In one embodiment, the invention provides method of the invention using compounds according to any one of Formulae III, III-A, III-D, III-H, III-I, III-N, III-O, III-P, III-S and III-T, and any subclasses or classes described above, wherein $R^1$ is H, $R^2$ is independently halogen, $C_{1-7}$alkoxy, hydroxy, $C_{1-7}$alkyl or halo-$C_{1-7}$alkyl, n is 0, 1 or 2 and X and $X^1$ are independently OH or —O—$C_{1-7}$alkyl, or a pharmaceutically acceptable salt thereof. In a further aspect of this embodiment, the invention pertains to method of the invention using compounds according to anyone of Formulae III, III-A, III-I, III-N, III-O, III-S and III-T, and any other classes and subclasses described above, wherein n is 1 or 2; $R^2$ is meta-chloro or meta-fluoro and the other optional $R^2$ group is halo, $C_{1-7}$alkyl, halo-$C_{1-7}$alkyl, hydroxy and $C_{1-7}$alkoxy, or a pharmaceutically acceptable salt thereof. In yet another embodiment, the invention provides method of using compounds according to Formula III-F or III-G, wherein $A^1$ is —$CH_2$—, —$CH_2CH_2$—, —$CH_2CH_2CH_2$, p is 0, X and $X^1$ are independently OH or —O—$C_{1-7}$alkyl, $R^1$ is H and $R^{2a}$ is chloro; or a pharmaceutically acceptable salt thereof.

In another embodiment, the invention pertains to the use of a compound according to anyone of Formulae III-D to III-G, or a pharmaceutically acceptable salt thereof, in the manufacture of a medicament, for the treatment, amelioration and/or prevention of contrast-induced nephropathy, in a subject in need of such treatment, wherein $A^1$ is a linear $C_{1-7}$alkylene, which is optionally substituted with one or more substituents independently selected from the group consisting of halo, $C_{1-7}$alkoxy, hydroxy, O-acetate and $C_{3-7}$cycloalkyl; in which two geminal alkyl can optionally combine to form a $C_{3-7}$cycloalkyl.

In a further embodiment, the invention pertains to the use of a compound according to anyone of Formulae III-D to III-G, or a pharmaceutically acceptable salt thereof, in the manufacture of a medicament, for the treatment, amelioration and/or prevention of contrast-induced nephropathy, in a subject in need of such treatment, wherein $A^1$ is —$CH_2$—, —$CH_2CH_2$—, —$CH_2CH_2CH_2$. In a further embodiment, the invention pertains to the use of a compound according to Formula III-F or III-G, or a pharmaceutically acceptable salt thereof, in the manufacture of a medicament, for the treatment, amelioration and/or prevention of contrast-induced nephropathy, in a subject in need of such treatment, wherein $A^1$ is —$CH_2$—, —$CH_2CH_2$—, —$CH_2CH_2CH_2$.

In one embodiment, the invention provides the use of a compound according to any one of Formulae III-A to III-T or a pharmaceutically acceptable salt thereof, in the manufacture of a medicament, for the treatment, amelioration and/or prevention of contrast-induced nephropathy, in a subject in need of such treatment, wherein $R^1$ is H.

In one embodiment, the invention provides the use of a compound according to any one of Formulae III, III-A, III-D, III-E, III-H, III-I, III-L, III-M, III-N, III-O, III-S and III-T, and any other classes and subclasses described above, or a pharmaceutically acceptable salt thereof, in the manufacture of a medicament, for the treatment, amelioration and/or prevention of contrast-induced nephropathy, in a subject in need of such treatment, wherein $R^1$ is H, $R^2$ is independently halo, $C_{1-7}$alkoxy, hydroxy, $C_{1-7}$alkyl or halo-$C_{1-7}$alkyl, n is 0, 1 or 2 and X and $X^1$ are independently OH or —O—$C_{1-7}$alkyl. In a further aspect of this embodiment, the invention pertains the use of a compound according to anyone of Formulae III, III-A, III-D, III-E, III-H, III-I, III-l, III-M, III-N, III-O, III-P, III-S and III-T, and any classes and subclasses described above, or a pharmaceutically acceptable salt thereof, in the manufacture of a medicament, for the treatment, amelioration and/or prevention of contrast-induced nephropathy, in a subject in need of such treatment, wherein n is 1 or 2; $R^2$ is meta-chloro or meta-fluoro and the other optional $R^2$ group is halo, $C_{1-7}$alkyl, halo-$C_{1-7}$alkyl, hydroxy and $C_{1-7}$alkoxy. In another embodiment, the invention pertains to the use of a compound according to Formula III-F or III-G, wherein $A^1$ is —$CH_2$—, —$CH_2CH_2$—, —$CH_2CH_2CH_2$, p is 0, X and $X^1$ are independently OH or —O—$C_{1-4}$alkyl, $R^1$ is H and $R^{2a}$ is chloro; or a pharmaceutically acceptable salt thereof.

Other embodiments of the invention are the use of compounds exemplified in U.S. application Ser. No. 12/788,794 (US 2010/0305145) and Ser. No. 12/788,766 (US 2010/0305131), each of which is herein incorporated by reference in its entirety, in the manufacture of a medicament, for the treatment, amelioration and/or prevention of contrast-induced nephropathy, in a subject in need of such treatment.

Other embodiments of the invention are method of invention using compounds exemplified in U.S. application Ser. No. 12/788,794 (US 2010/0305145) and Ser. No. 12/788,766 (US 2010/0305131), each of which is herein incorporated by reference in its entirety, for the treatment, amelioration and/or prevention of contrast-induced nephropathy, in a subject in need of such treatment.

In yet another embodiment, the invention pertains to a method of treating and/or preventing contrast-induced nephropathy in a subject, by administering to the subject a therapeutically effective amount of a compound of Formula IV:

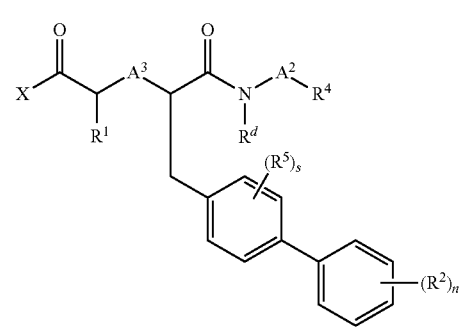

IV wherein:
X is OH, —O—$C_{1-7}$alkyl, —$NR^bR^c$, —$NHS(O)_2$—$C_{1-7}$alkyl or —$NHS(O)_2$-benzyl; wherein $R^b$ and $R^c$ for each occurrence are independently H or $C_{1-7}$alkyl;

$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy or $C_{1-6}$ alkoxy; for each occurrence, $R^2$ is independently $C_{1-6}$-alkoxy, hydroxy, halo, $C_{1-6}$-alkyl, cyano or trifluoromethyl;

$A^3$ is O or $NR^e$;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{1-7}$-cycloalkyl, wherein each heteroaryl, aryl or cycloalkyl are optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$alkyl or halo-$C_{1-7}$alkyl; or $R^d, A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

In another embodiment, the invention pertains to the use of a compound according to Formula IV, or a pharmaceutically acceptable salt thereof, in the manufacture of a medicament, for the treatment, amelioration and/or prevention of contrast-induced nephropathy, in a subject in need of such treatment, wherein X, $R^1$, $R^2$, $R^4$, $R^5$, $R^d$, $R^e$, $A^2$, $A^3$, n and s are as defined supra in formula IV.

In a further aspect of this embodiment, the invention pertains to the method of treating and/or preventing contrast-induced nephropathy in a subject, by administering to the subject a therapeutically effective amount of a compound of Formula IVA:

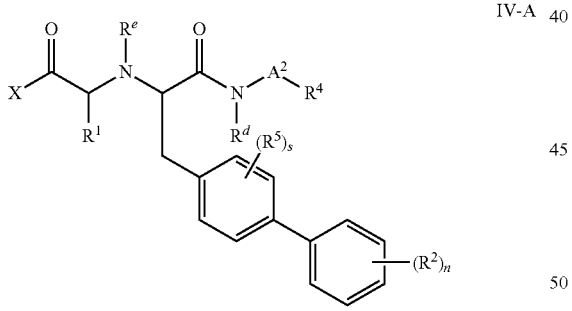

IV-A

Wherein:

X represent OH or O—$C_{1-6}$-alkyl;

$R^1$ is H, $C_{1-6}$ alkyl or $C_{6-10}$-aryl-$C_{1-6}$ alkyl;

for each occurrence, $R^2$ is independently $C_{1-6}$-alkoxy, hydroxy, halo, $C_{1-6}$-alkyl, cyano or trifluoromethyl;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{3-7}$cycloalkyl, wherein each heteroaryl, aryl or cycloalkyl are optionally substituted with one or more groups independently selected from the group consisting of $C_{1-6}$alkyl, halo, halo-$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$ alkyl or halo-$C_{1-7}$alkyl; or $R^d, A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

In a further aspect, the invention pertains to the use of a compound according to Formula IV-A, or a pharmaceutically acceptable salt thereof, in the manufacture of a medicament, for the treatment, amelioration and/or prevention of constrast-induced nephropathy, in a subject in need of such treatment, wherein X, $R^1$, $R^2$, $R^4$, $R^5$, $R^d$, $R^e$, $A^2$, n and s are as defined supra in formula IV-A.

In a further embodiment, the invention pertains to the method of treating, ameliorating or preventing contrast-induced nephropathy in a subject, comprising administering to the subject a therapeutically useful amount of a compound according to anyone of the following formulae IV-B to IV-D:

Formula IV-B

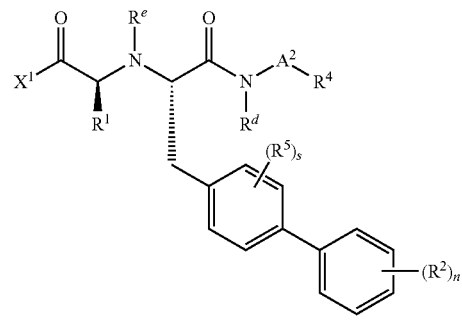

Formula IV-C

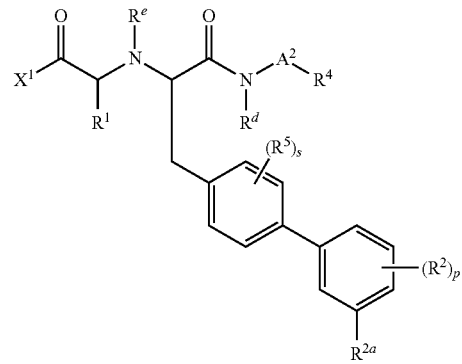

-continued

Formula IV-D

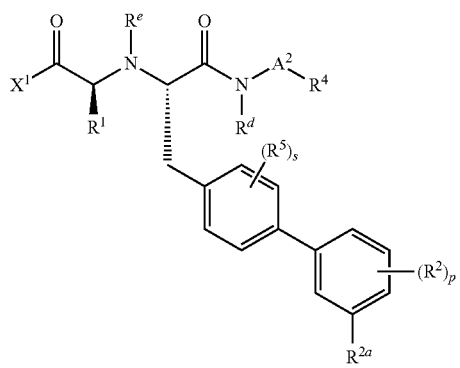

or a pharmaceutically acceptable salt thereof, wherein $X^1$, $R^1$, $R^2$, $R^4$, $R^5$, $R^9$, $A^2$, n and s are as defined in Formula IV or IV-A, p is 0, 1, 2, 3 or 4, $R^{29}$ is halo.

In another embodiment, the invention pertains to the use of a compound according to anyone of Formulae IV-B to IV-D, or a pharmaceutically acceptable salt thereof, in the manufacture of a medicament, for the treatment, amelioration and/or prevention of constrast-induced nephropathy, in a subject in need of such treatment, wherein $X^1$, $R^1$, $R^2$, $R^4$, $R^5$, $R^e$, $A^2$, n and s are as defined in Formula IV or IV-A, p is 0, 1, 2, 3 or 4, $R^{2a}$ is halo.

In another embodiment, the invention pertains to method of the invention using compounds according to anyone of Formulae IV and IV-A to IV-D, or any of any other classes and subclasses described supra, or a pharmaceutically acceptable salt thereof, wherein $R^e$ is H.

In another embodiment, the invention pertains to the use of a compound according to anyone of Formulae IV and IV-A to IV-D, or any of any other classes and subclasses described supra, or a pharmaceutically acceptable salt thereof, in the manufacture of a medicament, for the treatment, amelioration and/or prevention of contrast-induced nephropathy, in a subject in need of such treatment, wherein $R^e$ is H.

In another embodiment, the invention pertains to method of the invention using compounds according to anyone of Formulae IV and IV-A to IV-D or any of any other classes and subclasses described supra, or a pharmaceutically acceptable salt thereof, wherein $R^d$ is H.

In another embodiment, the invention pertains to the use of a compound according to anyone of Formulae IV and IV-A to IV-D, or any of any other classes and subclasses described supra, or a pharmaceutically acceptable salt thereof, in the manufacture of a medicament, for the treatment, amelioration and/or prevention of contrast-induced nephropathy, in a subject in need of such treatment, wherein $R^d$ is H.

In another embodiment, the invention pertains to method of the invention using compounds according to anyone of Formulae IV and IV-A to IV-D or any of any other classes and subclasses described supra, or a pharmaceutically acceptable salt thereof, wherein s is 0.

In another embodiment, the invention pertains to the use of a compound according to anyone of Formulae IV and IV-A to IV-D or any of any other classes and subclasses described supra, or a pharmaceutically acceptable salt thereof, in the manufacture of a medicament, for the treatment, amelioration and/or prevention of contrast-induced nephropathy, in a subject in need of such treatment, wherein s is 0.

The following embodiments can be used independently, collectively or in any combination or sub-combination:

In one embodiment, the invention includes use of a compound according to anyone of Formulae I, II, II-N to II-Q, III, III-P to III-R, IV and IV-A to IV-D, or a pharmaceutically acceptable salt thereof, wherein $A^2$ is $(CH_2)_p$ and p is 0, 1, 2 or 3, in the manufacture of a medicament, for the treatment, amelioration and/or prevention of contrast-induced nephropathy, in a subject in need of such treatment.

In one aspect of this embodiment, p is 0, therefore $A^2$ is a bond. In another aspect of this embodiment, $A^2$ is $CH_2$ or $CH_2$—$CH_2$.

In another aspect of this embodiment, the invention provides the use of a compound according to anyone of Formulae I, II, II-N to II-Q, III, III-P to III-R, IV and IV-A to IV-D, or a pharmaceutically acceptable salt thereof, in the manufacture of a medicament, for the treatment, amelioration and/or prevention of contrast-induced nephropathy, in a subject in need of such treatment, wherein $R^4$ is an optionally substituted $C_{6-10}$aryl; wherein the substituents are as defined supra in Formula I, II, III or IV.

Representative examples of aryl are benzoimidazolone, benzoisothiazolone or phenyl. In one further aspect of this embodiment, $R^4$ is phenyl. Substituents on the phenyl ring include for example, halo (e.g. F, Cl), hydroxy, halo-$C_{1-7}$alkyl (e.g. $CF_3$), $C_{1-7}$alkoxy or $C_{1-7}$alkyl.

In yet another aspect of this embodiment, the invention provides the use of a compound according to anyone of Formulae I, II, II-N to II-Q, III, III-P to III-R, IV and IV-A to IV-D or a pharmaceutically acceptable salt thereof, in the manufacture of a medicament, for the treatment, amelioration and/or prevention of contrast-induced nephropathy, in a subject in need of such treatment, wherein $R^4$ is an optionally substituted bicyclic heteroaryl; wherein the substituents are as defined supra in Formula I, II, III or IV.

In yet another aspect of this embodiment, the invention provides the use of a compound according to anyone of Formulae I, II, II-N to II-Q, III, III-P to III-R, IV and IV-A to IV-D, or a pharmaceutically acceptable salt thereof, in the manufacture of a medicament, for the treatment, amelioration and/or prevention of contrast-induced nephropathy, in a subject in need of such treatment, wherein $R^4$ is an optionally substituted 5- or 6-membered heteroaryl; wherein the substituents are as defined supra in Formula I, II, III or N.

In one aspect of this embodiment, $R^4$ is a 6-membered ring heteroaryl selected from the group consisting of pyrazinyl, pyridinyl, pyrimidinyl, oxo-pyranyl (e.g. pyranone, optionally substituted pyran-4-one, pyran-2-one such as 3-hydroxy-pyran-4-one, 3-hydroxy-pyran-2-one), and oxo-pyridinyl (e.g. pyridinone, optionally substituted pyridin-4-one or pyridin-2-one such as for example 3-hydroxy-1-methyl-pyridin-4-one or 1-benzyl-pyridin-2-one); or pyrimidinone (i.e. oxo-pyrimidinyl). In another aspect of this embodiment $R^4$ is a 5-membered ring heteroaryl selected from the group consisting of oxazole, pyrrole, pyrazole, isooxazole, triazole, tetrazole, oxadiazole (e.g. 1-oxa-3,4-diazole, 1-oxa-2,4-diazole), oxadiazolone (e.g. oxadiazol-2-one), thiazole, isothiazole, thiophene, imidazole and thiadiazole. In a particular aspect of this embodiment, $R^4$ is tetrazole. Other representative examples of $R^4$ are oxazolone, thiazolone, oxadiazolone triazolone, oxazolone, imidazolone, pyrazolone. In a further embodiment, the optional substituents on $C_{6-10}$aryl and heteroaryl are selected from hydroxy, $C_{1-7}$alkyl, $C_{1-7}$alkoxy, halo, halo-$C_{1-7}$alkyl or benzyl.

In yet another aspect of the above embodiment, the invention provides the use of a compound according to anyone of Formulae I, II, II-N to II-Q, III, III-P to III-R, IV and IV-A to IV-D, or a pharmaceutically acceptable salt thereof, wherein $R^4$ is a bicyclic heteroaryl, in the manufacture of a medicament, for the treatment, amelioration and/or prevention of contrast-induced nephropathy, in a subject in need of such treatment. In a further embodiment includes $R^4$ is indolyl, benzothiazolyl or benzimidazolyl. Representative examples of $R^4$ are the following:

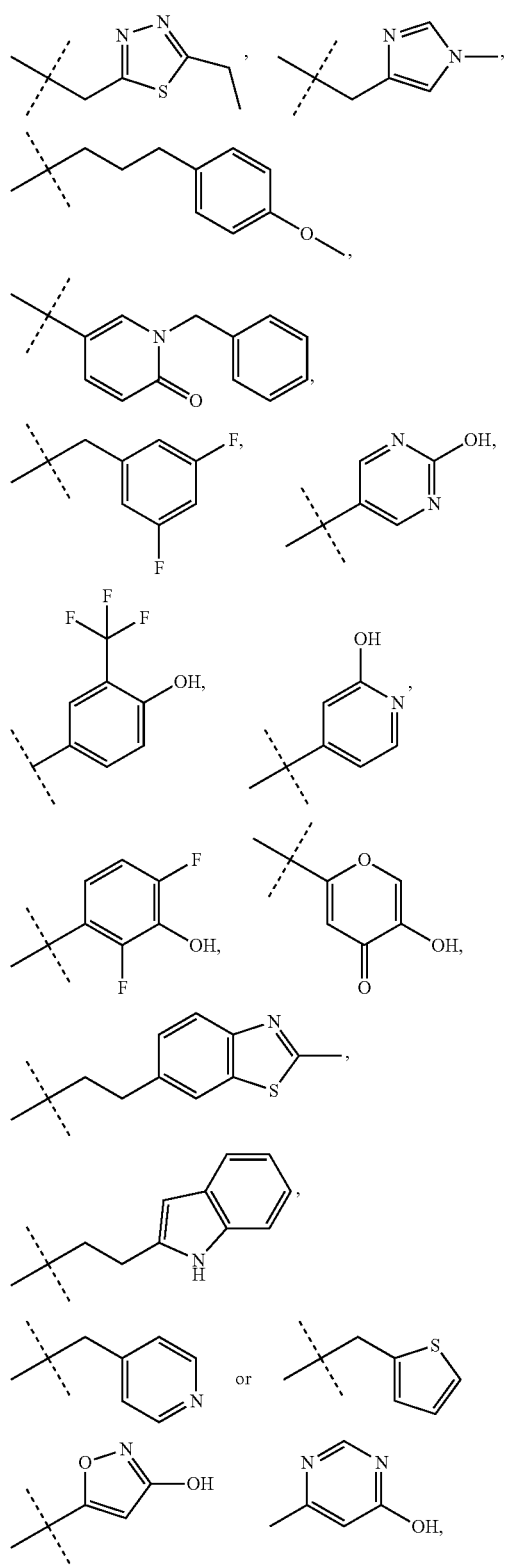

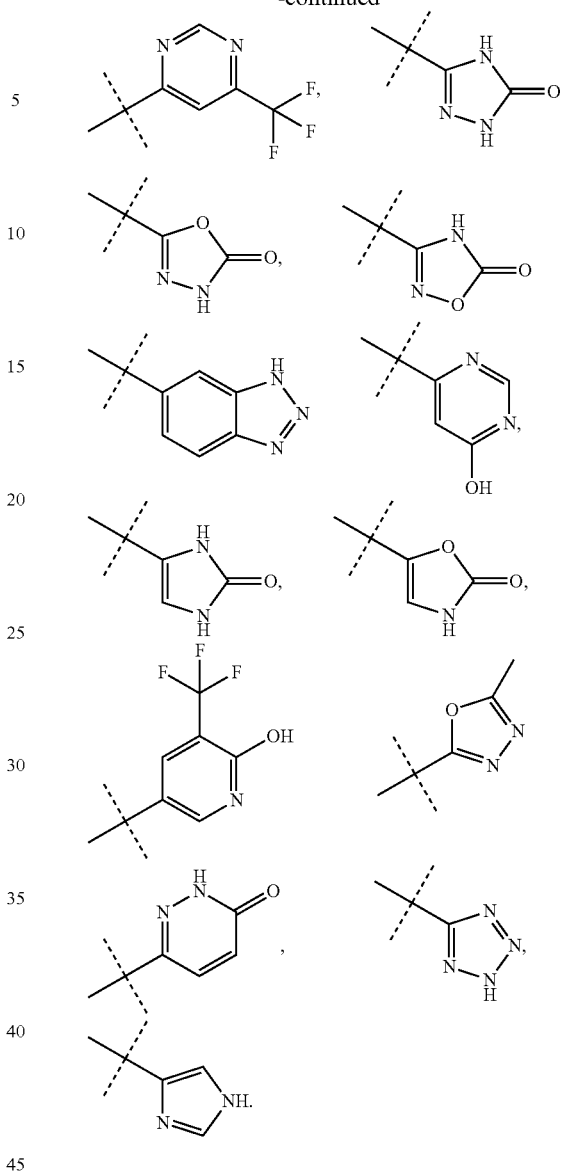

In one embodiment, the invention provides the use of a compound according to any one of Formulae I, II, II-A to II-S, III, III-A to III-T, IV, IV-A to IV-D or a pharmaceutically acceptable salt thereof, in the manufacture of a medicament, for the treatment, amelioration and/or prevention of contrast-induced nephropathy, in a subject in need of such treatment, wherein $R^1$ is methyl.

In another embodiment, the invention provides the use of a compound according to any one of Formulae I, II, II-A, II-D, II-E, II-H, II-I, II-L II-M, II-M, II-N, II-O, II-R, II-S, III, III-A, III-D, III-E, III-H, III-I, III-L, III-M, III-N, III-O, III-P, III-S, IV, IV-A and IV-B or a pharmaceutically acceptable salt thereof, in the manufacture of a medicament, for the treatment, amelioration and/or prevention of contrast-induced nephropathy, in a subject in need of such treatment, wherein each $R^2$ is independently halo, alkyl, alkoxy, hydroxy, haloalkyl and n is 0, 1 or 2.

In a further embodiment the invention pertains to the use of a compound according to anyone of Formulae I, II, II-A, II-D, II-E, II-H, II-I, II-L, II-M, II-M, II-N, II-O, II-R, II-S, III, III-A, III-D, III-E, III-H, III-I, III-L, III-M, III-N, III-O, III-P, III-S, IV, IV-A and IV-B, or a pharmaceutically acceptable salt thereof, in the manufacture of a medicament, for the treatment, amelioration and/or prevention of contrast-induced nephropathy, in a subject in need of such treatment, wherein n is 1, 2, 3, 4 or 5, $R^2$ is halo in the meta position and the other optional $R^2$ groups are independently halo, $C_{1-7}$alkyl, $C_{1-7}$alkoxy, hydroxy, haloalkyl. In yet a further embodiment, the invention provides the use of a compound according to any one of Formulae I, II, II-A, II-D, II-E, II-H, II-I, II-L, II-M, II-M, II-N, II-O, II-R, II-S, III, III-A, III-D, III-E, III-H, III-I, III-L, III-M, III-N, III-O, III-P, III-S, IV, IV-A and IV-B, or a pharmaceutically acceptable salt thereof, in the manufacture of a medicament, for the treatment, amelioration and/or prevention of contrast-induced nephropathy, in a subject in need of such treatment, wherein n is 1 or 2, $R^2$ is meta-chloro and the other optional $R^2$ group is halo, $C_{1-7}$alkyl, $C_{1-7}$alkoxy, hydroxy, haloalkyl.

In another embodiment, the invention provides the use of a compound according to anyone of Formulae II-B, II-C, II-F, II-G, II-J, II-K, II-P, II-Q, III-B, III-C, III-F, III-G, III-J, III-K, III-Q, III-R, IV-C and IV-D, or a pharmaceutically acceptable salt thereof, wherein p is 0, $R^{2a}$ is chloro.

In yet another embodiment, the invention provides use of a compound according to any one of Formulae I, II, II-A to II-S, II, III-A to III-T, IV and IV-A to IV-D, or a pharmaceutically acceptable salt thereof, in the manufacture of a medicament, for the treatment, amelioration and/or prevention of contrast-induced nephropathy, in a subject in need of such treatment, wherein X and $X^1$ (when present) are independently OH or —O—$C_{1-7}$alkyl (e.g. O-ethyl, O-methyl, O-propyl or O-butyl). In one particular aspect of this embodiment X and $X^1$ are OH. In another aspect of this embodiment, X and $X^1$ are independently —O—$C_{1-7}$alkyl in which alkyl is substituted with $C_{6-10}$aryl, heteroaryl, heterocyclyl, C(O)NH$_2$, C(O)NH—$C_{1-6}$alkyl, or C(O)N($C_{1-6}$alkyl)$_2$. Representative examples of X or $X^1$ are —O—CH$_2$—C(O)N(CH$_3$)$_2$, —O—CH$_2$—CH$_2$-morpholine, —O—CH$_2$-dioxolone or —O-benzyl. In yet another aspect of this embodiment, X and $X^1$ are —O—$C_{6-10}$aryl. A representative examples of —O—$C_{6-10}$aryl is —O-(2,3-dihydro-1H-indene).

In a further embodiment, the invention pertains to the use of a compound according to anyone of Formulae I, II, II-H to II-K, III, III-L and III-M, or a pharmaceutically acceptable salt thereof, in the manufacture of a medicament, for the treatment, amelioration and/or prevention of contrast-induced nephropathy, in a subject in need of such treatment, wherein $Y^1$, $Y^2$ and $Y^3$ form together with the ring atoms to which they are attached a 5-membered heteroaryl ring selected from furan, thiophene, pyrrole, pyrazole, oxazole, thiazole, oxadiazole, thiadiazole, and triazole.

One further embodiment includes use of a compound according to anyone of Formulae I, II, II-H to II-K, III, III-L and III-M, or a pharmaceutically acceptable salt thereof, in the manufacture of a medicament, for the treatment, amelioration and/or prevention of contrast-induced nephropathy, in a subject in need of such treatment, wherein the 5-membered heteroaryl is one of the following:

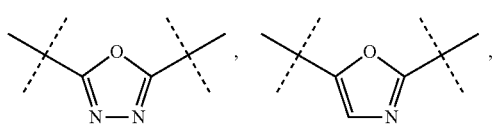

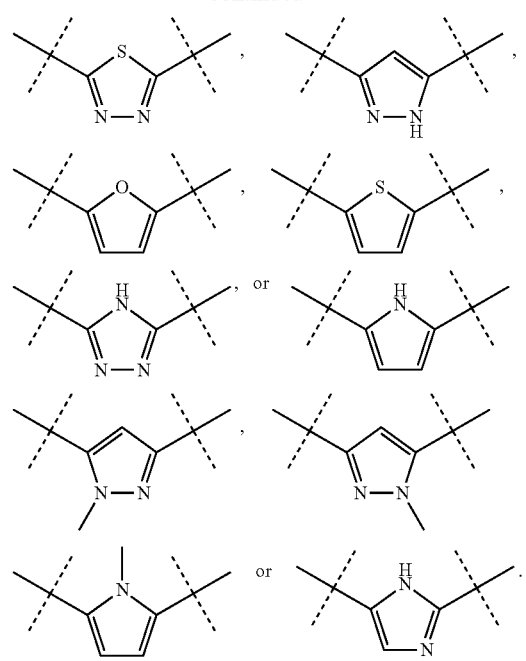

In one aspect of this embodiment, the invention pertains to the use of a compound of anyone of Formulae I, II, II-A to II-G, III and III-D to III-K or a pharmaceutically acceptable salt thereof, in the manufacture of a medicament, for the treatment, amelioration and/or prevention of contrast-induced nephropathy, in a subject in need of such treatment, wherein $A^1$ is phenyl, pyridine or pyrimidine.

One further embodiment includes use of a compound according to anyone of Formulae I, II, II-A to II-G, II-L, II-M, III, III-D to III-K, III-N and III-O or a pharmaceutically acceptable salt thereof, in the manufacture of a medicament, for the treatment, amelioration and/or prevention of contrast-induced nephropathy, in a subject in need of such treatment, wherein $A^1$ is one of the following:

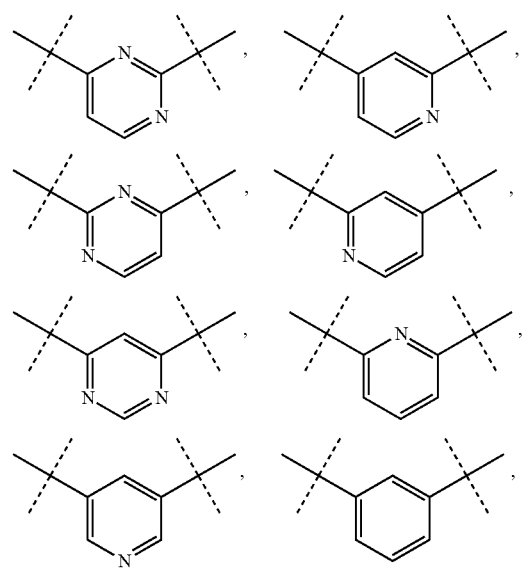

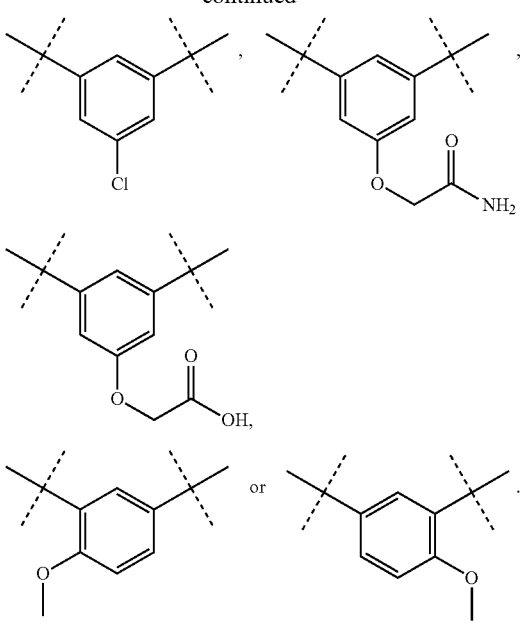

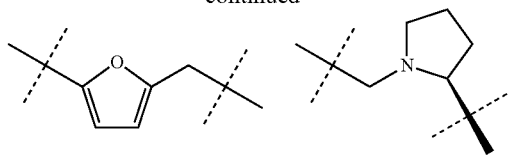

In a further embodiment, the invention pertains to the use of a compound according to any one of Formulae I, II, II-A to II-G, III and III-D to III-K, or a pharmaceutically acceptable salt thereof, in the manufacture of a medicament, for the treatment, amelioration and/or prevention of contrast-induced nephropathy, in a subject in need of such treatment, wherein $A^1$ is —$C_{1-4}$alkylene-$C_{6-10}$-aryl-, —$C_{1-4}$alkylene-heteroaryl- or —$C_{1-4}$alkylene-heterocyclyl-, —$C_{6-10}$aryl-$C_{1-4}$-alkylene-, -heteroaryl-$C_{1-4}$alkylene or -heterocyclyl-$C_{1-4}$alkylene-. In one aspect of this embodiment, $A^1$ is —$C_{1-4}$alkylene-$C_{6-10}$-aryl-, —$C_{1-4}$alkylene-heteroaryl- or —$C_{1-4}$alkylene-heterocyclyl-, wherein the alkylene portion is attached to C(O)NH group and the aryl, heteroaryl or heterocyclyl moities are attached to $C(O)X^1$. In another aspect of this embodiment, $A^1$ is —$CH_2$-phenyl- or -phenyl-$CH_2$—. In another aspect of this embodiment, $A^1$ is —$CH_2$-heteroaryl or -heteroaryl-$CH_2$—. In a further embodiment, $A^1$ is —$CH_2$-heterocyclyl or -heterocyclyl-$CH_2$—. Representative examples of $A^1$ are the following:

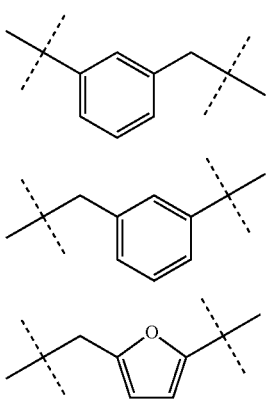

In another embodiment, the invention provides the use of a compound according to any one of the formulae I, II, II-A to II-G, III and III-D to III-K, or of any classes and subclasses described herein, or a pharmaceutically acceptable salt thereof, in the manufacture of a medicament, for the treatment, amelioration and/or prevention of contrast-induced nephropathy, in a subject in need of such treatment, wherein $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence is independently H, $C_{1-7}$alkyl or $CH_2C(O)OH$.

One further embodiment includes the use of a compound according to anyone of Formulae I, II, II-A to II-G, III and III-D to III-K, in the manufacture of a medicament, for the treatment, amelioration and/or prevention of contrast-induced nephropathy, in a subject in need of such treatment, wherein $A^1$ is one of the following:

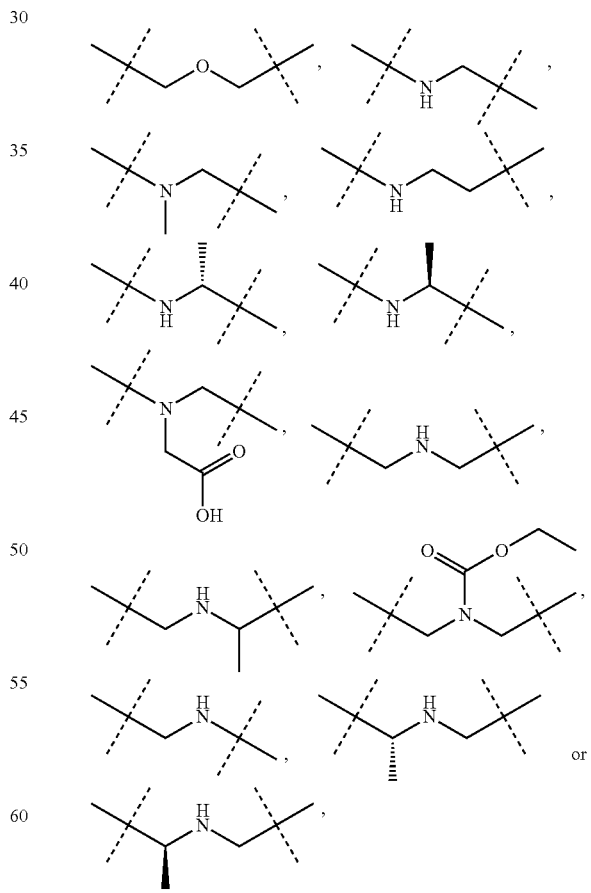

In yet another embodiment, the invention provides the use of a compound according to any one of Formulae I, II, II-A to II-G, III and III-D to III-K, or of any classes and subclasses described herein, or a pharmaceutically acceptable salt thereof, in the manufacture of a medicament, for the treatment, amelioration and/or prevention of contrast-induced nephropathy, in a subject in need of such treatment, wherein $A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$, and $OCH_2C(O)NH_2$. In one aspect of this embodiment, the invention provides the use of a compound according to any one of Formulae I, II, II-A to II-G, III and III-D to III-K, or a pharmaceutically acceptable salt thereof, wherein $A^1$ is a $C_{3-7}$cycloalkyl or a heterocyclyl. One further embodiment includes the use of a compound according to any one of Formulae I, II, II-A to II-G, III and III-D to III-K, or a pharmaceutically acceptable salt thereof, in the manufacture of a medicament, for the treatment, amelioration and/or prevention of contrast-induced nephropathy, in a subject in need of such treatment, wherein $A^1$ is one of the following:

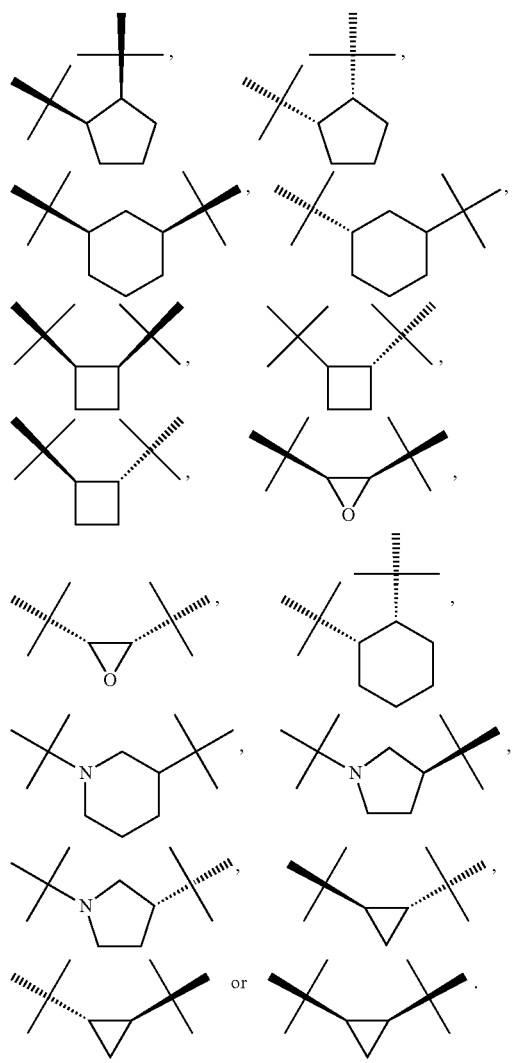

In a further embodiment, the invention includes the use of a compound according to anyone of Formulae I, II, II-A to II-G, III and III-D to III-K, or a pharmaceutically acceptable salt thereof, in the manufacture of a medicament, for the treatment, amelioration and/or prevention of contrast-induced nephropathy, in a subject in need of such treatment, wherein $A^1$ has the following formulae:

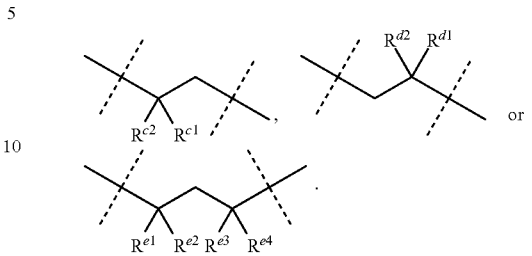

in which $R^{c1}$, $R^{c2}$, $R^{d1}$, $R^{d2}$, $R^{e1}$, $R^{e2}$, $R^{e3}$ and $R^{e4}$ are independently H, halo, $C_{3-7}$cycloalkyl, or $C_{1-7}$alkyl; and alternatively $R^{c1}$ and $R^{c2}$ or $R^{d1}$ and $R^{d2}$ can form together with the atoms to which they are attached a $C_{3-7}$cycloalkyl. In a further embodiment, at least one of $R^{c2}$ and $R^{c1}$ is other than H, or at least one of $R^{d2}$ and $R^{d1}$ is other than H, or at least one of $R^{e1}$, $R^{e2}$, $R^{e3}$, $R^{e4}$ is other than H. In some representative examples, $A^1$ is one of the following:

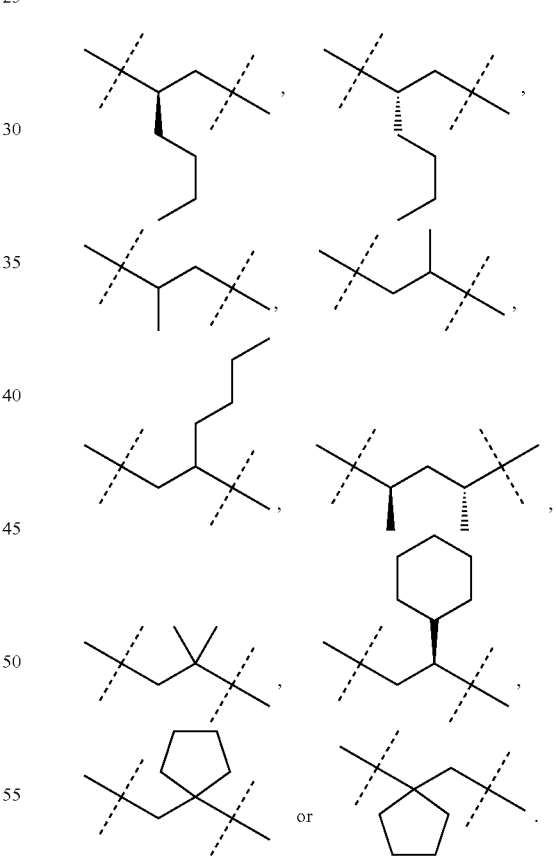

Yet another further embodiment includes use of a compound according to anyone of Formulae I, II, II-A to II-G, III and III-D to III-K, or of any classes and subclasses described herein, or a pharmaceutically acceptable salt thereof, in the manufacture of a medicament, for the treatment, amelioration and/or prevention of contrast-induced nephropathy, in a subject in need of such treatment, wherein $A^1$ has the following formulae:

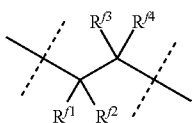

in which $R^{f1}$, $R^{f2}$, $R^{f3}$ and $R^{f4}$ are independently H, halo, O-acetate or $C_{1-7}$alkyl. In a further embodiment, one of $R^{f1}$, $R^{f2}$, $R^{f3}$ and $R^{f4}$ is other than H. In some representative examples, $A^1$ is one of the following:

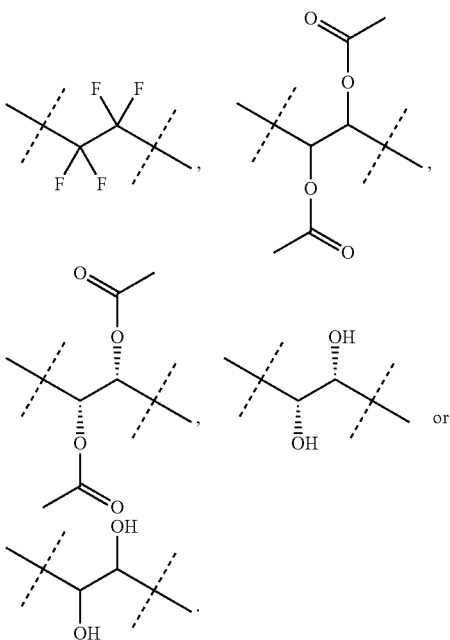

In another embodiment, the invention pertains to a method of treating, amelioration or preventing contrast-induced nephropathy, comprising administering to the subject a therapeutically effective amount of a compound according to Formula I, wherein $A^3$, $R^2$, $R^3$, $R^5$, $B^1$, X, n and s groups are those defined by the $A^3$, $R^1$, $R^2$, $R^3$, $R^5$, $B^1$, X, n and s groups in the Examples section below.

In another embodiment, the invention pertains to the use of a compound according to Formula I, wherein $A^3$, $R^1$, $R^2$, $R^3$, $R^5$, $B^1$, X, n and s groups are those defined by the $A^3$, $R^1$, $R^2$, $R^3$, $R^5$, $B^1$, X, n and s groups in the Examples section below, in the manufacture of a medicament, for the treatment, amelioration and/or prevention of contrast-induced nephropathy, in a subject in need of such treatment.

In another embodiment, the invention pertains to a method of treating, ameliorating or preventing contrast-induced nephropathy in a subject, comprising administering to the subject a therapeutically effective amount of a compound listed in the Examples section below or a pharmaceutically acceptable salt thereof. In another embodiment, the invention pertains to the use of a compound listed in the Examples section below or a pharmaceutically acceptable salt thereof, in the manufacture of a medicament, for the treatment, amelioration and/or prevention of contrast-induced nephropathy, in a subject in need of such treatment.

In another embodiment, the invention pertains to method of treating, ameliorating or preventing contrast-induced nephropathy in a subject, comprising administering to the subject a therapeutically effective amount of a compound disclosed in U.S. patent application Ser. No. 12/788,794 (US 2010/0305145), U.S. patent application Ser. No. 12/788,766 (US 2010/0305131) and U.S. provisional application 61/359,914 (U.S. patent application Ser. No. 12/947,029: US 2011/0124695), each of which is herein incorporated by reference, or a pharmaceutically acceptable salt thereof. In another embodiment, the invention pertains to the use of a compound disclosed in U.S. patent application Ser. No. 12/788,794 (US 2010/0305145), U.S. patent application Ser. No. 12/788,766 (US 2010/0305131) and U.S. provisional application 61/359,914 (which is U.S. patent application Ser. No. 12/947,029: US 2011/0124695), or a pharmaceutically acceptable salt thereof, in the manufacture of a medicament, for the treatment, amelioration and/or prevention of contrast-induced nephropathy, in a subject in need of such treatment.

In another embodiment, the invention pertains to method of treating, ameliorating or preventing contrast-induced nephropathy in a subject, comprising administering to the subject a therapeutically effective amount of a compound disclosed in U.S. provisional application 61/414,163, which is herein incorporated by reference, or a pharmaceutically acceptable salt thereof. In another embodiment, the invention pertains to the use of a compound disclosed in U.S. provisional application 61/414,163, or a pharmaceutically acceptable salt thereof, in the manufacture of a medicament, for the treatment, amelioration and/or prevention of contrast-induced nephropathy, in a subject in need of such treatment.

In another embodiment, the invention pertains to the use of a compound according to anyone of Formulae I, II, IIA to II-S, III, III-A to III-T, IV, IV-A to IV-D or any classes and subclasses described supra; or of Examples 1 to 38 or a pharmaceutically acceptable salt thereof, in the manufacture of a medicament for the prevention, amelioration or treatment of contrast-induced nephropathy.

In another embodiment, the invention pertains to the method of treating, preventing or ameliorating contrast-induced nephropathy in a subject in need thereof, comprising administering to the subject a compound according to anyone of Formulae I, II, IIA to II-S, III, III-A to III-T, IV, IV-A to IV-D or any classes and subclasses described supra; or of Examples 1 to 38, or a pharmaceutically acceptable salt thereof.

It will be noted that the structure of some of the compounds for use in this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)- configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis- (Z)- or trans- (E)- form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate; citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3H$, $^{13}C$, and $^{14}C$ are present. In one embodiment, the atoms in the formulae herein occur in their natural abundance. In another embodiment, one or more hydrogen atom may be enriched in $^2H$; or/and one or more carbon atom may be enriched in $^{11}C$, $^{13}C$ or $^{14}C$; or/and one or more nitrogen may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to anyone of the formulae I, II, II-A to II-S, III, III-A to III-T, IV and IV-A to IV-D. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds according to anyone of formulae I, II, II-A to II-S, III, III-A to III-T, IV and IV-A to IV-D can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds according to anyone of formulae I, II, II-A to II-S, III, III-A to III-T, IV and IV-A to IV-D that contain groups capable of acting as donors and/or acceptors for hydrogen bonds may be capable of forming co-crystals with suitable co-crystal formers. These co-crystals may be prepared from compounds according to anyone of formulae I, II, II-A to II-S, III, III-A to III-T, IV and IV-A to IV-D by known co-crystal forming procedures. Such procedures include grinding, heating, co-subliming, co-melting, or contacting in solution compounds according to anyone of formulae I, II, II-A to II-S, III, III-A to III-T, IV and IV-A to IV-D with the co-crystal former under crystallization conditions and isolating co-crystals thereby formed. Suitable co-crystal formers include those described in WO 2004/078163. Hence the invention further provides co-crystals comprising a compound according to anyone of formulae I, II, II-A to II-S, III, III-A to III-T, IV and IV-A to IV-D or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease or a symptom thereof (i) ameliorated by the inhibition of neutral endopeptidase EC 3.4. 24.11 or (ii) associated with neutral endopeptidase EC 3.4. 24.11 activity, or (iii) characterized by abnormal activity of neutral endopeptidase EC 3.4. 24.11; or (2) reduce or inhibit the activity of neutral endopeptidase EC 3.4. 24.11; or (3) reduce or inhibit the expression of neutral endopeptidase EC 3.4. 24.11. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of neutral endopeptidase EC 3.4. 24.11; or at least partially reduce or inhibit the expression of neutral endopeptidase EC 3.4. 24.11

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Scheme:

The compounds of the invention can be synthesized using the methods described in the following schemes, examples, and by using art recognized techniques. All compounds described herein are included in the invention as compounds. Compounds of the invention may be synthesized according to at least one of the methods described in schemes 1-3.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds according to anyone of formulae I, II, II-A to II-S, III, III-A to III-T, IV and IV-A to IV-D can be prepared according to the Schemes 1 to 16 provided infra.

The compounds of the invention of formula I, II or III wherein $B^1$ is NHC(O) and $R^3$ is $A^1$-C(O)$X^1$ can be prepared by hydrolysis of intermediates A to C wherein X, $X^1$, $A^1$, $A^3$, $R^1$, $R^2$, $R^5$, Ring C, s and n have the definition of Formula I, supra; and $P^1$ and $P^2$ are appropriate protecting groups selected from, but not limited to, methyl, ethyl, isopropyl, tert-butyl, methoxybenzyl or benzyl.

Intermediate A

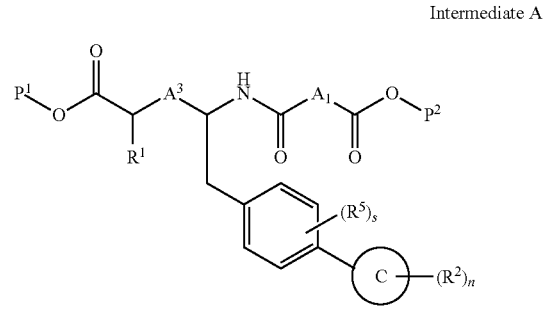

Intermediate B

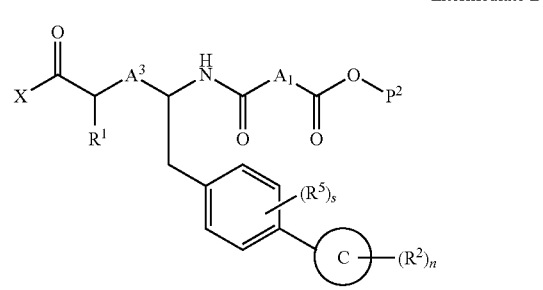

Intermediate C

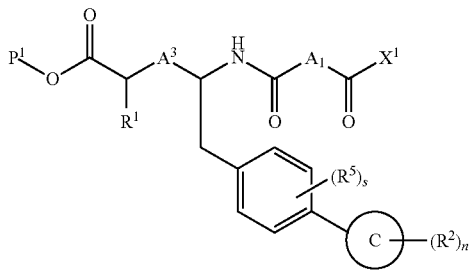

The compounds of the invention of formula I or III wherein $B^1$ is C(O)NH and $R^3$ is $A^1$-C(O)$X^1$ can be prepared by hydrolysis of intermediate D, E or F wherein X, $X^1$, $A^1$, $A^3$, $R^1$, $R^2$, $R^5$, Ring C, s and n have the definition of Formula I, supra; and $P^1$ and $P^2$ can be appropriate protecting groups selected from, but not limited to, methyl, ethyl, isopropyl, tert-butyl, methoxybenzyl or benzyl.

Intermediate D

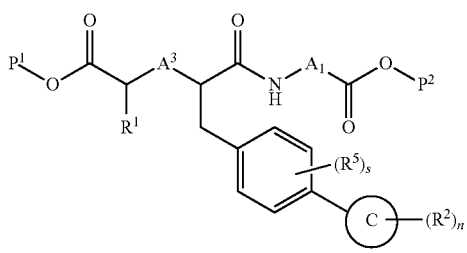

Intermediate E

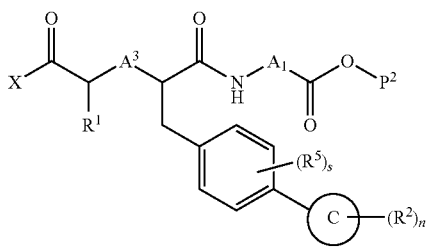

Intermediate F

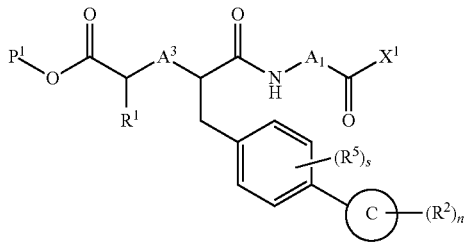

The compounds of the invention of formula I, II or III wherein $R^3$ is $A^2$-$R^4$, can be prepared by hydrolysis of intermediate G wherein $A^2$, $R^1$, $R^2$, $R^4$, $R^5$, Ring C, s and n have the definition of Formula I, supra; $A^3$ is $CH_2$ or absent, and $P^1$ can be appropriate protecting group selected from, but not limited to, methyl, ethyl, isopropyl, tert-butyl, methoxybenzyl or benzyl.

Intermediate G

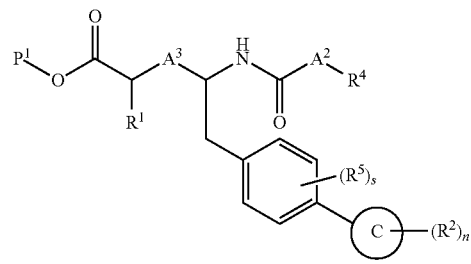

Intermediate H

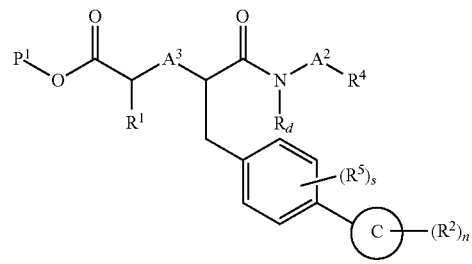

Standard methods can be applied for the hydrolysis of Intermediates A to H using a base selected from, but not limited to, NaOH, KOH or LiOH, or an acid selected from, but not limited to, TFA, HCl or $BCl_3$. When $P^1$ or $P^2$ is benzyl or methoxybenzyl, preferable method of deprotection is hydrogenation in the presence of a catalyst such as, but not limited to, palladium-on-carbon under hydrogen.

The intermediate A, B, C or G can be prepared using the following process comprising: condensing an intermediate I or J wherein X, $P^1$, $R^1$, $R^2$, $R^5$, Ring C, s and n are as previously described and $A^3$ is $CH_2$ or absent:

Intermediate I

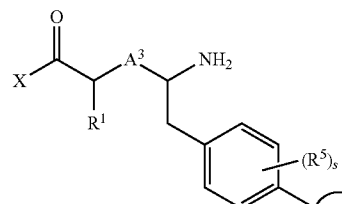

Intermediate J

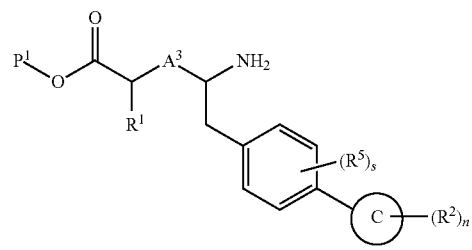

with an intermediate K, L or M wherein $X^1$, $A^1$, $A^2$, $R^4$ and $P^2$ are previously described.

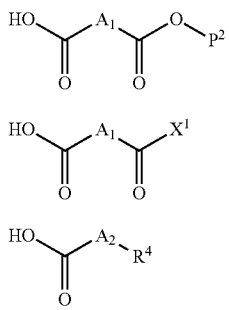

Known condensation methods may be applied including, but not limited to, conversion of the intermediate K, L or M to their corresponding acid halide, using reagents such as thionyl chloride or oxalyl chloride, or conversion of intermediate K, L or M to mixed anhydride using reagents such as ClC(O)O-isobutyl or 2,4,6-trichlorobenzoyl chloride followed by reaction of the acid halide or mixed anhydride with the intermediate I or J in a presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine). Alternatively, the intermediate K, L, or M can be coupled with I or J using coupling reagents such as DCC, EDCl, PyBOP or BOP in presence or absence of a reagent such as 1-hydroxybenazotriazole, 1-hydroxy-7-azabenzotriazole or pentafluorophenol.

Scheme 1 illustrates the synthesis of an intermediate C by reaction of intermediate J with an anhydride:

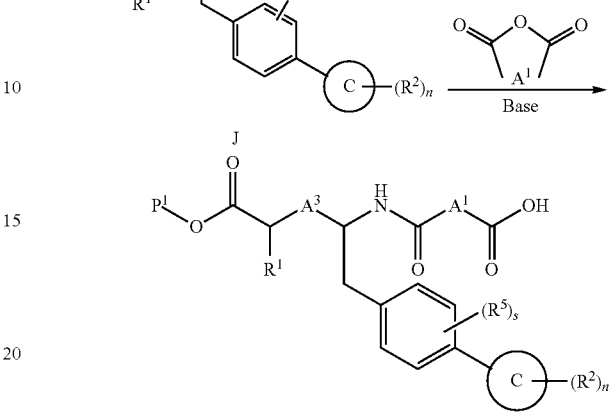

Intermediate J, or salts thereof, was prepared according to the route described in the U.S. Pat. No. 5,217,996 or in WO2008083967 wherein $P^1$ is alkyl or benzyl and $R^1$, $R^2$, $R^5$, $A^3$, Ring C, s and n are defined as in Formula I, II, III or IV supra.

Intermediate G wherein $R^4$ is a tetrazole can be synthesized according to Scheme 1A:

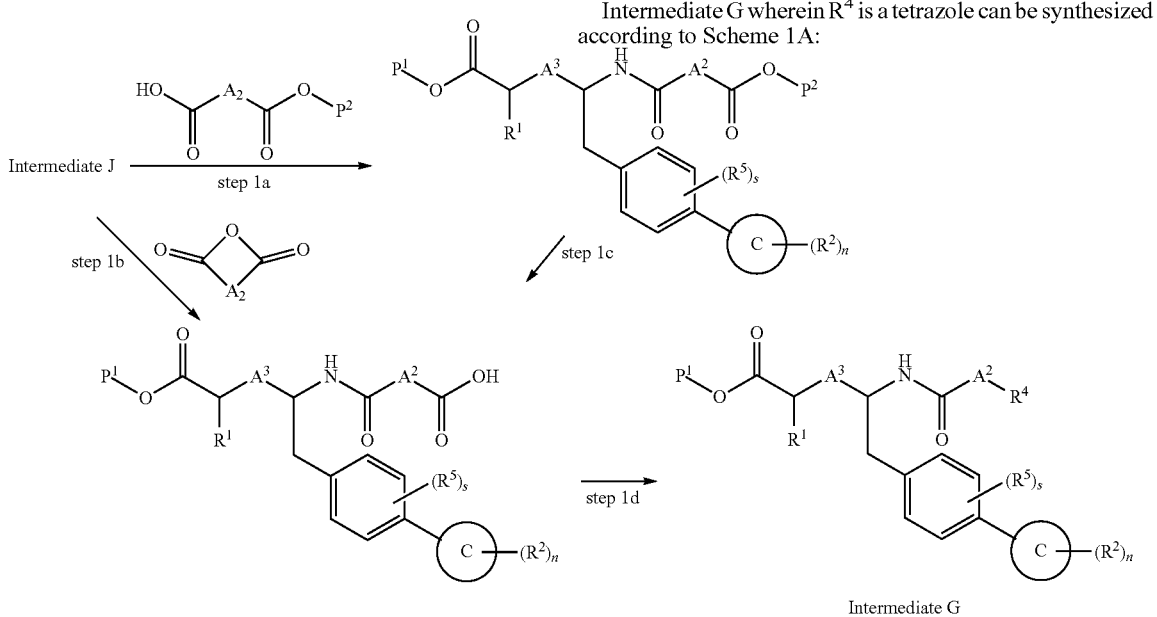

wherein $A^2$, $R^1$, $R^2$, $R^4$, $R^5$, $P^1$, $P^2$, Ring C, s and n are as previously defined above and $A^3$ is $CH_2$ or absent.

In step 1a, intermediate J is reacted with an appropriate carboxylic acid using standard coupling reagents selected from, but not limited to, DCC, EDCl, PyBOP or BOP in presence or absence of a reagent such as 1-hydroxybenazotriazole, 1-hydroxy-7-azabenzotriazole or pentafluorophenol; followed by removal of $P^2$ protecting group in step 1c using a base selected from, but not limited to, NaOH, KOH or LiOH, or an acid selected from, but not limited to, TFA or HCl, or hydrogenation with a catalyst such as, but not limited to, palladium-on-carbon under hydrogen. Alternatively, intermediate J is reacted with an appropriate anhydride in the presence of a base selected from, but not limited to, pyridine, triethylamine or diisopropylethylamine (step 1b); followed by conversion of the carboxylic acid into a tetrazole (step 1b) using similar method as described in *Journal of Medicinal Chemistry* 1998, 41, 1513.

The intermediate D, E, F or G can be prepared using the following process comprising: condensing an intermediate N or Q wherein X, $P^1$, $R^1$, $R^2$, $A^3$, $R^5$, Ring C, s and n are as defined above;

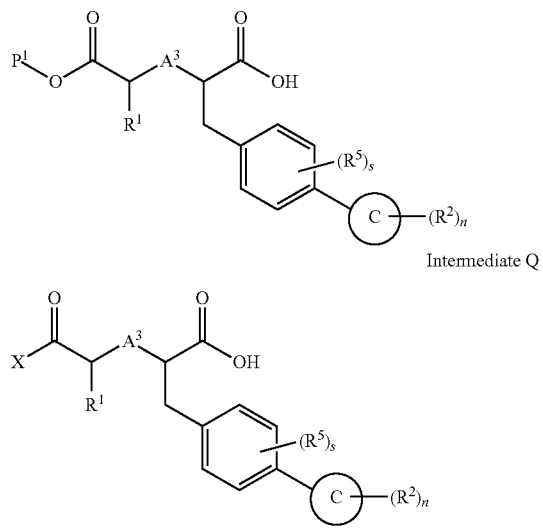

Intermediate N

Intermediate Q with an intermediate R, S or T wherein $X^1$, $A^1$ and $P^2$ have the meaning as defined above.

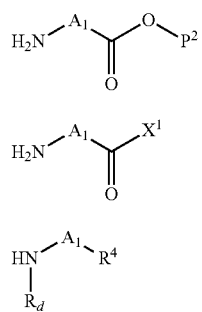

Intermediate R

Intermediate S

Intermediate T

Known condensation methods may be applied including, but not limited to, conversion of the intermediate N or Q to acid halide, using reagents such as thionyl chloride or oxalyl chloride, or conversion of intermediate N or Q to mixed anhydride using reagents such as ClC(O)O-isobutyl or 2,4,6-trichlorobenzoyl chloride followed by reaction of the acid chloride or mixed anhydride with the intermediate R, S or T in a presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine); Alternatively, the intermediate N or Q can be coupled with the intermediate R, S or T using a reagent such as DCC, EDCl, PyBOP or BOP in presence or absence of a reagent such as 1-hydroxybenazotriazole, 1-hydroxy-7-azabenzotriazole or pentafluorophenol.

The intermediate N or Q wherein $A^3$ is absent can be prepared according to the following general procedures described in Scheme 2:

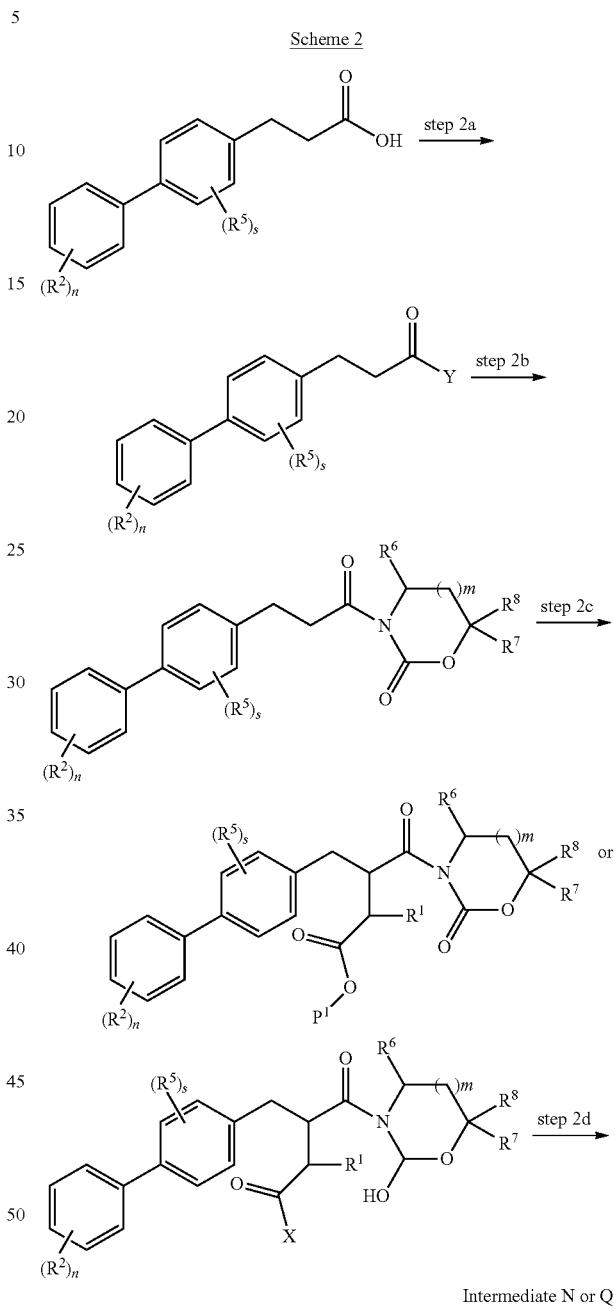

Scheme 2

Intermediate N or Q wherein $R^1$, $R^2$, $R^5$, X and n are as defined above and wherein m=0 or 1; $P^1$ is a protecting group selected from, but not limited to, hydrogen, methyl, ethyl, propyl, tert-butyl, methoxymethyl, tert-butyldimethylsilyl, tetrahydrofuranyl, benzyl, allyl or phenyl; $R^6$ is for example hydrogen, methyl, ethyl, isopropyl, benzyl or phenyl; $R^7$ and $R^8$ are independently hydrogen, methyl, ethyl, isopropyl, benzyl or phenyl. Y is selected from, but not limited to, chloro, bromo, iodo, benzotriazoloxy, pyridinium, N,N-dimethylaminopyridinium, pentafluorophenoxy, phenoxy, 4-chlorophenoxy, —OCO$_2$Me, —OCO$_2$Et, tert-butoxycarbonyl or —OCC(O)O-isobutyl.

In step (2a), standard methods can be applied to prepare the corresponding acid halide, such as the use of thionyl chloride, oxalyl chloride; or standard methods to prepare the mixed anhydride or the acyl pyridinium cation can be applied, such as the use of pivaloyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), 2,4,6-trichlorobenzoyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), or ClC(O)O-i-Bu with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine); or standard methods to prepare the activated ester can be applied, such as the use of 1-hydroxybenazotriazole, 1-hydroxy-7-azabenzotriazole or pentafluorophenol in the presence of a coupling reagent (e.g. DCC, EDCl) or BOP.

In step (2b), standard methods to prepare the N-acyloxazolidinones (m=0) can be employed. Illustrative examples of this chemistry are outlined in *Aldrichchimica Acta* 1997, Vol. 30, pp. 3-12 and the references therein; or standard methods to prepare the N-acyloxazinanone (m=1) can be employed. An illustrative example of this chemistry is outlined in *Organic and Biomolecular Chemistry* 2006, Vol. 4, No. 14, pp. 2753-2768. In step (2c), standard methods for alkylation can be employed. An illustrative example is outlined in *Chemical Reviews* 1996, 96(2), 835-876 and the references therein.

In step (2d), standard methods for cleavage of N-acyloxazolidinone or N-acyloxazinanone can be employed. Illustrative examples of this chemistry are outlined in *Aldrichchimica Acta* 1997, Vo. 30, pp. 3-12 and the references therein.

The intermediate I or J can be prepared according to the following general procedures described in Schemes 3, 4 or 5: Scheme 3 describes the synthesis of intermediate I or J wherein $A^3$ is absent.

Scheme 3

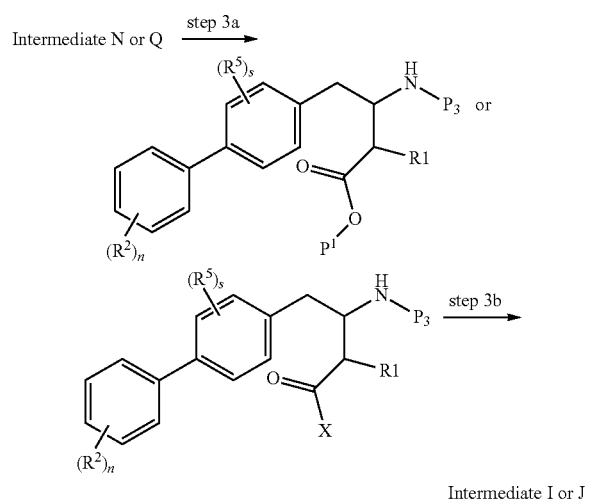

wherein $R^1$, $R^2$, $R^5$, X, Ring C, s and n are as defined above and wherein $P_3$ is a protecting group selected from, but not limited to, tert-butyl, benzyl, triphenylphosphynyl, tertbutoxycarbonyl, benzyloxycarbonyl, allyloxycarbonyl, acetyl or trifluoroacetyl.

In step (3a), standard methods for introduction of the amine part can be employed, such as using: either simultaneous treatment with or stepwise treatment via the corresponding acyl azide formation by using thionyl chloride (or $ClCO_2R^9$), $NaN_3$ (or $TMSN_3$) and $R^{10}OH$ (wherein $R^9$ and $R^{10}$ are hydrogen, methyl, ethyl, tert-butyl, allyl, benzyl or 4-methoxybenzyl); or either simultaneous treatment with or stepwise treatment via the corresponding acyl azide formation with DPPA and $R^{10}OH$ (wherein $R^{10}$ is defined as above); or standard methods for conversion to the corresponding carboxamide followed by treatment with $NH_3$ equivalent and either simultaneous treatment with or stepwise treatment with LTA or hypervalent iodine reagents (e.g. PIDA, PIFA, PhI(OH)OTs, PhIO) and $R^{10}OH$ (wherein $R^{10}$ is defined as above); or standard methods for conversion to the corresponding carboxamide and either simultaneous treatment with or stepwise treatment with $Br_2$ and MOH (wherein M is defined herein e.g. Na, K, Ba or Ca); or standard methods for conversion to the corresponding carboxamide and treatment with MOZ or $NaBrO_2$ (wherein Z is defined herein e.g. Cl or Br); or standard methods for conversion to the corresponding carboxamide and treatment with $Pb(OAc)_4$ and $R^{10}OH$ (wherein $R^{10}$ is defined as above); or standard methods for conversion to the corresponding hydroxamic acid followed by treatment with $H_2NOH$ or $H_2NOTMS$ and treatment with $Ac_2O$, $Boc_2O$, $R^{11}COCl$, $R^{11}SO_2Cl$, $R^{11}PO_2Cl$ (wherein $R^{11}$ is defined herein e.g. Me, Et, tBu or phenyl), thionyl chloride, EDCl, DCC, or 1-chloro-2,4-dinitrobenzene in the presence or absence of a base (e.g. pyridine, $Na_2CO_3$aq, triethylamine, DIPEA) and treatment with $R^{10}OH$ in the presence of a base (e.g. DBU, ZOH, DIPEA) (wherein $R^{10}$ and Z are defined as above).

In step (3b), standard methods for removing $P_3$ protecting groups can be applied, such as base hydrolysis using NaOH, KOH, or LiOH, acid hydrolysis using TFA or HCl, or hydrogenation using palladium-on-carbon under hydrogen. This synthetic scheme can be applied to the synthesis of Intermediates I or J wherein $A^3$ is $CH_2$.

Scheme 4 describes an alternative synthesis of Intermediate I or J wherein $A^3$ is absent:

Scheme 4

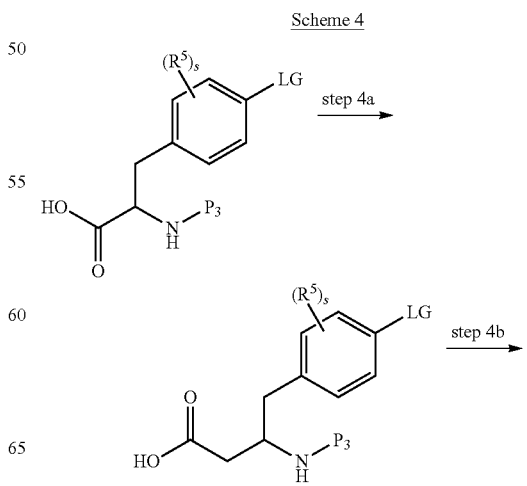

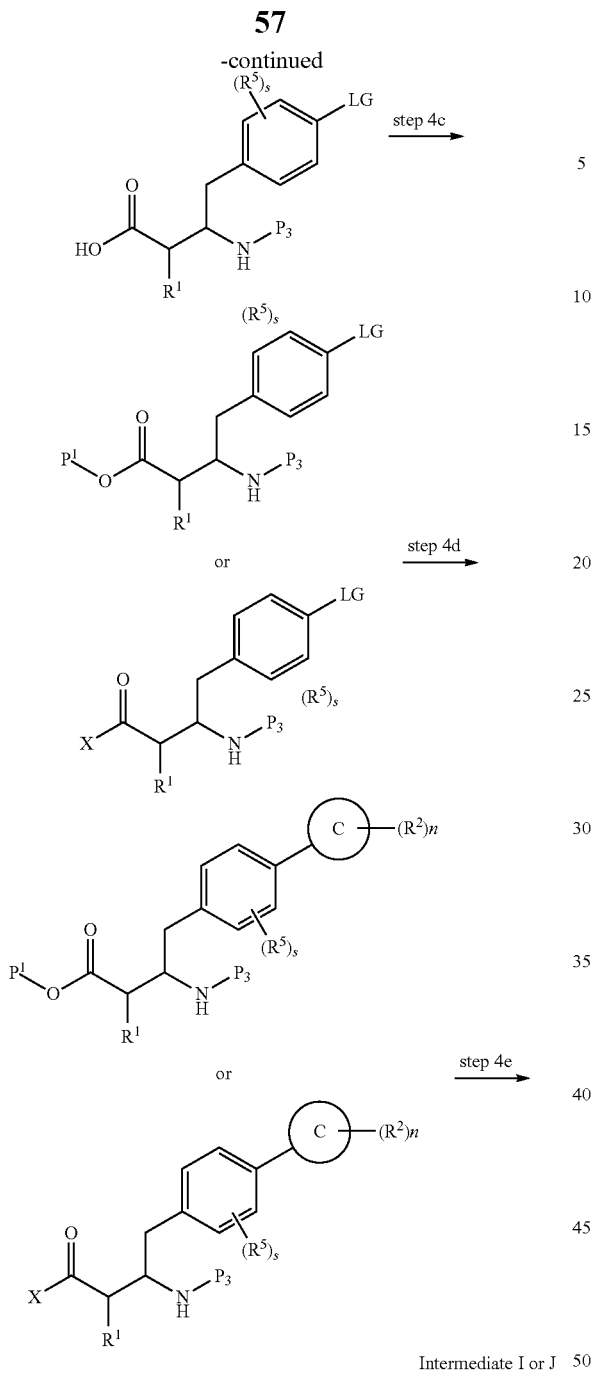

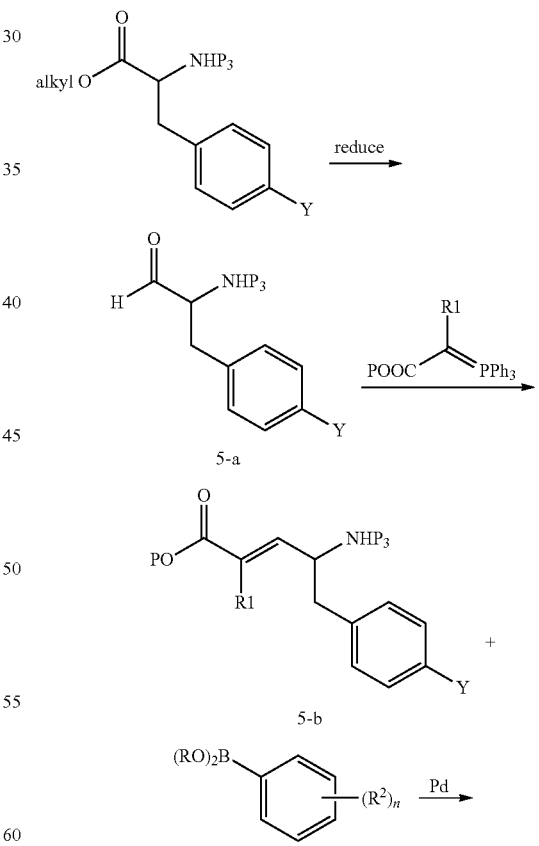

($R^{10}O)_2CHNMe_2$, CDI/DBU/$R^{10}OH$ wherein $R^{10}$ has the same meaning as defined above, or isobutylene/$H_2SO_4$ (for tert-butyl ester).

In step (4d), standard methods for Suzuki coupling reaction can be applied, such as using a palladium (or nickel) species [e.g. $Pd(PPh_3)_4$, $PdCl_2$(dppf), $Pd(OAc)_2$/a phosphine (e.g. $PPh_3$, dppf, $PCy_3$, $P(tBu)_3$, XPhos), Pd/C, $Pd_2(dba)_3$/a phosphine (e.g. $PPh_3$, dppf, $PCy_3$, $P(tBu)_3$, XPhos), $Ni(COD)_2$/a phosphine (or dppe, dppb, $PCy_3$, Ni(dppf)$Cl_2$], a base (e.g. KF, CsF, $K_3PO_4$, $Na_2CO_3$, $K_2CO_3$, $Cs_2CO_3$, NaOH, KOH, NaO-t-Bu, KO-t-Bu), and $(R^2)$n-PhB(OH)$_2$ [or $(R^2)$n-PhBF$_3$K].

In step (4e), standard methods for removing $P_3$ protecting groups can be applied, such as base hydrolysis using NaOH, KOH, or LiOH, acid hydrolysis using TFA or HCl, or hydrogenation using palladium-on-carbon under hydrogen.

The synthetic scheme 4 can be applied to the synthesis of Intermediates I or J wherein $A^3$ is $CH_2$.

Scheme 5 illustrates the synthesis of intermediate J wherein $A^3$ is $CH_2$, which is useful for the preparation of compounds of Formula I or II.

wherein LG is a leaving group selected from, but not limited to, Cl, Br, I, OMs, OTs or OTf. In step (4a), standard methods for Arndt-Eistert homologation can be employed. An illustrative example of this chemistry is outlined in "Enantioselective synthesis of β-amino acids, $2^{nd}$ Edition", John Wiley and Sons, Inc., NJ (2005), either directly or analogously.

In step (4b), standard methods for alkylation can be employed, such as using $R^1$LG in the presence of a base such as LDA, NHMDS, LHMDS or KHMDS.

In step (4c), standard methods to protect the carboxylic acid can be employed, such as using TMSCHN$_2$ (for methyl ester), $P^1$LG/base (e.g. $K_2CO_3$, NaHCO$_3$, $Cs_2CO_3$ or $K_3PO_4$), thionyl chloride (or oxalyl chloride)/$R^{10}OH$, DCC (or EDCl)/DMAP/$R^{10}OH$, BOP/$R^{10}OK$ (or $R^{10}ONa$),

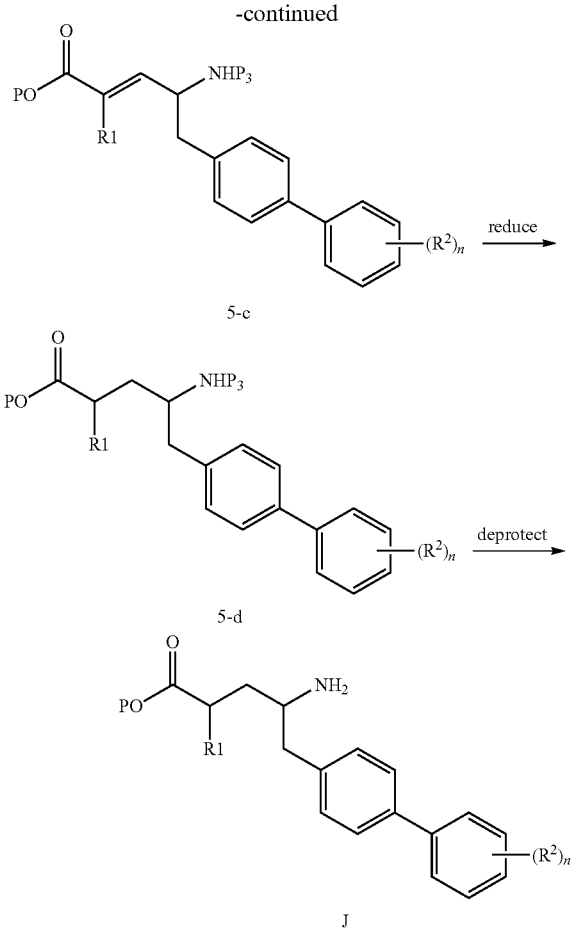

Aldehyde 5-a is prepared by reduction of a protected amino acid ester with a reducing agent such as, but not limited to, diisobutyl aluminum hydride. The protecting group $P_3$ can be chosen from, but not limited to, Boc or Cbz and group Y can be chosen from, but not limited to, halogen or triflate. Intermediate 5-b is prepared from intermediate 5-a by methodology such as, but not limited to, a Wittig reaction employing an appropriate phosphorus reagent such as, but not limited to, a triphenyl phosphonium ylide. The substituted biphenyl intermediate 5-c is prepared from Intermediate 5-b by methodology such as, but not limited to, a Suzuki reaction employing reactants such as, but not limited to, aryl- or heteroarylboronic acids or aryl- or heteroarylboronic esters catalyzed by a palladium(0) complex such as, but not limited to, tetrakis(triphenylphosphine)palladium or dichloro[1,1'-bis(diphenylphosphino)ferrocene]palladium(II) dichloromethane adduct. The olefin of Intermediate 5-c is reduced to furnish Intermediate 5-d by hydrogenation in the presence of a catalyst such as, but not limited to, platinum-on-carbon or platinum oxide at atmospheric or elevated pressure. Alternatively, the reduction can be performed using chiral catalysts and ligands such as, but not limited to, those described in patent application WO2008031567. The protecting group $P_3$ can be removed with an acid selected from, but not limited to, TFA or HCl, or hydrogenation with a catalyst such as, but not limited to, palladium-on-carbon under hydrogen to generate intermediate J.

Alternatively, the intermediate I or J may be prepared be following the synthetic routes outlined in *Tetrahedron Letters*, 2008, Vol. 49, No. 33, pp. 4977-4980 either directly or analogously and converting the obtained boronic acid into a substituted biphenyl by methods outlined in *Organic Letters*, 2002, Vol. 4, No. 22, pp. 3803-3805.

Alternatively, the intermediate I or J may be prepared be following the synthetic routes outlined in *Tetrahedron: Asymmetry*, 2006, Vol. 17, No. 2, pp. 205-209 either directly or analogously.

Alternatively, the intermediate I or J may be prepared by methods of Mannich reaction. Illustrative examples of this chemistry are outlined in "Enantioselective synthesis of—amino acids, $2^{nd}$ Edition", John Wiley and Sons, Inc., NJ (2005), either directly or analogously.

Alternatively, the intermediate I or J may be prepared by enolate addition. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate I or J may be prepared by methods of aza-Michael reaction. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate I or J may be prepared following the synthetic route outlined in Synlett, 2006, No. 4, pp. 539-542, either directly or analogously.

Scheme 6 illustrate the synthesis of a compound of Formula I or III, or a salt thereof, wherein $B^1$ is NHC(O), Ring C is a phenyl, s is 0, X is OH and $R^3$ is $A^1C(O)X^1$ wherein $X^1$ is an —O—$C_{1-7}$alkyl.

Scheme 6

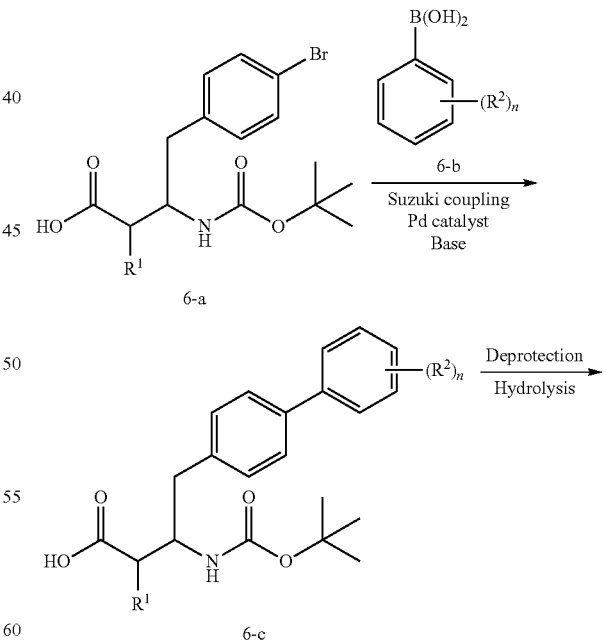

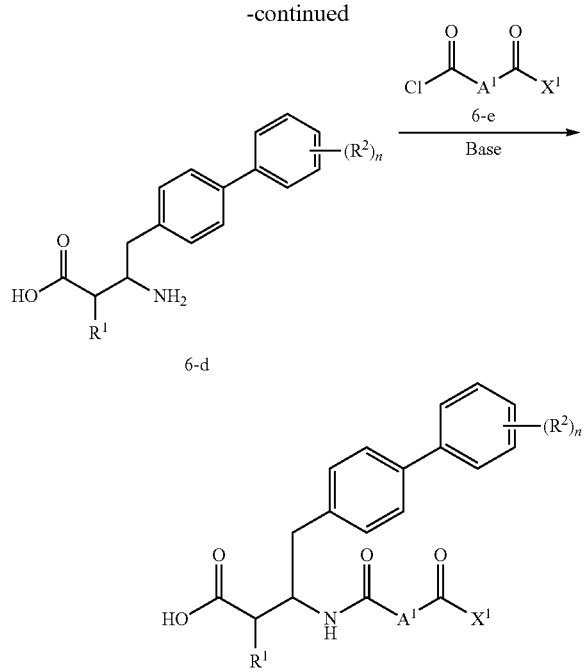

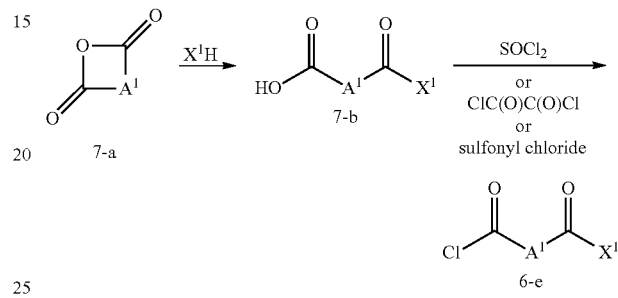

A compound of Formula 6-a is converted into a compound of Formula I or III wherein $B^1$ is NHC(O), X is OH and $R^3$ is $A^1C(O)X^1$ wherein $X^1$ is an —O—$C_{1-7}$alkyl or a salt thereof, wherein $R^1$, $A^1$, $R^2$ and n are as defined in Formula I, according to the method described in Scheme 5. Compound of Formula 6-a undergoes Suzuki coupling reaction with a boronic acid 6-b, or an ester thereof, in the presence of a catalyst and a base to generate a compound of Formula 6-c or a salt thereof. The Suzuki coupling reaction is well known in the art and is carried out using standard procedures. Examples of Suzuki coupling reaction are described in the exemplification section of the description. Example of palladium catalyst which can be used for the coupling are $PdCl_2(dppf)_2.CH_2Cl_2$, $Pd(PPh_3)_4$, $PdCl_2(PPh_3)_2$, or other catalyst as described in step (4d) of scheme 4. Example of a base which can be used for the coupling are $Na_2CO_3$, $K_2CO_3$, $K_3PO_4$ or other base described in step (4d) of Scheme 4. The Suzuki coupling reaction can be carried out in a solvent. Examples of a solvent are DME, DMF, $CH_2Cl_2$, ethanol, methanol, dioxane, water or toluene, or a mixture thereof. One example of Suzuki conditions is $Pd(PPh_3)_2Cl_2$ and $Na_2CO_3$. In one embodiment the solvent is water or THF or a mixture thereof.

Compound 6-c or salt thereof, wherein $R^1$, $R^2$ and n are as defined in Formula I or III, is then hydrolyzed to generate the amine 6-d or salt thereof. The hydrolysis can be carried out under acidic condition. An example of hydrolysis condition is HCl hydrolysis which generates the hydrochloric salt of compound 6-d. The HCl hydrolysis can be carried out in a solvent. Example of a solvent is dioxane, water or THF or a mixture thereof. For example, the HCl hydrolysis can be carried out using an HCl aqueous solution in THF.

The amine 6-d, or salt thereof, is then converted into a compound of Formula I or III wherein $B^1$ is NHC(O), X is OH and $R^3$ is $A^1C(O)X^1$ wherein $X^1$ is —O—$C_{1-7}$alkyl or a salt thereof, wherein $R^1$, $A^1$, $R^2$ and n are as defined in Formula I or III, by reaction with an acyl chloride of Formula 6-e, in the presence or absence of a base. Examples of a base are NaOH, $Na_2CO_3$, $K_2CO_3$, KOH, LiOH or other base described supra for reaction of an Intermediate I or J with an acid halide. The amide formation can be carried out in a solvent. Examples of a solvent are water, acetonitrile, THF or a mixture thereof.

For example, a HCl salt of compound 6-d can be reacted with an acyl chloride of Formula 6-e in the presence of NaOH and $Na_2CO_3$. An example of solvent is a mixture of acetonitrile and water.

Compound of Formula 6-e can be prepared from a compound of Formula 7-a, according to the method described in Scheme 7.

Scheme 7

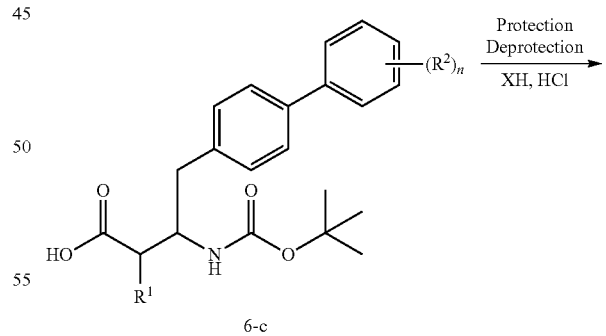

Compound of Formula 7-a is reacted with $X^1H$ wherein $X^1$ is —O—$C_{1-7}$alkyl to generate the acid 7-b or salt thereof. The reaction can be carried out in a solvent. Examples of a solvent are toluene, benzene or a mixture thereof. In one embodiment the solvent is toluene. Examples of a reagent $X^1H$ are methanol, ethanol, propanol or butanol. Compound of Formula 7-b is then converted to an acyl chloride 6-e by reacting with thionyl chloride, oxalyl chloride or sulfonyl chloride.

A compound of Formula I or III, or a salt thereof, wherein $B^1$ is NHC(O), Ring C is phenyl, s is 0, X is —O—$C_{1-7}$alkyl, and $R^3$ is $A^1C(O)X^1$ wherein $X^1$ is an —OH and wherein $R^1$, $A^1$, $R^2$ and n are as defined in Formula I or III, can be synthesized as outlined in Scheme 8:

Scheme 8

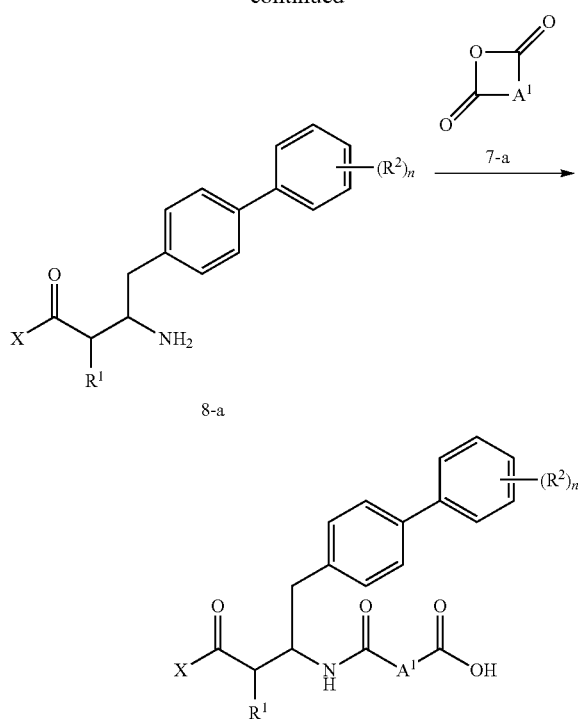

Compound of Formula 6-c, or a salt thereof, wherein $R^1$, $R^2$ and n are as defined in Formula I or III, is converted to compound of Formula 8-a, or a salt thereof; wherein $R^1$, $R^2$ and n are as defined in Formula I or III, and X is —O—$C_{1-7}$alkyl; by reaction with XH under acidic condition. Examples of XH are methanol, ethanol, propanol or butanol.

Compound of Formula 6-c, or salt thereof, is prepared as described in Scheme 6.

Compound 8-a is then converted to a compound of Formula I or III, or salt thereof, wherein $B^1$ is NHC(O), X is —O—$C_{1-7}$alkyl, and $R^3$ is $A^1C(O)X^1$ wherein $X^1$ is an —OH, by reaction with anhydride reagent 7-a. Optionally a base can be used in the last step of Scheme 8. Example of a base is NaOH, $Na_2CO_3$, $K_2CO_3$, KOH, LiOH or other base described supra for reaction of an Intermediate H or I with a mixed anhydride. In one particular example the reaction of compound of Formula 8-a with an anhydride of Formula 7-a is carried out in the presence of isopropyl acetate. Compounds of the invention of Examples 1-1, 1-2, 1-4, 1-5, 1-6, 1-10, 1-14 and the like can be prepared according to Schemes 6, 7 and 8.

Scheme 9 illustrates the synthesis of compounds according to anyone of Formula I, II or III wherein $R^3$ is $A^1$-C(O)$X^1$ and $A^1$ is a linear $C_{1-4}$alkylene wherein one carbon is replaced by a nitrogen atom or $A^1$ is a heterocyclyl or heteroaryl.

Scheme 9

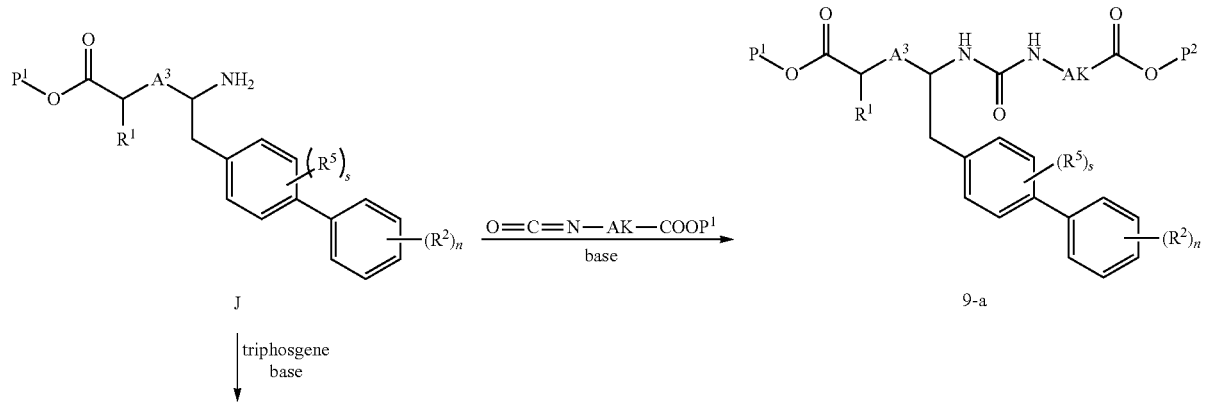

-continued

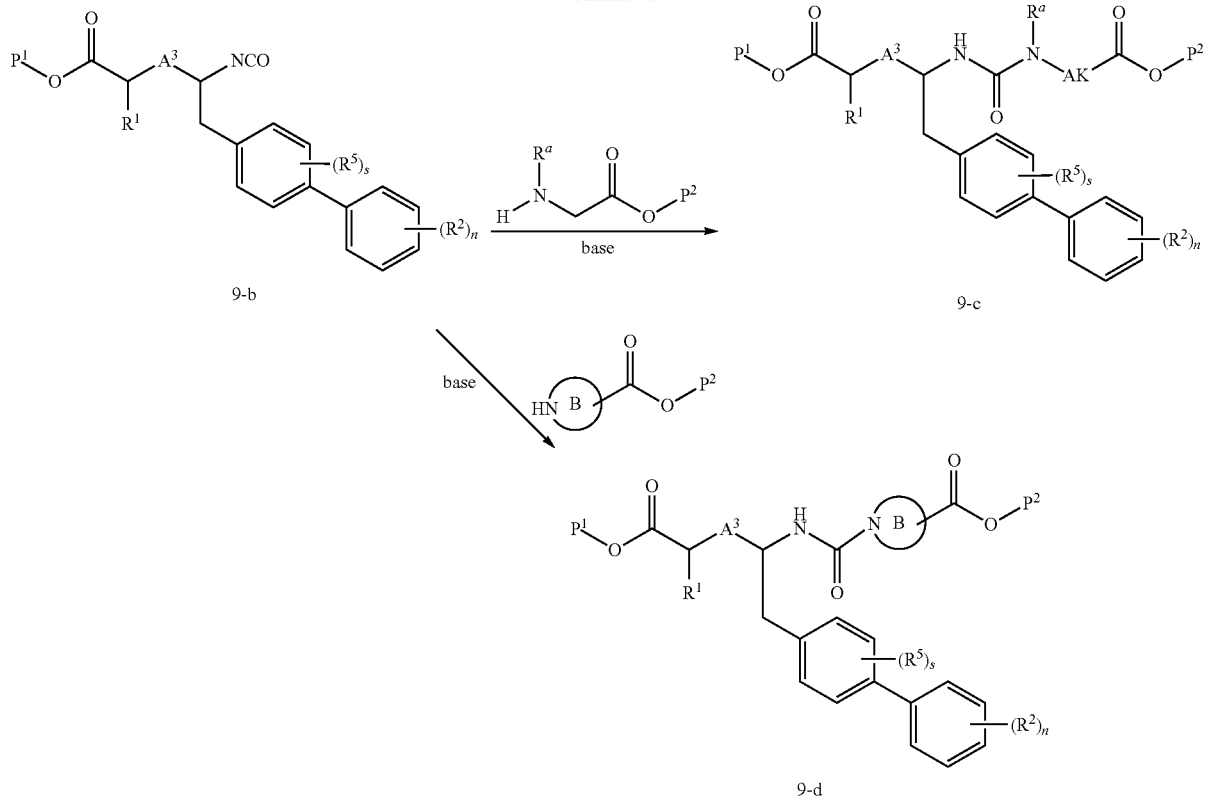

Compounds according to anyone of Formulae I, II or III wherein $R^3$ is $A^1$-C(O)$X^1$ and $A^1$ is a linear $C_{1-4}$alkylene wherein one carbon is replaced by a nitrogen atom, represented by compounds 9-a, are prepared from intermediate J by reaction with an alkyl isocyanate, wherein $P^2$ is alkyl or benzyl and AK is an alkyl, in the presence of a base such as, but not limited to, pyridine, triethylamine and diisopropylethylamine. Alternatively, intermediate J is converted to isocyanate 9-b with reagents such as, but not limited to, triphosgene in the presence of a base such as, but not limited to NaHCO$_3$. Substituted analogs, represented by compounds 9-c, are prepared by reacting compound 9-b with an appropriate protected amino acid in the presence of a base such as, but not limited to NaHCO$_3$. Similarly, compounds according to anyone of Formulae I, II or III wherein $A^1$ is a heterocyclyl or a heteroaryl containing a Nitrogen atom which is linked to C(O)NH amide bond, and represented by compounds 9-d, are prepared from the reaction of compound 9-b with protected cyclic amino acids wherein B is heterocyclyl or heteroaryl and the carboxylate group can be attached at any position not occupied by a heteroatom. Compounds 9-a to 9-d are converted to their corresponding carboxylic acids ($P^1$, $P^2$=H) by standard hydrolytic methods using a base such as, but not limited to, NaOH or LiOH. The hydrolysis reactions are performed at either ambient or elevated temperatures. When $P^1$ or $P^2$ is benzyl, the preferable method of deprotection is hydrogenation in the presence of a catalyst such as, but not limited to, palladium-on-carbon at atmospheric or elevated pressure.

Scheme 10 illustrates the synthesis of intermediate H wherein $A^3$ is NR$^e$. The intermediate H can be prepared according to the following general procedures described in Scheme 1 wherein $A^1$, $P^1$, $R^1$, $R^2$, $R^3$, $R^4$, $R^5$, $R^6$, s and n are as previously defined.

Scheme 10

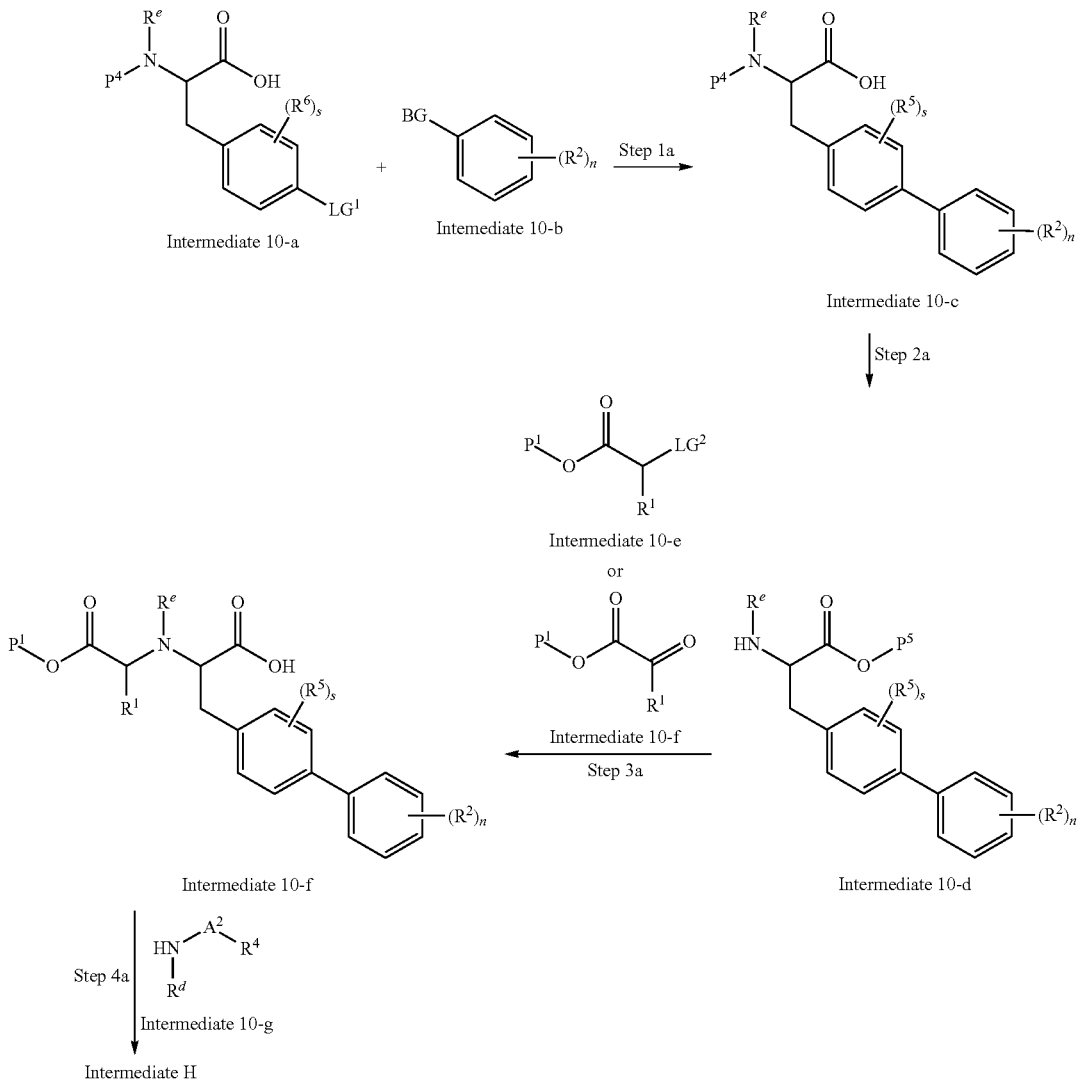

In step 1a, the intermediate 10-c can be prepared by cross-coupling of an intermediate 10-a wherein $P^3$ is an appropriate protecting groups selected from, but not limited to, t-butoxycarbonyl, benzyloxycarbonyl, fluorenylmethyloxycarbonyl, benzyl, or methoxybenzyl and wherein $LG^1$ is a leaving group selected from, but not limited to, halo (e.g. bromo, chloro, or iodo) or trifluoromethanesulfonyloxy with an intermediate 10-b wherein $R^2$ and n are as previously described and wherein BG is an appropriate groups selected from, but not limited to, boronic acid, trifluoroborate or boronic ester. Known coupling methods may be applied including Suzuki-Miyaura coupling of the intermediate 10-a with the intermediate 10-b using palladium species such as, but not limited to, $Pd(PPh_3)_4$, $PdCl_2(dppf)$, $Pd(PPh_3)_2Cl_2$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

In step 2a, the intermediate 10-d can be prepared by appropriate protection of an intermediate 10-c wherein $P^5$ is a protection group such as, but not limited to, t-butyl, methyl, benzyl, fluorenylmethyl, allyl or methoxybenzyl; followed by an appropriate deprotection of the $P^4$ group. For example, in the case where $P^4$ is t-butoxycarbonyl, deprotection can be carried out using HCl in an appropriate solvent such as t-butylmethylether, THF, dioxane and/or isopropylacetate.

In step 3a, the intermediate 10-g can be prepared by reacting an intermediate 10-d wherein $R^2$, $R^5$, $R^6$, s, m, and $P^5$ are as previously defined with an intermediate 10-e wherein $R^1$ and $P^1$ are as previously defined above and wherein $LG^2$ is a leaving group selected from, but not limited to, trifluoromethansulfonyloxy, toluenesulfonyloxy, methansulfonyloxy, iodo, bromo, and chloro, followed by deprotection of the $P^5$ using an appropriate method. For example, when $P^5$ is allyl, deprotection can be carried out using a catalytic amount of PdO (e.g. $Pd(PPh_3)_4$) in an appropriate solvent. Alternatively, the intermediates 10-g can be prepared by reacting an intermediate 10-d with an intermediate 10-f wherein $R^1$ and $P^1$ are as defined above, followed by deprotection of the $P^5$ using an appropriate method. Known coupling methods may be applied including alkylation of the intermediate 10-d with the intermediate 10-e using a base such as, but not limited to, tertiary amine (e.g. triethylamine or N,N-diisoproplyl ethylamine), pyridine, or $K_2CO_3$; or reductive amination condition of intermediate 10-d with the intermediate 10-f, under condition such as hydrogenation in the presence of a catalyst such as palladium-on-carbon or reduction using a reductive reagent (e.g. $NaBH_4$, $NaBH(OAc)_3$, or $NaBH_3CN$) in the presence of or absence of an acid such as acetic acid, TFA, or $Ti(i-PrO)_4$.

In step 4a, the intermediate H can be prepared by coupling an intermediate 10-g wherein $P^1$, $R^1$, $R^2$, $R^e$, $R^6$, s and n are as previously described with an intermediate 10-h wherein $A^2$, $R^4$, and $R^d$ are previously described. Known coupling methods may be applied including, but not limited to, conversion of the intermediate 10-g to a corresponding oxazolidine-2,5-dione, using reagents such as triphosgene, carbonyldiimidazole, 4-nitrophenyl chloroformate, or disuccinimidyl carbonate, conversion of the intermediate 10-g to a corresponding acid halide, using reagents such as thionyl chloride or oxalyl chloride, or conversion of the intermediate 10-g to a corresponding mixed anhydride using reagents such as ClC(O)O-isobutyl, 2,4,6-trichlorobenzoyl chloride or propyl phosphonic acid anhydride cyclic trimer (T3P), followed by reaction of the oxazolidine-2,5-dione, the acid halide, or the mixed anhydride with the intermediate 10-h in a presence or absence of a base such as tertiary amine (e.g. triethylamine or N,N-diisoproplyl ethylamine) or $K_2CO_3$. Alternatively, the intermediate 10-g can be coupled with the intermediate 10-h using peptide condensation reagents including, but not limited to, dicyclohexylcarbodiimide (DCC), diisopropylcarbodiimide (DIC), 1-ethyl-3-(3-dimethylaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine.

Scheme 11 illustrates the synthesis of Intermediate N wherein $A^3$ is $NR^e$ and Ring C is phenyl. The intermediate N or 10-g can also be prepared according to the following procedures described in Scheme 11 wherein BG, $LG^1$, $LG^2$, $P^1$, $P^5$, $R^1$, $R^2$, $R^5$, $R^e$, s and n are as previously defined.

Scheme 11

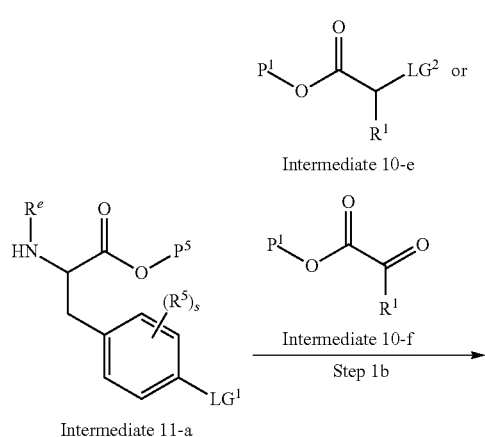

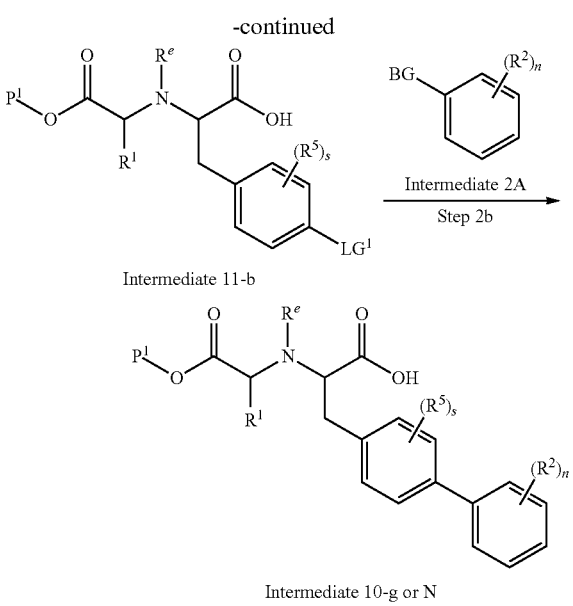

In step 1b, the intermediate 11-b can be prepared by reacting an intermediate 11-a where in $LG^1$, $R^5$, $R^6$, s and $P^5$ are previously described with an intermediate 10-e wherein $R^1$, $P^1$, and $LG^2$ are as previously described, followed by an appropriate deprotection of the protecting group $P^5$. Alternatively, the intermediates 11-b can be prepared by reacting an intermediate 11-a with an intermediate 11-f wherein $P^1$ and $R^1$ are as previously described, followed by an appropriate deprotection of the protecting group $P^5$. Known reaction methods may be applied including alkylation of the intermediate 11-a with the intermediate 11-e using a base such as, but not limited to, tertiary amine (e.g. triethylamine or N, N-diisoproplyl ethylamine), pyridine, or $K_2CO_3$, or reductive amination condition of intermediate 11-a with the intermediate 11-e, under condition such as hydrogenation in the presence of a catalyst such as palladium-on-carbon or reduction using a reducing reagent (e.g. $NaBH_4$, $NaBH(OAc)_3$, or $NaBH_3CN$) in the presence of or absence of an acid such as acetic acid, TFA, or $Ti(i-PrO)_4$.

In step 2b, the intermediate 10-g or N can be prepared by cross-coupling of an intermediate 11-b wherein $LG^1$, $P^1$, $R^5$, $R^e$, $R^1$ and s with an intermediate 10-b wherein BG, n, and $R^2$ are as previously described. Known coupling methods may be applied including Suzuki-Miyaura coupling of the intermediate 11-b with the intermediate 10-b using palladium species such as, but not limited to, $Pd(PPh_3)_4$, $PdCl_2(dppf)$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

The intermediates 11-b can also be prepared according to the following general procedure described in Scheme 12 wherein $LG^1$, $P^1$, $P^5$, $R^5$, $R^e$, $R^1$ and s are as previously described.

Scheme 12

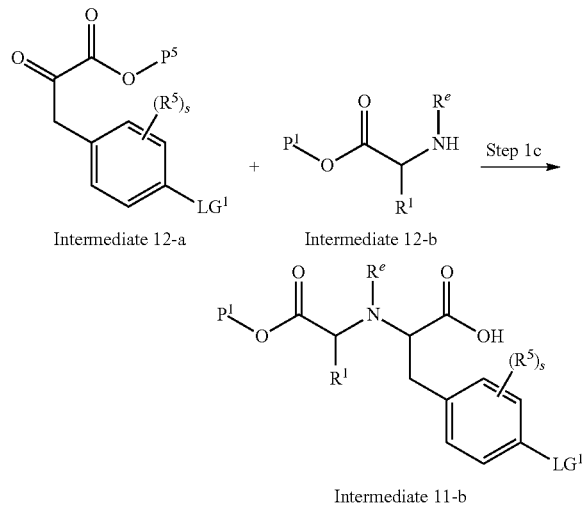

Intermediate 12-a  Intermediate 12-b

Intermediate 11-b

In step 1c, the intermediate 11-b can be prepared by reductive amination of the intermediate 12-a wherein $LG^1$, $R^5$, s and $P^5$ are as previously described with the intermediate 12-b wherein $R^e$ and $R^1$ are as previously described. Known reductive amination methods may be applied including a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i\text{-}PrO)_4$. The intermediate 12-a can be prepared according to the reported procedure. The illustrative example of this chemistry is outlined in WO 2006015885.

The intermediate 10-g or N wherein $A^3$ is $NR^e$ and Ring C is phenyl can also be prepared according to the following general procedures described in Scheme 13 wherein m, $P^1$, $P^5$, $R^1$, $R^e$, $R^5$ and $R^2$ are as previously described.

Scheme 13

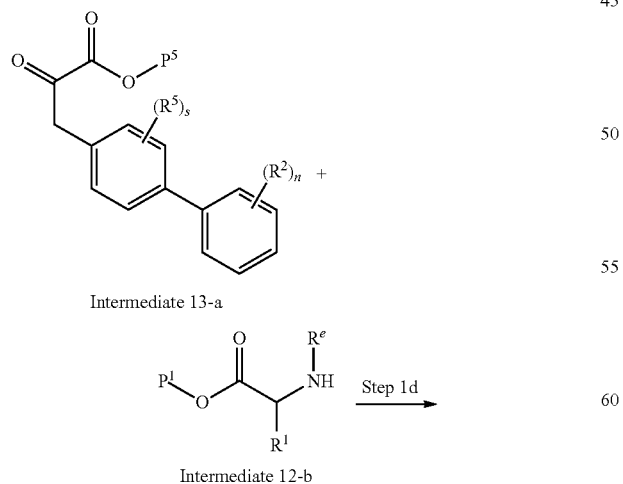

Intermediate 13-a

Intermediate 12-b

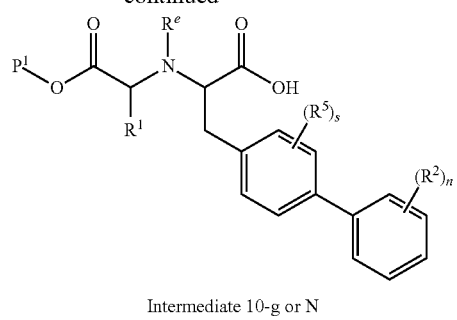

Intermediate 10-g or N

In step 1d, the intermediate 10-g can be prepared by reductive amination of the intermediate 13-a wherein n, $P^5$, $R^5$, $R^e$, s and $R^2$ are as previously described with the intermediate 12-b wherein $P^1$, $R^e$ and $R^1$ are as previously described. Known reductive amination methods may be applied including a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i\text{-}PrO)_4$. The intermediates 12-b can be prepared according to the reported procedure. The illustrative example of this chemistry is outlined in WO 2006015885.

The intermediate H wherein $A^3$ is $NR^e$, can also be prepared according to the following procedures described in Scheme 14 wherein $A^2$, $LG^2$, $P^1$, $P^4$, $R^1$, $R^2$, $R^5$, $R^e$, $R^d$, s and n are as previously described.

Scheme 14

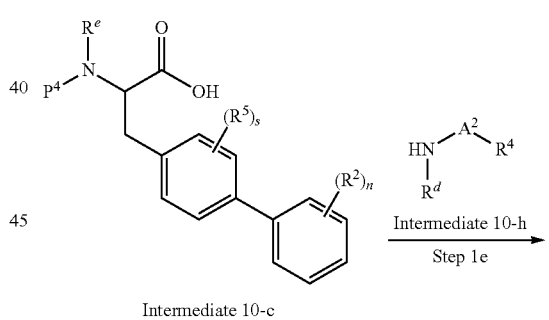

Intermediate 10-c

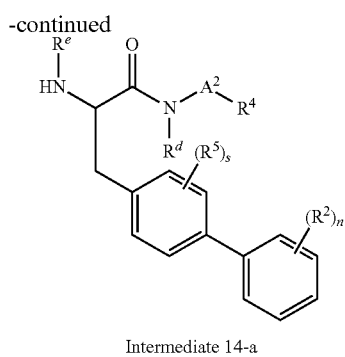

Intermediate 14-a

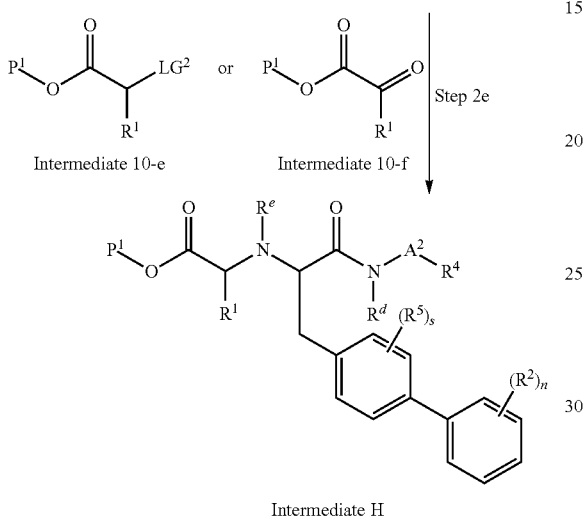

Intermediate H

In step 1e, the intermediate 14-a can be prepared by coupling an intermediate 10-c with an intermediate 10-h. Known coupling methods may be applied including, but not limited to, conversion of the intermediate 10-c to a corresponding oxazolidine-2,5-dione, using reagents such as triphosgene, carbonyldiimidazole, 4-nitrophenyl chloroformate, or disuccinimidyl carbonate, conversion of the intermediate 10-c to a corresponding acid halide, using reagents such as thionyl chloride or oxalyl chloride, or conversion of the intermediate 10-c to a corresponding mixed anhydride using reagents such as ClC(O)O-isobutyl or 2,4,6-trichlorobenzoyl chloride, followed by reaction of the oxazolidine-2,5-dione, the acid halide, or the mixed anhydride with the intermediate 10-h in a presence or absence of a base such as tertiary amine (e.g. triethylamine or N,N-diisoproplyl ethylamine) or $K_2CO_3$ and an appropriate deprotection of $P^2$ protecting group. Alternatively, the intermediate 10-c can be coupled with the intermediate 10-h using peptide condensation reagents including, but not limited to, dicyclohexylcarbodiimide (DCC), diisopropylcarbodiimide (DIC), 1-ethyl-3-(3-dimethyllaminopropyl) carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine followed by an appropriate deprotection of $P^4$ protecting group.

In step 2e, the intermediate H can be prepared by reacting an intermediate 14-a with an intermediate 10-e wherein $LG^2$ is as previously described. Alternatively, the intermediates A can be prepared by reacting an intermediate 14-a with an intermediate 10-f. Known reaction methods may be applied including alkylation of the intermediate 14-a with the intermediate 10-e using a base such as, but not limited to, tertiary amine (e.g. triethylamine or N,N-diisoproplylethylamine), pyridine, or $K_2CO_3$ or reductive amination of the intermediate 14-a with the intermediate 104 under a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i\text{-}PrO)_4$.

The intermediates H wherein $A^3$ is $NR^o$ and Ring C is phenyl can also be prepared according to the following procedures described in Scheme 15 wherein $A^2$, BG, $LG^1$, $P^1$, $R^1$, $R^2$, $R^4$, $R^5$, $R^e$, $R^d$, s and n are as previously described.

Scheme 15

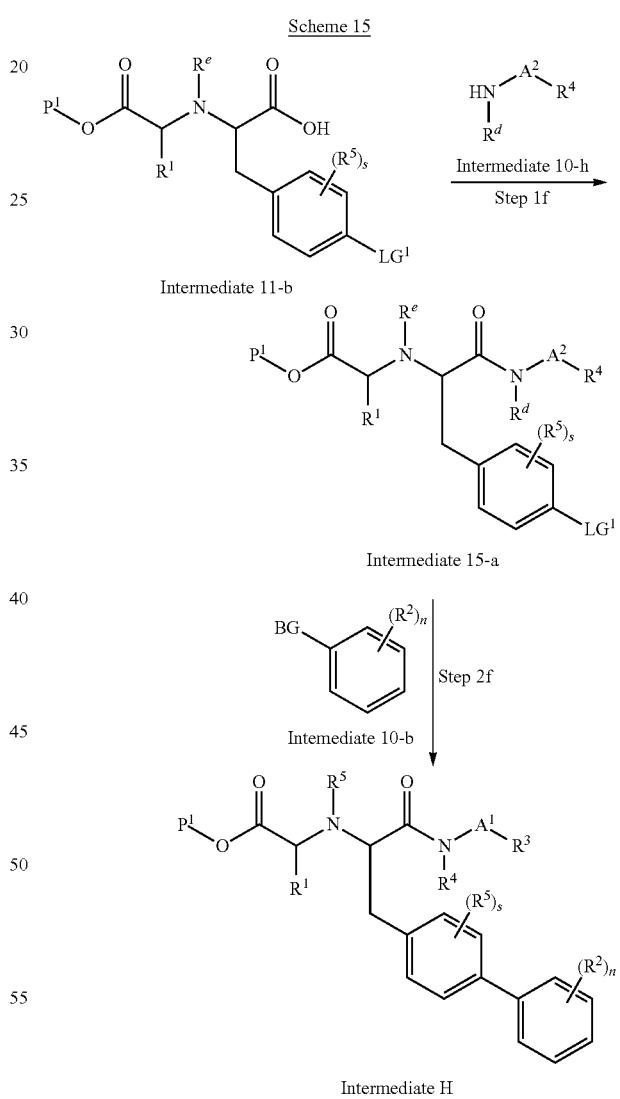

In step 1f, an intermediate 15-a can be prepared by coupling the intermediate 11-b wherein $LG^1$, $P^1$, $R^e$, $R^5$, s and $R^1$ are as previously described with an intermediate 10-h. Known coupling methods may be applied including, but not limited to, conversion of the intermediate 11-b to a corresponding oxazolidine-2,5-dione, using reagents such as triphosgene, carbonyldiimidazole, 4-nitrophenyl chloroformate, or disuccinimidyl carbonate, conversion of the intermediate 11-b to a corresponding acid halide, using reagents such as thionyl chloride or oxalyl chloride, or conversion of the intermediate 11-b to a corresponding mixed anhydride using reagents such as ClC(O)O-isobutyl or 2,4,6-trichlorobenzoyl chloride, followed by reaction of the oxazolidine-2,5-dione, the acid halide, or the mixed anhydride with the intermediate 10-h in a presence or absence of a base such as tertiary amine (e.g. triethylamine or N,N-diisoproplyl ethylamine) or $K_2CO_3$. Alternatively, the intermediate 11-b can be coupled with the intermediate 10-h using peptide condensation reagents including, but not limited to, dicyclohexylcarbodiimide (DCC), diisopropylcarbodiimide (DIC), 1-ethyl-3-(3-dimethyllaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine.

In step 2f, the intermediate H can be prepared by cross-coupling of an intermediate 15-a wherein $A^2$, $LG^1$, $P^1$, $R^1$, $R^4$, $R^5$, $R^2$, $R^d$, n, s and $R^e$ are as previously described with an intermediate 10-b wherein $R^2$, m, and BG are as previously described. Known coupling methods may be applied including Suzuki-Miyaura coupling of the intermediate 15-a with the intermediate 10-b using palladium species such as, but not limited to, $Pd(PPh_3)_4$, $PdCl_2(dppf)$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

The intermediates 15-a can also be prepared according to the following procedures described in Scheme 16 wherein $A^2$, $LG^1$, $LG^2$, $P^1$, $P^4$, $R^1$, $R^2$, $R^4$, $R^5$, $R^e$, $R^d$, s and n are as previously described.

Scheme 16

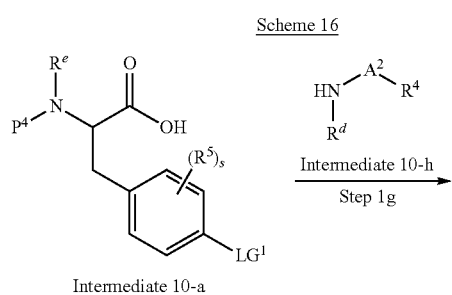

Intermediate 10-a

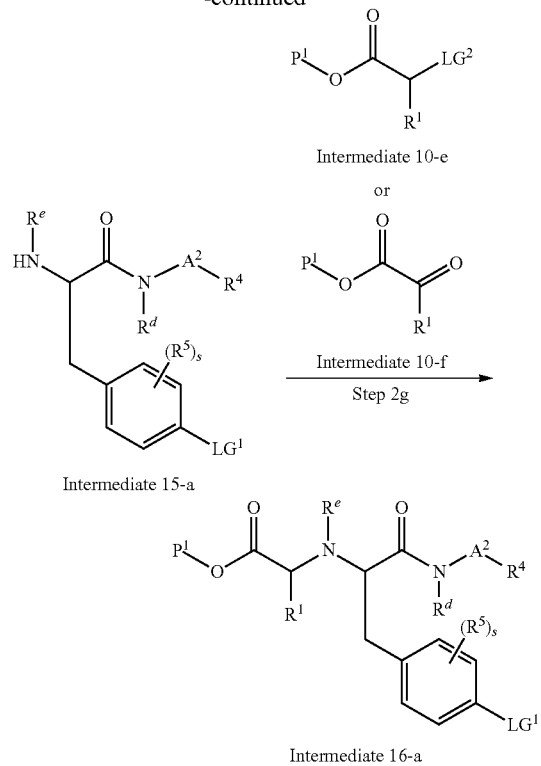

In step 1g, an intermediate 16-a can be prepared by coupling the intermediate 10A wherein $P^4$, $R^5$, $R^e$, s and $LG^1$ are as previously described with an intermediate 10-h wherein $A^2$, $R^4$, and $R^d$ are as previously described followed by an appropriate deprotection of the protecting group $P^4$. Known coupling methods may be applied including, but not limited to, conversion of the intermediate 10-a to corresponding oxazolidine-2,5-dione, using reagents such as triphosgene, carbonyldiimidazole, 4-nitrophenyl chloroformate, or disuccinimidyl carbonate, conversion of the intermediate 10-a to corresponding acid halide, using reagents such as thionyl chloride or oxalyl chloride, or conversion of the intermediate 10-a to corresponding mixed anhydride using reagents such as ClC(O)O-isobutyl or 2,4,6-trichlorobenzoyl chloride, followed by reaction of the oxazolidine-2,5-dione, the acid halide, or the mixed anhydride with the intermediate 10-h in a presence or absence of a base such as tertiary amine (e.g. triethylamine or N,N-diisoproplyl ethylamine) or $K_2CO_3$. Alternatively, the intermediate 10-a can be coupled with the intermediate 10-h using peptide condensation reagents including, but not limited to, dicyclohexylcarbodiimide (DCC), diisopropylcarbodiimide (DIC), 1-ethyl-3-(3-dimethyllaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine.

In step 2g, the intermediate 16-a can be prepared by reacting an intermediate 15-a wherein $A^2$, $LG^1$, $R^4$, $R^5$, $R^e$, s and $R^d$ are as previously defined with an intermediate 10-e $LG^1$, $R^4$, wherein $R^1$, $P^1$, and $LG^2$ are as previously defined. Alternatively, the intermediates 14A can be prepared by reacting an intermediate 16-a wherein $A^2$, $LG^1$, $R^4$, $R^5$, $R^e$, s and $R^d$ are as previously defined with an intermediate 10-f wherein $R^1$ and $P^1$ areas previously described. Known reaction methods may be applied including alkylation of the intermediate 16-a with the intermediate 10-e using a base such as, but not limited to, tertiary amine (e.g. triethylamine or N,N-diisopropyl ethylamine), pyridine, or $K_2CO_3$ or reductive amination of the intermediate 16-a with the intermediate 10-f under a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i-PrO)_4$.

Intermediate H wherein Ring C is heteroaryl can be synthesized according to Schemes 10 to 16 by replacing the phenyl boronic acid or ester 10-b with the corresponding heteroaryl boronic acid or ester.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention or a pharmaceutically acceptable salt thereof and one or more pharmaceutically acceptable carriers for use in the prevention, amelioration or treatment of contrast-induced nephropathy. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
- a) diluents, e.g., lactose, dextrose, sucrose, mannitol, sorbitol, cellulose and/or glycine;
- b) lubricants, e.g., silica, talcum, stearic acid, its magnesium or calcium salt and/or polyethyleneglycol; for tablets also
- c) binders, e.g., magnesium aluminum silicate, starch paste, gelatin, tragacanth, methylcellulose, sodium carboxymethylcellulose and/or polyvinylpyrrolidone; if desired
- d) disintegrants, e.g., starches, agar, alginic acid or its sodium salt, or effervescent mixtures; and/or
- e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art in the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I, II, II-A to II-S, III, III-A to III-T, IV and IV-A to IV-D, for use in the method of the invention, or a pharmaceutically acceptable salt thereof, in free form or in pharmaceutically acceptable salt form, exhibit valuable pharmacological properties, e.g. neutral endopeptidase EC 3.4. 24.11 modulating properties, e.g. as indicated in in vitro and in vivo tests as provided in the next sections and are therefore indicated for the treatment, amelioration and/or prevention of contrast-induced nephropathy.

Human Endogenous atrial natriuretic peptides (ANP) infusions have been available in Japan for use in acute decompensated heart failure since 1997. Morikawa et al. showed recently that a 48 hour infusion of ANP was able to decrease the incidence of CIN in an at-risk population undergoing cardiac catheterization by over 70% (*Journal of the American College of Cardiology*, Vol 53, No 12, 2009, 1040-1046). The general clinical rationale for this study was also based on a number of other studies in the surgical literature that show ANP infusions can decrease renal failure in post-operative settings. ANP has been shown to be efficacious in a dog model of contrast nephropathy and can function both as a modulator of renal medullary flow, as well as an enhancer of glomerular filtration. In the former case, an increase in renal medullary perfusion will counteract the vasoconstriction that is known to occur as a result of circulating intravenous contrast dye. In the latter case, the increase in glomerular filtration will increase fluid flow through the renal tubules, decrease the transit time of the contrast dye, and thereby decrease the exposure of the renal tubular epithelium to the highly toxic dye. In addition, ANP has been shown to enhance antiproliferative and antifibrotic profiles in renal mesangial and interstitial cells, and may provide longer term renal protective benefits as well. NEP inhibitors, by virtue of increasing ANP, particularly in the kidney, are proposed to have similar benefits to ANP itself.

Endogenous atrial natriuretic peptides, (also called atrial natriuretic factor; ANF) have diuretic, natriuretic and vasorelaxant functions in mammals. The natural ANF peptide is metabolically inactivated, in particular by a degrading enzyme which has been recognized to correspond to the enzyme neutral endopeptidase (NEP) EC 3.4.24.11, also responsible for e.g. the metabolic inactivation of enkephalins.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEP) should increase renal levels of ANP in particular and therefor be useful for the treatment, amelioration and/or prevention of contrast-induced nephropathy.

Clinical Study to Demonstrate the Efficacy of NEP Inhibition in contrast-induced Nephropathy Contrast-induced nephropathy is commonly defined by an increase from baseline creatinine of ≥0.5 mg/dL and/or 25% over baseline after exposure to iodinated intravenous contrast. Associated with this increase in creatinine is a decline in glomerular filtration rate (GFR). GFR is most commonly estimated using equations that utilize serum creatinine, i.e measuring creatinine clearance. For example, the following equations are used to measure GFR:

$$\text{Cockcroft-Gault} = (140 - \text{age}) \times \text{Mass} \times (0.85 \text{ if female}) / 72 \times \text{serum creatinine (mg/dL)}$$

$$\text{MDRD (modified diet and renal disease)} = 186 \times \text{serum creatinine}^{-1.154} \times \text{age}^{-0.203} \times (1.21 \text{ if black}) \times (0.742 \text{ if female})$$

GFR will be measured during proof of concept clinical trial which is to be performed in patients with chronic renal insufficiency who are undergoing planned cardiac catheterization. The GFR values allow to measure the efficacy of NEP inhibitors in the treatment of contrast-induced nephropathy. Since the estimated GFR takes into account serum creatinine as one of its parameters, it gives an excellent approximation of the rate of contrast-induced nephropathy. GFR's increase is to be observed when the patient is successfully treated with a NEP inhibitor.

Human ANP infusion at a rate of 0.042 μg/kg/min has been shown to reduce the incidence of contrast-induced nephropathy by 70% in a study of patients with chronic renal insufficiency undergoing cardiac catheterization (Morikawa et al. *Journal of American College of Cardiology*, Vol. 53, No 12, 2009, 1040-1046). In this study no biomarker measure of ANP activity was measured.

A biomarker study is designed and involves the infusion of human ANP in subjects with chronic renal insufficiency. The dose of human ANP used is identical to that used in the Morikawa study that showed efficacy in reducing the rate of contrast-induced nephropathy in cardiac catheterization patients. The pharmacokinetic and biomarker study of ANP infusion is designed to determine the level of increase in urinary cGMP as marker for ANP's effects in the kidney. In particular, the level of urinary cGMP is to serve as a target to be achieved by NEP inhibition in the first-in-human studies. Based in the biomarker study, a dose of NEP inhibitor is then selected in order to reach the urinary cGMP level as previously determined in the human ANP infusion study.

Renal Function Assessment in Rats
Background

The effects of compounds of the invention (in the effective dose range of 0.1-100 mg/kg p.o.) on GFR were assessed in adult (~9 months old), male, cannulated Sprague-Dawley rats by the FITC-inulin clearance method. Four to 6 rats each was administered a NEP inhibitor according to the invention (in the effective dose range of 0.1-100 mg/kg p.o.) or its vehicle (1 ml/kg of 0.5% methylcellulose (MC)+0.1% Tween 80). Thirty min after the compound or vehicle administration, a bolus of FITC-inulin (10 mg/kg) was injected i.v. Blood samples were collected for 120 min thereafter to determine GFR D/AUC, where D is the injected dose of FITC-inulin and AUC is the area under the FITC-inulin plasma concentrations/time relationship from 0 to infinity).

Methods

FITC-Inulin Preparation

A fluorescein isothiocyanate (FITC)-inulin stock solution was prepared by weighing the FITC-inulin powder, adding it to saline (50 mg/ml), and heating it in boiling water until dissolved. The solution was filtered and dialyzed overnight to remove unbound FITC. The next day, the dialysate was again filtered to sterilize it.

Animal Preparation

Approximately 1-2 weeks before the study, femoral arterial and venous catheters were implanted in the rats under isoflurane anesthesia. The catheters were exteriorized through a spring tether/swivel system and the instrumented rats were housed in specialized cages.

In vivo Procedures

On the experimental day, rats were administered a NEP inhibitor or its vehicle by oral gavage. Thirty min later, FITC-inulin (10 mg/kg i.v. bolus) was administered via the venous catheter. Blood samples were withdrawn from the arterial catheter at 3, 7, 10, 15, 30, 60, 90, and 120 min after the FITC-inulin injection for plasma FITC-inulin and compound concentrations.

Arterial pressure was continuously monitored throughout the experiment.

Ex vivo Analyses

The stock solution of FITC-inulin was serially diluted to generate a standard curve. The dosing solution was also diluted and analyzed to determine the exact amount of FITC-inulin injected. Plasma samples, standard samples, and dosing solution samples were analyzed on black 96-well plates with a spectrophotometer at 485 nm excitation frequency and 530 nm emission frequency. Concentrations of FITC-inulin in the plasma and dosing solution were determined by linear regression from the standard curve. FITC-inulin AUC(0-infinity) was derived by WinNonlin for each rat's plasma concentration-time curves. GFR (FITC-inulin clearance) was calculated for each animal as the injected dose divided by the AUC.

Results

| Example # | Dose (mg/kg) | n* | % GFR increase |
|---|---|---|---|
| Example 34 | 100 | 4 | 37 |
| Example 1-2 | 0.1 | 5 | 23 |
| Example 31 | 0.1 | 5 | 27 |
| Example 3-12 | 1 | 4 | 32 |
| Example 35 | 1 | 4 | 22 |
| Example 9-7 | 1 | 4 | 35 |

*n is the number of rats per treatment

GFR in the vehicle-treated rats was 0.78±0.02 (SEM) ml/min/100 g body weight. GFR was 22-37% higher in the NEP inhibitor-treated rats relative to the vehicle-treated rats. These results indicate that a single injection of a NEP inhibitor according to the invention at an effective dose range of 0.1-100 mg/kg p.o. in this rat model is not only renally safe but also augments GFR, thereby supporting the contrast-induced nephropathy indication in humans. There were no changes in arterial pressure in the NEP inhibitor-treated rats vs. the vehicle-treated rats indicating that the compound increased GFR independently of blood pressure changes.

The pharmaceutical composition or combination of the present invention for use in the prevention, treatment and/or prevention of contrast-induced nephropathy, can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the severity of the contrast-induced nephropathy disorder. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound for use in the method according to the present invention can be assessed by the following in vitro & in vivo methods and/or by the following in vitro & in vivo methods well-described in the art. See A fluorescence lifetime-based assay for protease inhibitor profiling on human kallikrein 7 Doering K, Meder G, Hinnenberger M, Woelcke J, Mayr L M, Hassiepen U Biomol Screen. 2009 January; 14(1):1-9.

In particular, the in vitro inhibition of recombinant human neutral endopeptidase (NEP, EC 3.4.24.11) can be determined as follows:

Recombinant human neutral endopeptidase (expressed in insect cells and purified using standard methods, final concentration 7 μM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys(PT14)-Arg-Arg-Leu-Trp-OH to a final concentration of 0.7 μM. Substrate hydrolysis leads to an increase fluorescence lifetime (FLT) of PT14 measured by the means of a FLT reader as described by Doering et al. (2009). The effect of the compound on the enzymatic activity was determined after 1 hour (t=60 min) incubation at room temperature. The IC50 values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory efficacy in accordance to Table 1, provided infra.

TABLE 1

Inhibitory Activity of Compounds

| Example # | Human NEP $IC_{50}$ (nM) |
|---|---|
| Example 3-11 | 18 |
| Example 3-12 | 15 |
| Example 3-13 | 15 |
| Example 5-1 | 38 |
| Example 5-2 | 7 |
| Example 5-3 | 4 |
| Example 5-4 | 3 |
| Example 5-5 | 67 |
| Example 5-6 | 42 |
| Example 5-7 | 2.3 |
| Example 5-8 | 0.7 |
| Example 5-9 | 0.5 |
| Example 5-10 | 2.7 |
| Example 5-11 | 0.7 |
| Example 6-1 | 75 |
| Example 8-1 | 56 |
| Example 9-1 | 1.1 |
| Example 9-6 | 0.5 |
| Example 9-5 | 0.07 |
| Example 9-7 | 0.4 |
| Example 10-1 | 0.2 |
| Example 11-1 | 0.8 |
| Example 12-1 | 1.2 |
| Example 14-1 | 283 |
| Example 15-1 | 267 |
| Example 16-3 | 250 |
| Example 16-5 | 1 |
| Example 16-8 | 7.3 |
| Example 17 | 350 |
| Example 18-1 | 450 |
| Example 19 | 93 |
| Example 20 | 142 |
| Example 23 | 14 |
| Example 29 | 0.04 |
| Example 29-1 | 0.03 |
| Example 29-2 | 0.3 |
| Example 32-1 | 0.09 |
| Example 32-2 | 0.3 |
| Example 32-3 | 11 |
| Example 32-4 | 2.4 |
| Example 32-5 | 91 |
| Example 32-6 | 0.2 |
| Example 32-7 | 0.2 |
| Example 36 | 0.3 |

The compounds of the invention have been found to have IC50 values in the range of about 0.01 nM to about 10,000 nM for NEP. Preferably the compounds for use in the invention have an $IC_{50}$ equal to or below 5000 nM. More preferably the compounds for use in the invention have an $IC_{50}$ equal to or below 1000 nM.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention pertains to the method of treating, ameliorating or preventing contrast-induced nephropathy in a subject, comprising administering to the subject a product comprising a compound according to anyone of formulae I, II, II-A to II-S, III, III-A to III-T, IV and IV-A to IV-D, or a pharmaceutically acceptable salt thereof, and at least one other therapeutic agent as a combined preparation for simultaneous, separate or sequential use in therapy.

Products provided as a combined preparation for use in the method of the invention, include a composition comprising the compound according to anyone of formulae I, II, II-A to II-S, III, III-A to III-T, IV and IV-A to IV-D, or a pharmaceutically acceptable salt thereof, and the other therapeutic agent(s) together in the same pharmaceutical composition, or the compound according to anyone of formulae I, II, II-A to II-S, III, III-A to III-T, IV and IV-A to IV-D, or a pharmaceutically acceptable salt thereof, and the other therapeutic agent(s) in separate form, e.g. in the form of a kit.

In one embodiment, the invention pertains to the method of treating, ameliorating or preventing contrast-induced nephropathy in a subject, comprising administering to the subject a pharmaceutical composition comprising a compound according to anyone of formulae I, II, II-A to II-S, III, III-A to III-T, IV and IV-A to IV-D, or a pharmaceutically acceptable salt thereof, and at least one other therapeutic agent as a combined preparation for simultaneous, separate or sequential use in therapy. Optionally, the pharmaceutical composition for use in the method of the invention may comprise a pharmaceutically acceptable excipient, as described above.

In one embodiment, the invention provides a kit for use in the method of the invention, comprising two or more separate pharmaceutical compositions, at least one of which contains a compound according to anyone of formulae I, II, II-A to II-S, III, III-A to III-T, IV and IV-A to IV-D, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (ii) in the patient themselves, e.g. during sequential administration of the compound of the invention and the other therapeutic agent.

Accordingly, the invention provides the use of a compound according to anyone of formulae I, II, II-A to II-S, III, III-A to III-T, IV and IV-A to IV-D, or a pharmaceutically acceptable salt thereof, for treating, ameliorating or preventing contrast-induced nephropathy, wherein the medicament is prepared for administration with another therapeutic agent. The invention also provides the use of another therapeutic agent for treating, ameliorating or preventing constrast-induced nephropathy, wherein the medicament is administered with a compound according to anyone of formulae I, II, II-A to II-S, III-A to III-T, IV and IV-A to IV-D, or a pharmaceutically acceptable salt thereof.

The invention also provides a compound according to anyone of formulae I, II, II-A to I-S, III, III-A to III-T, IV and IV-A to IV-D, or a pharmaceutically acceptable salt thereof, for use in a method of treating, ameliorating or preventing constrast-induced nephropathy, wherein the compound according to anyone of formulae I, II, II-A to II-S, III, III-A to III-T, IV, and IV-A to IV-D, or a pharmaceutically acceptable salt thereof, is prepared for administration with another therapeutic agent. The invention also provides another therapeutic agent for use in a method of treating, ameliorating, or preventing contrast-induced nephropathy, wherein the other therapeutic agent is prepared for administration with a compound according to anyone of formulae I, II, II-A to II-S, III, III-A to III-T, IV and IV-A to IV-D, or a pharmaceutically acceptable salt thereof.

The invention also provides a compound according to anyone of formulae I, II, II-A to II-S, III, III-A to III-T, IV and IV-A to IV-D, or a pharmaceutically acceptable salt thereof, for use in a method of treating, ameliorating or preventing constrast-induced nephropathy, wherein the compound according to anyone of formulae I, II, II-A to II-S, III, III-A to III-T, IV and IV-A to IV-D or a pharmaceutically acceptable salt thereof, is administered with another therapeutic agent. The invention also provides another therapeutic agent for use in a method of treating, ameliorating or preventing constrast-induced nephropathy, wherein the other therapeutic agent is administered with a compound according to anyone of formulae I, II, II-A to III, III-A to III-T, IV and IV-A to IV-D, or a pharmaceutically acceptable salt thereof.

The invention also provides the use of a compound according to anyone of formulae I, II, II-A to II-S, III, III-A to III-T, IV and IV-A to IV-D, or a pharmaceutically acceptable salt thereof, for treating, ameliorating or preventing constrast-induced nephropathy, wherein the patient has previously (e.g. within 24 hours) been treated with another therapeutic agent. The invention also provides the use of another therapeutic agent for treating, ameliorating or preventing constrast-induced nephropathy, wherein the patient has previously (e.g. within 24 hours) been treated with a compound according to anyone of formulae I, II, II-A to II-S, III, III-A to III-T, IV and IV-A to IV-D, or a pharmaceutically acceptable salt thereof.

In one embodiment, the other therapeutic agent is selected from: an adenosine-receptor antagonist, a calcium channel blockers, an antioxidant, an anti-apoptotic agent, a MAP kinase inhibitor, a prostacyclin or prostacyclin analogue, an endothelin receptor antagonist, an iron chelator and a dopamine receptor agonist.

The term "in combination with" a second agent or treatment includes co-administration of the compound of the invention (e.g., a compound according to anyone of Formulae I, II, II-A to II-S, III, III-A to III-T, IV and IV-A to IV-D or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of contrast-induced nephropathy.

Examples of second agents include an adenosine-receptor antagonist, a calcium channel blocker, an anti-apoptotic agent, an antioxidant, a MAP kinase inhibitor, a prostacyclin or prostacyclin analogue, endothelin antagonist and a dopamine receptor agonist or a pharmaceutically acceptable salt thereof.

The term "adenosine-receptor antagonist" includes methylxanthines, xanthine alkaloids and other xanthine derivatives, or a pharmaceutically acceptable salt thereof. Examples include theophylline and caffeine.

The term "anti-apoptotic agent" includes any drug known or postulated to prevent programmed cell death through various cellular pathways. Examples include N-acetylcystin, 3-[5-amino-4-(3-cyanobenzoyl)-pyrazol-1-yl]-N-cyclopropyl-4-methyl-benzamide or a pharmaceutically acceptable salt thereof.

The term "anti-oxidant agent" includes any drug known or postulated to prevent the development of reactive oxygen species through various cellular pathways. Examples include vitamin E, polyphenols, N-Acetylcystine, glutathione or, pharmaceutically acceptables salt thereof.

The term "MAP kinase inhibitor" includes any drug known or postulated to inhibit the activity of the Mitogen Activated Protein kinase. Examples include compounds of PCT application Number WO 2005/009973. Examples of compounds of the application are 3-(5-amino-4-benzoyl-pyrazol-1-yl)-N-cyclopropyl-4-methyl-benzamide; 3-[5-amino-4-(3-iodo-benzoyl)-pyrazol-1-yl]-N-cyclopropyl-4-methyl-benzamide; 3-[5-amino-4-(3-hydroxymethyl-benzoyl)-pyrazol-1-yl]-N-cyclopropyl-4-methyl-benzamide; 3-[5-amino-4-(3-hydroxy-benzoyl)-pyrazol-1-yl]-N-cyclopropyl-4-methyl-benzamide; 3-[5-amino-4-(4-methyl-benzoyl)-pyrazol-1-yl]-N-cyclopropyl-4-methyl-benzamide; and 3-[5-amino-4-(3-cyanobenzoyl)-pyrazol-1-yl]-N-cyclopropyl-4-methyl-benzamide or a pharmaceutically acceptable salt thereof.

Other examples of MAP kinase inhibitors include Doramapimod (BIBR-796), VX-702, Talmapimod (SC10-469), GSK-1120212, BAY-86-9766 and MSC-1936369B.

The term "prostacyclin or prostacyclin analogue" includes eicosanoids and synthetic analogues thereof. Examples include epoprostenol, trepostinil, iloprost, ciloprost; or a pharmaceutically acceptable salt thereof.

The term "endothelin antagonist" includes any drug known or postulated to prevent binding of the endothelin receptor, or activation of the endothelin receptor signaling, either directly or indirectly. Examples include avosentan, bosentan, sixtasentan, ambrisentan, atrasentan, tazosentan, or pharmaceutically acceptables salt thereof. Examples of indirect inactivation of endothelin receptor signaling includes relaxin or a pharmaceutically acceptable salt thereof.

The term "dopamine receptor agonist" includes any drug known or postulated to activate the dopamineric G-protein receptor. Examples include dopamine, fenoldopam, bromocriptine, pergolide, ropinirole, pramipexole, piribedil, rotigotine, or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or a pharmaceutically acceptable salt thereof.

The term "iron chelator" includes deferipone.

Second agent of particular interest include MAP kinase inhibitor or endothelin antagonist.

EXEMPLIFICATION OF THE INVENTION

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXEMPLIFICATION OF THE INVENTION

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the example 5-1 to 15-3 have been found to have $IC_{50}$ values in the range of about 0.01 nM to about 10,000 nM for NEP.

ABBREVIATIONS

ATP: adenosine 5'-triphosphate
Alloc: allyloxycarbonyl
BOP: benzotriazole1-yloxy)tris(dimethylamino)phosphonium hexafluorophosphate
BOPCl: Bis(2-oxo-3-oxazolidinyl)-phosphonic chloride
br: broad
Ac: Acetyl
Aq: aqueous
Bn: benzyl
Bu, i-bu and t-Bu: butyl, isobutyl and t-butyl
CDI: 1,1'-carbonyldiimidazole
DBU: 1,8-diazabicyclo[5.4.0]undec-7-ene
DIAD: diisopropyl azodicarboxylate
d: doublet
dd: doublet of doublets
DIEA: diethylisopropylamine
DMF: N,N-dimethylformamide
DIPEA: N,N-diisopropylethylamine
Dppb: 1,2-bis(diphenylphosphino)butane
DAD: diode array detector
DPPA: diphenylphosphorylazide
EDTA: ethylenediamine tetraacetic acid
Et and EtOAc: ethyl and ethyl acetate
FITC fluorescein isothiocyanate
HATU: O-(7-azobenzotriazol-1-yl)-1,1,3,3-tetramethyluroniumhexafluorophosphate
HPLC: high pressure liquid chromatography
H: Hour(s)
IR: infrared
KHMDS: potassium bis(trimethylsilyl)amide
LTA: lead tetraacetate
MeOD: methanol-d4
MS: mass spectrometry
min: minutes
Ms: mesyl
M and mM: Molar and millimolar
MC: methylcellulose
Ph: Phenyl
ppm: parts per million
PyBOP: benzotriazol-1-yloxy Tripyrrolidinophosphoniumhexafluorophosphate
PS: polymer supported
PIDA: iodobenzene bis(trifluoroacetate)
RP: reverse phase
s: singlet and t: triplet
q: quartet
TFA: trifluoroacetic acid
TEA: triethylamine
Tf: triflate
TLC: thin layer chromatography
μL, mL and L: microliter, milliliter and liter
WSC: water soluble carbodiimide (N-Ethyl-N'-(3-dimethylaminopropyl)carbodiimide
Wt: weight AS: Aldosterone Synthase
BOC: tertiary butyl carboxy
BINAP: racemic 2,2'-bis(diphenyl phosphino)-1,1'-binaphthyl
HBTU: 2-(1H-benzotriazole-1-yl)-1,1,3,3-tetramethyluronium-hexafluorophosphate
bs: broad singlet
Atm: atmosphere
calcd: calculated
Cbz: benzyloxycarbonyl
Pr and i-Pr: propyl and isopropyl
COD: 1,5-cyclooctadiene
DCC: 1,3-dicyclohexylcarbodiimide
DAST: (diethylamino)sulfur trifluoride
DCM: dichloromethane
DME: 1,4-dimethoxyethane
DMSO: dimethylsulfoxide
DMAP: N,N-dimethylaminopyridine
Dppe: 1,2-bis(diphenylphosphino)ethane
DTT: dithiothreitol
EDCl, EDIC: N-Ethyl-N'-(3-dimethylaminopropyl)carbodiimide hydrochloride
ESI: electrospray ionization
EDC: N-Ethyl-N'-(3-dimethylaminopropyl)carbodiimide hydrochloride
HPLC-RT: Retention time
HOBt: 1-hydroxy-7-azabenzotriazole
LC and LCMS: liquid chromatography and liquid chromatography and mass spectrometry
HOAt: 1-hydroxy-7-azabezotriazole
LDA: lithium diisopropylamide
LHMDS: lithium bis(trimethylsilyl)amide
NHMDS: sodium bis(trimethylsilyl)amide
MeOH: methanol
m: multiplet
m/z: mass to charge ratio
Me: methyl
Mg: milligram
n.d.: not determined
NMR: nuclear magnetic resonance
Pr and iPr: propyl and isopropyl
Pd/C: Palladium on Carbom
RT: room temperature
PIFA: iodobenzene diacetate
SEM: standard error of the mean
Ts tosyl
THF: tetrahydrofuran
PMBCl: para-methoxybenzylchloride
tBu: tert-butyl
Tris-HCl: aminotris(hydroxymethyl)methane hydrochloride
TMS: Trimethylsilyl
TMSCl: trimethylsilyl chloride
UV: ultraviolet The conditions for measuring the retention times are as follows:

HPLC Condition A:

Column: INERTSIL C8-3, 3 μm×33 mm×3.0 mm at 40° C.

Flow rate: 2 ml/min
Mobile phase: A) 5 mM aqueous HCOONH4, B) MeOH/CH3CN (1/1, v/v)
Gradient: linear gradient from 5% A to 95% B in 2 min
Detection: DAD-UV at 200-400 nm
HPLC Condition B:
Column: INERTSIL C8-3, 3 μm×33 mm×3.0 mm at 40° C.
Flow rate: 2 ml/min
Mobile phase: A) 5 mM aqueous HCOONH4, B) MeOH/CH3CN (1/1, v/v)
Gradient: linear gradient from 40% A to 95% B in 2 min
Detection: DAD-UV at 200-400 nm
HPLC Condition C:
Column: INERTSIL C8-3, 3 μm×33 mm×3.0 mm at 40° C.
Flow rate: 2 ml/min
Mobile phase: A) (5 mM $NH_4^+HCOO^-$)/water, B) MeOH/$CH_3CN$ (1/1, v/v)
Gradient: linear gradient from 5 to 95% B in 2 min
Detection: DAD-UV at 200-400 nm
HPLC Condition D:
Column: INERTSIL C8-3, 3 μm×33 mm×3.0 mm at 40° C.
Flow rate: 2 ml/min
Mobile phase: A) 0.1% aqueous Formic acid, B) MeOH/$CH_3CN$ (1/1, v/v)
Gradient: linear gradient from 5% B to 95% B in 2 min
Detection: DAD-UV at 200-400 nm
HPLC Condition E:
Column: Inertsil C8-3, 3 μm×33 mm×3.0 mm at 40° C.
Flow rate: 2 ml/min
Mobile phase: A) methanol/acetonitrile (1/1, v/v), B) 5 mM aqueous $HCOONH_4$
Gradient: linear gradient from 40% B to 95% A in 2 min
Detection: UV at 214 nm
HPLC Condition F:
Column: INERTSIL C8-3, 3 μm×33 mm×3.0 mm at 40° C.
Flow rate: 2 mL/min
Mobile phase: $H_2O$ (5 mM NH4+HCOO−)
Gradient: linear gradient from 5% to 95% MeCN in 2 min
Detection: DAD-UV at 200-400 nm
HPLC Condition G:
Column: INERTSIL C8-3, 3 μm×33 mm×3.0 mm at 40° C.
Flow rate: 2 mL/min
Mobile phase: 0.1% Formic acid
Gradient: linear gradient from 5% to 95% MeCN/MeOH in 2 min
Detection: UV at 215 nm
HPLC Condition H:
Column: Inertsil C8-3, 3 μm×33 mm×3.0 mm at 40° C.
Flow rate: 2 ml/min
Mobile phase: A) $H_2O$ (5 mM NH4+HCOO−), B) 50% MeOH/50% MeCN
Gradient: linear gradient from 40% B to 95% B in 2 min
Detection: UV at 214 nm
HPLC Condition I:
Column: INERTSIL C8-3, 3 μm×33 mm×3.0 mm at 40° C.
Flow rate: 2 mL/min
Mobile phase: A) 0.5 mM ammonium formate in $H_2O$; B) 50% MeOH in $CH_3CN$
Gradient: linear gradient from 5% B to 95% B in 2 min
Detection: DAD-UV at 210-400 nm
HPLC Condition J:
Column: INERTSIL C8-3, 3 μm×33 mm×3.0 mm at 40° C.
Flow rate: 2 mL/min
Mobile phase: A) 0.5 mM ammonium formate in $H_2O$; B) 50% MeOH in $CH_3CN$
Gradient: linear gradient from 40% B to 95% B in 2 min
Detection: DAD-UV at 210-400 nm
HPLC Condition K:
Column: INERTSIL C8-3, 3 μm×33 mm×3.0 mm at 40° C.
Flow rate: 2 mL/min
Mobile phase: A) 0.1% formic acid in $H_2O$; B) 50% MeOH in $CH_3CN$
Gradient: linear gradient from 40% B to 95% B in 2 min
Detection: DAD-UV at 210-400 nm The relative stereochemistry was determined using two dimensional NMR. Under the reaction condition, it would be unexpected that the stereocenter bearing the bisphenyl-methyl group racemize. Therefore, the absolute stereochemistry was determined based on the relative stereochemistry and the absolute stereochemistry of the stereocenter bearing the bisphenyl-methyl group.

Example 1-1

Synthesis of (R)-4-(1-(biphenyl-4-yl)-4-ethoxy-4-oxobutan-2-ylamino)-4-oxobutanoic acid

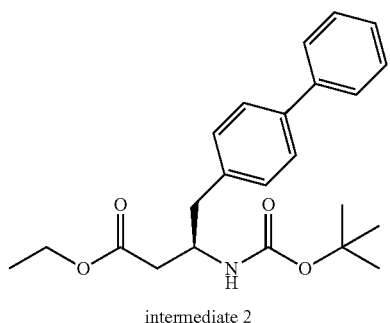

intermediate 2

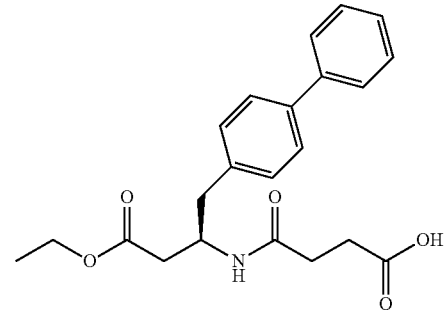

To (R)-ethyl-4-(biphenyl-4-yl)-3-(tert-butoxycarbonylamino)butanoate (230.1 mg, 0.600 mmol) is added a solution of HCl in 1,4-dioxane (3.00 mL, 12.00 mmol) at room temperature. After stirring for 1 hour, the reaction mixture is concentrated under reduced pressure to give (R)-3-amino-4-biphenyl-4-yl-butyric acid ethyl ester hydrochloride. A solution of (R)-3-amino-4-biphenyl-4-yl-butyric acid ethyl ester hydrochloride, succinic anhydride (72.1 mg, 0.720 mmol) and DIPEA (0.126 mL, 0.720 mmol) in dichloromethane (4 mL) is allowed to stir for 1 hour. The reaction is quenched with 10% aqueous citric acid and extracted with dichloromethane. The organic layer is separated and concentrated under reduced pressure. The obtained residue is purified by flash column chromatography on CN-modified silica gel (eluent: heptane/EtOAc=100:0 to 0:100) and by RP-HPLC (SunFire C18, $H_2O$ (0.1% TFA)/$CH_3CN$) to give (R)-4-(1-(biphenyl-4-yl)-4-ethoxy-4-oxobutan-2-ylamino)-4-oxobutanoic acid (148.2 mg). HPLC retention time=1.64 minutes (condition A); MS (m+1)=384.1; 1H NMR (400 MHz, ACETONI- TRILE-d3) δ ppm 1.21 (t, J=7.07 Hz, 3 H) 2.31-2.39 (m, 2 H) 2.40-2.56 (m, 4 H) 2.77-2.92 (m, 2 H) 4.08 (q, J=7.24 Hz, 2 H) 4.33-4.48 (m, 1 H) 6.62 (d, J=8.34 Hz, 1 H) 7.30 (d, J=8.08 Hz, 2 H) 7.32-7.39 (m, 1 H) 7.41-7.49 (m, 2 H) 7.54-7.60 (m, 2H) 7.60-7.67 (m, 2 H) 10.02 (br. s., 1 H).

Example 1-2

Synthesis of (R)-4-(1-(3'-chlorobiphenyl-4-yl)-4-ethoxy-4-oxobutan-2-ylamino)-4-oxobutanoic acid

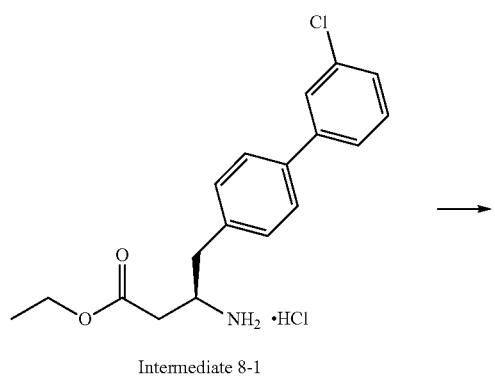

Intermediate 8-1

→

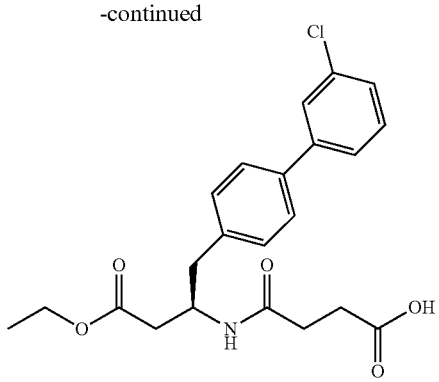

A solution of (R)-ethyl 3-amino-4-(3'-chlorobiphenyl-4-yl)butanoate hydrochloride (400 mg, 1.13 mmol), succinic anhydride (136 mg, 1.36 mmol) and DIPEA (0.237 mL, 1.36 mmol) in dichloromethane (5 mL) is allowed to stir for 2.5 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(3'-chlorobiphenyl-4-yl)-4-ethoxy-4-oxobutan-2-ylamino)-4-oxobutanoic acid (255 mg). HPLC retention time=1.15 minutes (condition B); MS (m+1)=418.0; 1H NMR (400 MHz, CHLOROFORM-d) δ ppm 1.29 (t, J=7.08 Hz, 3 H) 2.46-2.58 (m, 4 H) 2.64-2.67 (m, 2 H) 2.87 (A of ABX, $J_{ab}$=13.6 Hz, $J_{bx}$=7.8 Hz, 1 H) 2.99 (B of ABX, $J_{ab}$=13.6 Hz, $J_{bx}$=6.6 Hz, 1 H) 4.12-4.24 (m, 2 H) 4.47-4.55 (m, 1 H) 6.50 (br d, J=8.8 Hz, 1 H) 7.24-7.37 (m, 4 H) 7.43-7.46 (m, 1 H) 7.48-7.52 (m, 2H) 7.55-7.56 (m, 1 H).

Chiral HPLC retention time=3.59 min. Column: Daicel CHIRALPAK AD-H (4.6×100 mm); flow rate=1 ml/min.; eluent: EtOH (containing 0.1% TFA)/heptane=4/6.

Following compounds are prepared using similar procedure as described in example 1-2:

| Example # | Product | Starting Material | Condition | HPLC-RT (condition) | MS (M+1) |
|---|---|---|---|---|---|
| Example 1-3 | (R)-4-(4-(benzyloxy)-1-(3'-chlorobiphenyl-4-yl)-4-oxobutan-2-ylamino)-4-oxobutanoic acid | Intermediate 8-4 | DIPEA, DCM, RT | 1.37 min. (B) | 480.2 |

-continued

| Example # | Product | Starting Material | Condition | HPLC-RT (condition) | MS (M + 1) |
|---|---|---|---|---|---|
| Example 1-4 | | Intermediate 8-1 | Pyridine, RT | 1.32 min. (C) | 490.2 |
| Example 1-5 | | Intermediate 23 | DIPEA, DCM, RT | 1.52 min. (B) | 506.4 |

Example 1-3

1H NMR (400 MHz, CHLOROFORM-d) δ ppm 2.41-2.45 (m, 2 H) 2.50-2.64 (m, 4 H) 2.81-2.87 (m, 1 H) 2.95-3.00 (m, 1 H) 4.49-4.56 (m, 1 H) 5.12 (A of AB, J=12.1 Hz, 1 H) 5.18 (B of AB, J=12.1 Hz, 1 H) 6.39 (d, J=8.1 Hz, 1 H) 7.18-7.54 (m, 13 H).

Example 1-4

1H NMR (400 MHz, DMSO-d6): 1H NMR (400 MHz, DMSO-d6): δ ppm 1.22-1.25 (t, J=7.07 Hz, 3H), 2.61-2.63 (m, 2H), 2.91 (d, J=7.07 Hz, 2H), 4.09 (q, J=7.07 Hz, 2H), 4.52-4.59 (m, 1H), 7.32-7.34 (m, 3H), 7.04 (t, J=7.83 Hz, 1H), 7.52-7.56 (m, 3H), 7.59 (t, J=2.02 Hz, 1H).

Example 1-5

1H NMR (400 MHz, CHLOROFORM-d) δ ppm 2.03-2.13 (m, 2 H), 2.44 (t, J=6.3 Hz, 2 H), 2.64 (t, J=6.6 Hz, 2 H), 2.70 (dd, J=16.2, 5.6 Hz, 1 H), 2.78 (dd, J=16.2, 5.1 Hz, 1 H), 2.83-2.98 (m, 5 H), 3.04 (dd, J=13.9, 6.8 Hz, 1 H), 4.57-4.69 (m, 1 H), 6.51 (d, J=8.8 Hz, 1 H), 6.79 (dd, J=8.1, 2.3 Hz, 1 H), 6.90 (d, J=1.8 Hz, 1 H), 7.18 (d, J=8.1 Hz, 1 H), 7.26-7.31 (m, 3 H), 7.34 (t, J=7.7 Hz, 1 H), 7.43 (dt, J=7.3, 1.5 Hz, 1 H), 7.49 (d, J=8.1 Hz, 2 H), 7.54 (t, J=1.8 Hz, 1 H), 9.34 (br. s., 1 H).

Example 1-6

Synthesis of (R)-4-(1-(2',5'-dichlorobiphenyl-4-yl)-4-ethoxy-4-oxobutan-2-ylamino)-4-oxobutanoic acid

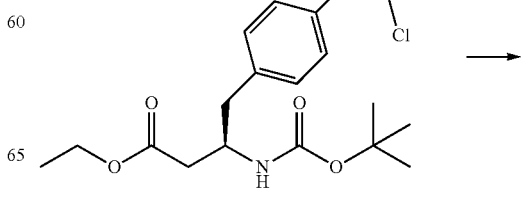

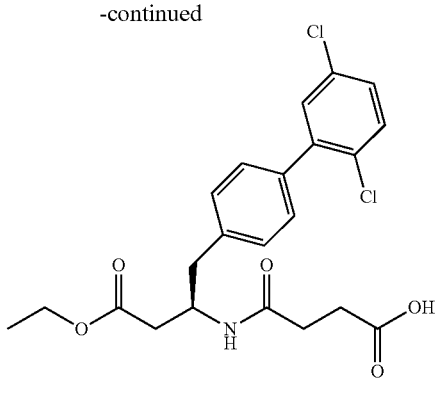

To (R)-ethyl 3-(tert-butoxycarbonylamino)-4-(2',5'-dichlorobiphenyl-4-yl)butanoate (Intermediate 11: 1.09 g, 2.33 mmol) is added a solution of 4 M HCl in 1,4-dioxane (5.81 mL, 23.3 mmol) at room temperature. After stirring for 2 hours, the reaction mixture is concentrated under reduced pressure to give (R)-ethyl 3-amino-4-(2',5'-dichlorobiphenyl-4-yl)butanoate hydrochloride. Next, a solution of the product, succinic anhydride (280 mg, 2.80 mmol) and DIPEA (0.489 mL, 2.80 mmol) in dichloromethane (15 mL) is allowed to stir for 2 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(2',5'-dichlorobiphenyl-4-yl)-4-ethoxy-4-oxobutan-2-ylamino)-4-oxobutanoic acid (553 mg) as a white solid; HPLC retention time=1.02 minutes (condition B); MS (m+1)=452.14; 1H NMR (400 MHz, CHLOROFORM-d) δ ppm 1.29 (t, J=7.2 Hz, 3 H) 2.47-2.67 (m, 6 H) 2.89 (A of ABX, $J_{ab}$=13.7 Hz, $J_{ax}$=7.8 Hz, 1 H) 3.00 (B of ABX, $J_{ab}$=13.7 Hz, $J_{bx}$=6.7 Hz, 1 H) 4.12-4.24 (m, 2 H) 4.49-4.57 (m, 1 H) 6.53 (br d, J=8.8 Hz, 1 H) 7.23-7.26 (m, 3 H) 7.32-7.40 (m, 4 H).

Following compounds are prepared using similar procedure as described in example 1-6:

| Example | Product | Starting Material | HPLC-RT (condition) | MS (M + 1) |
|---|---|---|---|---|
| Example 1-7 | (R)-3-(3-Carboxy-propionylamino)-4-(3'-chloro-biphenyl-4-yl)-butyric acid 5-methyl-2-oxo-[1,3]dioxol-4-yl | Intermediate 9-3 | 1.12 min. (B) | 502.2 |
| Example 1-8 | (R)-3-(3-Carboxy-propionylamino)-4-(3'-chloro-biphenyl-4-yl)-butyric acid dimethylcarbamoylmethyl ester | Intermediate 9-4 | 0.89 min. (B) | 475.3 |

| Example | Product | Starting Material | HPLC-RT (condition) | MS (M + 1) |
|---|---|---|---|---|
| Example 1-9 | (R)-3-(3-Carboxy-propionylamino)-4-(3'-chloro-biphenyl-4-yl)-butyric acid 2-morpholin-4-yl-ethyl ester | Intermediate 9-5 | 0.99 min. (B) | 503.5 |

Example 1-7

1H NMR (400 MHz, CHLOROFORM-d) δ ppm 2.17 (s, 3 H), 2.44 (t, J=6.2 Hz, 2 H), 2.48-2.57 (m, 1 H), 2.57-2.73 (m, 3 H), 2.87 (dd, J=13.6, 7.6 Hz, 1 H), 2.98 (dd, J=13.9, 7.1 Hz, 1 H), 4.47-4.58 (m, 1 H), 4.84 (s, 2 H), 6.32 (d, J=8.6 Hz, 1 H), 7.23 (d, J=8.1 Hz, 2 H), 7.30 (d, 1 H), 7.35 (t, J=7.7 Hz, 1 H), 7.44 (d, J=7.3 Hz, 1 H), 7.49 (d, J=8.1 Hz, 2 H), 7.54 (s, 1 H).

Example 1-8

1H NMR (400 MHz, CHLOROFORM-d) δ ppm 2.48-2.59 (m, 3 H), 2.61-2.71 (m, 3 H), 2.91-3.06 (m, 8 H), 4.53-4.63 (m, 1 μl), 4.67 (d, J=14.7 Hz, 1 H), 5.03 (d, J=14.7 Hz, 1 H), 7.30 (dt, J=7.8, 1.8 Hz, 1 H), 7.32-7.38 (m, 3 H), 7.45 (dt, J=7.6, 1.5 Hz, 1 H), 7.50 (d, J=8.1 Hz, 2 H), 7.55 (t, J=1.8 Hz, 1 H), 8.08 (d, J=9.3 Hz, 1 H).

Example 1-9

1H NMR (400 MHz, DMSO-d6) δ ppm 2.20-2.32 (m, 2 H), 2.32-2.41 (m, 2 H), 2.42-2.50 (m, 1 H), 2.57 (dd, J=15.4, 5.6 Hz, 1 H), 2.80 (d, J=36.1 Hz, 2 H), 3.15 (br. s., 2 H), 3.31-3.50 (m, 4 H), 3.52-4.05 (m, 4 H), 4.25-4.40 (m, 3 H), 7.31 (d, J=8.3 Hz, 2 H), 7.39-7.43 (m, 1 H), 7.48 (t, J=7.8 Hz, 1 H), 7.60-7.67 (m, 3 H), 7.70 (t, J=1.8 Hz, 1 H), 8.02 (d, J=8.6 Hz, 1 H), 10.06 (br. s., 1 H), 12.17 (br. s., 1 H).

Example 1-10

Synthesis of (R)-4-(1-(5'-chloro-2'-fluorobiphenyl-4-yl)-4-ethoxy-4-oxobutan-2-ylamino)-4-oxobutanoic acid

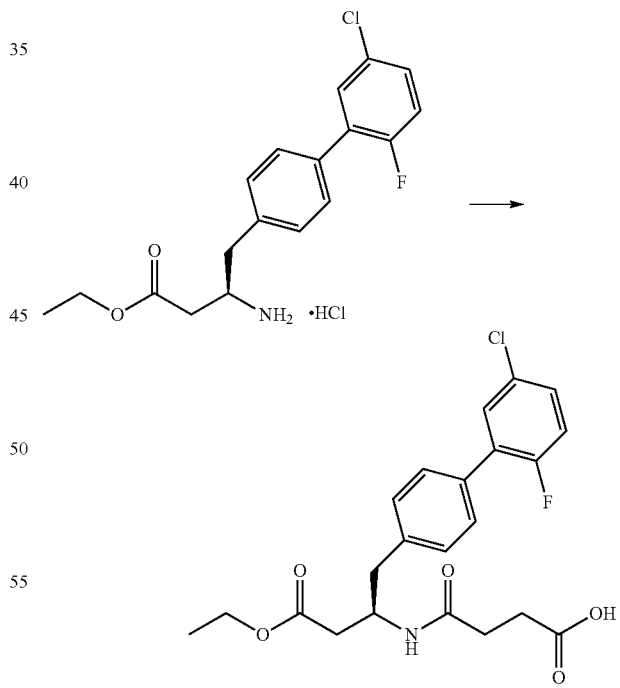

A solution of (R)-ethyl 3-amino-4-(5'-chloro-2'-fluorobiphenyl-4-yl)butanoate hydrochloride (Intermediate 8-5: 293 mg, 0.777 mmol), succinic anhydride (93 mg, 0.932 mmol) and DIPEA (0.204 mL, 1.165 mmol) in dichloromethane (4 mL) is allowed to stir for 1.5 hours. The reaction is quenched with 1 M aqueous HCl and extracted with dichloromethane. The organic layer is separated and concentrated under reduced pressure. The resulting residue is purified by preparative HPLC using a gradient of 20% MeCN/water (0.1% TFA) to 100% MeCN to give (R)-4-(1-(5'-chloro-2'-fluorobiphenyl-4-yl)-4-ethoxy-4-oxobutan-2-ylamino)-4-oxobutanoic acid (294 mg). HPLC retention time=1.03 minutes (condition B); MS (m+1)=436.2; 1H NMR (400 MHz, CHLOROFORM-d) δ ppm 1.28 (t, J=7.07 Hz, 3 H) 2.46-2.58 (m, 4 H) 2.64-2.68 (m, 2 H) 2.87 (A of ABX, $J_{ab}$=13.64 Hz, $J_{ax}$=7.83 Hz, 1 H) 2.99 (B of ABX, $J_{ab}$=13.64 Hz, $J_{bx}$=6.57 Hz, 1 H) 4.11-4.22 (m, 2 H) 4.47-4.56 (m, 1 H) 6.60 (br d, J=8.59 Hz, 1 H) 7.05-7.10 (m, 1 H) 7.23-7.27 (m, 3 H) 7.39-7.41 (m, 1 H) 7:44-7.46 (m, 2 H).

Following compounds are prepared using similar procedure as described in example 1-10:

| Example # | Product | Starting Material | Condition | HPLC-RT (condition) | MS (M + 1) |
|---|---|---|---|---|---|
| Example 1-11 | 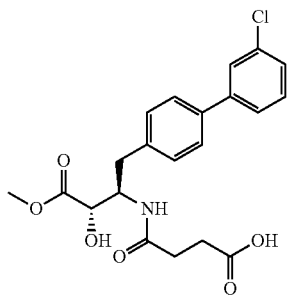<br>(2S,3R)-3-(3-Carboxy-propionylamino)-4-(3'-chloro-biphenyl-4-yl)-2-hydroxy-butyric acid methyl ester | 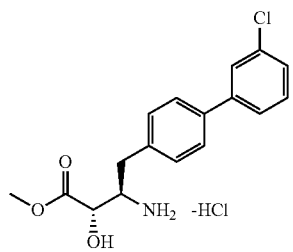 [SMILES: COC(=O)[C@@H](O)[C@H](N)Cc1ccc(-c2cccc(Cl)c2)cc1 ; "-HCl"] | 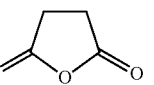<br>Et₃N, DCM | 1.29 min. (A) | 420.0 |
| | 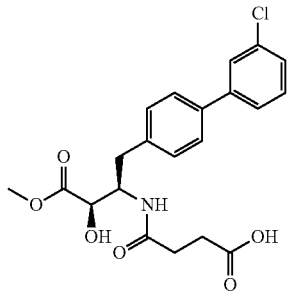<br>(2R,3R)-3-(3-Carboxy-propionylamino)-4-(3'-chloro-biphenyl-4-yl)-2-hydroxy-butyric acid methyl ester | 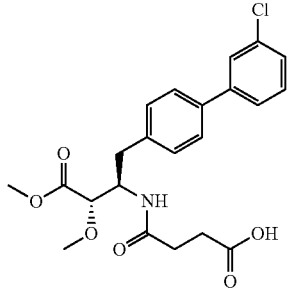<br>Intermediate 23-1 | | | |
| Example 1-12 | 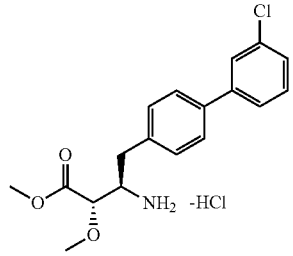<br>(2S,3R)-3-(3-Carboxy-propionylamino)-4-(3'-chloro-biphenyl-4-yl)-2-methoxy-butyric acid methyl ester | 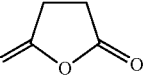 | DIPEA, DCM | 1.21 min. (A) | 434.2 |

-continued

| Example # | Product | Starting Material | Condition | HPLC-RT (condition) | MS (M + 1) |
|---|---|---|---|---|---|
| | (2R,3R)-3-(3-Carboxy-propionylamino)-4-(3'-chloro-biphenyl-4-yl)-2-methoxy-butyric acid methyl ester | Intermediate 24 | | | |
| Example 1-13 | (2S,3R)-3-(3-Carboxy-propionylamino)-4-(3'-chloro-biphenyl-4-yl)-2-fluoro-butyric acid methyl ester | | Et₃N, DCM | 0.83 min. (B) | 422.1 |
| | (2R,3R)-3-(3-Carboxy-propionylamino)-4-(3'-chloro-biphenyl-4-yl)-2-fluoro-butyric acid methyl ester | Intermediate 25 | | | |
| Example 1-14 | | | Et₃N, DCM | 0.98 min. (B) | 432 |

Example 2-1

Synthesis of (R)-3-(3-carboxy-propionylamino)-4-(4'-fluoro-biphenyl-4-yl)-butyric acid ethyl ester

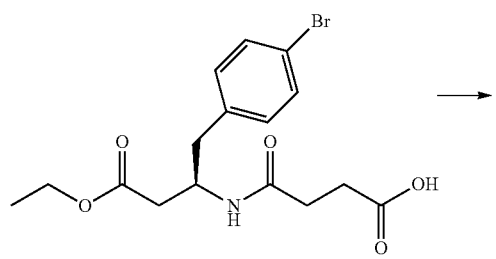

→

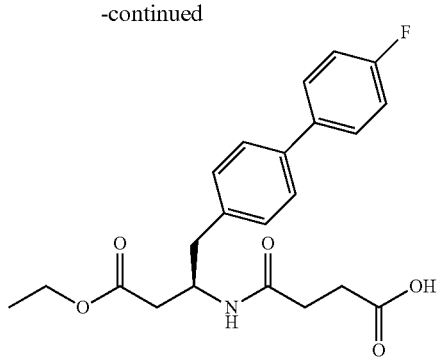

A mixture of (R)-4-(1-(4-bromophenyl)-4-ethoxy-4-oxobutan-2-ylamino)-4-oxobutanoic acid (Intermediate 3-1: 50 mg, 0.129 mmol), 4-fluorophenylboronic acid (27.2 mg, 0.194 mmol), Pd(Ph$_3$P)$_4$ (14.96 mg, 0.013 mmol) and aqueous Na$_2$CO$_3$ (0.129 mL, 0.259 mmol) in toluene (1 mL) is allowed to stir at 95° C. under nitrogen. After stirring for 13 hours, the solution is cooled to ambient temperature and then quenched with aqueous 1 M HCl. The products are extracted with ethyl acetate, washed with brine, dried over MgSO$_4$, filtered, and concentrated under reduced pressure. The obtained residue is purified by RP-HPLC (SunFire C18, H$_2$O (0.1% TFA)/CH$_3$CN), and then lyophilized to give (R)-3-(3-carboxy-propionylamino)-4-(4'-fluoro-biphenyl-4-yl)-butyric acid ethyl ester (29.2 mg). HPLC retention time=1.26 minutes (condition B); MS (m+1)=402.2; 1H NMR (400 MHz, CHLOROFORM-d) δ ppm 1.29 (t, J=7 Hz, 3 H) 2.47-2.67 (m, 6 H) 2.87 (A of ABX, Jab=13.7 Hz, Jax=7.9 Hz, 1 H) 2.99 (B of ABX, Jab=13.7 Hz, Jbx=6.6 Hz, 1 H) 4.12-4.23 (m, 2 H) 4.47-4.55 (m, 1 H) 6.52 (br d, J=8.6 Hz, 1 H) 7.08-7.14 (m, 2 H) 7.24 (d, J=8.4 Hz, 2 H) 7.46-7.55 (m, 4 H).

Following compounds are prepared using similar procedure as described in example 2-1:

| Example | Product | Reagent (condition) | HPLC MS (M + 1) |
|---|---|---|---|
| Example 2-2 | 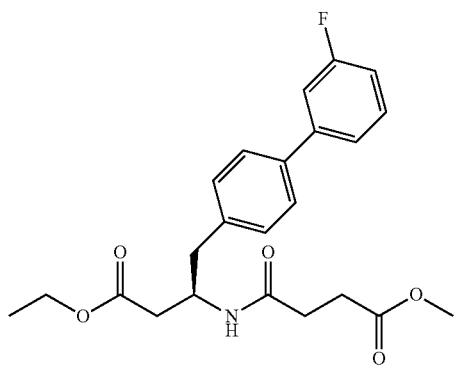 [SMILES: CCOC(=O)C[C@@H](Cc1ccc(-c2cccc(F)c2)cc1)NC(=O)CCC(=O)OC] | Pd(PPh$_3$)$_4$, m-fluorophenylboronic acid, aq. 2M Na$_2$CO$_3$, (R)-ethyl 4-(4-bromophenyl)-3-(4-methoxy-4-oxobutanamido)butanoate. | 1.24 min. (B)  416.1 |
| Example 2-3 | 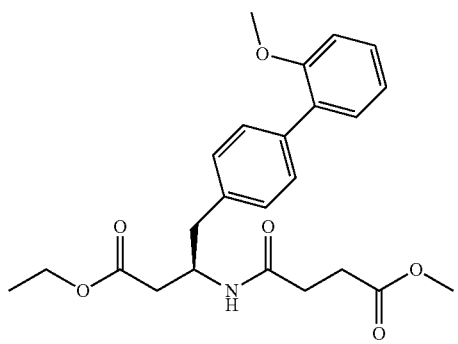 [SMILES: CCOC(=O)C[C@@H](Cc1ccc(-c2ccccc2OC)cc1)NC(=O)CCC(=O)OC] | Pd(PPh$_3$)$_4$, o-methoxyphenylboronic acid, aq. 2M Na$_2$CO$_3$, (R)-ethyl 4-(4-bromophenyl)-3-(4-methoxy-4-oxobutanamido)butanoate. | 1.22 min. (B)  428.2 |

-continued

| Example | Product | Reagent | HPLC-RT (condition) | MS (M + 1) |
|---|---|---|---|---|
| Example 2-4 | 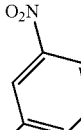 | Pd(PPh3)4, 3-nitrophenylboronic acid, aq. 2M Na2CO3, (R)-ethyl 4-(4-bromophenyl)-3-(4-methoxy-4-oxobutanamido)butanoate. | 1.16 min. (B) | 443.2 |
| Example 2-5 | 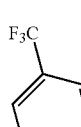 | Pd(PPh3)4, 3-(trifluoromethyl)phenyl boronic acid, aq. 2M Na2CO3, (R)-ethyl 4-(4-bromophenyl)-3-(4-methoxy-4-oxobutanamido)butanoate. | 1.39 min. (G) | 466.1 |
| Example 2-6 | 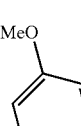 | Pd(PPh3)4, 3-methoxyphenylboronic acid, aq. 2M Na2CO3, (R)-ethyl 4-(4-bromophenyl)-3-(4-methoxy-4-oxobutanamido)butanoate. | 1.19 min. (G) | 428.2 |
| Example 2-7 | 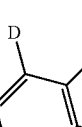 | PdCl2(dppf)·CH2Cl2 complex, phenyl-d5-boronic acid, aq. 2M Na2CO3, (R)-tert-butyl 4-(1-(4-bromophenyl)-4-ethoxy-4-oxobutan-2-ylamino)-4-oxobutanoate | 1.42 min. (B) | 445.2 |

Example 2-2

1H NMR (400 MHz, CHLOROFORM-d) δ ppm 1.29 (t, J=7 Hz, 3 H) 2.43-2.65 (m, 6 H) 2.84-3.02 (m, 2 H) 3.67 (s, 3 H) 4.12-4.23 (m, 2 H) 4.47-4.55 (m, 1 H) 6.30 (br d, J=8.6 Hz, 1 H) 7.00-7.05 (m, 1 H) 7.26-7.29 (m, 3 H) 7.34-7.41 (m, 2 H) 7.51 (d, J=8.3 Hz, 2 H).

Example 2-3

1H NMR (400 MHz, CHLOROFORM-d) δ ppm 1.28 (t, J=7 Hz, 3 H) 2.44-2.66 (m, 6 H) 2.84-3.01 (m, 2 H) 3.68 (s, 3 H) 3.81 (s, 3 H) 4.11-4.23 (m, 2 H) 4.48-4.56 (m, 1 H) 6.26 (br d, J=8.8 Hz, 1 H) 6.97-7.04 (m, 2 H) 7.22 (d, J=8.1 Hz, 2 H) 7.29-7.33 (m, 2 H) 7.46-7.48 (m, 2 H).

Example 2-4

1H NMR (400 MHz, CHLOROFORM-d) δ ppm 1.30 (t, J=7.1 Hz, 3 H) 2.41-2.65 (m, 6 H) 2.67-2.92 (m, 1 H) 3.00-3.05 (m, 1 H) 3.68 (s, 3 H) 4.14-4.22 (m, 2 H) 4.48-4.56 (m, 1 H) 6.33 (br d, J=8.6 Hz, 1 H) 7.32 (d, J=8.3 Hz, 2 H) 7.56-7.62 (m, 3 H) 7.89-7.91 (m, 1 H) 8.18-8.20 (m, 1 H) 8.44 (t, J=8.0 Hz, 1 H).

Example 2-5

1H NMR (400 MHz, CHLOROFORM-d) δ ppm 1.29 (t, J=7.2 Hz, 3 H) 2.44-2.65 (m, 6 H) 2.86-2.91 (m, 1 H) 2.98-3.03 (m, 1 H) 3.67 (s, 3 H) 4.13-4.22 (m, 2 H) 4.47-4.56 (m, 1 H) 6.33 (br d, J=8.8 Hz, 1 H) 7.29 (d, J=8.2 Hz, 2 H) 7.53 (d, J=8.2 Hz, 2 H) 7.56-7.60 (m, 2 H) 7.75 (d, J=7.6 Hz, 1 H) 7.81 (s, 1 H).

Example 2-6

1H NMR (400 MHz, CHLOROFORM-d) δ ppm 1.28 (t, J=7.2 Hz, 3 H) 2.43-2.65 (m, 6 H) 2.84-2.89 (m, 1 H) 2.96-3.01 (m, 1 H) 3.67 (s, 3 H) 3.86 (s, 3 H) 4.11-4.23 (m, 2 H) 4.47-4.55 (m, 1 H) 6.30 (br d, J=8.8 Hz, 1 H) 6.87-6.90 (m, 1 H) 7.10-7.11 (m, 1 H) 7.15-7.17 (m, 1 H) 7.24-7.26 (m, 2 H) 7.34 (t, J=7.8 Hz, 2 H) 7.51-7.53 (m, 2 H).

Example 2-7

1H NMR (400 MHz, CHLOROFORM-d) δ ppm 1.28 (t, J=7.2 Hz, 3 H) 1.43 (s, 9 H) 2.36-2.56 (m, 6 H) 2.84-3.01 (m, 4 H) 4.11-4.22 (m, 2 H) 4.47-4.56 (m, 1 H) 6.30-6.35 (m, 1 H) 7.25-7.27 (m, 2 H) 7.51-7.54 (m, 2 H).

Example 2-8

Synthesis of (R)-4-(4-ethoxy-1-(5'-fluoro-2'-methoxybiphenyl-4-yl)-4-oxobutan-2-ylamino)-4-oxobutanoic acid To a solution of (R)-tert-butyl 4-(1-(4-bromophenyl)-4-ethoxy-4-oxobutan-2-ylamino)-4-oxobutanoate, intermediate 13, (100 mg, 0.23 mmol) and 5-fluoro-2-methoxyphenylboronic acid (57.6 mg, 0.34 mmol) in toluene (1 mL) and EtOH (0.1 mL) is added Pd(PPh$_3$)$_4$ (26.1 mg, 0.023 mmol) and Na$_2$CO$_3$ (47.9 mg, 0.45 mmol). After stirring at 95° C. under nitrogen for 18 hours, the solution is cooled to ambient temperature and then quenched with aqueous 1 M HCl. The crude is diluted with ethyl acetate, the organic layer is washed with brine, dried over Na$_2$SO$_4$, filtered, and concentrated under reduced pressure % The obtained residue is purified by flash column chromatography on silica gel (eluent: heptane/EtOAc=100:0 to 30:70) to give (R)-tert-butyl 4-(4-ethoxy-1-(5'-fluoro-2'-methoxybiphenyl-4-yl)-4-oxobutan-2-ylamino)-4-oxobutanoate (65 mg). HPLC retention time=1.44 minutes (condition B); MS (m+1)=488.3; 1H NMR (400 MHz, CHLOROFORM-d) δ ppm 1.32 (t, J=7.1 Hz, 3 H) 1.48 (s, 9 H) 2.41-2.48 (m, 2 H) 2.51-2.63 (m, 4 H) 2.90 (dd, J=13.6, 6 Hz, 1 H) 3.02 (dd, J=13.6, 6 Hz, 1 H) 3.81 (s, 3 H) 4.14-4.29 (m, 2 H) 4.49-4.63 (m, 1 H) 6.44 (d, J=8.6 Hz, 1 H) 6.89-6.97 (m, 1 H) 6.98-7.05 (m, 1 H) 7.05-7.11 (m, 1 H) 7.27 (d, J=8.1 Hz, 2 H) 7.49 (d, J=8.1 Hz, 2 H).

A solution of (R)-tert-butyl 4-(4-ethoxy-1-(5'-fluoro-2'-methoxybiphenyl-4-yl)-4-oxobutan-2-ylamino)-4-oxobutanoate, (65 mg, 0.13 mmol) in 4M HCl in 1,4-dioxane (671 µL, 2.68 mmol) is stirred at room temperature. After stirring for 1 hour, the reaction mixture is concentrated under reduced pressure. The obtained residue is purified by RP-HPLC (SunFire C18, H$_2$O (0.1% TFA)/CH$_3$CN), and then lyophilized to give (R)-4-(4-ethoxy-1-(5'-fluoro-2'-methoxybiphenyl-4-yl)-4-oxobutan-2-ylamino)-4-oxobutanoic acid (23 mg).

HPLC retention time=1.66 minutes (condition D); MS (m+1) =432.3; 1H NMR (400 MHz, DMSO-$d_6$) δ ppm 1.17 (t, J=7.1 Hz, 3 H) 2.21-2.32 (m, 2 H) 2.32-2.40 (m, 2 H) 2.40-2.48 (m, 2 H) 2.77 (d, J=6.8 Hz, 2 H) 3.74 (s, 3 H) 4.03 (q, J=7.1 Hz, 2 H) 4.19-4.33 (m, 1 H) 7.04-7.20 (m, 3 H) 7.23 (d, J=8.1 Hz, 2 H) 7.43 (d, J=8.1 Hz, 2 H) 7.93 (d, J=8.3 Hz, 1 H)

Following compounds are prepared using similar procedure as described in example 2-8:

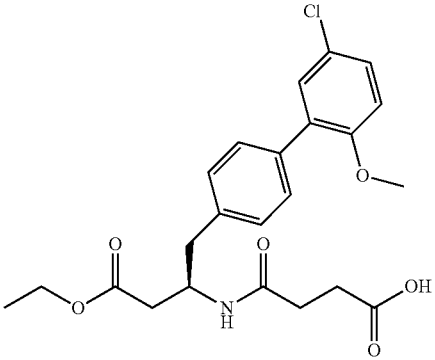

| Example | Product | Reagent | LCMS-RT (condition) | MS (M + 1) |
|---|---|---|---|---|
| Example 2-9 | (R)-4-(1-(5'-chloro-2'-methoxybiphenyl-4-yl)-4-ethoxy-4-oxobutan-2-ylamino)-4-oxobutanoic acid | Pd(PPh$_3$)$_4$, 5-chloro-2-methoxyphenylboronic acid, aq. 2M Na$_2$CO$_3$, (R)-tert-butyl 4-(1-(4-bromophenyl)-4-ethoxy-4-oxobutan-2-ylamino)-4-oxobutanoate. | 1.63 min. (D) | 448.2 |

Example 2-9

1H NMR (400 MHz, CD$_3$OD) δ ppm 1.23 (t, J=7.1 Hz, 3 H) 2.36-2.58 (m, 6 H) 2.85 (d, J=7.1 Hz, 2 H) 3.76 (s, 3 H) 4.10 (q, J=7.1 Hz, 2 H) 4.40-4.57 (m, 1 H) 7.01 (d, J=8.6 Hz, 1 H) 7.17-7.30 (m, 4 H) 7.39 (d, J=8.1 Hz, 2 H)

Example 3-1

Synthesis of (R)-6-(1-(biphenyl-4-yl)-4-ethoxy-4-oxobutan-2-ylcarbamoyl)pyrimidine-4-carboxylic acid

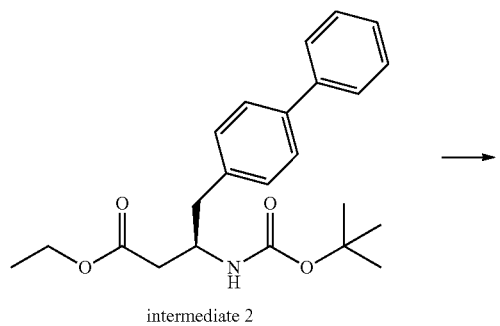

intermediate 2

→

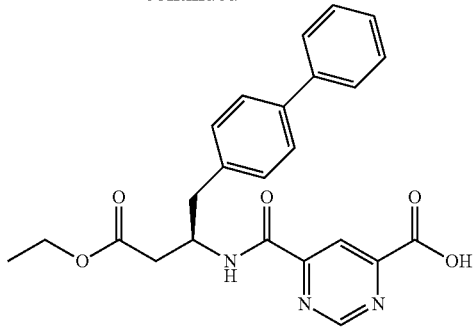

To (R)-ethyl-4-(biphenyl-4-yl)-3-(tert-butoxycarbonylamino)butanoate (300 mg, 0.782 mmol) is added a solution of 4M HCl in 1,4-dioxane (3.92 mL, 15.65 mmol) at room temperature. After stirring for 1 hour, the reaction mixture is concentrated under reduced pressure to give (R)-3-amino-4-biphenyl-4-yl-butyric acid ethyl ester hydrochloride.

Next, to a suspension of pyrimidine-4,6-dicarboxylic acid (325 mg, 1.935 mmol), (R)-3-amino-4-biphenyl-4-yl-butyric acid ethyl ester hydrochloride (250 mg, 0.774 mmol), WSC hydrochloride (148 mg, 0.774 mmol) and HOAt (105 mg, 0.774 mmol) in DMF (4 mL) and H$_2$O (1 mL) is added DIPEA (0.135 mL, 0.774 mmol). After stirring for 14 hours, the reaction is quenched with H2O, and the products are extracted with EtOAc, washed with brine, dried over Na$_2$SO$_4$, filtered, and concentrated under reduced pressure.

The obtained residue is purified by RP-HPLC (SunFire C18, H$_2$O (0.1% TFA)/CH$_3$CN), and then lyophilized to give (R)-6-(1-(biphenyl-4-yl)-4-ethoxy-4-oxobutan-2-ylcarbamoyl)pyrimidine-4-carboxylic acid (84.8 mg). HPLC retention time=1.32 minutes (condition B); MS (m+1)=434.1; 1H NMR (400 MHz, DMSO-d6) δ ppm 1.12 (t, J=7.0 Hz, 3 H) 2.65 (A of ABX, Jab=15.4 Hz, Jax=5.8 Hz, 1 H) 2.73 (B of ABX, Jab=15.4 Hz, Jbx=7.9 Hz) 2.91 (A of ABX, Jab=13.6 Hz, Jax=6.1 Hz, 1 H) 3.01 (B of ABX, Jab=13.6 Hz, Jbx=8.2 Hz, 1 H) 4.01 (q, J=7.0 Hz, 2 H) 4.59-4.68 (m, 1 H) 7.29-7.35 (m, 3 H) 7.41-7.45 (m, 2 H) 7.55-7.63 (m, 4 H) 8.32 (d, J=1.35 Hz, 1 H) 9.19 (d. J=9.1 Hz, 1 H) 9.50 (d, J=1.35 Hz, 1 H) 14.11 (br s, 1 H).

Following compounds are prepared using similar procedure as described in example 3-1:

| Example # | Product | Reagent | HPLC-RT (condition) | MS (M + 1) |
|---|---|---|---|---|
| Example 3-2 | (R)-4-biphenyl-4-yl-3-[(2-hydroxy-pyrimidine-5-carbonyl)-amino]-butyric acid ethyl ester | | 1.56 min. (A) | 406.2 |

Example 3-2

1H NMR (400 MHz, DMSO-d6) δ ppm 1.14 (t, J=7.1 Hz, 3 H) 2.57 (d, J=7.1 Hz, 2 H) 2.83-2.92 (m, 2 H) 4.03 (q, J=7.1 Hz, 2 H) 4.43-4.52 (m, 1 H) 7.29-7.36 (m, 3 H) 7.42-7.46 (m, 2 H) 7.58-7.65 (m, 4 H) 8.30 (d, J=8.4 Hz, 1 H) 8.64 (br s, 1 H).

Example 3-3

Synthesis of (R)-benzyl 3-(4-butoxy-4-oxobutanamido)-4-(3'-chlorobiphenyl-4-yl)butanoate

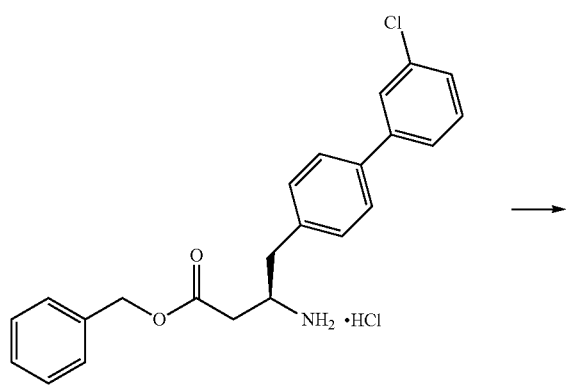

→

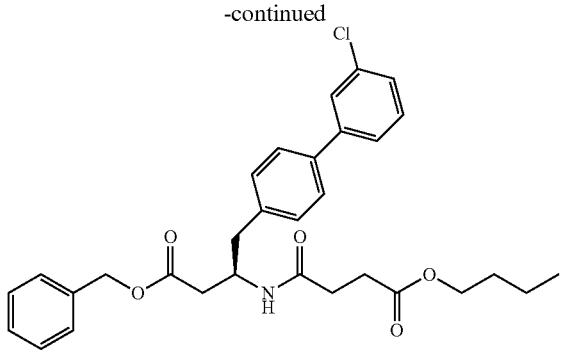

A mixture of (R)-benzyl 3-amino-4-(3'-chlorobiphenyl-4-yl)butanoate hydrochloride (Intermediate 8-4: 150 mg, 0.360 mmol), 4-butoxy-4-oxobutanoic acid (107 mg, 0.540 mmol, 88% purity), EDCl (104 mg, 0.540 mmol), DIPEA (0.094 ml, 0.540 mmol) and HOAt (73.6 mg, 0.540 mmol) in DMF (2 ml) is allowed to stir at room temperature for 1 hour. The reaction mixture is diluted with water, and then the precipitated solid is collected on a funnel, washed with H2O, and dried under reduced pressure to give crude. The obtained residue is purified by silica gel flash column chromatography (heptane/EtOAc=100:0 to 0:100) to give (R)-benzyl 3-(4-butoxy-4-oxobutanamido)-4-(3'-chlorobiphenyl-4-yl)butanoate (178.9 mg); HPLC retention time=1.47 minutes (condition B); MS (m+1)=536.42; 1H NMR (400 MHz, CHLOROFORM-d) δ ppm 0.90-0.94 (m, 3 H) 1.31-1.40 (m, 2 H) 1.56-1.63 (m, 2 H) 2.39-2.42 (m, 2 H) 2.48-2.62 (m, 4 H) 2.84 (A of ABX, $J_{ab}$=13.6 Hz, $J_{ax}$=8.1 Hz, 1 H) 2.97 (B of ABX, $J_{ab}$=13.6 Hz, $J_{bx}$=6.6 Hz, 1 H) 4.07 (t, J=6.7 Hz, 2 H)

4.48-4.56 (m, 1 H) 5.12 (A of AB, J=12.1 Hz, 1 H) 5.18 (B of AB, J=12.1 Hz, 1 H) 6.27 (br d, J=7.7 Hz, 1 H) 7.20 (d, J=8.3 Hz, 1 H) 7.29-7.39 (m, 7 H) 7.42-7.47 (m, 3 H) 7.54-7.55 (m, 1 H).

Following compounds are prepared using similar procedure as described in example 3-3:

| Example # | Product | Starting Material |
|---|---|---|
| Example 3-4 | 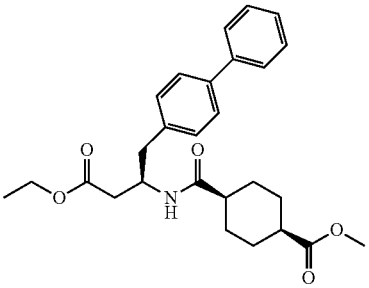<br>(1S,4s)-methyl 4-((R)-1-(biphenyl-4-yl)-4-ethoxy-4-oxobutan-2-ylcarbamoyl)cyclohexanecarboxylate | 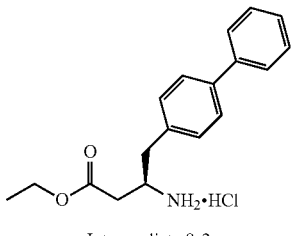<br>Intermediate 8-2 |
| Example 3-5 | 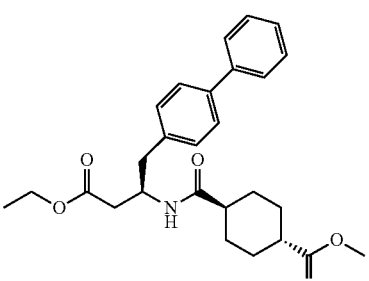<br>(1R,4r)-methyl 4-((R)-1-(biphenyl-4-yl)-4-ethoxy-4-oxobutan-2-ylcarbamoyl)cyclohexanecarboxylate | 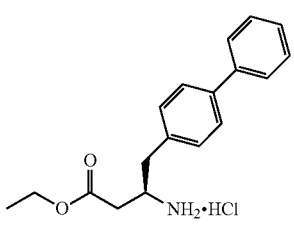<br>Intermediate 8-2 |
| Example 3-6 | 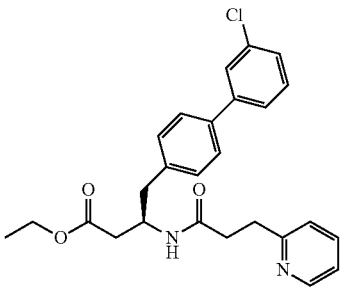<br>(R)-ethyl 4-(3'-chlorobiphenyl-4-yl)-3-(3-(pyridin-2-yl)propanamido)butanoate | 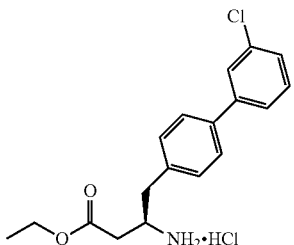<br>Intermediate 8-1 |

-continued
Example 3-7
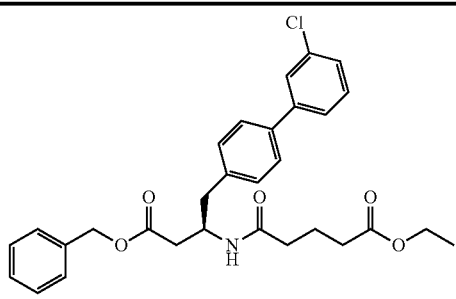
(R)-ethyl 5-(4-(benzyloxy)-1-(3′-chlorobiphenyl-4-yl)-4-oxobutan-2-ylamino)-5-oxopentanoate
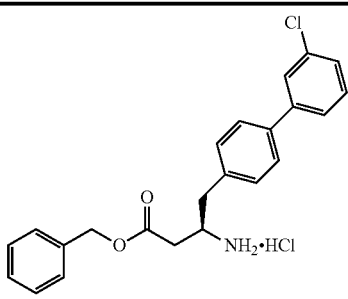
Intermediate 8-1
Example 3-8
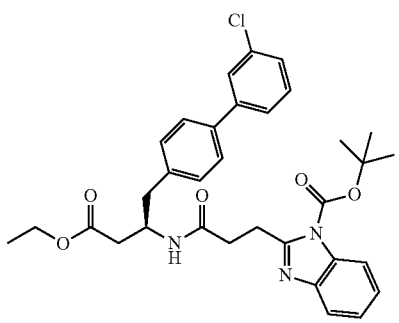
(R)-tert-butyl 2-(3-(1-(3′-chlorobiphenyl-4-yl)-4-ethoxy-4-oxobutan-2-ylamino)-3-oxopropyl)-1H-benzo[d]imidazole-1-carboxylate
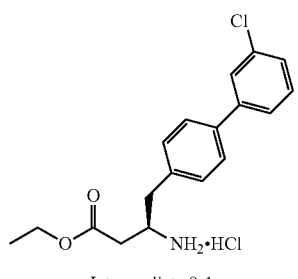
Intermediate 8-1
| Example # | Condition | HPLC-RT (condition) | MS (M + 1) |
|---|---|---|---|
| Example 3-4 | 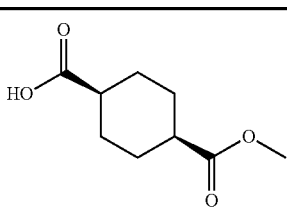 EDCl, HOAt, DIPEA, DMF, RT | 1.42 min. (B) | 452.2 |
| Example 3-5 | 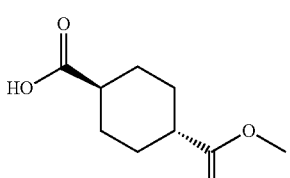 | 1.42 min. (B) | 452.3 |

Example 3-4

1H NMR (400 MHz, CHLOROFORM-d) δ ppm 1.29 (t, J=7.1 Hz, 3 H) 1.53-2.20 (m, 9 H) 2.46-2.57 (m, 3 H) 2.86 (A of ABX, $J_{ab}$=13.6 Hz, $J_{ax}$=7.8 Hz, 1 H) 2.98 (B of ABX, $J_{ab}$=13.6 Hz, $J_{bx}$=6.6 Hz, 1 H) 3.65 (s, 3 H) 4.11-4.23 (m, 2 H) 4.47-4.55 (m, 1 H) 6.23 (br d, J=8.6 Hz, 1 H) 7.24-7.26 (m, 2 H) 7.31-7.35 (m, 1 H) 7.41-7.45 (m, 2 H) 7.51-7.59 (m, 4 H).

Example 3-5

1H NMR (400 MHz, CHLOROFORM-d) δ ppm 1.29 (t, J=7.2 Hz, 3 H) 1.36-1.51 (m, 4 H) 1.84-1.94 (m, 2 H) 1.98-2.06 (m, 3 H) 2.24-2.32 (m, 1H) 2.50 (A of ABX, $J_{ab}$=16.2 Hz, $J_{ax}$=5.3 Hz, 1 H) 2.53 (B of ABX, $J_{ab}$=16.2 Hz, $J_{bx}$=5.1 Hz, 1 H) 2.86 (A of ABX, $J_{ab}$=13.6 Hz, $J_{ax}$=7.8 Hz, 1 H) 2.98 (B of ABX, $J_{ab}$=13.6 Hz, $J_{bx}$=6.6 Hz, 1 H) 3.66 (s, 3 H) 4.11-4.23 (m, 2 H) 4.46-4.55 (m, 1 H) 6.19 (br d, J=8.8 Hz, 1 H) 7.24-7.26 (m, 2 H) 7.31-7.36 (m, 1 H) 7.41-7.45 (m, 2 H) 7.51-7.58 (m, 4 H).

Example 3-6

1H NMR (400 MHz, CHLOROFORM-d) δ ppm 1.26 (t, J=7.2 Hz, 3 H) 2.41-2.51 (m, 4 H) 2.62-2.66 (m, 2 H) 2.84 (A of ABX, $J_{ab}$=13.6 Hz, $J_{ax}$=7.6 Hz, 1 H) 2.92 (B of ABX, $J_{ab}$=13.6 Hz, $J_{bx}$=6.6 Hz, 1 H) 3.06-3.10 (m, 2 H) 4.08-4.19 (m, 2 H) 4.46-4.55 (m, 1 H) 6.78 (d, J=8.9 Hz, 1 H) 7.10-7.12 (m, 1 H) 7.16 (d, J=7.8 Hz, 1 H) 7.20-7.22 (m, 2 H) 7.29-7.31 (m, 1 H) 7.35 (t, J=7.7 Hz, 1 H) 7.42-7.47 (m, 3 H) 7.54-7.59 (m, 2 H) 8.48 (d, J=1.0 Hz, 1 H).

Example 3-7

1H NMR (400 MHz, CHLOROFORM-d) δ ppm 1.23 (t, J=7.2 Hz, 3 H) 1.86-1.92 (m, 2 H) 2.14-2.18 (m, 2 H) 2.24-2.28 (m, 2 H) 2.50-2.63 (m, 2 H) 2.82-2.99 (m, 2 H) 4.11 (q, J=7.2 Hz, 2 H) 4.53-4.54 (m, 1 H) 5.12 (A of AB, J=12.1 Hz, 1 H) 5.18 (B of AB, J=12.1 Hz, 1 H) 6.12-6.14 (m, 1 H) 7.19-7.54 (m, 13 H).

Example 3-8

1H NMR (400 MHz, CHLOROFORM-d) δ ppm 1.26 (t, J=7.2 Hz, 3 H) 1.67 (s, 9 H) 2.46-2.57 (m, 2 H) 2.74-2.96 (m, 4 H) 3.41-3.45 (m, 2 H) 4.09-4.17 (m, 2 H) 4.50-4.59 (m, 1 H) 6.95 (br d, J=8.6 Hz, 1 H) 7.18 (d, J=8.1 Hz, 2 H) 7.27-7.42 (m, 7 H) 7.51 (t, J=1.8 Hz, 1 H) 7.61-7.65 (m, 1 H) 7.86-7.93 (m, 1 H).

Example 3-9

Synthesis of (R)-ethyl 4-(3'-aminobiphenyl-4-yl)-3-(4-methoxy-4-oxobutanamido)butanoate A suspension of (R)-ethyl 3-(4-methoxy-4-oxobutanamido)-4-(3'-nitrobiphenyl-4-yl)butanoate (Example 2-4: 123 mg, 0.278 mmol) and Pd/C (59.2 mg, 0.028 mmol) in EtOH (2 ml) is allowed to stir under hydrogen at room temperature for 5.5 hours. The reaction mixture is filtered, and the solution is concentrated to give (R)-ethyl 4-(3'-aminobiphenyl-4-yl)-3-(4-methoxy-4-oxobutanamido)butanoate (105 mg); HPLC retention time=0.84 minutes (condition B); MS (m+1)=413.1; 1H NMR (400 MHz, CHLOROFORM-d) δ ppm 1.28 (t, J=7.2 Hz, 3 H) 2.41-2.65 (m, 6 H) 2.85-3.00 (m, 2 H) 3.67 (s, 3 H) 4.11-4.22 (m, 2 H) 4.46-4.54 (m, 1 H) 6.31 (br d, J=8.8 Hz, 1 H) 6.71-6.74 (m, 1 H) 6.95-7.02 (m, 2 H) 7.21-7.25 (m, 3 H) 7.48-7.50 (m, 2 H).

Following compounds are prepared using similar procedure as described in example 3-9:

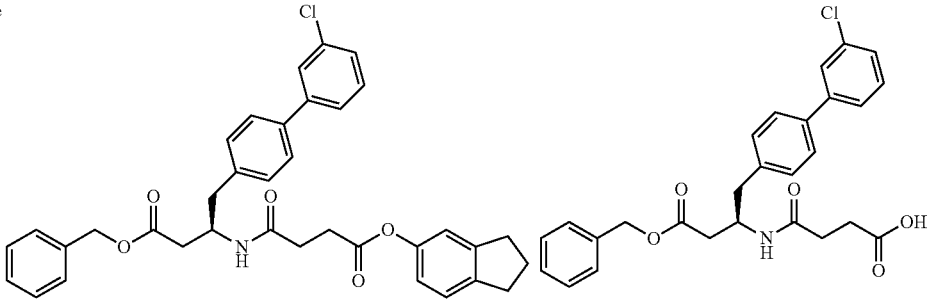

| Example # | Product | Condition | HPLC-RT (condition) | MS (M + 1) |
|---|---|---|---|---|
| Example 3-10 | (R)-benzyl 4-(3'-chlorobiphenyl-4-yl)-3-(4-(2,3-dihydro-1H-inden-5-yloxy)-4-oxobutanamido)butanoate | Example 1-3, PyBOP, indanol, DCM, RT | 1.73 min. (B) | 596.5 |

Example 3-10

1H NMR (400 MHz, CHLOROFORM-d) δ ppm 2.03-2.11 (m, 2H) 2.48-2.62 (m, 4 H) 2.81-2.90 (m, 7 H) 2.95-3.00 (m, 1 H) 4.49-4.58 (m, 1 H) 5.07-5.18 (m, 2 H) 6.23 (br d, J=8.6 Hz, 1 H) 6.79-6.82 (m, 1 H) 6.92 (s, 1 H) 7.15-7.20 (m, 3 H) 7.29-7.45 (m, 10 H) 7.52-7.53 (m, 1 H)

Example 3-11

Synthesis of (S)-benzyl 1-(2-((R)-1-(biphenyl-4-yl)-4-ethoxy-4-oxobutan-2-ylamino)-2-oxoethyl)pyrrolidine-2-carboxylate trifluoroacetic acid salt

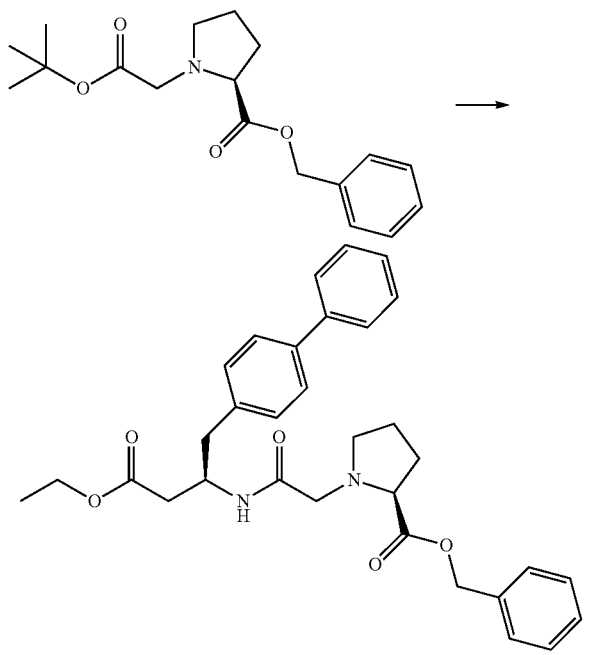

To a solution of (S)-benzyl 1-(2-tert-butoxy-2-oxoethyl)pyrrolidine-2-carboxylate (Intermediate 10: 200 mg, 0.626 mmol) and triethylsilane (0.250 ml, 1.565 mmol) in DCM (3 ml), TFA (0.965 ml, 12.52 mmol) is added at room temperature. After stirring for 24 hours, the reaction is concentrated to give crude.

To a suspension of the crude, (R)-ethyl 3-amino-4-(biphenyl-4-yl)butanoate hydrochloride (266 mg, 0.832 mmol), WSC.HCl (0.180 g, 0.939 mmol) and HOAt (128 mg, 0.939 mmol) in DMF (4 ml), DIPEA (0.328 ml, 1.878 mmol) is added. After stirring for 4 hours, the reaction is diluted with H$_2$O and EtOAc. The products are extracted with EtOAc, washed with brine, dried over Na$_2$SO$_4$, filtered, and concentrated. The crude is subjected twice to column chromatography (heptane/EtOAc=100:0 to 0:100). Then, the obtained product is purified by preparative HPLC using a gradient of 20% MeCN/water (0.1% TFA) to 100% MeCN to give (S)-benzyl 1-(2-((R)-1-(biphenyl-4-yl)-4-ethoxy-4-oxobutan-2-ylamino)-2-oxoethyl)pyrrolidine-2-carboxylate trifluoroacetic acid salt (28.5 mg) as a pale yellow solid; HPLC retention time=1.84 minutes (condition D); MS (m+1)=529.3; 1H NMR (400 MHz, CHLOROFORM-d) δ ppm 1.25-1.28 (m, 3 H) 1.74-1.85 (m, 2 H) 1.91-1.98 (m, 1 H) 2.09-2.19 (m, 1 H) 2.35-2.41 (m, 1 H) 2.46 (A of ABX, Jab=15.7 Hz, Jax=6.6 Hz, 1 H) 2.59 (B of ABX, J$_{ab}$=13.7 Hz, J$_{bx}$=5.7 Hz, 1 H) 2.78-2.83 (m, 1 H) 2.86 (A of ABX, J$_{ab}$=13.8 Hz, J$_{ab}$=8.1 Hz, 1 H) 2.99 (B of ABX, J$_{ab}$=13.7 Hz, J$_{bx}$=6.4 Hz, 1 H) 3.08 (A of AB, J=16.5 Hz, 1 H) 3.35 (B of AB, J=16.5 Hz, 1 H) 3.41 (dd, J=9.1 and 5.1 Hz, 1 H) 4.11-4.20 (m, 2 H) 4.46-4.55 (m, 1 H) 5.10 (A of AB, J=12.4 Hz, 1 H) 5.13 (B of AB, J=12.4 Hz, 1 H) 7.26-7.27 (m, 2 H) 7.31-7.38 (m, 6 H) 7.40-7.44 (m, 2 H) 7.49-7.56 (m, 4 H) 7.74 (br d, J=8.6 Hz, 1 H).

Example 3-12

Synthesis of (R)-3-(4-butoxy-4-oxobutanamido)-4-(3'-chlorobiphenyl-4-yl)butanoic acid

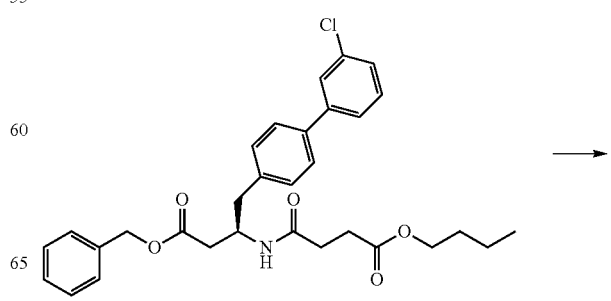

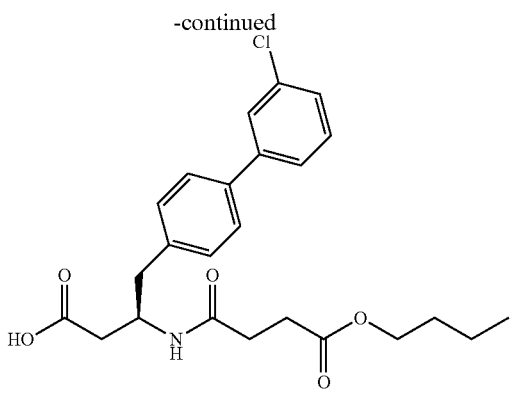

A suspension of (R)-benzyl 3-(4-butoxy-4-oxobutanamido)-4-(3'-chlorobiphenyl-4-yl)butanoate (Example 3-3: 178.9 mg, 0.334 mmol) and Pd/C (71.0 mg, 0.033 mmol) in EtOAc (3 ml) is allowed to stir under hydrogen at room temperature for 1.5 hours. The reaction mixture is filtered, and concentrated to give crude. The resulting residue is purified by preparative HPLC using a gradient of 20% MeCN/water (0.1% TFA) to 100% MeCN to give (R)-3-(4-butoxy-4-oxobutanamido)-4-(3'-chlorobiphenyl-4-yl)butanoic acid (90.7 mg) as a white solid; HPLC retention time=1.27 minutes (condition B); MS (m+1)=446.24; 1H NMR (400 MHz, CHLOROFORM-d) δ ppm 0.91 (t, J=7.5 Hz, 3 H) 1.31-1.40 (m, 2 H) 1.55-1.62 (m, 2 H) 2.43-2.47 (m, 2 H) 2.52-2.69 (m, 4 H) 2.93 (A of ABX, $J_{ab}$=13.7 Hz, $J_{ax}$=7.7 Hz, 1 H) 3.00 (B of ABX, $J_{ab}$=13.7 Hz, $J_{bx}$=6.8 Hz, 1 H) 4.07 (t, J=6.7 Hz, 2 H) 4.49-4.57 (m, 1 H) 6.31 (br d, J=8.6 Hz, 1 H) 7.26-7.37 (m, 4 H) 7.43-7.46 (m, 1 H) 7.49-7.52 (m, 2 H) 7.55 (br t, J=1.8 Hz, 1 H).

Chiral HPLC retention time=4.33 min. Column: Daicel CHIRALPAK IA (4.6×100 mm); flow rate=1 ml/min.; eluent: EtOH (containing 0.1% TFA)/heptane=10/90 to 70/30 in 10 min. (linear gradient).

Following compounds are prepared using similar procedure as described in example 3-11:

| Example # | Product | Condition | HPLC-RT (condition) | MS (M + 1) |
|---|---|---|---|---|
| Example 3-13 | (R)-4-(3'-chlorobiphenyl-4-yl)-3-(5-ethoxy-5-oxopentanamido)butanoic acid | Pd/C, H₂, EtOAc, RT Example 3-7 | 1.08 min. (B) | 432.4 |
| Example 3-14 | (R)-4-(3'-chlorobiphenyl-4-yl)-3-(4-(2,3-dihydro-1H-inden-5-yloxy)-4-oxobutanamido)butanoic acid | Pd/C, H₂, EtOAc, acetone, RT Example 3-10 | 1.36 min. (B) | 506.4 |

Example 3-13

1H NMR (400 MHz, CHLOROFORM-d) δ ppm 1.23 (t, J=7.1 Hz, 3 H) 1.86-1.93 (m, 2 H) 2.57 (A of ABX, $J_{ab}$=16.3 Hz, $J_{ax}$=5.7 Hz, 1 H) 2.64 (B of ABX, $J_{ab}$=16.3 Hz, $J_{bx}$=5.2 Hz, 1 H) 2.94 (A of ABX, $J_{ab}$=13.7 Hz, $J_{ax}$=7.6 Hz, 1 H) 2.99 (B of ABX, $J_{ab}$=13.7 Hz, $J_{bx}$=7.2 Hz, 1 H) 4.10 (q, J=7.1 Hz, 2 H) 4.51-4.60 (m, 1 H) 6.17 (br d, J=8.6 Hz, 1 H) 7.26-7.37 (m, 4 H) 7.43-7.45 (m, 1 H) 7.49-7.52 (m, 2 H) 7.55 (br t, J=1.8 Hz, 1 H).

Example 3-14

1H NMR (400 MHz, CHLOROFORM-d) δ ppm 2.07 (quint, J=7.4 Hz, 2 H) 2.51-2.63 (m, 4 H) 2.82-3.02 (m, 8 H) 4.50-4.59 (m, 1 H) 6.28 (d, J=8.6 Hz, 1 H) 6.78-6.81 (m, 1 H) 6.91 (d, J=1.8 Hz, 1 H) 7.26-7.36 (m, 6 H) 7.41-7.44 (m, 1 H) 7.47-7.50 (m, 2 H) 7.53-7.54 (m, 1 H).

Example 3-15

Synthesis of (R)-ethyl 4-(3'-chlorobiphenyl-4-yl)-3-(5-oxo-4,5-dihydro-1,3,4-oxadiazole-2-carboxamido)butanoate

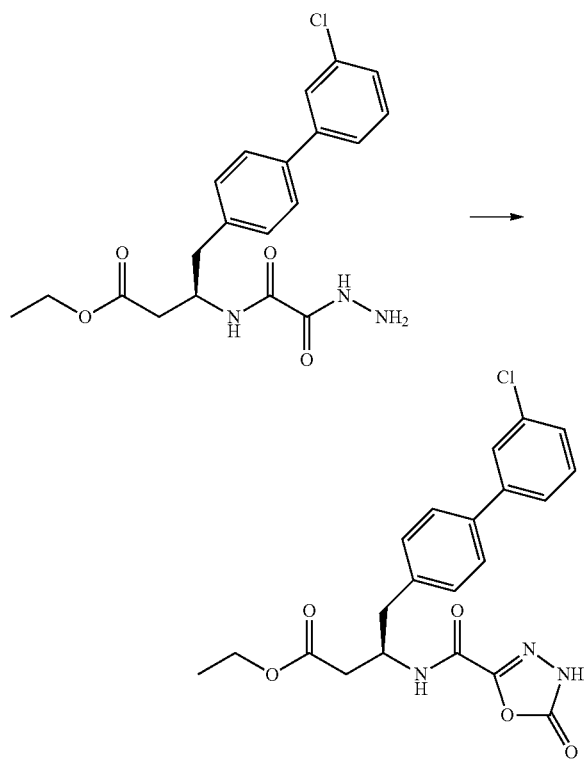

To a solution of (R)-ethyl 4-(3'-chlorobiphenyl-4-yl)-3-(2-hydrazinyl-2-oxoacetamido)butanoate, (intermediate 15: 289 mg, 0.72 mmol) in THF (8.5 mL) is added CDI (139 mg, 0.86 mmol) at room temperature. After stirring for 18 hour at room temperature, the reaction is quenched with H₂O and 1M HCl, and the crude is diluted with EtOAc. The organic layer is washed with brine, dried over Na₂SO₄, filtered, and concentrated under reduced pressure. The obtained residue is purified by RP-HPLC (SunFire C18, H₂O (0.1% TFA)/CH₃CN) and then lyophilized to give (R)-ethyl 4-(3'-chlorobiphenyl-4-yl)-3-(5-oxo-4,5-dihydro-1,3,4-oxadiazole-2-carboxamido)butanoate (100 mg). HPLC retention time=1.67 minutes (condition A); MS (m+1)=430.2; 1H NMR (400 MHz, DMSO-d₆) δ ppm 1.14 (t, J=7.1 Hz, 3 H) 2.52-2.70 (m, 2 H) 2.84 (dd, J=13.7, 8.4 Hz, 1 H) 2.90 (dd, J=13.7, 8.4 Hz, 1 H) 4.02 (q, J=7.1 Hz, 2 H) 4.42-4.58 (m, 1 H) 7.30 (d, J=8.1 Hz, 2 H) 7.37-7.43 (m, 1 H) 7.47 (t, J=7.8 Hz, 1 H) 7.57-7.66 (m, 3 H) 7.70 (t, J=1.9 Hz, 1 H) 8.98 (d, J=8.8 Hz, 1 H) 12.94 (s, 1 H).

Example 3-16

Synthesis of (R)-3-(3-Carboxymethyl-ureido)-4-(3'-chloro-biphenyl-4-yl)-butyric acid ethyl ester

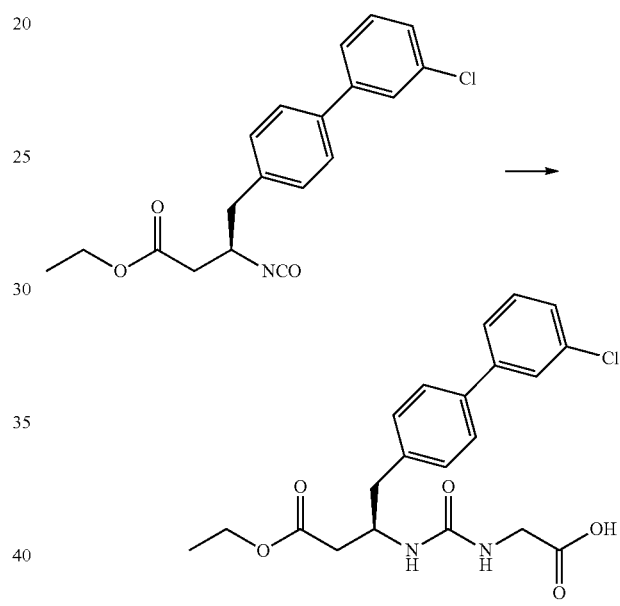

To a solution of t-butyl 2-aminoacetate (19.08 mg, 0.145 mmol) and DIEA (18.8 mg, 0.145 mmol) in DMF (1 mL) is added Intermediate 21 (50 mg, 0.145 mmol) and the mixture is stirred at room temperature for 2 hours. The solvent is removed under reduced pressure to give (R)-3-(3-tert-butoxycarbonylmethyl-ureido)-4-(3'-chloro-biphenyl-4-yl)-butyric acid ethyl ester.

Next, to a solution of the above diester (70 mg, 0.147 mmol) in methylene chloride (2 mL) is added TFA (4 mL) and the mixture is stirred at room temperature for 18 hours. The solvents are removed under reduced pressure and the residue is purified by preparative HPLC using a gradient of 35% MeCN/water to 100% MeCN (+0.1% TFA). Lyophilization of the proper fractions gives the title compound; HPLC Retention time 1.42 minutes (condition C); MS 419.1 (M+1); 1H NMR (400 MHz, DMSO-d6): δ ppm 1.17 (t, J=7.07 Hz, 3H), 2.41 (d, J=7.07 Hz, 2H), 2.77-2.79 (m, 2H), 3.66-3.68 (m, 2H), 4.04 (q, J=7.07 Hz, 2H), 4.08-4.15 (m, 1H), 6.13 (t, J=5.81 Hz, 1H), 6.24 (d, J=8.59 Hz, 1H), 7.28-7.30 (m, 2H), 7.39-7.42 (m, 1H), 7.48 (t, J=7.83 Hz, 1H), 7.62-7.64 (m, 3H), 7.71 (t, J=1.77 Hz, 1H), 12.42 (s, 1H).

Example 4-1

Synthesis of (R)-4-biphenyl-4-yl-3-(2-1H-tetrazol-5-yl-acetylamino)-butyric acid ethyl ester

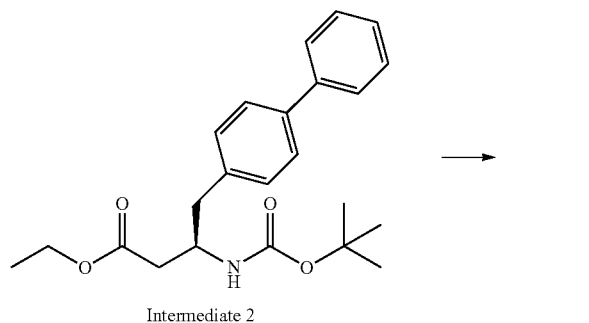

To a solution of (R)-4-biphenyl-4-yl-3-tert-butoxycarbonylamino-butyric acid ethyl ester (100 mg, 0.261 mmol) in DCM (3 mL) at room temperature is added TFA (1 mL, 12.98 mmol) and the mixture is stirred at room temperature for 0.5 hour. The mixture is concentrated under reduced pressure to give (R)-3-amino-4-biphenyl-4-yl-butyric acid ethyl ester trifluoroacetic salt. HPLC retention time=1.50 minutes (condition C); MS (m+1)=384.

Next, to a suspension of (R)-3-amino-4-biphenyl-4-yl-butyric acid ethyl ester trifluoroacetic salt (0.074 g, 0.261 mmol) in DCM (10 mL) at room temperature is added 1H-tetrazole-5-acetic acid (0.050 µg, 0.392 mmol). To the mixture at ice bath temperature is added bis(2-oxo-3-oxazolidinyl)phosphinic chloride (0.100 g, 0.392 mmol) and quickly followed by DIPEA (0.137 ml, 0.783 mmol). The reaction mixture is slowly warmed up to room temperature and stirred overnight. The reaction is extracted with DCM. The combined organic layer is washed with saturated NaHCO₃, saturated NH₄Cl, brine and dried over anhydrous sodium sulfate, filtered and concentrated under reduced pressure to give (R)-4-biphenyl-4-yl-3-(2-1-tetrazol-5-yl-acetylamino)-butyric acid ethyl ester. HPLC retention time=1.04 minutes (condition E); MS (m+1)=394.

Example 4-2

Synthesis of (R)-ethyl 4-(biphenyl-4-yl)-3-(6-(methylsulfonamido)nicotinamido)butanoate

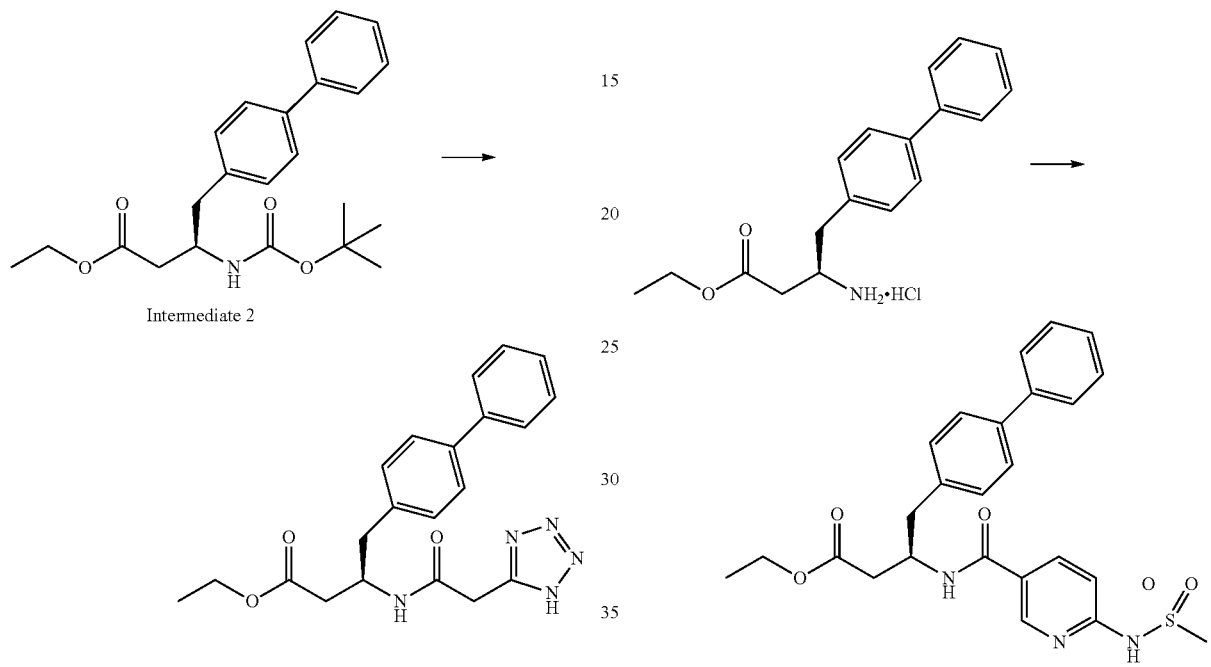

To a solution of (R)-ethyl 3-amino-4-(3'-chlorobiphenyl-4-yl)butanoate hydrochloride (Intermediate 8-1: 103 mg, 0.32 mmol) and 6-(methylsulfonamido)nicotinic acid, intermediate 16, (84 mg, 0.39 mmol) in CH₂Cl₂ (2 mL) and DMF (2 mL) is added TEA (0.18 mL, 1.29 mmol) and HATU (159 mg, 0.42 mmol) at room temperature. The crude is stirred at room temperature for 2 hrs. The crude is quenched with saturated NaHCO₃, diluted in EtOAc.

The organic layer is washed with six times with water, brine, dried over MgSO₄, filtered, and concentrated. The crude is purified via RP-HPLC (SunFire C18, H₂O (0.1% TFA)/CH₃CN) to give (R)-ethyl 4-(biphenyl-4-yl)-3-(6-(methylsulfonamido)nicotinamido)butanoate as a white solid (4.1 mg). HPLC retention time=1.61 minutes (condition A); MS (m+1)=482.3. 1H NMR (400 MHz, CHLOROFORM-d) δ ppm 1.22 (t, J=7.2 Hz, 3 H), 2.56 (t, J=4.8 Hz, 2 H), 2.84-2.92 (m, 1 H), 3.05 (dd, J=13.6, 6.1 Hz, 1 H), 3.16 (s, 3 H), 4.08-4.18 (m, 2 H), 4.57-4.71 (m, 1 H), 7.03 (d, J=8.3 Hz, 1 H), 7.10 (d, J=8.3 Hz, 1 H), 7.22 (d, J=8.3 Hz, 2 H), 7.26-7.31 (m, 1 H), 7.33-7.40 (m, 2 H), 7.44-7.54 (m, 5 H), 7.98 (dd, J=8.8, 2.3 Hz, 1 H), 8.52 (s, 1 H).

Following compounds are prepared using similar procedure as described in example 4-2:

| Example # | Product | Reagent | LCMS-RT (condition) | MS (M + 1) |
|---|---|---|---|---|
| Example 4-3 | 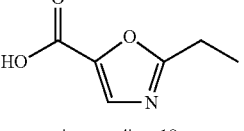<br>(R)-ethyl 4-(3'-chlorobiphenyl-4-yl)-3-(2-ethyloxazole-5-carboxamido)butanoate | 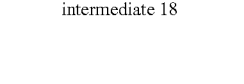<br>intermediate 18 | 1.60 min (A) | 441.3 |
| Example 4-4 | 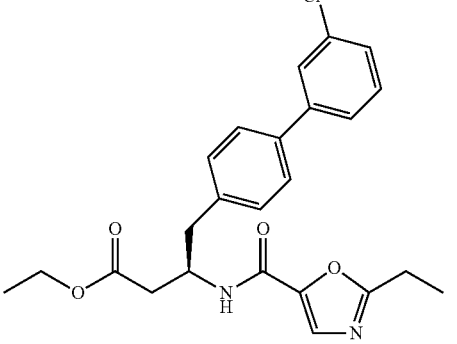<br>(R)-ethyl 4-(3'-chlorobiphenyl-4-yl)-3-(3-hydroxy-1H-pyrazole-5-carboxamido)butanoate | 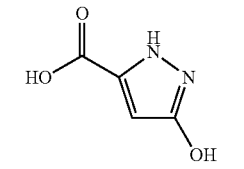 | 1.82 min (A) | 428.2 |
| Example 4-5 | <br>(R)-ethyl 4-(3'-chlorobiphenyl-4-yl)-3-(5-oxo-4,5-dihydro-1H-1,2,4-triazole-3-carboxamido)butanoate | 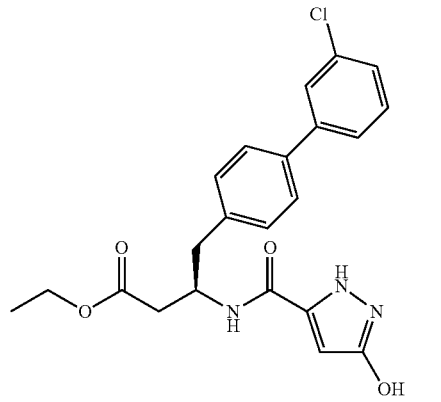<br>EDCI and HOAt used instead of HATU | 1.86 min (D) | 429.2 |

Example 4-3

1H NMR (400 MHz, DMSO-$d_6$) δ ppm 1.13 (t, J=7.2 Hz, 3 H) 1.25 (t, J=7.6 Hz, 3 H) 2.53-2.65 (m, 2 H) 2.80 (q, J=7.6 Hz, 2 H) 2.84-2.96 (m, 2 H) 4.02 (q, J=7.1 Hz, 2 H) 4.42-4.60 (m, 1 H) 7.31 (d, J=8.3 Hz, 2 H) 7.37-7.42 (m, 1 H) 7.47 (t, J=7.8 Hz, 1 H) 7.59 (s, 1 H) 7.60-7.65 (m, 3 H) 7.69 (t, J=1.9 Hz, 1 H) 8.48 (d, J=8.6 Hz, 1 H)

Example 4-4

1H NMR (400 MHz, DMSO-$d_6$) δ ppm 1.13 (t, J=7.1 Hz, 3 H) 2.52-2.65 (m, 2 H) 2.85 (dd, J=13.6, 5.8 Hz, 1 H) 2.91 (dd, J=13.6, 5.8 Hz, 1 H) 4.02 (q, J=7.1 Hz, 2 H) 4.38-4.60 (m, 1 H) 5.89 (s, 1 H) 7.31 (d, J=8.3 Hz, 2 H) 7.37-7.42 (m, 1 H) 7.46 (t, J=7.8 Hz, 1 H) 7.58-7.65 (m, 3 H) 7.69 (t, J=1.8 Hz, 1 H) 8.10 (d, J=8.6 Hz, 1 H)

Example 4-5

1H NMR (400 MHz, CD₃OD) δ ppm 1.22 (t, J=7.2 Hz, 3 H) 2.56-2.72 (m, 2 H) 2.95 (d, J=7.3 Hz, 2 H) 4.11 (q, J=7.2 Hz, 2 H) 4.53-4.73 (m, 1 H) 7.28-7.36 (m, 3 H) 7.39 (t, J=7.8 Hz, 1 H) 7.48-7.55 (m, 3 H) 7.58 (t, J=1.8 Hz, 1 H)

Example 4-6

Synthesis of (R)-ethyl 4-(5'-fluoro-7-methoxybiphenyl-4-yl)-3-(oxazole-5-carboxamido)butanoate

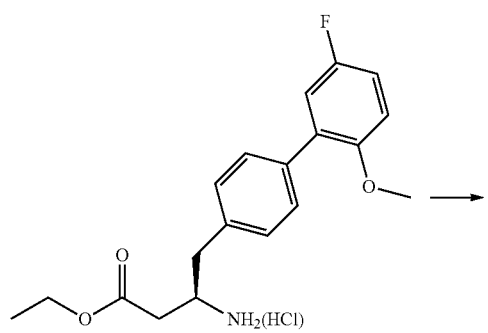

To a solution of oxazole-5-carboxylic acid (70 mg, 0.61 mmol) in DMF (1.5 mL) and DCM (1.5 mL) is added (R)-ethyl 3-amino-4-(5'-fluoro-2'-methoxybiphenyl-4-yl)butanoate hydrochloride, intermediate 8-3, (150 mg, 0.41 mmol), HATU (233 mg, 0.61 mmol), and TEA (284 µL, 2.04 mmol). After stirring for 2 hours, the reaction is quenched with H₂O, and the crude is diluted with EtOAc, the organic layer is washed with brine, dried over Na₂SO₄, filtered, and concentrated under reduced pressure. The obtained residue is purified by RP-HPLC (SunFire C18, H₂O (0.1% TFA)/CH₃CN), and then lyophilized to give (R)-ethyl 4-(5'-fluoro-2'-methoxybiphenyl-4-yl)-3-(oxazole-5-carboxamido)butanoate (157 mg). HPLC retention time=1.50 minutes (condition A); MS (m+1)=427.4; 1H NMR (400 MHz, CHLOROFORM-d) δ ppm 1.19 (t, J=7.2 Hz, 3 H) 2.46-2.62 (m, 2 H) 2.86 (dd, J=13.6, 8.1 Hz, 1 H) 3.02 (dd, J=13.6, 6.1 Hz, 1 H) 3.67 (s, 3 H) 4.05-4.15 (m, 2 H) 4.52-4.69 (m, 1 H) 6.76-6.82 (m, 1 H) 6.83-6.96 (m, 2 H) 7.11-7.21 (m, 3 H) 7.37 (d, J=8.1 Hz, 2 H) 7.61 (s, 1 H) 7.80 (s, 1 H)

Following compounds are prepared using similar procedure as described in example 4-6:

| Example 4-7 | 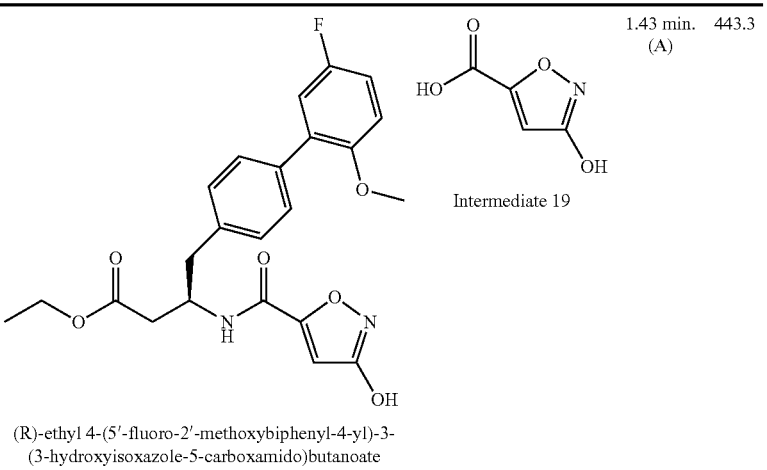 | 1.43 min. 443.3 (A) |
|---|---|---|

(R)-ethyl 4-(5'-fluoro-2'-methoxybiphenyl-4-yl)-3-(3-hydroxyisoxazole-5-carboxamido)butanoate -continued

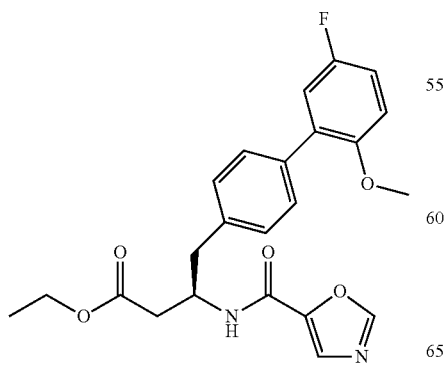

Example 4-7

1H NMR (400 MHz, CD₃OD) δ ppm 1.21 (t, J=7.1 Hz, 3 H) 2.61-2.68 (m, 2 H) 2.95 (d, J=7.1 Hz, 2 H) 3.74 (s, 3 H)

4.10 (q, J=7.1 Hz, 2 H) 4.60-4.73 (m, 1 H) 6.43 (s, 1 H) 6.98-7.06 (m, 3 H) 7.27 (d, J=8.1 Hz, 2 H) 7.38-7.48 (m, 2 H) 8.78 (d, J=8.8 Hz, 1 H)

Example 4-8

Synthesis of 5-[(R)-1-(3'-Chloro-biphenyl-4-ylm-ethyl)-2-ethoxycarbonyl-ethylcarbamoyl]-1H-pyrazole-3-carboxylic acid

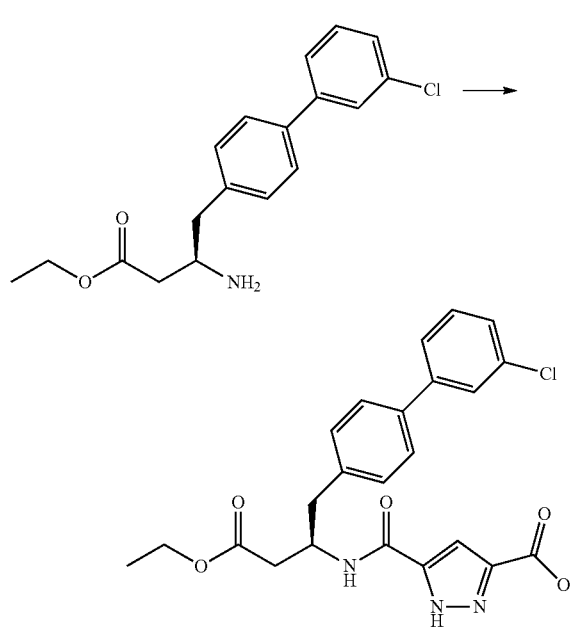

To a mixture of Intermediate 8-1 (130 mg, 0.367 mmol), 1H-pyrazole-3,5-dicarboxylic acid (74.5 mg, 0.477 mmol), EDCl (91 mg, 0.477 mmol) and HOBt (64.5 mg, 0.477 mmol) in DMF (3 mL) is added triethylamine (149 mg, 0.203 mmol) and the mixture is stirred at room temperature for 18 hours. Any insoluble material is removed by filtration and the filtrate is chromatographed by HPLC using a gradient of 10% MeCN/water to 100% MeCN (+0.1% TFA). Lyophilization of the proper fractions gives the title compound; HPLC Retention time 1.31 minutes (condition C); MS 456.2 (M+1); 1H NMR (400 MHz, DMSO-d6) δ ppm 1.12 (t, J=7.07 Hz, 3H), 2.54-2.67 (m, 2H), 2.84-2.97 (m, 2H), 4.02 (q, J=7.07 Hz, 2H), 4.54 (m, 1H), 7.11 (s, broad, 1H), 7.32 (d, J=8.08 Hz, 2H), 7.39 (m, 1H), 7.46 (t, 1H), 7.62 (d, J=8.08 Hz, 3H), 7.69 (s, 1H), 8.41 (s, broad, 1H).

Example 4-9

(R)-4-(3'-Chloro-biphenyl-4-yl)-3-[(3-hydroxy-isoxazole-5-carbonyl)-amino]-butyric acid ethyl ester

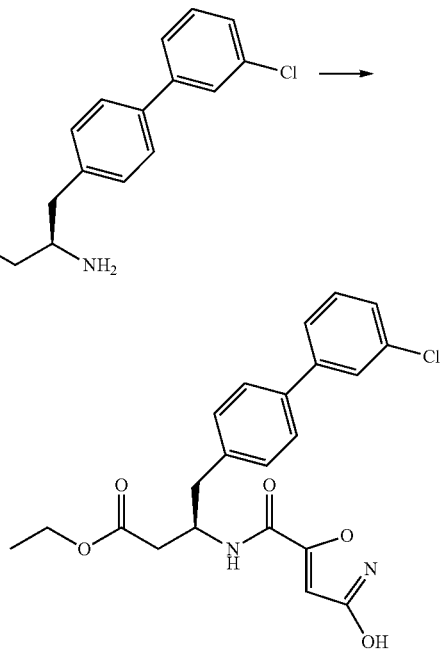

To a solution of intermediate 8-1 (40.6 mg, 0.315 mmol) and HATU (144 mg, 0.378 mmol) in DMF (2 mL) is added pyridine (74.7 mg, 0.76 mL, 0.944 mmol) and the mixture is stirred at room temperature for 15 minutes. Then Intermediate 19 is added and stirring is continued for 2 hours. Any insoluble is removed by filtration and the filtrate is chromatographed by HPLC using a gradient of 10% MeCN/water to 100% MeCN (+0.1% TFA). Lyophilization of the proper fractions gives the title compound. HPLC Retention time 1.36 minutes (condition C); MS 429.1 (M+1); 1H NMR (400 MHz, DMSO-d6) δ ppm 1.13 (t, J=7.07 Hz, 3 H) 2.60 (dd, J=6.95, 3.66 Hz, 2 H) 2.81-2.95 (m, 2 H) 4.02 (q, J=7.24 Hz, 2 H) 4.49 (d, J=7.83 Hz, 1 H) 6.49 (s, 1 H) 7.31 (d, J=8.34 Hz, 2 H) 7.37-7.43 (m, 1 H) 7.47 (t, J=7.83 Hz, 1 H) 7.59-7.66 (m, 3 H) 7.70 (t, J=1.89 Hz, 1 H) 8.83 (d, J=8.84 Hz, 1 H).

Example 4-10

(R)-3-[(5-Carboxymethyl furan-2-carbonyl)-amino]-4-(3'-chloro-biphenyl-4-yl)-butyric acid ethyl ester and Example 4-11

(R)-3-[(5-Carboxymethyl-furan-2-carbonyl)-amino]-4-(3'-chloro-biphenyl-4-yl)-butyric acid

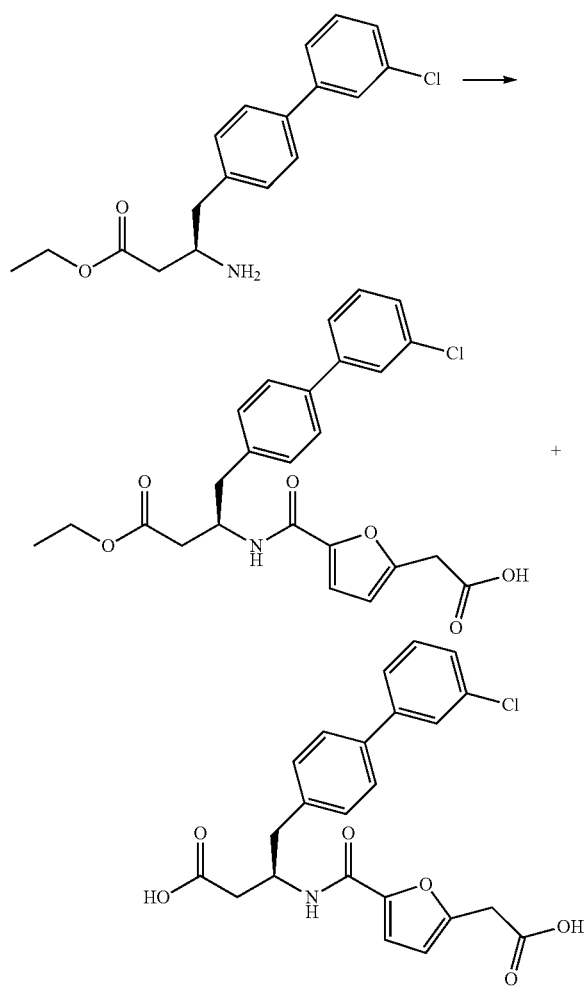

The reaction is performed similar to Example 4-8 using Intermediate 8-1 and Intermediate 20 to give (R)-4-(3'-chloro-biphenyl-4-yl)-3-[(5-methoxycarbonylmethyl-furan-2-carbonyl)-amino]-butyric acid ethyl ester. HPLC Retention time 1.38 minutes (condition C).

Next, to a solution of the above diester (235 mg, 0.486 mmol) in EtOH (5 mL) is added 1N NaoH (0.486 mL) and the mixture is stirred at room temperature for 4 hours. The solvent is removed under reduced pressure and water (4 mL) is added. The solution is acidified with 1N HCl and the mixture is extracted with EtOAc. The organic phase is dried over sodium sulfate and the solvent is removed under reduced pressure.

The residue is purified by preparative HPLC using a gradient of 10% MeCN/water to 100% MeCN (+0.1% TFA). Lyophilization of the proper fractions gives the title compounds.

(R)-3-[(5-Carboxymethyl-furan-2-carbonyl)-amino]-4-(3'-chloro-biphenyl-4-yl)-butyric acid ethyl ester. HPLC Retention time 1.35 minutes (condition C); MS 470.0 (M+1); 1H NMR (400 MHz, DMSO-d6) δ ppm 1.13 (t, J=7.07 Hz, 3H), 2.50-2.64 (m, 2H), 2.81-2.95 (m, 2H), 3.74 (s, 2H), 4.01 (q, J=7.07 Hz, 2H), 4.51 (m, 1H), 6.99 (d, J=3.28 Hz, 1H), 7.31 (d, J=8.34 Hz, 2H), 7.38-7.41 (m, 1H), 7.47 (t, 1H), 7.62 (d, J=8.08 Hz, 3H), 7.69 (t, 1H), 8.24 (d, J=8.84 Hz, 1H).

(R)-3-[(5-Carboxymethyl-furan-2-carbonyl)-amino]-4-(3'-chloro-biphenyl-4-yl)-butyric acid. HPLC Retention time 0.94 minutes (condition C); MS 442.0 (M+1); 1H NMR (400 MHz, DMSO-d6) δ ppm 2.44-2.58 (m, 2H), 2.81-2.94 (m, 2H), 3.74 (s, 2H), 4.48 (m, 1H), 6.39 (d, J=3.28 Hz, 1H), 6.99 (d, J=3.54 Hz, 1H), 7.30 (d, J=8.34 Hz, 2H), 7.38-7.41 (m, 1H), 7.47 (t, 1H), 7.62 (d, J=8.34 Hz, 3H), 7.70 (t, J=1.77 Hz, 1H), 8.22 (d, J=8.84 Hz, 1H).

Example 4-12

(R)-4-(3'-Chloro-biphenyl-4-yl)-3-[(2H-tetrazole-5-carbonyl)-amino]-butyric acid ethyl ester

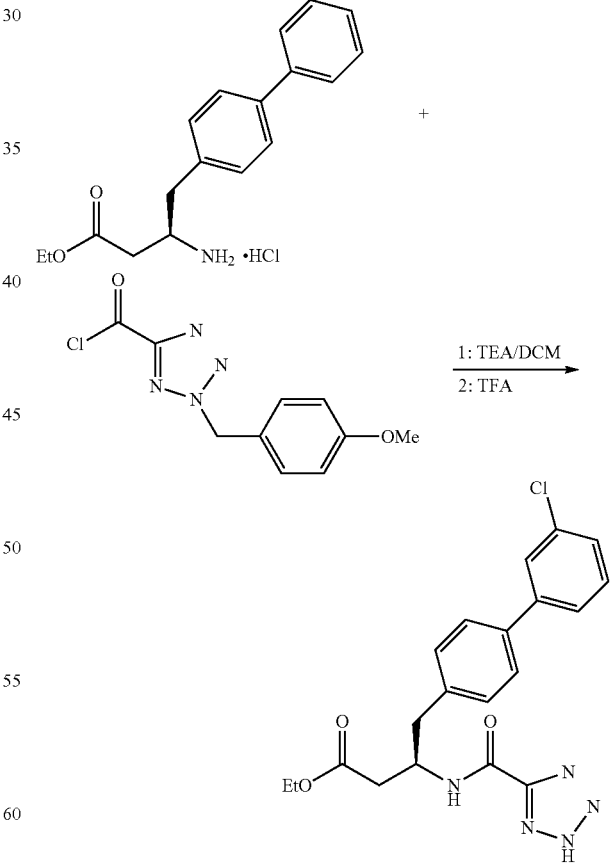

To a solution of intermediate 8-1 in DCM (8 ml) at room temperature is added 2-(4-methoxy-benzyl)-2H-tetrazole-5-carbonyl chloride and followed by TEA (Intermediate 22: 0.293 ml, 2.100 mmol). The reaction is stirred at room temperature for 5 min. The reaction is quenched by brine and is extracted with DCM. The combined organic layer is washed with brine and dried over anhydrous sodium sulfate, filtered and concentrated under reduced pressure. The residue is purified by column chromatography (15% to 40% EtOAc/Heptane). The obtained residue in TFA (5 ml, 64.9 mmol) is heated at 80° C. for 0.5 hours. The reaction is concentrated under reduced pressure to give (R)-4-(3'-chloro-biphenyl-4-yl)-3-[(2H-tetrazole-5-carbonyl)-amino]-butyric acid ethyl ester.

HPLC retention time=1.31 minutes (condition B); MS (m+1)=414.1; 1H NMR (400 MHz, DMSO-$d_6$) δ ppm 1.11 (t, J=7.1 Hz, 3 H), 2.63 (dd, J=15.4, 5.6 Hz, 1 H), 2.72 (dd, J=15.4, 8.3 Hz, 1 H), 2.86-2.99 (m, 2 H), 4.02 (q, J=7.1 Hz, 2 H), 4.55-4.67 (m, 1 H), 7.32 (d, J=8.1 Hz, 2 H), 7.37-7.42 (m, 1 H), 7.46 (t, J=7.8 Hz, 1 H), 7.60 (d, J=8.1 Hz, 3 H), 7.68 (t, J=1.8 Hz, 1 H), 9.37 (d, J=8.8 Hz, 1 H).

Example 4-13

Synthesis of (R,E)-ethyl 4-(4-(benzyloxy)-1-(3'-chlorobiphenyl-4-yl)-4-oxobutan-2-ylamino)-4-oxobut-2-enoate

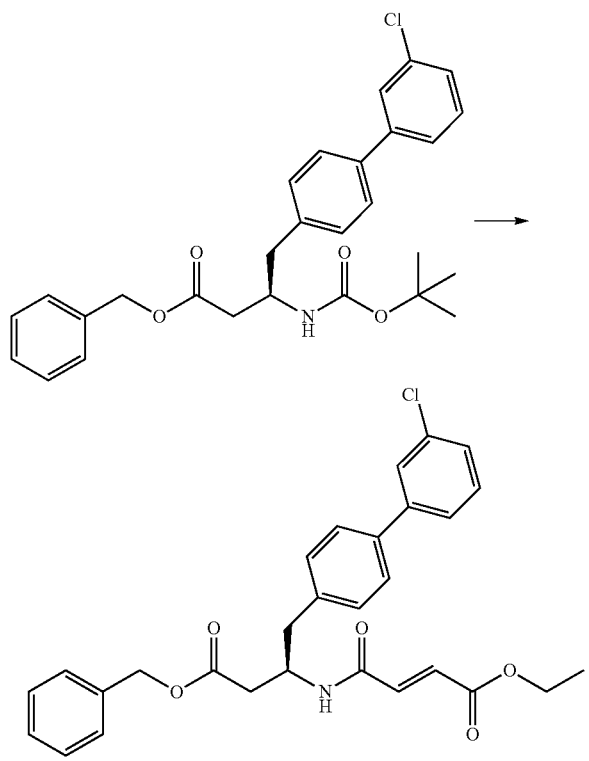 [SMILES: CC(C)(C)OC(=O)N[C@@H](CC(=O)OCc1ccccc1)Cc1ccc(-c2cccc(Cl)c2)cc1 ; CCOC(=O)/C=C/C(=O)N[C@@H](CC(=O)OCc1ccccc1)Cc1ccc(-c2cccc(Cl)c2)cc1]

To (R)-benzyl 3-amino-4-(3'-chlorobiphenyl-4-yl)butanoate (Intermediate 9-2: 87.6 mg, 0.183 mmol) is added a solution of HCl in 1,4-dioxane (0.456 mL, 1.825 mmol) at room temperature. After stirring for 3 hours, the reaction mixture is concentrated under reduced pressure to give (R)-benzyl 3-amino-4-(3'-chlorobiphenyl-4-yl)butanoate hydrochloride. A mixture of (R)-benzyl 3-amino-4-(3'-chlorobiphenyl-4-yl)butanoate hydrochloride, fumaric acid monoethyl ester (33.4 mg, 0.220 mmol), EDCl (63.3 mg, 0.330 mmol), DIPEA (0.058 ml, 0.330 mmol) and HOAt (44.9 mg, 0.330 mmol) in DMF (1.8 ml) is allowed to stir at room-temperature for 3 hour. The reaction mixture is diluted with water, and then the products are extracted with EtOAc. The organic layer is washed with NH$_4$OH, 1M HClaq and brine, dried over Na2SO4, filtered, and concentrated to give crude. The obtained residue is purified by silica gel flash column chromatography (heptane/EtOAc=100:0 to 0:100) to give (R,E)-ethyl 4-(4-(benzyloxy)-1-(3'-chlorobiphenyl-4-yl)-4-oxobutan-2-ylamino)-4-oxobut-2-enoate (72.9 mg); HPLC retention time=1.40 minutes (condition B); MS (m+1)=506.3; 1H NMR (400 MHz, CHLOROFORM-d) δ ppm 1.31 (t, J=7.1 Hz, 3 H) 2.58 (A of ABX, $J_{ab}$=16.4 Hz, $J_{ax}$=5.3 Hz, 1 H) 2.6 (B of ABX, $J_{ab}$=16.4 Hz, $J_{bx}$=5.1 Hz, 1 H) 2.88 (A of ABX, $J_{ab}$=13.6 Hz, $J_{ax}$=8.1 Hz, 1 H) 3.03 (B of ABX, $J_{ab}$=13.6 Hz, $J_{bx}$=6.3 Hz, 1 H) 4.24 (q, J=7.1 Hz, 2 H) 4.56-4.64 (m, 1 H) 5.12 (A of AB, J=12.1 Hz, 1 H) 5.18 (B of AB, J=12.1 Hz, 1 H) 6.57 (br d, J=9.1 Hz, 1 H) 6.77 (A of AB, J=15.4 Hz, 1 H) 6.81 (B of AB, J=15.4 Hz, 1 H) 7.19 (br d, J=8.1 Hz, 2 H) 7.29-7.47 (m, 10 H) 7.53-7.54 (m, 1 H).

Example 4-14

Synthesis of (R)-ethyl 4-(3'-chlorobiphenyl-4-yl)-3-(2-(ethoxycarbonylamino)acetamido)butanoate

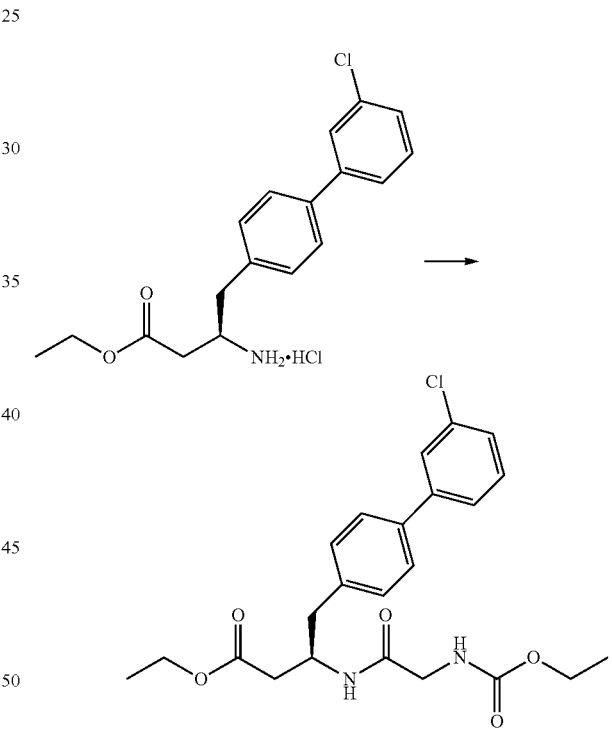

A mixture of (R)-ethyl 3-amino-4-(3'-chlorobiphenyl-4-yl)butanoate hydrochloride (173 mg, 0.488 mmol), 2-(ethoxycarbonylamino)acetic acid (86 mg, 0.488 mmol), EDCl (140 mg, 0.732 mmol), DIPEA (0.128 ml, 0.732 mmol) and HOAt (100 mg, 0.732 mmol) in DMF (2.5 ml) is allowed to stir at room temperature for 1 hour. The reaction mixture is diluted with water, and then the precipitated solid is collected on a funnel, washed with H2O, and dried under reduced pressure to give crude. The obtained residue is purified by silica gel flash column chromatography (heptane/EtOAc=100:0 to 0:100) to give (R)-ethyl 4-(3'-chlorobiphenyl-4-yl)-3-(2-(ethoxycarbonylamino)acetamido)butanoate (161 mg); HPLC retention time=1.16 minutes (condition B); MS (m+1)=447.3; 1H NMR (400 MHz, CHLOROFORM-d)

δ ppm 1.25 (t, J=7.07 Hz, 3 H) 1.29 (t, J=7.07 Hz, 3 H) 2.50 (A of ABX, $J_{ab}$=16.2 Hz, $J_{ax}$=5.3 Hz, 1 H) 2.54 (B of ABX, $J_{ab}$=16.2 Hz, $J_{bx}$=5.3 Hz, 1 H) 2.89 (A of ABX, $J_{ab}$=13.6 Hz, $J_{ax}$=7.8 Hz, 1 H) 2.99 (B of ABX, $J_{ab}$=13.6 Hz, $J_{bx}$=6.6 Hz, 1 H) 3.80 (be d, J=5.8 Hz, 2 H) 4.12-4.23 (m, 4 H) 4.48-4.56 (m, 1 H) 5.15 (br s, 1 H) 6.64 (br d, J=8.8 Hz, 1 H) 7.25-7.27 (m, 2 H) 7.29-7.38 (m, 2 H) 7.43-7.46 (m, 1 H) 7.49-7.52 (m, 2 H) 7.55-7.56 (m, 1 H).

Following compounds are prepared using similar procedure as described in example 4-14:

| Example # | Product | Starting Material | Condition | HPLC-RT (condition) | MS (M + 1) |
|---|---|---|---|---|---|
| Example 4-15 | 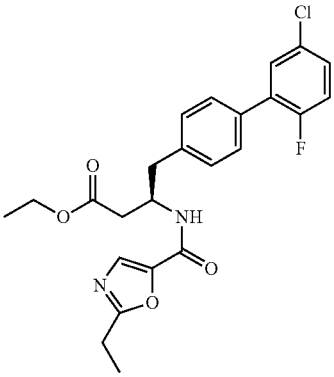<br>(R)-4-(5'-chloro-2'-fluoro-biphenyl-4-yl)-3-[(2-ethyl-oxazole-5-carbonyl)-amino]-butyric acid ethyl ester | 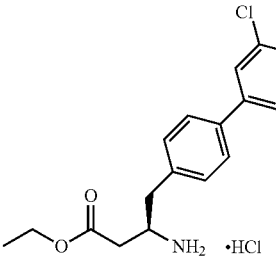 | HATU, TEA, DMF/DCM, rt | 1.81 min. (A) | 459.1 |

Example 4-15

1H NMR (400 MHz, CD3OD) δ ppm 1.20 (t, J=7.2 Hz, 3 H) 1.33 (t, J=7.7 Hz, 3 H) 2.66 (d, J=6.8 Hz, 2 H) 2.83 (q, J=7.6 Hz, 2 H) 2.98 (d, J=7.1 Hz, 2 H) 4.10 (q, J=7.1 Hz, 2 H) 4.65-4.79 (m, 1 H) 7.14 (dd, J=10.2, 8.7 Hz, 1 H) 7.30 (ddd, J=8.8, 4.1, 2.8 Hz, 1 H) 7.32-7.37 (m, 2 H) 7.37-7.46 (m, 3 H) 7.54 (s, 1 H) 8.49 (d, J=8.8 Hz, 1 H).

Example 5-1

Synthesis of (R)-4-(biphenyl-4-yl)-3-(3-carboxypropanamido)butanoic acid

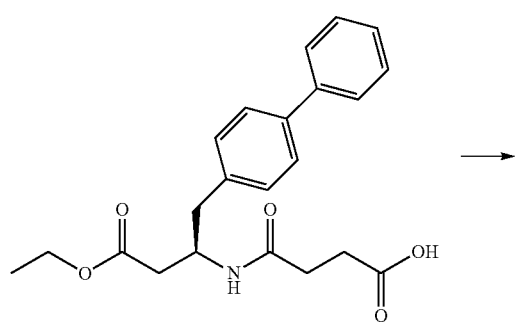

Example 1-1

→

-continued

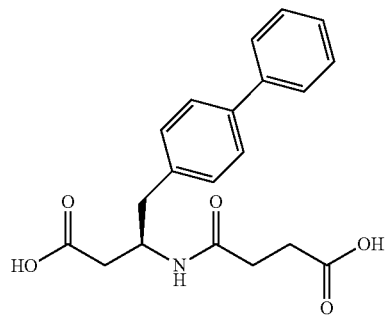

To a solution of (R)-4-(1-(biphenyl-4-yl)-4-ethoxy-4-oxobutan-2-ylamino)-4-oxobutanoic acid (61.2 mg, 0.160 mmol) in THF (1.6 mL) and methanol (0.2 mL), aqueous 1M NaOH solution (0.638 mL, 0.638 mmol) is added at room temperature. After stirring for 45 minutes, the reaction is quenched with aqueous 0.1 M HCl and is extracted with ethyl acetate. The organic layer is washed with brine, dried over $Na_2SO_4$, filtered, and concentrated under reduced pressure to give (R)-4-(biphenyl-4-yl)-3-(3-carboxypropanamido)butanoic acid (54.9 mg). HPLC retention time=1.33 minutes (condition A); MS (m+1)=356.1; 1H NMR (400 MHz, CD3OD) δ ppm 2.40-2.56 (m, 6 H) 2.83-2.94 (m, 2 H) 4.43-4.50 (m, 1 H) 7.29-7.32 (m, 3 H) 7.41 (t, 2 H, J=7.7 Hz) 7.53-7.60 (m, 4 H).

Following compounds are prepared using similar procedure as described in example 5-1:

| Example # | Product | Starting Material | Hydrolysis Condition | HPLC-RT (condition) | MS (M + 1) |
|---|---|---|---|---|---|
| Example 5-2 | 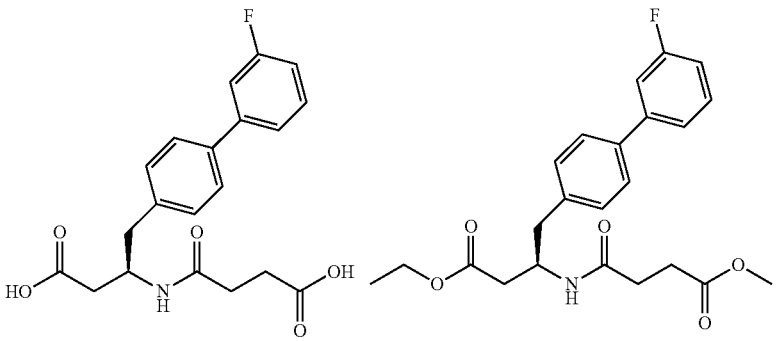<br>(R)-3-(3-carboxy-propionylamino)-4-(3'-fluoro-biphenyl-4-yl)-butyric acid | <br>Example 2-2 | Aq. NaOH, THF, MeOH, rt | 0.69 min. (B) | 374.0 |
| Example 5-3 | 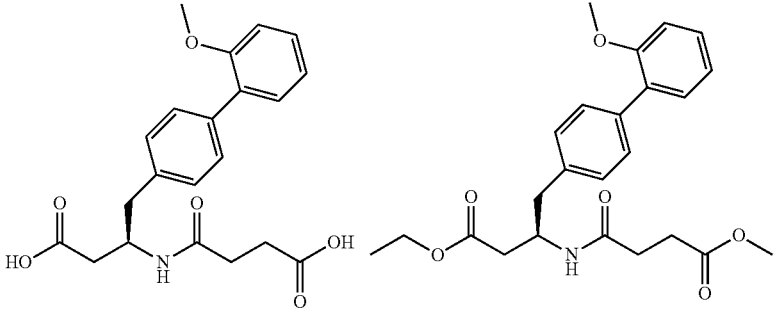<br>(R)-3-(3-carboxy-propionylamino)-4-(2'-methoxy-biphenyl-4-yl)-butyric acid | <br>Example 2-3 | Aq. NaOH, THF, MeOH, rt | 0.61 min. (B) | 386.1 |
| Example 5-4 | 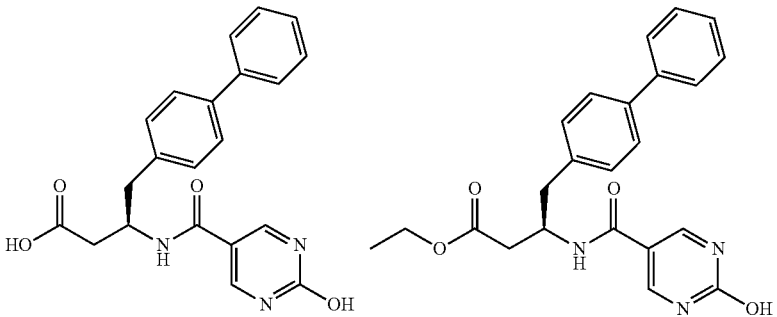<br>(R)-4-Biphenyl-4-yl-3-[(2-hydroxy-pyrimidine-5-carbonyl)-amino]-butyric acid | <br>Example 3-2 | aq. NaOH, THF, MeOH, RT | 1.28 min. (A) | 377.9 |
| Example 5-5 | 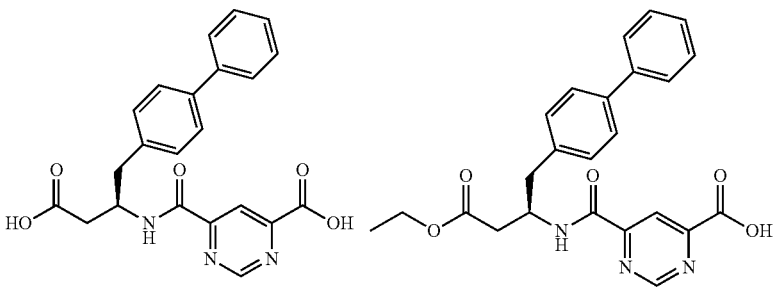<br>6-((R)-1-Biphenyl-4-ylmethyl-2-carboxy-ethylcarbamoyl)-pyrimidine-4-carboxylic acid | <br>Example 3-1 | aq. NaOH, THF, MeOH, RT | 0.80 min. (B) | 406.0 |
| Example 5-6 | 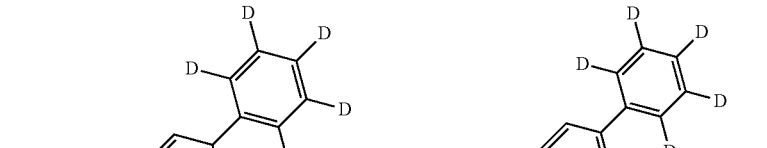 |  | aq. NaOH, THF, MeOH, 50° C. | 0.68 min. (B) | 361.2 |

Example 5-2

1H NMR (400 MHz, CD3OD) δ ppm 2.39-2.44 (m, 2 H) 2.46-2.55 (m, 4 H) 2.86 (A of ABX, Jab=13.6 Hz, Jax=7.6 HZ, 1 H) 2.92 (B of ABX, Jab=13.6 Hz, Jbx=6.3 HZ, 1 H) 4.42-4.49 (m, 1 H) 7.01-7.06 (m, 1 H) 7.32 (br d, J=8.1 Hz, 2 H) 7.39-7.45 (m, 2 H) 7.55 (d, J=8.1 Hz, 2 H)

Example 5-3

1H NMR (400 MHz, CD3OD) δ ppm 2.40-2.52 (m, 6 H) 2.83-2.92 (m, 2 H) 3.77 (s, 3 H) 4.44-4.47 (m, 1 H) 6.96-7.05 (m, 2 H) 7.23-7.30 (m, 4 H) 7.39-7.41 (m, 2 H)

Example 5-4

1H NMR (400 MHz, DMSO-d6) δ ppm 2.46-2.59 (m, 2 H), 2.86-2.88 (m, 2 H), 4.41-4.49 (m, 1 H), 7.29-7.36 (m, 3 H), 7.42-7.46 (m, 2 H), 7.58-7.65 (m, 4 H), 8.26 (d, J=8 Hz, 1 H), 8.64 (br s, 2 H) 12.24 (br. s., 1 H).

Example 5-5

1H NMR (400 MHz, DMSO-d6) δ ppm 2.54-2.70 (m, 2 H), 2.88-3.03 (m, 2H), 4.56-4.65 (m, 1 H), 7.29-7.34 (m, 3 H), 7.41-7.45 (m, 2 H), 7.55-7.63 (m, 4 H), 8.33 (s, 1 H), 9.15 (d, J=9.1 Hz, 1 H), 9.49 (s, 1 H), 12.30 (br s, 1 H), 14.11 (br s, 1 H).

Example 5-6

1H NMR (400 MHz, CD3OD) δ ppm 2.39-2.55 (m, 6 H) 2.85 (A of ABX, Jab=13.6 Hz, Jax=7.5 HZ, 1 H) 2.90 (B of ABX, Jab=13.6 Hz, Jbx=6.3 HZ, 1 H) 4.42-4.49 (m, 1 H) 6.86-6.92 (m, 1 H) 7.31 (d, J=8.1 Hz, 2 H) 7.53-7.55 (m, 2 H).

Example 5-7

Synthesis of (R)-4-(1-carboxy-3-(5'-fluoro-2'-methoxybiphenyl-4-yl)propan-2-ylamino)-4-oxobutanoic acid

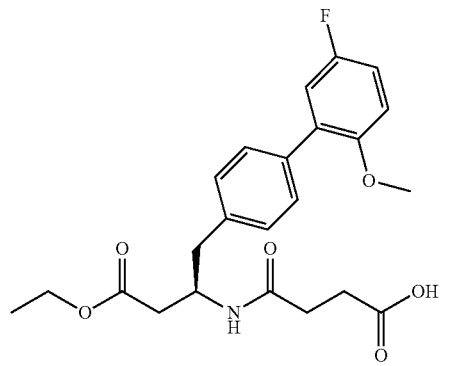

→

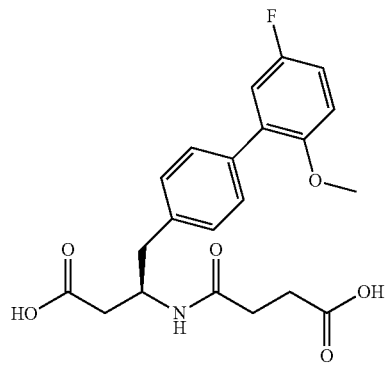

To a solution of (R)-4-(4-ethoxy-1-(5'-fluoro-2'-methoxybiphenyl-4-yl)-4-oxobutan-2-ylamino)-4-oxobutanoic acid (Example 2-8: 83 mg, 0.192 mmol) in MeOH (2 mL) is added 1N NaOH (4 mL, 4 mmol) After stirring at room temperature for 2 hours, the crude is concentrated under reduced pressure to remove MeOH and is diluted with EtOAc. The organic layer is washed with brine, dried over Na2SO4, filtered and concentrated under reduced pressure. The obtained residue is purified by RP-HPLC (SunFire C18, H2O (0.1% TFA)/CH3CN), and then lyophilized to give (R)-4-(1-carboxy-3-(5'-fluoro-2'-methoxybiphenyl-4-yl)propan-2-ylamino)-4-oxobutanoic acid (58 mg). HPLC retention time=1.46 minutes (condition D); MS (m+1)=404.2; 1H NMR (400 MHz, CD3OD) δ ppm 2.36-2.59 (m, 6 H) 2.84 (dd, J=13.4, 6.3 Hz, 1H) 2.91 (dd, J=13.4, 6.3 Hz, 1 H) 3.75 (s, 3 H) 4.34-4.56 (m, 1 H) 6.95-7.08 (m, 3 H) 7.26 (d, J=8.1 Hz, 2 H) 7.42 (d, J=8.3 Hz, 2 H)

Following compounds are prepared using similar procedure as described in example 5-7:

| Example # | Product | Starting Material | Hydrolysis Condition | LCMS-RT (condition) | MS (M + 1) |
|---|---|---|---|---|---|
| Example 5-8* | R-4-(1-carboxy-3-(5'-chloro-2'-methoxybiphenyl-4-yl)propan-2-ylamino)-4-oxobutanoic acid | Example 2-9 | Aq. NaOH, MeOH, rt | 1.52 min. (D) | 420.1 |
| Example 5-9 | R-4-(3'-chlorobiphenyl-4-yl)-3-(5-oxo-4,5-dihydro-1,3,4-oxadiazole-2-carboxamido)butanoic acid | Example 3-15 | Aq. NaOH, MeOH, rt | 1.53 min. (D) | 402.2 |
| Example 5-10 | R-4-(3'-chlorobiphenyl-4-yl)-3-(2-ethyloxazole-5-carboxamido)butanoic acid | Example 4-3 | Aq. NaOH, MeOH, rt | 1.60 min. (D) | 413.3 |
| Example 5-11 | | | Aq. NaOH, MeOH, rt | 1.37 min. (D) | 415.1 |

Example 5-8

1H NMR (400 MHz, CD$_3$OD) δ ppm 2.36-2.60 (m, 6 H) 2.84 (dd, J=13.4, 6.1 Hz, 1 H) 2.91 (dd, J=13.4, 6.1 Hz, 1 H) 3.77 (s, 3 H) 4.34-4.58 (m, 1 H) 7.03 (d, J=8.6 Hz, 1 H) 7.18-7.31 (m, 4 H) 7.39 (d, J=8.1 Hz, 2 H)

Example 5-9

1H NMR (400 MHz, DMSO-d$_6$) δ ppm 2.51-2.63 (m, 2 H) 2.84 (dd, J=13.6, 8.3 Hz, 1 H) 2.89 (dd, J=13.6, 8.3 Hz, 1 H) 4.40-4.55 (m, 1 H) 7.30 (d, J=8.3 Hz, 2 H) 7.37-7.42 (m, 1 H) 7.47 (t, J=7.8 Hz, 1 H) 7.58-7.66 (m, 3 H) 7.70 (t, J=1.9 Hz, 1 H) 8.95 (d, J=8.6 Hz, 1 H) 12.93 (s, 1 H)

Example 5-10

1H NMR (400 MHz, DMSO-d$_6$) δ ppm 1.25 (t, J=7.6 Hz, 3 H) 2.51-2.59 (m, 2 H) 2.80 (q, J=7.6 Hz, 2 H) 2.84-2.94 (m, 2 H) 4.41-4.56 (m, 1 H) 7.31 (d, J=8.1 Hz, 2 H) 7.37-7.42 (m, 1 H) 7.47 (t, J=7.8 Hz, 1 H) 7.59 (s, 1 H) 7.63 (d, J=8.3 Hz, 3 H) 7.70 (t, J=1.9 Hz, 1 H) 8.45 (d, J=8.6 Hz, 1 H) 12.27 (br. s., 1 H)

Example 5-11

1H NMR (400 MHz, CD$_3$OD) δ ppm 2.64 (d, J=6.3 Hz, 2 H) 2.97 (d, J=7.1 Hz, 2 H) 3.74 (s, 3 H) 4.58-4.73 (m, 1 H) 6.43 (s, 1 H) 6.96-7.08 (m, 3 H) 7.27 (d, J=8.1 Hz, 2 H) 7.42 (d, J=8.1 Hz, 2 H) 8.71 (d, J=8.3 Hz, 1 H)

Example 5-12

1H NMR (400 MHz, CD$_3$OD) δ ppm 2.38-2.56 (m, 6 H) 2.85 (dd, J=13.4, 7.3 Hz, 1 H) 2.89 (dd, J=13.4, 7.3 Hz, 1 H) 4.40-4.52 (m, 1 H) 7.26-7.35 (m, 3 H) 7.36-7.46 (m, 2 H) 7.52-7.61 (m, 3 H)

Example 6-1

Synthesis of (R)-3-(biphenyl-4-ylmethyl)-4-(2-carboxyethylamino)-4-oxobutanoic acid

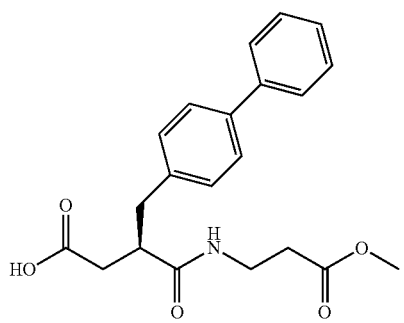

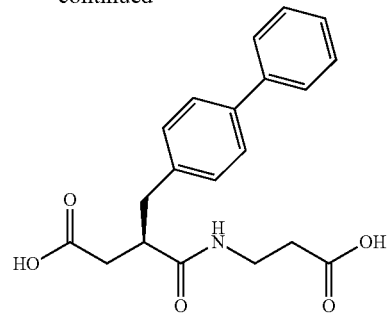

To a solution of (R)-3-(biphenyl-4-ylmethyl)-4-(3-methoxy-3-oxopropylamino)-4-oxobutanoic acid (Intermediate 5: 22.1 mg, 0.060 mmol) in THF (0.6 mL) and methanol (0.1 mL), aqueous 1M NaOH (0.12 mL, 0.12 mmol) is added at room temperature. After stirring for 3 hours, additional aqueous 1M NaOH (0.12 mL, 0.12 mmol) is added. The reaction mixture is allowed to stir for 30 minutes and quenched with 0.5 mL of aqueous 1M HCl and 0.5 mL of brine. The mixture is extracted twice with ethyl acetate, and the organic layer is concentrated under reduced pressure to give (R)-3-(biphenyl-4-ylmethyl)-4-(2-carboxyethylamino)-4-oxobutanoic acid (16.4 mg). HPLC retention time=1.04 minutes (condition A); MS (m+1)=356.1; 1H NMR (400 MHz, DMSO-d6) δ ppm 2.13-2.31 (m, 3 H) 2.59-2.65 (m, 1 H) 2.81-2.90 (m, 2 H) 3.12-3.27 (m, 2 H) 7.26 (d, 2 H, J=8 Hz) 7.34 (t, 1 H, J=7.4 Hz) 7.45 (t, 2 H, J=7.7 Hz) 7.57 (d, 2 H, J=8.1 Hz) 7.63-7.65.

Example 7-1

Synthesis of (R)-3-biphenyl-4-ylmethyl-N-carboxymethyl-succinamic acid

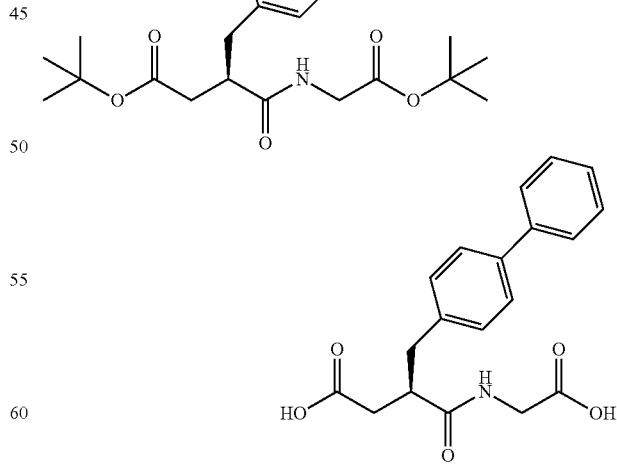

A solution of (R)-tert-butyl 3-(biphenyl-4-ylmethyl)-4-(2-tert-butoxy-2-oxoethylamino)-4-oxobutanoate (Intermediate 6-1: 40 mg, 0.088 mmol) and TFA (0.5 mL, 6.49 mmol) in DCM (1.5 mL) is allowed to stir for 2 hours at room temperature. The reaction is concentrated under reduced pressure, and the obtained residue is suspended in DCM (0.5 mL) and heptane (2 mL), and collected on a funnel, giving (R)-3-biphenyl-4-ylmethyl-N-carboxymethyl-succinamic acid (9.6 mg). HPLC retention time=1.26 minutes (condition A); MS (m+1)=342.0; 1H NMR (400 MHz, CD3OD) δ ppm 2.39 (dd, J=16.67, 5.31 Hz, 1 H) 2.63-2.82 (m, 2 H) 2.98-3.14 (m, 2 H) 3.84 and 3.95 (AB, 2 H, J=17.8 Hz) 7.26-7.33 (m, 3 H) 7.40 (t, J=7.71 Hz, 2 H) 7.56 (dd, J=19.96, 8.08 Hz, 4 H).

Example 8-1

Synthesis of (R)-4-biphenyl-4-yl-3-[(1H-tetrazole-5-carbonyl)-amino]-butyric acid

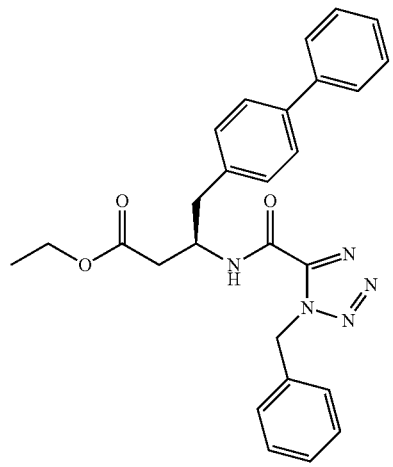

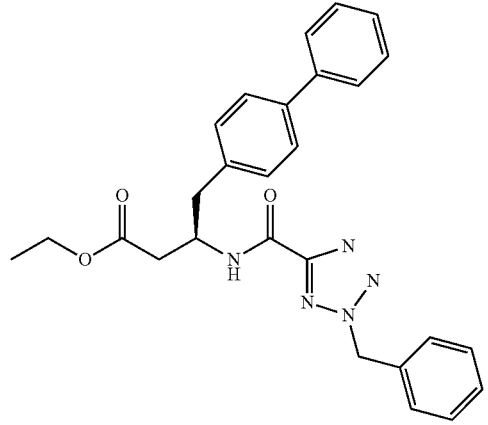

Intermediate 7

-continued

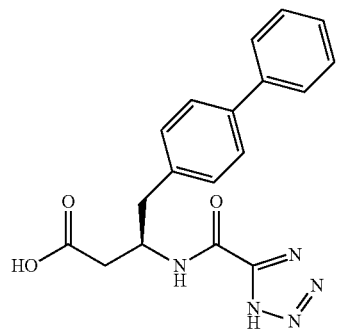

To a mixture of (R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester (180 mg, 0.383 mmol) in EtOH (1 mL) and THF (1 mL) is added aqueous 1M LiOH (2 mL). After stirring for 0.5 hour, the reaction mixture is acidified with aqueous 1M HCl. The mixture is extracted with ethyl acetate, dried over Na$_2$SO$_4$, and concentrated under reduced pressure. The residue is dissolved in MeOH and hydrogenated with 10% Pd/C at room temperature for 3 hours and at 40° C. for 2 hours. The reaction mixture is concentrated and purified by reverse phase HPLC to give (R)-4-biphenyl-4-yl-3-[(1H-tetrazole-5-carbonyl)-amino]-butyric acid. HPLC retention time=1.18 minutes (condition D); MS (m+1)=352; $^1$H NMR (400 MHz, DMSO-d6) δ ppm 2.56 (dd, J=5.81, 15.92 Hz, 1H), 2.67 (dd, J=7.58, 15.92 Hz, 1H), 2.85-2.99 (m, 2H), 4.55-4.64 (m, 1H), 7.26-7.35 (m, 3H), 7.43 (dd, J=7.83, 7.83 Hz, 2H), 7.56 (d, J=8.08 Hz, 2H), 7.62 (d, J=7.07 Hz, 2H), 9.28 (d, 8.84 Hz, 1H), 12.28 (s, 1H).

Example 9-1

Synthesis of (R)-4-(1-carboxy-3-(3'-chlorobiphenyl-4-yl)propan-2-ylamino)-4-oxobutanoic acid

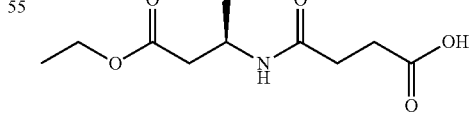

-continued

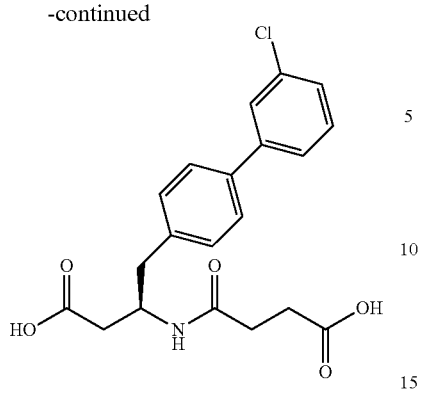

To a solution of (R)-4-(1-(biphenyl-4-yl)-4-ethoxy-4-oxobutan-2-ylamino)-4-oxobutanoic acid (Example 1-2: 110 mg, 0.263 mmol) in THF (2 mL) and methanol (0.2 mL), aqueous 1M NaOH solution (1.053 mL, 1.053 mmol) is added at room temperature. After stirring for 1 hour, the reaction is quenched with 0.1 M aqueous HCl, and the solution is diluted with DCM (15 ml) and allowed to stir for 1.5 hours. The precipitated solid is collected on a funnel, washed with water, DCM, heptane and then DCM in that order, and dried under reduced pressure to (R)-4-(1-carboxy-3-(3'-chlorobiphenyl-4-yl)propan-2-ylamino)-4-oxobutanoic acid (66 mg). HPLC retention time=0.87 minutes (condition B); MS (m+1)=390.0; 1H NMR (400 MHz, CD$_3$OD) δ ppm 2.39-2.55 (m, 6 μl) 2.86 (A of ABX, J$_{ab}$=13.6 Hz, J$_{ax}$=7.6 Hz, 1 H) 2.92 (B of ABX, J$_{ab}$=13.6 Hz, J$_{bx}$=6.2 Hz, 1 H) 4.42-4.49 (m, 1 H) 7.30-7.34 (m, 3 H) 7.40 (t, J=7.4 Hz, 1 H) 7.51-7.56 (m, 3 H) 7.60 (t, J=1.8 Hz, 1 H).

Following compounds are prepared using similar procedure as described in example 9-1:

| Example # | Product | Starting Material | Hydrolysis Condition | HPLC-RT (condition) | MS (M + 1) |
|---|---|---|---|---|---|
| Example 9-2 | (R)-4-(3'-chlorobiphenyl-4-yl)-3-(3-(pyridin-2-yl)propanamido)butanoic acid | Example 3-6 | Aq. NaOH, THF, MeOH, RT | 1.39 min. (A) | 423.3 |
| Example 9-3 | (R)-3-(3-(1H-benzo[d]imidazol-2-yl)propanamido)-4-(3'-chlorobiphenyl-4-yl)butanoic acid | Example 3-8 | Aq. NaOH, THF, MeOH, RT | 1.50 min. (B) | 462.3 |

-continued

| Example # | Product | Starting Material | Hydrolysis Condition | HPLC-RT (condition) | MS (M + 1) |
|---|---|---|---|---|---|
| Example 9-4 | 5-[(R)-2-Carboxy-1-(3'-chloro-biphenyl-4-ylmethyl)-ethylcarbamoyl]-1H-pyrazole-3-carboxylic acid | Example 4-8 | Aq. NaOH, EtOH, 50° C. | 1.09 min. (C) | 428.2 |
| Example 9-5 | (R)-4-(3'-Chloro-biphenyl-4-yl)-3-[(3-hydroxy-isoxazole-5-carbonyl)-amino]-butyric acid | Example 4-9 | Aq. NaOH, EtOH, rt | 1.17 min. (C) | 401.0 |
| Example 9-6 | N-[(R)-2-Carboxy-1-(3'-chloro-biphenyl-4-ylmethyl)-ethyl]-2,2,3,3-tetrafluoro-succinamic acid | Example 1-4 | Aq. NaOH, EtOH, rt | 1.16 min. (C) | 462.2 |
| Example 9-7 | | | Aq. NaOH, MeOH, rt | 1.73 min. (D) | 431.1 |

Example 9-2

1H NMR (400 MHz, CD$_3$OD) δ ppm 2.47 (A of ABX, J$_{ab}$=15.7 Hz, J$_{ax}$=7.7 HZ, 1 H) 2.54 (B of ABX, J$_{ab}$=15.7 Hz, Jbx=5.8 Hz, 1 H) 2.64-2.75 (m, 2 H) 2.80 (A of ABX, J$_{ab}$=13.7 Hz, J$_{ax}$=8.3 Hz, 1 H) 2.92 (B of ABX, J$_{ab}$=13.7 Hz, J$_{bx}$=5.9 Hz, 1 H) 3.17-3.21 (m, 2 H) 4.43-4.50 (m, 1 H) 7.28-7.35 (m, 3 H) 7.39-7.43 (m, 1 H) 7.51-7.54 (m, 3 H) 7.59 (br t, J=1.9 Hz, 1 H) 7.69-7.75 (m, 2 H) 8.29-8.32 (m, 1 H) 8.61 (d, J=4.6 Hz, 1 H).

Example 9-3

1H NMR (400 MHz, CD$_3$CN+D$_2$O) δ ppm 2.43-2.56 (m, 2 H) 2.71-2.91 (m, 4 H) 3.21-3.34 (m, 2 H) 4.39-4.46 (m, 1 H) 7.27 (d, J=8.3 Hz, 2 H) 7.34-7.49 (m, 7 H) 7.55-7.56 (m, 1 H) 7.65-7.70 (m, 2 H).

Example 9-4

1H NMR (400 MHz, DMSO-d6) δ ppm 2.46-2.60 (m, 2H), 2.84-2.96 (m, 2H), 4.51 (m, 1H), 7.31 (d, J=8.34 Hz, 2H), 7.38-7.41 (m, 1H), 7.46 (t, 1H), 7.62 (d, J=8.34 Hz, 3H), 7.69 (t, 1H).

Example 9-5

1H NMR (400 MHz, DMSO-d6) δ ppm) 2.75-2.99 (m, 1H) 4.47 (d, J=7.58 Hz, 1 H) 6.49 (s, 1 H) 7.30 (d, J=8.34 Hz, 1 H) 7.37-7.43 (m, 1 H) 7.47 (t, J=7.83 Hz, 1 H) 7.63 (d, J=8.08 Hz, 2 H) 7.70 (t, J=1.77 Hz, 1 H) 8.80 (d, J=8.59 Hz, 1 H) 11.69 (s, 1 H) 12.04-12.58 (m, 1 H).

Example 9-6

1H NMR (400 MHz, DMSO-d6): 1H NMR (400 MHz, DMSO-d6): δ ppm 2.44-2.52 (m, 2H), 2.83-2.85 (d, J=6.82 Hz, 2H), 4.29-4.38 (m, 1H), 7.28-7.30 (d, J=8.34 Hz, 2H), 7.40-7.43 (t, J=7.83 Hz, 1H), 7.62-7.65 (m, 3H), 7.71-7.72 (t, J=1.77 Hz, 1H), 9.42-9.45 (M, 1H), 12.32 (s, 1H).

Example 9-7

1H NMR (400 MHz, CD$_3$OD) δ ppm 1.32 (t, J=7.6 Hz, 3 H) 2.66 (d, J=6.8 Hz, 2 H) 2.83 (q, J=7.6 Hz, 2 H) 2.98 (dd, J=13.6, 7.8 Hz, 1 H) 3.03 (dd, J=14.7, 6.8 Hz, 1 H) 4.61-4.80 (m, 1 H) 7.13 (dd, J=18.9, 10.1 Hz, 1 H) 7.25-7.32 (m, 1 H) 7.32-7.37 (m, 2 H) 7.37-7.45 (m, 3 H) 7.54 (s, 1 H).

Example 10

Synthesis of (R)-4-(1-carboxy-3-(3'-chlorobiphenyl-4-yl)propan-2-ylamino)-4-oxobutanoic acid

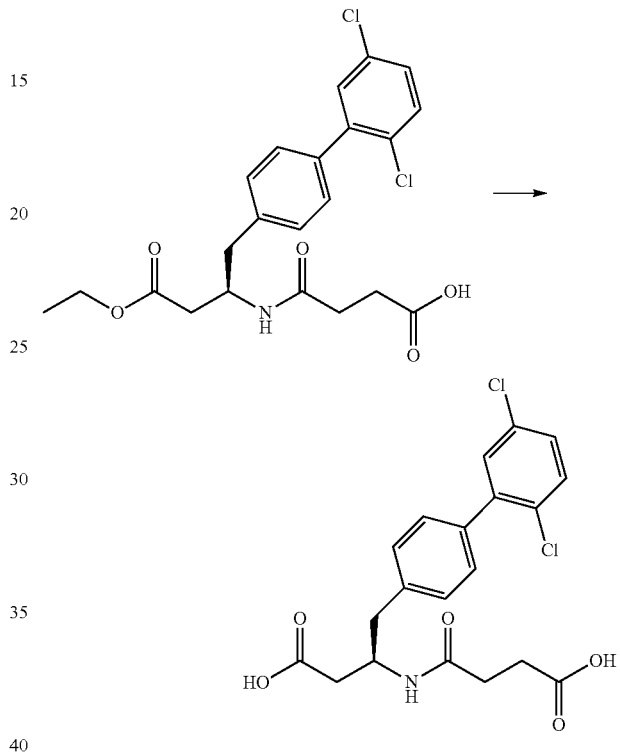

To a solution of (R)-4-(1-(2',5'-dichlorobiphenyl-4-yl)-4-ethoxy-4-oxobutan-2-ylamino)-4-oxobutanoic acid (Example 1-6: 106 mg, 0.234 mmol) in THF (2 ml) and MeOH (0.1 ml), 1M aqueous NaOH solution (1.406 mL, 1.406 mmol) is added at room temperature. After stirring for 4.5 hours, the reaction is quenched with 0.1 M aqueous HCl (3 ml), and the products are extracted with EtOAc. The combined organic layer is washed with brine, dried over Na$_2$SO$_4$, filtered, and concentrated under reduced pressure. The crude is triturated in DCM. The precipitates are collected on a funnel, washed with DCM, and dried under reduced pressure to give (R)-4-(1-carboxy-3-(3'-chlorobiphenyl-4-yl)propan-2-ylamino)-4-oxobutanoic acid (64.0 mg) as white solid; HPLC retention time=1.24 minutes (condition A); MS (m+1) =424.07; 1H NMR (400 MHz, CD$_3$OD) δ ppm 2.38-2.42 (m, 2 H) 2.45-2.57 (m, 4 H) 2.87 (A of ABX, J$_{ab}$=13.6 Hz, J$_{ax}$=7.6

Hz, 1 H) 2.95 (B of ABX, J$_{ab}$=13.6 Hz, J$_{bx}$=6.1 Hz, 1 H) 4.44-4.51 (m, 1 H) 7.30-7.37 (m, 6 H) 7.47 (d, J=8.4 Hz, 1 H).

Example 11-1

Synthesis of (R)-3-(3-Carboxymethyl-ureido)-4-(3'-chloro-biphenyl-4-yl)-butyric acid

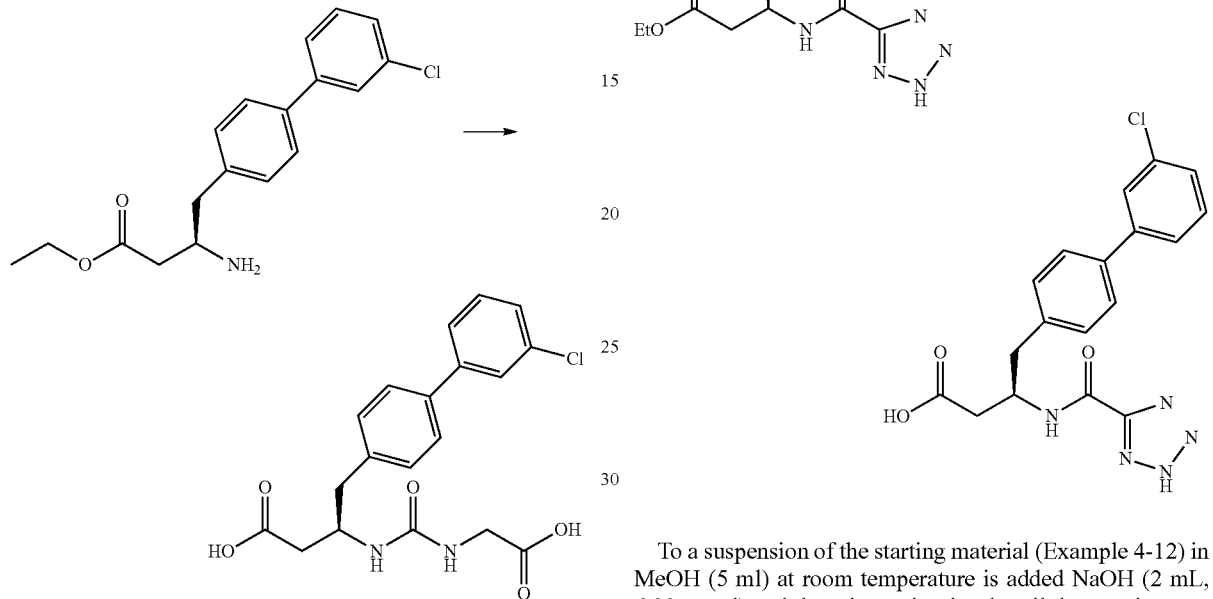

To a solution of Intermediate 8-1 (90 mg, 0.254 mmol) and ethyl isocyanatoacetate (Intermediate 16-1: 39.4 mg, 0.305 mmol) in DMF (3 mL) is added pyridine (2.93 g, 37.1 mmol) and the mixture is stirred at room temperature for 2 hours. The solvent is removed under reduced pressure and the residue is used directly in the next step. Next, the above residue is dissolved in EtOH (1 mL) and 1N NaOH (3 mL, 3 mmol) is added. The mixture is stirred at room temperature for 2 hours then is acidified with 1N HCl. The mixture is extracted with EtOAc and the organic phase is washed with water, brine then dried over sodium sulfate. The solvent is removed under reduced pressure and the residue purified by preparative HPLC using a gradient of 10% MeCN/water to 100% MeCN (+0.1% TFA). Lyophilization of the proper fractions gives the title compound; HPLC Retention time 0.98 minutes (condition C); MS 391.3 (M+1); 1H NMR (400 MHz, DMSO-d6): δ ppm 2.34 (d, J=7.33 Hz, 2H), 2.79 (d, J=6.57 Hz, 2H), 3.67 (d, J=5.56 Hz, 2H), 4.04-4.12 (m, 1H), 6.15 (t, J=5.81 Hz, 1H), 6.23 (d, J=8.34 Hz, 1H), 7.28-7.30 (m, 2H), 7.39-7.42 (m, 1H), 7.48 (t, J=7.83 Hz, 1H), 7.62-7.65 (m, 3H), 7.71 (t, J=1.77 Hz, 1H), 12.32 (s, br, 2H).

Example 12-1

(R)-4-(3'-Chloro-biphenyl-4-yl)-3-[(2H-tetrazole-5-carbonyl)-amino]-butyric acid To a suspension of the starting material (Example 4-12) in MeOH (5 ml) at room temperature is added NaOH (2 mL, 6.00 mmol) and the mixture is stirred until the reaction was completed. The reaction mixture is acidified to pH<4 and purified by HPLC (15% to 60% acetonitrile-H$_2$O with 0.1% TFA) to give (R)-4-(3'-chloro-biphenyl-4-yl)-3-[(2H-tetrazole-5-carbonyl)-amino]-butyric acid (80 mg).

HPLC retention time=0.95 minutes (condition B); MS (m+1)=386.1; 1H NMR (400 MHz, DMSO-d$_6$) d ppm 2.52-2.61 (m, 1 H), 2.61-2.72 (m, 1 H), 2.84-2.99 (m, 2 H), 4.51-4.64 (m, 1 H), 7.31 (d, J=8.1 Hz, 2 H), 7.36-7.41 (m, 1 H), 7.46 (t, J=7.8 Hz, 1 H), 7.61 (d, J=8.3 Hz, 3 H), 7.68 (t, J=1.9 Hz, 1 H), 9.31 (d, J=8.8 Hz, 1 H), 12.32 (br. s., 1 H).

Example 13-1

[(R)-1-(3'-chloro-biphenyl-4-ylmethyl)-3-methanesulfonylamino-3-oxo-propyl]-succinamic acid

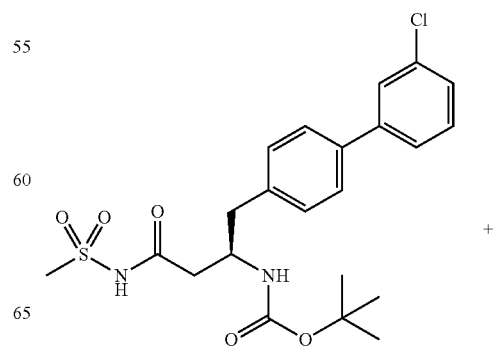

-continued

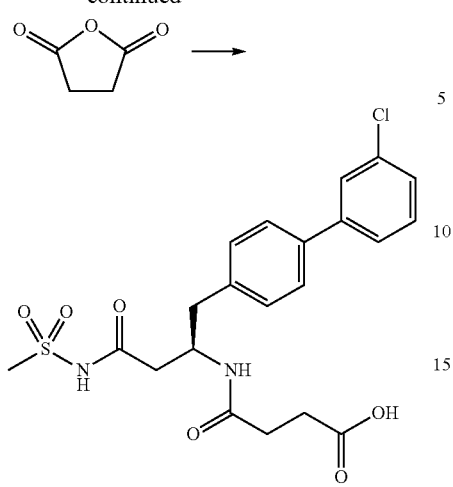

[(R)-1-(3'-Chloro-biphenyl-4-ylmethyl)-3-methanesulfonylamino-3-oxo-propyl]-carbamic acid tert-butyl ester (Intermediate 26: 150 mg, 0.321 mmol) is treated with 4M HCl in dioxane. After being stirred at room temperature for 1 h, the reaction mixture is concentrated in vacuo. To this residue in DCM (2 mL) are added succinic anhydride (48.2 mg, 0.482 mmol) and triethylamine (0.112 mL, 0.803 mmol). After being stirred at room temperature for 2 h, the reaction mixture is diluted with EtOAc and washed with 1M HCl and brine. The organic layer is dried over Na$_2$SO$_4$ and concentrated. The residue is purified by reverse phase HPLC (SunFire C18, 0.1% TFA in H$_2$O/CH$_3$CN) to give N—[(R)-1-(3'-chloro-biphenyl-4-ylmethyl)-3-methanesulfonylamino-3-oxo-propyl]-succinamic acid (63 mg). HPLC retentions time=1.32 minutes (condition A); MS (m+1)=467; 1H NMR (400 Mz, DMSO-d6) δ ppm 2.22-2.29 (m, 2 H), 2.32-2.54 (m, 4 H), 2.77 (d, 2 H, J=6.82 Hz), 3.17 (s, 3 H), 4.31 (dt, 1 H, J=7.33, 13.9 Hz), 7.28 (d, 2 H, J=8.08 Hz), 7.38-7.43 (m, 1 H), 7.48 (t, 1 H, J=7.83 Hz), 7.62 (d, 3 H, J=8.34 Hz), 7.70 (t, 1 H, J=2.02 Hz), 7.89 (d, 1 H, J=8.34 Hz), 11.70 (s, 1 H), 12.04 (s, 1 H).

Example 14-1

Synthesis of N-((1S,3R)-1-biphenyl-4-ylmethyl-3-carboxy-butyl)-isophthalamic acid

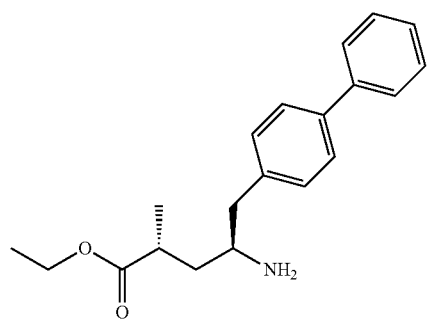

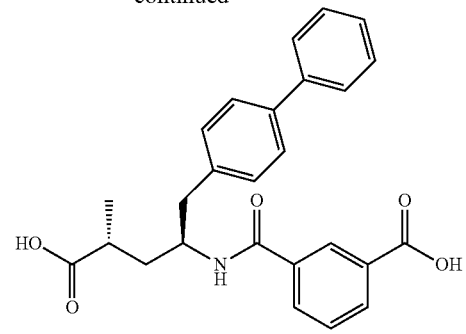

To a mixture of (2R,4S)-4-amino-5-biphenyl-4-yl-2-methyl-pentanoic acid ethyl ester hydrochloride (Intermediate 29: 70 mg, 0.201 mmol) and 3-chlorocarbonylbenzoic acid methyl ester (0.302 mmol) in methylene chloride (0.5 mL) is added pyridine (0.5 mL) and the mixture is stirred at room temperature for 24 hours. The solvents are removed under reduced pressure and ethyl acetate is added. The solution is washed with aqueous 1M HCl and brine and the organic phase is dried over sodium sulfate. The solvent is removed under reduced pressure and the residue is purified by column chromatography using methylene chloride to furnish N-((1S,3R)-1-biphenyl-4-ylmethyl-3-ethoxycarbonyl-butyl)-isophthalamic acid. Next, to a solution of N-((1S,3R)-1-biphenyl-4-ylmethyl-3-ethoxycarbonyl-butyl)-isophthalamic acid (0.287 mmol) in ethanol (10 mL) is added aqueous 1M NaOH (1.2 mL, 1.12 mmol) and the mixture is stirred at 50-60° C. for 5 hours. The ethanol is removed under reduced pressure and water is added. The solution is acidified with 1M HCl and the mixture is extracted with ethyl acetate. The organic phase is dried over sodium sulfate and the solvent is removed under reduced pressure. The residue is purified by preparative HPLC using a gradient of MeCN/water (0.1% TFA). The proper fractions are lyophilized to furnish N-((1S,3R)-1-biphenyl-4-ylmethyl-3-carboxy-butyl)-isophthalamic acid. HPLC Retention time 1.05 minutes (condition F); MS 432.3 (M+1); 1H NMR (400 MHz, DMSO-d6) δ ppm 1.09 (d, J=7.07 Hz, 3H), 1.60 (m, 1H), 1.89 (m, 1H), 2.47 (m, 1H), 2.86 (m, 2H), 4.27 (m, 1H), 7.27-7.35 (m, 3H), 7.34 (t, 1H), 7.43 (t, 2H), 7.55-7.66 (m, 5H), 8.01-8.07 (m, 2H), 8.39 (s, 1H), 8.47 (d, J=8.46 Hz, 1H).

Example 15-1

Synthesis of (2R,4S)-5-biphenyl-4-yl-4-(3-carboxy-3-methyl-butyrylamino)-2-methyl-pentanoic acid

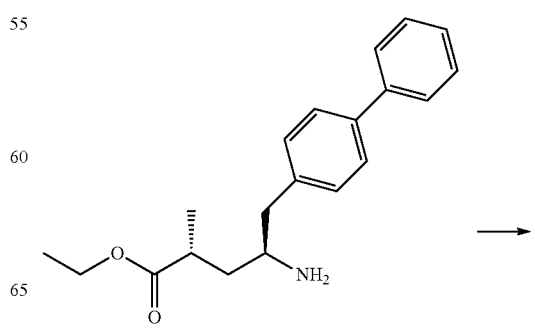

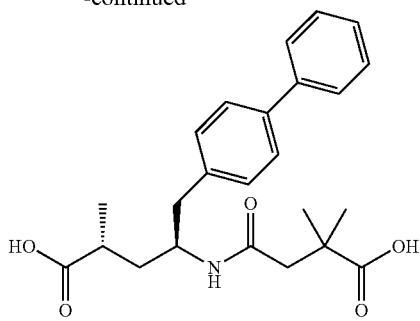

A solution of (2R,4S)-4-amino-5-biphenyl-4-yl-2-methyl-pentanoic acid ethyl ester hydrochloride (Intermediate 29: 100 mg, 0.287 mmol) and 3,3-dimethyl-dihydro-furan-2,5-dione (0.431 mmol) in 1:1 methylene chloride/pyridine (1.4 mL) is stirred at room temperature for 24 hours. The solvents are removed under reduced pressure and obtained residue is used directly in the subsequent hydrolysis reaction.

Next, to a solution of the obtained residue (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (2R,4S)-5-biphenyl-4-yl-4-(3-carboxy-3-methyl-butyrylamino)-2-methyl-pentanoic acid. HPLC Retention time 1.03 minutes (condition F); MS 412.4 (M+1); 1H NMR (400 MHz, DMSO-d6) δ ppm 0.97-1.07 (m, 9H), 1.32 (m, 1H), 1.72 (m, 1H), 2.25 (q, 2H), 2.45 (m, 1H), 2.64-2.74 (m, 2H), 3.91 (s, 1H), 7.25 (d, J=8.08 Hz, 2H), 7.34 (t, 1H), 7.45 (t, 2H), 7.56 (d, J=8.08 Hz, 2H), 7.64 (d, J=7.58 Hz, 2H), 7.88 (s, broad, 1H).

Following compounds are prepared using similar procedure as example 15-1 with appropriate reagents and conditions:

| Example # | Product | Reagent | Hydrolysis Condition | HPLC-RT (condition) | MS (M + 1) |
|---|---|---|---|---|---|
| Example 15-2 | (1S,2R)-2-((1S,3R)-1-biphenyl-4-ylmethyl-3-carboxy-butylcarbamoyl)-cyclopentanecarboxylic acid | | Aq. NaOH, EtOH, RT | 1.09 min. (F) | 424.4 |
| Example 15-3 | (2R,3S)-3-((1S,3R)-1-biphenyl-4-yl-methyl-3-carboxy-butylcarbamoyl)-oxirane-2-carboxylic acid | | Aq. NaOH, EtOH, 60° C. | 0.87 min. (F) | 398.3 |

| Example # | Product | Reagent | Hydrolysis Condition | HPLC-RT (condition) | MS (M + 1) |
|---|---|---|---|---|---|
| Example 15-4 | 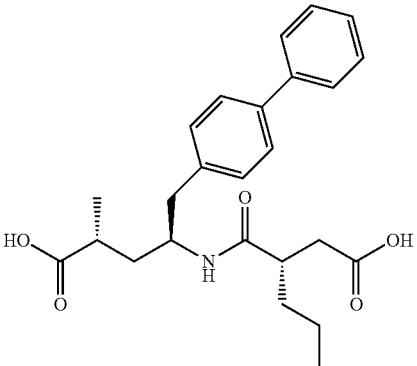<br>(S)-3-((1S,3R)-1-biphenyl-4-ylmethyl-3-carboxy-butylcarbamoyl)-heptanoic acid | 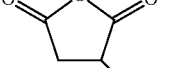<br>Pyridine used as solvent | Aq. NaOH, EtOH, RT | 1.28 min. (F) | 440.3 |
| Example 15-5 | 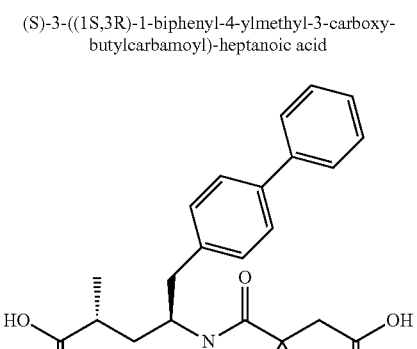<br>(2R,4S)-5-(biphenyl-4-yl)-4-(3-carboxy-2,2-dimethylpropanamido)-2-methylpentanoic acid | 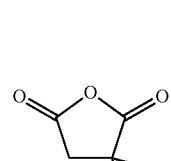<br>Pyridine used as solvent | Aq. NaOH, EtOH, RT | 1.13 min. (F) | 412.3 |

Example 15-2

1H NMR (400 MHz, MeCN-d3) δ ppm 1.07 (d, J=6.82 Hz, 3H), 1.47 (m, 1H), 1.61 (m, 2H), 1.73-1.95 (m, 4H), 2.45 (m, 1H), 2.73-2.96 (m, 5H), 4.0.6 (m, 1H), 6.64 (d, J=8.72 Hz, 1H), 7.29 (d, J=8.08 Hz, 2H), 7.35 (t, 1H), 7.45 (t, 2H), 7.57 (d, J=8.21 Hz, 2H), 7.64 (d, J=7.33 Hz, 2H).

Example 15-3

1H NMR (400 MHz, DMSO-d6) δ ppm 1.02 (d, J=7.20 Hz, 3H), 1.45 (m, 1H), 1.70 (m, 1H), 2.40 (m, 1H), 2.59 (m, 1H), 2.76 (m, 1H), 3.69 (d, J=5.05 Hz, 1H), 3.75 (d, J=5.05 Hz, 1H), 3.98 (m, 1H), 7.27 (d, J=8.08 Hz, 2H), 7.34 (t, 1H), 7.45 (t, 2H), 7.59 (d, J=8.21 Hz, 2H), 7.66 (d, J=7.20 Hz, 2H), 7.95 (d, J=8.59 Hz, 1H).

Example 15-4

1H NMR (400 MHz, MeOD-d4) δ ppm 0.88 (t, J=7.07 Hz, 3H), 1.15 (d, J=7.07 Hz, 3H), 1.43 (m, 7H), 1.90 (m, 1H), 2.24 (dd, J=6.69 Hz, 6.57 Hz, 1H), 2.39 (dd, J=7.58 Hz, 7.58 Hz, 1H), 2.57 (m, 2H), 2.81 (m, 2H), 4.15 (m, 1H), 7.30 (d, J=8.21 Hz, 2H), 7.41 (m, 2H), 7.51 (m, 2H), 7.57 (m, 2H).

Example 15-5

1H NMR (400 MHz, DMSO-d6) δ ppm 1.02 (m, 9H), 1.31 (m, 1H), 1.72 (m, 1H), 2.20 (m, 2H), 2.45 (m, 1H), 2.68 (m, 2H), 3.91 (m, 1H), 7.23 (d, J=8.08 Hz, 2H), 7.33 (d, J=7.20 Hz, 1H), 7.44 (d, J=7.83 Hz, 2H), 7.55 (d, J=8.08 Hz, 2H), 7.63 (dd, J=0.76 Hz, 1.14 Hz, 2H), 7.88 (s, 1H).

Example 16-1

Synthesis of (2R,4S)-5-biphenyl-4-yl-2-methyl-4-(2-thiophen-2-yl-acetylamino)-pentanoic acid

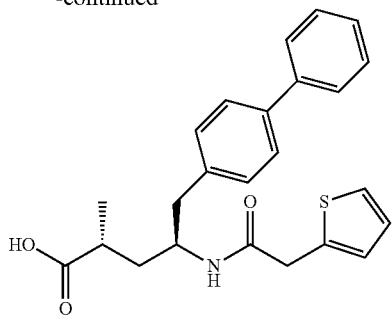

To a solution of thiophen-2-yl-acetic acid (0.144 mmol) in DMF (5 mL) is added HATU (0.216 mmol). After stirring the mixture at room temperature for 10 minutes, (2R,4S)-4-amino-5-biphenyl-4-yl-2-methyl-pentanoic acid ethyl ester hydrochloride (intermediate 29: 0.144 mmol) and triethylamine (0.359 mmol) is added and the mixture is stirred at room temperature for 18 hours. The mixture is poured into ethyl acetate and the mixture is washed with aqueous 1M HCl and brine. The organic phase is dried over magnesium sulfate and the solvent is removed under reduced pressure to give (2R,4S)-5-biphenyl-4-yl-2-methyl-4-(2-thiophen-2-yl-acetylamino)-pentanoic acid ethyl ester which is used directly in the subsequent hydrolysis reaction.

Next, to a solution of (2R,4S)-5-biphenyl-4-yl-2-methyl-4-(2-thiophen-2-yl-acetylamino)-pentanoic acid ethyl ester (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (2R,4S)-5-biphenyl-4-yl-2-methyl-4-(2-thiophen-2-yl-acetylamino)-pentanoic acid. HPLC Retention time 1.23 minutes (condition F); MS 408.3 (M+1); 1H NMR (400 MHz, MeOD-d4) δ ppm 1.16 (d, J=7.07 Hz, 3H), 1.50 (m, 1H), 1.96 (m, 1H), 2.52 (m, 1H), 2.72 (dd, J=7.71 Hz, 7.58 Hz, 1H), 2.84 (dd, J=5.81 Hz, 5.66 Hz, 1H), 3.64 (d, J=1.26 Hz, 2H), 4.20 (m, 1H), 6.82 (m, 1H), 6.89 (m, 1H), 7.21 (m, 3H), 7.32 (m, 1H), 7.42 (m, 2H), 7.46 (m, 2H), 7.57 (m, 2H), 7.95 (d, J=8.59 Hz, 1H).

Following compounds are prepared using similar procedure as example 16-1 with appropriate reagents and conditions:

| Example # | Product | Reagent | Hydrolysis Condition | HPLC-RT (condition) | MS (M + 1) |
|---|---|---|---|---|---|
| Example 16-2 | (2R,4S)-5-biphenyl-4-yl-4-(3-1H-indol-3-yl-propionylamino)-2-methyl-pentanoic acid | | Aq. NaOH, EtOH, RT | 1.31 min. (F) | 455.4 |
| Example 16-3 | (2R,4S)-5-biphenyl-4-yl-2-methyl-4-[4-(2-methyl-benzothiazol-6-yl)-butyrylamino]-pentanoic acid | Intermediate 32 | Aq. NaOH, EtOH, RT | 1.26 min. (F) | 501.3 |

-continued

| Example # | Product | Reagent | Hydrolysis Condition | HPLC-RT (condition) | MS (M + 1) |
|---|---|---|---|---|---|
| Example 16-4 | 5-((1S,3R)-1-biphenyl-4-ylmethyl-3-carboxy-butylcarbamoyl)-furan-2-carboxylic acid | (furan-2,5-dicarboxylic acid); EDIC and HOBt used instead of HATU | Aq. NaOH, EtOH, 60° C. | 1.18 min. (F) | 422.3 |
| Example 16-5 | 6-((2S,4R)-1-(biphenyl-4-yl)-4-carboxypentan-2-ylcarbamoyl)pyrimidine-4-carboxylic acid | (pyrimidine-4,6-dicarboxylic acid); EDIC and HOBt used instead of HATU | Aq. NaOH, EtOH, RT | 1.24 min. (F) | 434.2 |
| Example 16-6 | 1-(2-((2S,4R)-1-(biphenyl-4-yl)-4-carboxypentan-2-ylamino)-2-oxoethyl)cyclopentanecarboxylic acid | Intermediate 34 | Aq. NaOH, EtOH, RT | 1.25 min. (F) | 438.3 |
| Example 16-7 | (2R,4S)-5-biphenyl-4-yl-4-(3-carboxy-butyrylamino)-2-methyl-pentanoic acid | Intermediate 33 | Aq. NaOH, EtOH, RT | 0.98 min. (F) | 398.4 |
| Example 16-8 | | | Aq. NaOH, EtOH, RT | 0.98 min. (A) | 422.3 |

Example 16-2

1H NMR (400 MHz, Acetone-d6) δ ppm 1.28 (d, J=6.95 Hz, 3H), 1.54-1.70 (m, 2H), 2.09 (m, 1H), 2.67 (m, 1H), 2.81 (m, 1H), 3.06 (m, 2H), 3.26 (m, 2H), 4.47 (M, 1H), 7.25 (t, 1H), 7.34 (t, 1H), 7.36 (s, 1H), 7.49 (d, J=8.08 Hz, 2H), 7.60 (t, 2H), 7.69 (t, 2H), 7.7 (d, J=8.08 Hz, 2H), 7.80 (d, J=7.83 Hz, 1H), 7.88 (d, J=7.33 Hz, 2H).

Example 16-3

1H NMR (400 MHz, MeOD-d4) δ ppm 1.18 (d, J=7.07 Hz, 3H), 1.50 (m, 1H), 1.80 (m, 1H), 1.97 (m, 1H), 2.14 (m, 2H), 2.54 (m, 3H), 2.70 (m, 1H), 2.79 (s, 3H), 2.87 (dd, J=5.43 Hz, 1H), 4.28 (m, 1H), 7.21 (m, 2H), 7.29 (m, 4H), 7.41 (m, 2H), 7.46 (d, J=8.21 Hz, 2H), 7.57 (d, J=1.01 Hz, 1H), 7.67 (d, J=8.34 Hz, 1H), 7.81 (d, J=9.22 Hz, 1H).

Example 16-4

1H NMR (400 MHz, DMSO-d6) δ ppm 1.07 (d, J=7.07 Hz, 3H), 1.60 (m, 1H), 1.88 (m, 1H), 2.42 (m, 1H), 2.84 (m, 2H), 4.23 (m, 1H), 7.19 (d, J=3.66 Hz, 1H), 7.28 (m, 3H), 7.33 (t, 1H), 7.44 (t, 1H), 7.57 (d, J=8.34 Hz, 2H), 7.63 (d, J=8.08, 2H), 8.43 (d, J=8.84 Hz, 1H).

Example 16-5

1H NMR (400 MHz, DMSO-d6) δ ppm 1.07 (d, J=7.20 Hz, 3H), 1.72 (m, 1H), 1.91 (m, 1H), 2.42 (m, 1H), 2.85 (dd, J=7.45 Hz, 6.19 Hz, 1H), 2.96 (dd, J=7.96 Hz, 8.08 Hz, 1H), 4.32 (m, 1H), 7.30 (m, 3H), 7.43 (m, 2H), 7.54 (m, 2H), 7.62 (m, 2H), 8.33 (s, 1H), 9.03 (d, J=9.22 Hz, 1H), 9.51 (s, 1H), 12.04 (s, 1H), 14.16 (s, 1H).

Example 16-6

1H NMR (400 MHz, MeOD-d$_4$) δ ppm 1.16 (d, J=7.07 Hz, 3H), 1.53 (m, 7H), 1.96 (m, 3H), 2.55 (m, 3H), 2.74 (dd, J=7.83 Hz, 7.71 Hz, 1H), 2.84 (dd, J=6.95 Hz, 6.06 Hz, 1H), 4.17 (m, 1H), 7.30 (m, 3H), 7.42 (t, J=7.83 Hz, 2H), 7.51 (d, J=8.21 Hz, 2H), 7.56 (m, 2H).

Example 16-7

1H NMR (400 MHz, MeOD-d4) δ ppm 1.08 (d, J=7.07 Hz, 3H), 1.15 (d, J=7.07 Hz, 3H), 1.19 (t, J=7.07, 1H), 1.47 (m, 1H), 1.92 (m, 1H), 2.16 (dd, J=8.21 Hz, 8.21 Hz, 1H), 2.52 (dd, J=619 Hz, 6.32 Hz, 1H), 2.69 (dd, J=6.95 Hz, 7.83 Hz, 1H), 2.81 (m, 2H), 4.16 (m, 1H), 7.30 (m, 3H), 7.41 (m, 2H), 7.52 (m, 2H), 7.58 (m, 2H).

Example 16-8

1H NMR (400 MHz, DMSO-d6): 1H NMR (400 MHz, DMSO-d6): δ ppm 1.06-1.08 (d, J=7.07 Hz, 3H), 1.58-1.65 (m, 1H), 1.82-1.89 (m, 1H), 2.38-2.45 (m, 1H), 2.77-2.82 (m, 1H), 2.89-2.94 (m, 1H), 4.21-4.30 (m, 1H), 7.26-7.28 (m, 2H), 7.30-7.35 (m, 1H), 7.41-7.45 (m, 2H), 7.54-7.56 (m, 2H), 7.62-7.64 (m,2H), 7.67 (s, 1H), 7.89-7.91 (d, J=9.09 Hz, 1H), 12.01 (s, 1H).

Example 16-9

1H NMR (400 MHz, MeOD-d4): ppm 1.16-1.18 (d, J=7.07 Hz, 3H), 1.71-1.78 (m, 1H), 2.00-2.07 (m, 1H), 2.52-2.59 (m, 1H), 2.92-2.94 (m, 2H), 4.36-4.44 (m, 1H), 7.27-7.32 (m, 3 H), 7.37-7.41 (m, 2H), 7.50-7.58 (m, 5H), 8.61-8.63 (d, J=9.53, 1H).

Example 16-10

1H NMR (400 MHz, DMSO-d6) δ ppm 1.08 (d, J=7.07 Hz, 3 H) 1.34-1.46 (m, 1 H) 1.86 (ddd, J=13.64, 9.60, 4.04 Hz, 2 H) 1.91-2.06 (m, 2 H) 2.26-2.36 (m, 1 H) 2.43 (td, J=4.74, 2.65 Hz, 1 H) 2.70 (dd, J=13.39, 7.33 Hz, 1 H) 2.75-2.85 (m, 1 H) 3.04 (d, J=10.36 Hz, 1 H) 3.82 (d, J=15.41 Hz, 1 H) 3.96-4.10 (m, 2 H) 4.23 (br. s., 1 H) 7.27 (d, J=8.34 Hz, 2 H) 7.35 (t, J=7.33 Hz, 1 H) 7.46 (t, J=7.58 Hz, 2 H) 7.58 (d, J=8.08 Hz, 2 H) 7.61-7.67 (m, 2 H) 8.36 (d, J=8.59 Hz, 1 H).

Example 16-11

1H NMR (400 MHz, CD$_3$OD) δ ppm 1.18 (d, J=7.1 Hz, 3 H) 1.64-1.75 (m, 1 H) 2.00 (ddd, J=14.0, 10.0, 3.8 Hz, 1 H) 2.48-2.63 (m, 1 H) 2.86-2.91 (m, 2 H) 4.30-4.40 (m, 1 H) 7.25-7.33 (m, 4 H) 7.37-7.43 (m, 3 H) 7.52 (d, J=8.3 Hz, 2 H) 7.55-7.60 (m, 2 H)

Example 16-12

1H NMR (400 MHz, DMSO-d6) δ ppm 1.08 (d, J=7.07 Hz, 3H), 1.57 (m, 1H), 1.88 (m, 1H), 2.42 (m, 1H), 2.84 (m, 2H), 4.18 (m, 1H), 7.28 (d, J=8.21 Hz, 2H), 7.33 (t, 1H), 7.44 (t, 1H), 7.57 (d, J=8.21 Hz, 2H), 7.63 (d, J=8.08 Hz, 2H), 7.71 (d, J=3.92 Hz, 1H), 7.76 (d, J=3.92 Hz, 1H).

Example 17

Synthesis of 6-((1S,3R)-1-biphenyl-4-ylmethyl-3-carboxy-butylcarbamoyl)-4-oxo-4H-pyran-2-carboxylic acid

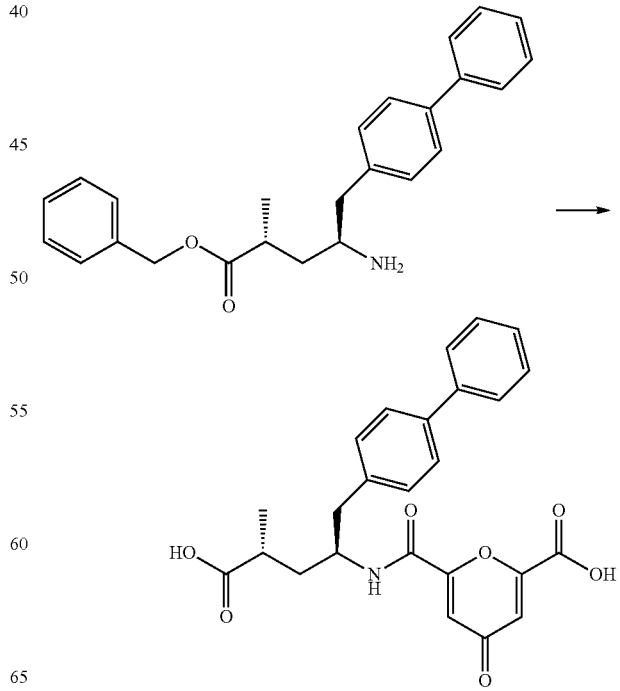

To a solution of 4-oxo-4H-pyran-2,6-dicarboxylic acid (99 mg. 0.535 mmol) in DMF (10 mL) is added HOBt (98 mg. 0.643 mmol) and EDCl (123 mg, 0.643 mmol) and the mixture is stirred at room temperature for 10 minutes. To this is then added (2R,4S)-4-amino-5-biphenyl-4-yl-2-methyl-pentanoic acid benzyl ester hydrochloride (Intermediate 30: 200 mg, 0.535 mmol) and triethylamine (0.224 mL, 1.61 mmol) and the mixture is stirred at room temperature for 48 hours. Water is added and the mixture is extracted with ethyl acetate. The organic phase is washed with water and brine and is dried over magnesium sulfate. The solvent is removed under reduced pressure and the residue is purified by preparative HPLC using a gradient of 10-100% MeCN/water (0.1% TFA) to elute the product, 6-((1S,3R)-3-benzyloxycarbonyl-1-biphenyl-4-ylmethyl-butylcarbamoyl)-4-oxo-4H-pyran-2-carboxylic acid. MS 540.2 (M+1). Next, to a solution of 6-((1S,3R)-3-benzyloxycarbonyl-1-biphenyl-4-ylmethyl-butylcarbamoyl)-4-oxo-4H-pyran-2-carboxylic acid (100 mg, 0.185 mmol) in methylene chloride (5 mL) is added BCl$_3$ (65.1 mg, 0.556 mmol) and the mixture is stirred at room temperature for 10 minutes. The mixture is acidified to pH 2-3 with aqueous 1M HCl and is extracted with ethyl acetate. The organic phase is washed with water and brine and is dried over magnesium sulfate. The solvent is removed under reduced pressure and the residue is purified by preparative HPLC using a gradient of 10-100% MeCN/water (0.1% TFA) to elute the product. The proper fractions are lyophilized to furnish 6-((1S,3R)-1-biphenyl-4-ylmethyl-3-carboxy-butylcarbamoyl)-4-oxo-4H-pyran-2-carboxylic acid. MS 450.1 (M+1); $^1$H-NMR (400 Hz, DMSO-d6); δ ppm 1.07 (d, J=7.07 Hz, 3H), 1.59 (m, 1H), 1.88 (m, 1H), 2.45 (m, 1H), 2.84 (d, J=6.69 Hz, 2H), 4.19 (m, 1H), 6.84 (s, 1H), 6.93 (s, 1H), 7.32 (dd, J=8.08 Hz, 6.57 Hz, 3H), 7.45 (t, J=7.83 Hz, 2H), 7.58 (d, J=8.21 Hz, 2H), 7.64 (d, J=7.33 Hz, 2H), 8.61 (d, J=8.72 Hz, 1H).

Example 18-1

Synthesis of (S)-1-((1S,3R)-1-biphenyl-4-ylmethyl-3-carboxy-butylcarbamoyl)-pyrrolidine-2-carboxylic acid

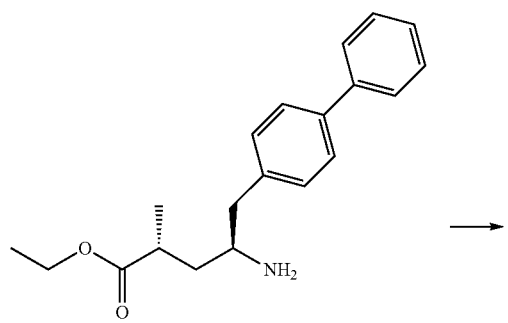

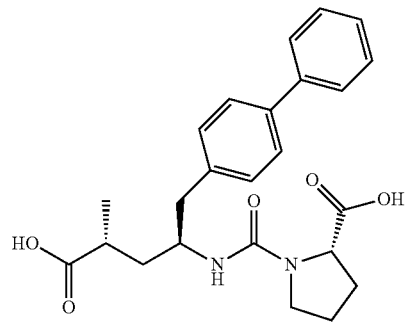

To a vigorously stirred 1:1 mixture of methylene chloride/8% aqueous NaHCO$_3$ (30 mL) at 0° C. is added triphosgene (114 mg, 0.384 mmol). After stirring the mixture at 0° C. for 5 minutes, (2R,4S)-4-amino-5-biphenyl-4-yl-2-methyl-pentanoic acid ethyl ester hydrochloride (Intermediate 29: 400 mg, 1.15 mmol) is added and stirring is continued for 15 minutes. The organic phase is separated and dried over sodium sulfate. The solvent is removed under reduced pressure to furnish (2R,4S)-5-biphenyl-4-yl-4-isocyanato-2-methyl-pentanoic acid ethyl ester.

Next, to a solution of (2R,4S)-5-biphenyl-4-yl-4-isocyanato-2-methyl-pentanoic acid ethyl ester (1.15 mmol) in methylene chloride (10 mL) is added (S)-pyrrolidine-2-carboxylic acid methyl ester (1.15 mmol) and diisopropylethylamine (2.3 mmol). The mixture is stirred at room temperature for 18 hours. The mixture is washed with aqueous 1M HCl and the organic phase is dried over sodium sulfate and the solvent is removed under reduced pressure. The residue is purified by column chromatography using hexane/methylene chloride to elute the product.

Next, to a solution of the obtained residue (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (S)-1-(1S,3R)-1-biphenyl-4-ylmethyl-3-carboxy-butylcarbamoyl)-pyrrolidine-2-carboxylic acid. HPLC Retention time 0.97 minutes (condition F); MS 425.3 (M+1); 1H NMR (400 MHz, DMSO-d6) δ ppm 1.03 (d, J=7.07 Hz, 3H), 1.43 (m, 1H), 1.71 (m, 1H), 1.86 (m, 3H), 2.09 (m, 1H), 2.45 (m, 1H), 2.66-2.83 (m, 2H), 3.84 (m, 1H), 6.00 (d, J=8.21 Hz, 1H), 7.27 (d, J=8.08 Hz, 2H), 7.34 (t, 1H), 7.45 (t, 2H), 7.57 (d, J=8.21 Hz, 2H), 7.65 (d, J=7.20, 2H).

Following compounds are prepared using similar procedure as example 18-1 with appropriate reagents and conditions:

| Example # | Product | Reagent | Hydrolysis Condition | HPLC-RT (condition) | MS (M + 1) |
|---|---|---|---|---|---|
| Example 18-2 | (2R,4S)-5-biphenyl-4-yl-4-(3-carboxymethyl-3-methyl-ureido)-2-methyl-pentanoic acid | Triethylamine instead of diisopropylethylamine | Aq. NaOH, EtOH, RT | 0.94 min. (F) | 399.3 |
| Example 18-3 | 1-((1S,3R)-1-biphenyl-4-ylmethyl-3-carboxy-butylcarbamoyl)-piperidine-3-carboxylic acid |  | Aq. NaOH, EtOH, RT | 1.15 min. (F) | 439.3 |

Example 18-2

1H NMR (400 MHz, DMSO-d6) δ ppm 1.02 (d, J=6.95 Hz, 3H), 1.43 (m, 1H), 1.70 (m, 1H), 2.45 (m, 1H), 2.66 (m, 1H), 2.78 (m, 2H), 2.79 (s, 2H), 3.81 (m, 3H), 7.26 (d, J=8.08 Hz, 2H), 7.34 (t, 1H), 7.45 (t, 2H), 7.56 (d, J=8.21 Hz, 2H), 7.65 (d, J=7.20 Hz, 2H).

Example 18-3

1H NMR (400 MHz, DMSO-d6) δ ppm 1.05 (d, J=7.07 Hz, 3H), 1.22 (m, 1H), 1.39-1.58 (m, 3H), 1.74 (m, 1H), 1.89 (m, 1H), 2.18 (m, 1H), 2.43 (m, 1H), 2.62-2.77 (m, 4H), 3.79 (t, 1H), 3.89 (m, 1H), 4.01 (m, 1H), 6.28 (d, J=8.34 Hz, 1H), 7.25 (d, J=7.83 Hz, 2H), 7.34 (t, 1H), 7.44 (t, 2H), 7.56 (d, J=8.34 Hz, 2H), 7.64 (d, J=7.20 Hz, 2H).

Example 19

Synthesis of (2R,4S)-5-biphenyl-4-yl-4-(3-carboxymethyl-ureido)-2-methyl-pentanoic acid

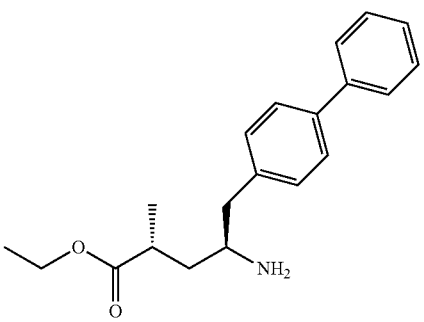

-continued

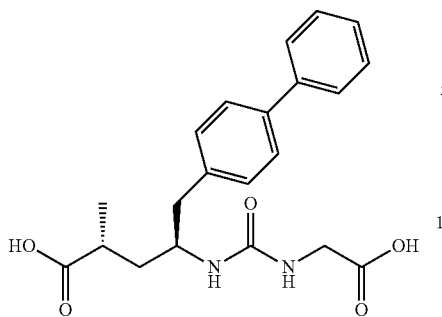

To a mixture of (2R,4S)-4-amino-5-biphenyl-4-yl-2-methyl-pentanoic acid ethyl ester hydrochloride (Intermediate 29: 50 mg, 0.161 mmol) and Isocyanato-acetic acid ethyl ester (0.161 mmol) in DMF (8 mL) is added pyridine (0.161 mmol) and the mixture is stirred at room temperature for 18 hours. Water is added and the mixture is extracted with ethyl acetate (3×). The combined organic layers are washed with water and brine then is dried over magnesium sulfate. The solvent is removed under reduced pressure to afford the ester product. This is used in the subsequent hydrolysis reaction.

Next, to a solution of the obtained residue (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (S)-1-((1S,3R)-1-biphenyl-4-ylmethyl-3-carboxy-butylcarbamoyl)-pyrrolidine-2-carboxylic acid. HPLC Retention time 0.91 minutes (condition F); MS 385.4 (M+1); 1H NMR (400 MHz, MeOD-d4) δ ppm 1.15 (d, J=7.20 Hz, 3H), 1.40 (m, 1H), 1.91 (m, 1H), 2.60 (m, 1H), 2.81 (d, J=6.32 Hz, 2H), 3.85 (d, J=1.89 Hz, 2H), 4.00 (m, 1H), 7.32 (m, 3H), 7.42 (m, 2H), 7.53 (m, 2H), 7.59 (m, 2H).

Example 20

Synthesis of 1-((1S,3R)-1-biphenyl-4-ylmethyl-3-carboxy-butylcarbamoyl)-1H-pyrazole-3-carboxylic acid

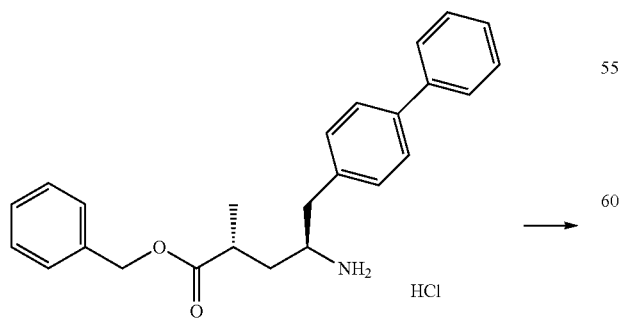

-continued

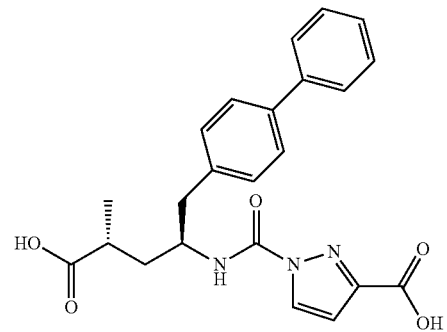 [SMILES: C[C@H](C[C@@H](Cc1ccc(-c2cccc(Cl)c2)cc1)NC(=O)c1ccc(C(=O)O)o1)C(=O)O]

To a vigorously stirred 1:1 mixture of methylene chloride/8% aqueous NaHCO₃ (6 mL) at 0° C. is added triphosgene (18 mg, 0.061 mmol). After stirring the mixture at 0° C. for 5 minutes, (2R,4S)-4-amino-5-biphenyl-4-yl-2-methyl-pentanoic acid benzyl ester hydrochloride (Intermediate 30: 75 mg, 0.183 mmol) is added and stirring is continued for 15 minutes. The organic phase is separated and dried over sodium sulfate. The solvent is removed under reduced pressure to furnish (2R,4S)-5-biphenyl-4-yl-4-isocyanato-2-methyl-pentanoic acid benzyl ester.

Next, to a solution of 1H-pyrazole-3-carboxylic acid (20.5 mg, 0.183 mmol) in DMF (1 mL) is added diisopropylethylamine (0.032 mL, 0.183 mmol). After 15 min a solution of the above (2R,4S)-5-biphenyl-4-yl-4-isocyanato-2-methyl-pentanoic acid benzyl ester in DMF (1 mL) is added dropwise and the mixture is stirred at room temperature for 18 hours. The mixture is purified by preparative HPLC using a gradient of 10% MeCN to 100% MeCN (0.1% TFA). Lyophilization of the appropriate fractions furnishes 1-((1S,3R)-3-benzyloxycarbonyl-1-biphenyl-4-ylmethyl-butylcarbamoyl)-1H-pyrazole-3-carboxylic acid.

Next, a solution of 1-((1S,3R)-3-benzyloxycarbonyl-1-biphenyl-4-ylmethyl-butylcarbamoyl)-1H-pyrazole-3-carboxylic acid (60 mg, 0.117 mmol) in EtOAc (10 mL) is hydrogenated over 10% Pd/C (40 mg) at 1 atm for 5 hours. The catalyst is filtered through Celite and the filtrate evaporated under reduced pressure. The residue is purified by preparative HPLC using a gradient of 10% MeCN to 100% MeCN (0.1% TFA). Lyophilization of the appropriate fractions furnishes 1-((1S,3R)-1-biphenyl-4-ylmethyl-3-carboxy-butylcarbamoyl)-1H-pyrazole-3-carboxylic acid. HPLC Retention time 0.96 minutes (condition F); MS 422.0 (M+1); 1H NMR (400 MHz, DMSO-d6) δ ppm 1.09 (d, J=7.07 Hz, 3H), 1.78 (m, 1H), 1.88 (m, 1H), 2.45 (m, 1H), 2.86 (m, 1H), 2.98 (m, 1H), 4.14 (m, 1H), 6.84 (d, J=2.65 Hz, 1H), 7.28 (d, J=8.34 Hz, 2H), 7.33 (t, 1H), 7.43 (t, 2H), 7.56

(d, J=8.34 Hz, 2H), 7.63 (d, J=7.07 Hz, 2H), 8.29 (d, J=2.78 Hz, 1H), 8.58 (d, J=9.09 Hz, 1H).

Example 21

(2R,4S)-5-biphenyl-4-yl-4-[(5-carbamoyl-thiophene-2-carbonyl)-amino]-2-methyl-pentanoic acid

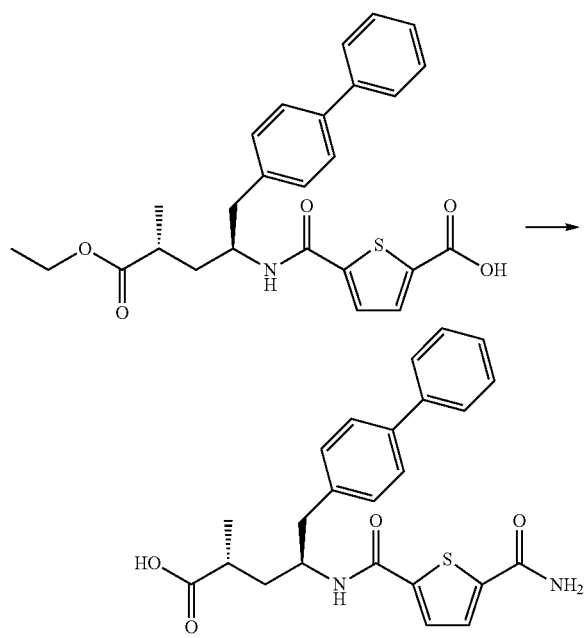

To a solution of 5-((1S,3R)-1-biphenyl-4-ylmethyl-3-ethoxycarbonyl-butylcarbamoyl)-thiophene-2-carboxylic acid (Example 26: 115 mg, 0.247 mmol) in THF (1 mL) at 0° C. is added diisopropylethylamine (63.8 mg, 0.494 mmol) followed by dropwise addition of a solution of isobutyl chloroformate (33.7 mg, 0.247 mmol) in THF (0.1 mL). The mixture is stirred at 0° C. for 30 minutes then ammonium hydroxide (0.3 mL of 14.8 M solution) is added. The mixture is allowed to warm to room temperature then aqueous 1M HCl (3 mL) is added. Most of the THF is removed under reduced pressure and the mixture is extracted with ethyl acetate. The organic phase is dried over sodium sulfate and the solvent is removed under reduced pressure to give (2R,4S)-5-biphenyl-4-yl-4-[(5-carbamoyl-thiophene-2-carbonyl)-amino]-2-methyl-pentanoic acid ethyl ester. MS 465.3 (M+1). Next, to a solution of (2R,4S)-5-biphenyl-4-yl-4-[(5-carbamoyl-thiophene-2-carbonyl)-amino]-2-methyl-pentanoic acid ethyl ester (115 mg, 0.248 mmol) in ethanol (8 mL) is added aqueous 1M NaOH (0.866 mL, 0.866 mmol) and the mixture is stirred at 50° C. for 3.5 hours. The ethanol is removed under reduced pressure and water is added to the residue. The resulting solution is acidified with aqueous 1M HCl and the resulting precipitate is filtered and washed with water. The solid is purified by preparative HPLC using 50% MeCN/water to elute the product. The appropriate fractions are lyophilized to give (2R,4S)-5-biphenyl-4-yl-4-[(5-carbamoyl-thiophene-2-carbonyl)-amino]-2-methyl-pentanoic acid. MS 437.2 (M+1); $^1$H-NMR (400 MHz, DMSO-d6); δ ppm 1.09 (d, J=7.20 Hz, 3H), 1.57 (m, 1H), 1.88 (m, 1H), 2.46 (m, 1H), 2.84 (m, 2H), 4.18 (m, 1H), 7.28 (d, J=8.21 Hz, 1H), 7.33 (t, 1H), 7.44 (t, 1H), 7.57 (d, J=8.21 Hz, 2H), 7.64 (d, J=7.33, 2H), 7.69 (m, 2H), 8.06 (s, 1H), 8.38 (d, J=8.59 Hz, 1H), 12.07 (s, broad, 1H).

Example 22

Synthesis of (2S,4S)-5-biphenyl-4-yl-4-((S)-3-carboxy-3-cyclohexyl-propionylamino)-2-methyl-pentanoic acid

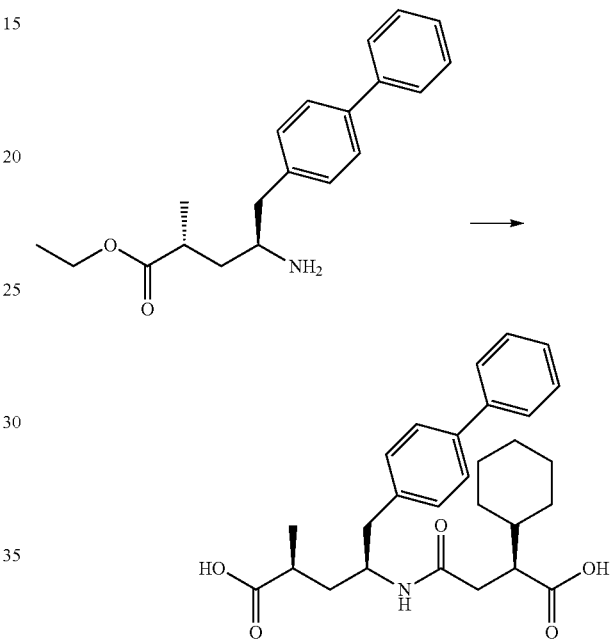

To a solution of (S)-2-cyclohexyl-succinic acid 1-methyl ester (0.144 mmol) in DMF (5 mL) is added HATU (0.216 mmol). After stirring the mixture at room temperature for 10 minutes, (2R,4S)-4-amino-5-biphenyl-4-yl-2-methyl-pentanoic acid ethyl ester hydrochloride (0.144 mmol) and triethylamine (0.359 mmol) is added and the mixture is stirred at room temperature for 18 hours. The mixture is poured into ethyl acetate and the mixture is washed with aqueous 1M HCl and brine. The organic phase is dried over magnesium sulfate and the solvent is removed under reduced pressure to give the ester product which is used directly in the subsequent hydrolysis reaction.

Next, to a solution of the obtained ester product (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified, and the diastereomers are separated, by preparative HPLC using a gradient of MeCN/water (0.1% TFA). The proper fractions are lyophilized to furnish (2S,4S)-5-biphenyl-4-yl-4-((S)-3-carboxy-3-cyclohexyl-propionylamino)-2-methyl-pentanoic acid. HPLC Retention time 1.21 minutes (condition F); MS 466.4 (M+1).

Example 23

Synthesis of (2R,4S)-5-biphenyl-4-yl-2-methyl-4-[(1H-tetrazole-5-carbonyl)-amino]-pentanoic acid

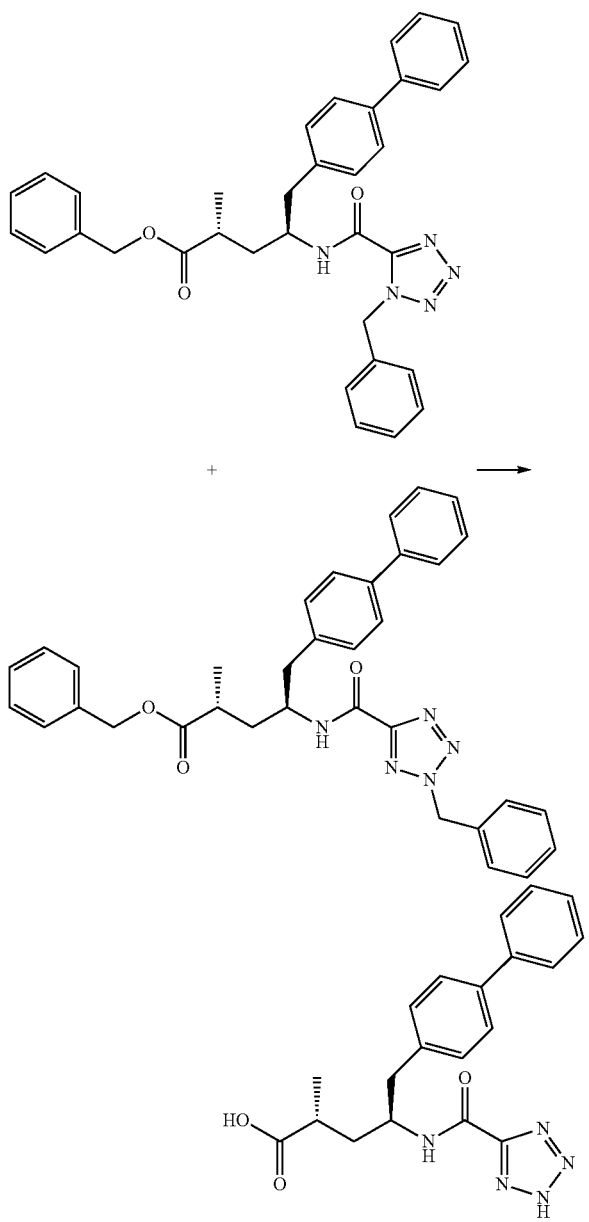

A mixture of Intermediate 31: (2R,4S)-4-[(1-benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester (126 mg, 0.225 mmol) in MeOH is hydrogenated with 10% Pd/C for 6 h. The reaction mixture is concentrated and purified by reverse phase HPLC to give (2R,4S)-5-biphenyl-4-yl-2-methyl-4-[(1H-tetrazole-5-carbonyl)-amino]-pentanoic acid. HPLC Retention time 1.16 minutes (condition H); MS 380.0 (M+1); $^1$H NMR (400 MHz, DMSO-d6) δ ppm 1.09 (d, J=7.20 Hz, 3H), 1.63-1.73 (m, 1H), 1.86-1.95 (m, 1H), 2.40-2.50 (m, 1H), 2.80-2.95 (m, 2H), 4.22-4.34 (m, 1H), 7.29-7.35 (m, 1H), 7.43 (dd, J=7.83, 7.83 Hz, 2H), 7.55 (d, J=10.23 Hz, 2H), 7.61-7.64 (2H, m), 9.16 (d, J=9.09 Hz, 1H), 12.03, (s, 1H).

Example 24

Synthesis of (2R,4S)-5-biphenyl-4-yl-4-(3,5-difluoro-4-hydroxy-benzoylamino)-2-methyl-pentanoic acid

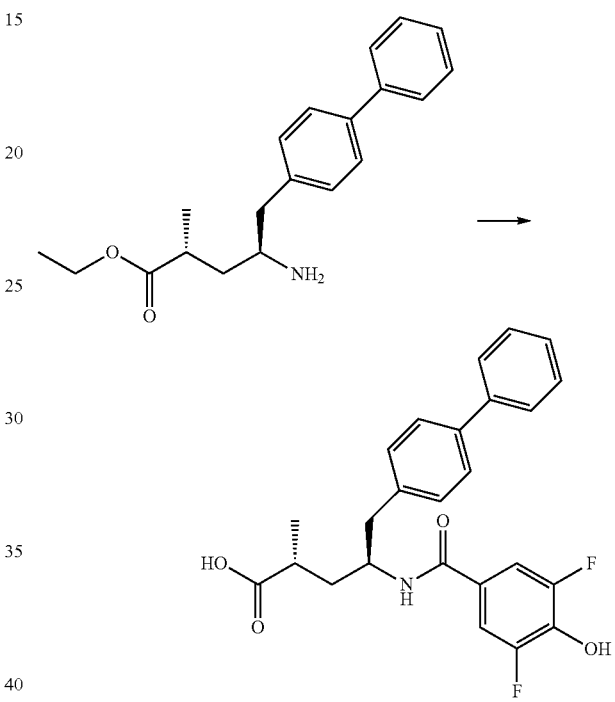

To a solution of (2R,4S)-4-amino-5-biphenyl-4-yl-2-methyl-pentanoic acid ethyl ester hydrochloride salt (200 mg, 0.58 mmol) in CH$_2$Cl$_2$ (2 mL) and DMF (2 mL) at rt is added 3,5-difluoro-4-methoxy benzoic acid (108 mg, 0.58 mmol) followed by an addition of TEA (0.32 mL, 2.3 mmol) and HATU (262 mg, 0.69 mmol). The mixture is stirred at r.t. for 4 hours and quenched with saturated NaHCO$_3$ and diluted in ethyl acetate. The organic layer is washed with water, brine, dried over MgSO$_4$, filtered, and concentrated under reduced pressure. The obtained material is purified by preparative silica gel thin-layer chromatography plates (eluent: EtOAc/hepane=3/2) to give 265 mg of (2R,4S)-5-biphenyl-4-yl-4-(3,5-difluoro-4-methoxy-benzoylamino)-2-methyl-pentanoic acid ethyl ester.

Next, to a solution of (2R,4S)-5-biphenyl-4-yl-4-(3,5-difluoro-4-methoxy-benzoylamino)-2-methyl-pentanoic acid ethyl ester (125 mg, 0.260 mmol) in DCM (2.6 mL) is slowly added BBr3 (2.60 mL, 2.60 mmol) under nitrogen. The reaction is stirred for 18 hours at rt. The reaction is quenched with MeOH, diluted with EtOAc, washed with H$_2$O and brine, dried over MgSO$_4$, and concentrated under reduced pressure. The obtained material is purified by preparative silica gel thin-layer chromatography (7% MeOH in DCM) to give 100 mg (2R,4S)-5-biphenyl-4-yl-4-(3,5-difluoro-4-hydroxy-benzoylamino)-2-methyl-pentanoic acid ethyl ester. Next, to a solution of (2R,4S)-5-biphenyl-4-yl-4-(3,5-difluoro-4-hydroxy-benzoylamino)-2-methyl-pentanoic acid ethyl ester (30 mg, 0.064 mmol) in MeOH (2 mL) at room temperature is added aqueous 1M NaOH (4 mL, 4.0 mmol). After stirring for 1 hour the reaction is quenched with aqueous 1M HCl (4 mL, 4.0 mmol). The mixture is concentrated under reduced pressure and filtered to remove NaCl salt. The obtained residue is purified by preparative silica gel thin-layer chromatography (7% MeOH in DCM) to give 17.1 mg of (2R,4S)-5-biphenyl-4-yl-4-(3,5-difluoro-4-hydroxy-benzoylamino)-2-methyl-pentanoic acid. HPLC Retention time 1.56 minutes (condition G); MS 440 (M+1); 1H NMR (400 MHz, ACETONITRILE-d3) δ ppm 1.19 (d, J=7.07 Hz, 3 H) 1.55 (ddd, J=14.27, 10.74, 3.79 Hz, 1 H) 1.90-1.96 (m, 1 H) 2.54-2.71 (m, 1 H) 2.91 (dd, J=6.69, 3.16 Hz, 2 H) 4.25-4.43 (m, 1 H) 6.49 (d, J=9.60 Hz, 2 H) 6.93 (d, J=8.84 Hz, 1 H) 7.33-7.42 (m, 3 H) 7.49 (t, J=7.71 Hz, 2 H) 7.61 (d, J=8.34 Hz, 2 H) 7.67 (dd, J=8.34, 1.26 Hz, 2 H).

Example 25-1

Synthesis of (2R,4S)-5-Biphenyl-4-yl-4-(3-carboxymethyl-benzoylamino)-2-methyl-pentanoic acid and Example 25-2

Synthesis of 3-[((1S,3R)-1-Biphenyl-4-ylmethyl-3-carboxy-butylcarbamoyl)-methyl]-benzoic acid

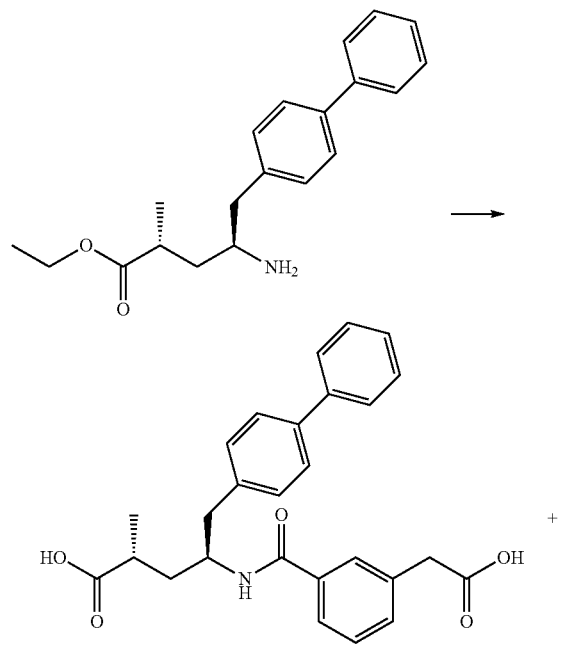

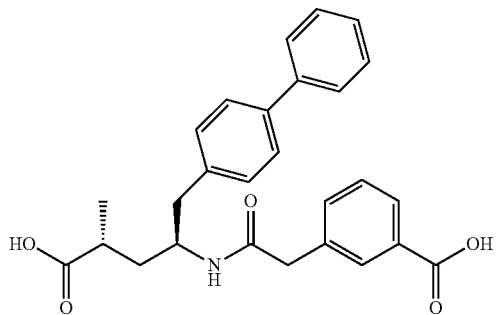

To a solution of Intermediate 29 (100 mg, 0.287 mmol), Intermediate 21 (57 mg, 0.316 mmol), EDCl (71.6 mg, 0.374 mmol) and HOBt (50.5 mg, 0.374 mmol) in DMF (3 mL) is added triethylamine (116 mg, 0.159 mL) and the mixture is stirred at room temperature for 18 hrs. Any insoluble material is removed by filtration and the solvent is removed under reduced pressure.

Next, the above residue is dissolved in EtOH (8 mL) and 1N NaOH (1.27 mL, 1.27 mmol) is added. The mixture is stirred at 50° C. for 5 hrs then the solvent is removed under reduced pressure. Water (5 mL) is added and the mixture is acidified with 1N HCl. The mixture is extracted with EtOAc and the organic phase is dried over sodium sulfate. The solvent is removed under reduced pressure and the residue is purified by preparative HPLC using a gradient of 10% MeCN/water to 100% MeCN (0.1% TFA) to elute the products (2R,4S)-5-biphenyl-4-yl-4-(3-carboxymethyl-benzoylamino)-2-methyl-pentanoic acid, HPLC Retention time 1.02 minutes (condition C); MS 446.3 (M+1); 1H NMR (400 MHz, DMSO-d6) δ ppm 1.08 (d, J=7.07 Hz, 3H), 1.58 (m, 1H), 1.88 (m, 1H), 2.46 (m, 1H), 2.79-2.90 (m, 2H), 3.62 (s, 2H), 4.25 (m, 1H), 7.29 (d, J=8.08 Hz, 2H), 7.34 (d, J=7.33 Hz, 1H), 7.40 (m, 2H), 7.43 (t, 2H), 7.57 (d, J=8.08 Hz, 2H), 7.63 (d, J=8.08 Hz, 2H), 7.68 (m, 2H), 8.22 (d, J=8.34 Hz, 1H) and 3-[((1S,3R)-1-biphenyl-4-ylmethyl-3-carboxy-butylcarbamoyl)-methyl]-benzoic acid, HPLC Retention time 1.03 minutes (condition C); MS 446.3 (M+1); 1H NMR (400 MHz, DMSO-d6) δ ppm 1.05 (d, J=7.07 Hz, 3H), 1.36 (m, 1H), 1.81 (m, 1H), 2.41 (m, 1H), 2.63-2.75 (m, 2H), 3.37-3.46 (m, 2H), 3.94 (m, 1H), 7.15 (d, J=8.08 Hz, 2H), 7.32-7.50 (m, 7H), 7.61 (d, J=7.33 Hz, 2H), 7.80 (m, 1H), 7.88 (s, 1H), 8.00 (d, J=8.59 Hz, 1H).

Following compounds are prepared and isolated after the coupling reaction and prior to the hydrolysis reaction described in the above example:

| Example # | Product | Coupling reaction described in | HPLC-RT (condition) | MS (M + 1) |
|---|---|---|---|---|
| Example 26 | 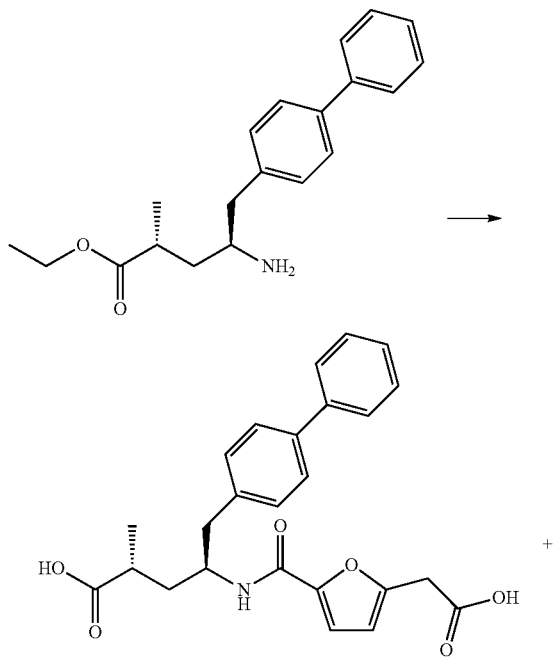

5-((1S,3R)-1-biphenyl-4-ylmethyl-3-ethoxycarbonyl-butylcarbamoyl)-thiophene-2-carboxylic acid | Example 16-12 | 1.23 min. (F) | 466.3 |

Example 26-1

Synthesis of (2R,4S)-5-Biphenyl-4-yl-4-[(5-carboxymethyl-furan-2-carbonyl)-amino]-2-methyl-pentanoic acid and

Example 26-2

Synthesis of 5-[((1S,3R)-1-Biphenyl-4-ylmethyl-3-carboxy-butylcarbamoyl)-methyl]-furan-2-carboxylic acid The title compounds are prepared analogous to Example 25-1 and Example 25-2 using Intermediates 29 and 36.

(2R,4S)-5-biphenyl-4-yl-4-[(5-carboxymethyl-furan-2-carbonyl)-amino]-2-methyl-pentanoic acid, HPLC Retention time 1.13 minutes (condition A); MS 436.3 (M+1); 1H NMR (400 MHz, DMSO-d6) δ ppm 1.07 (d, J=7.07 Hz, 3H), 1.55 (m, 1H), 1.85 (m, 1H), 2.41 (m, 1H), 2.75-2.88 (m, 2H), 3.74 (s, 2H), 4.19 (m, 1H), 6.39 (d, J=3.28 Hz, 1H), 7.01 (d, J=3.28 Hz, 1H), 7.27 (d, J=8.08 Hz, 2H), 7.33 (t, 1H), 7.44 (t, 2H), 7.56 (d, J=8.34 Hz, 2H), 7.64 (d, J=7.33 Hz, 2H), 8.08 (d, J=8.59 Hz, 1H).

5-[((1S,3R)-1-biphenyl-4-ylmethyl-3-carboxy-butylcarbamoyl)-methyl]-furan-2-carboxylic acid, HPLC Retention time 1.03 minutes (condition A); MS 436.3 (M+1); 1H NMR (400 MHz, DMSO-d6) δ ppm 1.06 (d, J=7.07 Hz, 3H), 1.36 (m, 1H), 1.81 (m, 1H), 2.42 (m, 1H), 2.67-2.78 (m, 2H), 3.54 (s, 2H), 3.97 (m, 1H), 6.30 (d, J=3.28 Hz, 1H), 7.12 (d, J=3.28 Hz, 1H), 7.23 (d, J=8.08 Hz, 2H), 7.34 (t, 1H), 7.45 (t, 2H), 7.56 (d, J=8.34 Hz, 2H), 7.64 (d, J=7.33 Hz, 2H), 8.05 (d, J=8.34 Hz, 1H).

Example 28

(2R,4S)-4-[(5-Carboxymethyl-furan-2-carbonyl)-amino]-5-(3'-chloro-biphenyl-4-yl)-2-methyl-pentanoic acid The title compound is prepared analogous to Example 26-1 and Example 26-2 using Intermediates 36 and 39.

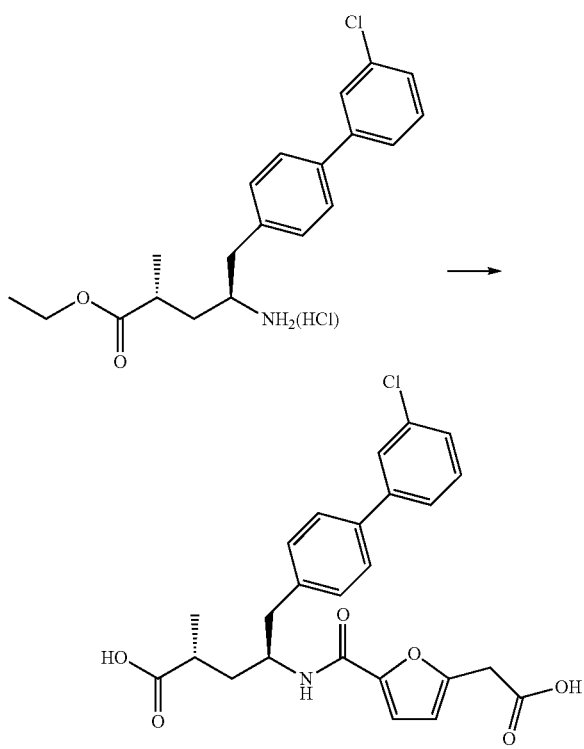

HPLC Retention time 1.37 minutes (condition A); MS (m+1)=470.0; 1H NMR (400 MHz, DMSO-d6) δ ppm 1.07 (d, J=7.07 Hz, 3H), 1.55 (m, 1H), 1.85 (m, 1H), 2.41 (m, 1H), 2.76-2.88 (m, 2H), 3.74 (s, 2H), 4.19 (m, 1H), 6.39 (d, J=3.28 Hz, 1H), 7.01 (d, J=3.28 Hz, 1H), 7.28 (d, J=8.08 Hz, 2H), 7.39 (m, 1H), 7.46 (t, 2H), 7.59-7.63 (m, 3H), 7.69 (m, 1H), 8.09 (d, J=8.84 Hz, 1H)

Example 29-1

Synthesis of (2R,4S)-5-(3'-Chloro-biphenyl-4-yl)-4-[(3-hydroxy-isoxazole-5-carbonyl)-amino]-2-methyl-pentanoic acid and Example 29-2

Synthesis of (2S,4S)-5-(3'-Chloro-biphenyl-4-yl)-4-[(3-hydroxy-isoxazole-5-carbonyl)-amino]-2-methyl-pentanoic acid

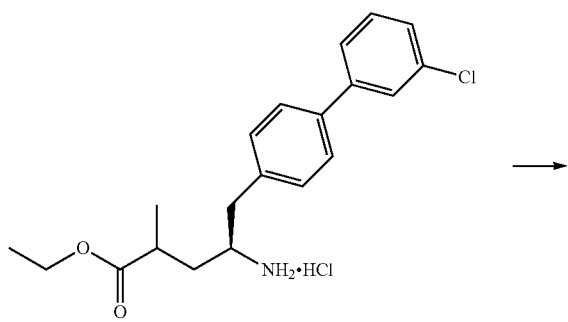

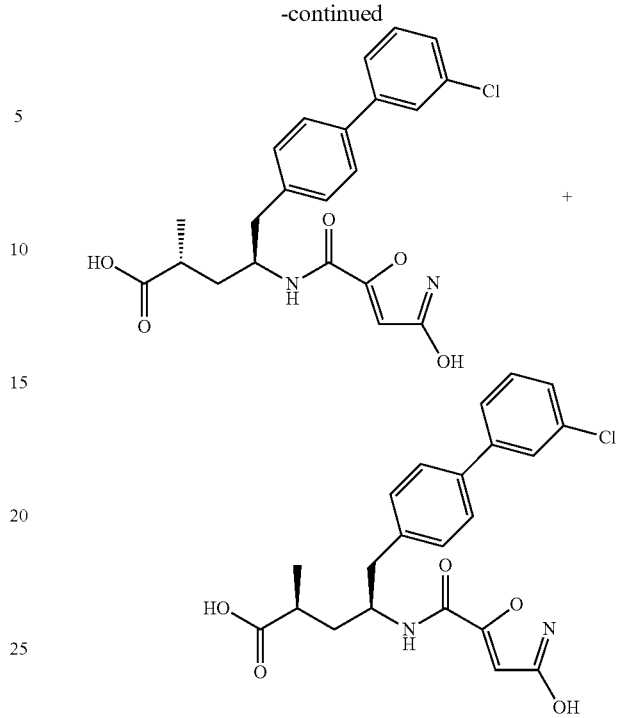

To a solution of 3-hydroxy-isoxazole-5-carboxylic acid (Intermediate 19) (74.6 mg, 0.578 mmol), HATU (264 mg, 0.694 mmol) in DMF (3 mL) is added pyridine (0.14 mL, 1.735 mmol) and the resulting mixture is stirred at room temperature for 15 minutes. Then (S)-4-amino-5-(3'-chloro-biphenyl-4-yl)-2-methyl-pentanoic acid ethyl ester hydrochloride (Intermediate 39) (200 mg, 0.578 mmol) is added and the mixture is stirred at room temperature for 2 hours. Any insoluble material is filtered and the filtrate purified by preparative HPLC using a gradient of 10% MeCN/water to 100% MeCN (0.1% TFA). The diastereomeric mixture is further purified by chiral HPLC on a Chirapak IA column using heptane/ethanol (80:20) (0.1% TFA) to elute each diastereomer, (2R,4S)-5-(3'-chloro-biphenyl-4-yl)-4-[(3-hydroxy-isoxazole-5-carbonyl)-amino]-2-methyl-pentanoic acid ethyl ester and (2S,4S)-5-(3'-chloro-biphenyl-4-yl)-4-[(3-hydroxy-isoxazole-5-carbonyl)-amino]-2-methyl-pentanoic acid ethyl ester.

Next, to a solution of (2R,4S)-5-(3'-chloro-biphenyl-4-yl)-4-[(3-hydroxy-isoxazole-5-carbonyl)-amino]-2-methyl-pentanoic acid ethyl ester (73 mg, 0.16 mmol) in ethanol (4 mL) is added 1N NaOH (2 mL) and the resulting mixture is stirred at room temperature for 2 hours. The mixture is acidified with 1N HCl and the solvent is removed under reduced pressure. The resulting residue is purified by preparative HPLC using a gradient of 10% MeCN/water to 100% MeCN (0.1% TFA) to give (2R,4S)-5-(3'-chloro-biphenyl-4-yl)-4-[(3-hydroxy-isoxazole-5-carbonyl)-amino]-2-methyl-pentanoic acid; HPLC Retention time 1.05 minutes (condition A): MS 429.1 (M+1); 1H NMR (400 MHz, DMSO-d6) δ ppm 1.07 (d, 3 H) 1.58 (ddd, J=13.89, 9.98, 4.42 Hz, 1 H) 1.87 (ddd, J=13.71, 9.66, 3.92 Hz, 1 H) 2.41 (ddd, J=9.54, 7.14, 4.55 Hz, 1 H) 2.82 (dd, J=6.69, 3.41 Hz, 2 H) 4.10-4.24 (m, 1 H) 6.50 (s, 1 H) 7.28 (d, J=8.34 Hz, 2 H) 7.36-7.42 (m, 1 H) 7.47 (t, J=7.83 Hz, 1 H) 7.58-7.65 (m, 3 H) 7.70 (t, J=1.89 Hz, 1 H) 8.66 (d, J=8.59 Hz, 1 H).

The second diastereomer, (2S,4S)-5-(3'-chloro-biphenyl-4-yl)-4-[(3-hydroxy-isoxazole-5-carbonyl)-amino]-2-methyl-pentanoic acid is prepared from the hydrolysis of (2R,4S)-5-(3'-chloro-biphenyl-4-yl)-4-[(3-hydroxy-isoxazole-5-carbonyl)-amino]-2-methyl-pentanoic acid ethyl ester analogous to the above example; HPLC Retention time 1.17 minutes (condition A): MS 429.3 (M+1); 1H NMR (400 MHz, DMSO-d6) δ ppm 1.06 (d, J=7.07 Hz, 3 H) 1.55 (ddd, J=13.64, 9.47, 3.92 Hz, 1 H) 1.96 (ddd, J=13.83, 10.67, 4.80 Hz, 1 H) 2.32 (ddd, J=9.09, 7.07, 5.05 Hz, 1 H) 2.86 (d, J=7.07 Hz, 2 H) 4.17-4.31 (m, 1 H) 6.50 (s, 1 H) 7.30 (d, J=8.34 Hz, 2 H) 7.36-7.43 (m, 1 H) 7.46 (t, J=7.83 Hz, 1 H) 7.56-7.65 (m, 3 H) 7.70 (t, J=1.89 Hz, 1 H) 8.68 (d, J=9.09 Hz, 1 H) 11.67 (s, 1 H).

The following compounds are prepared using similar procedure as example 29-1 with appropriate reagents and conditions:

| Example # | Product | Reagents | Hydrolysis Condition | HPLC-RT (condition) | MS (M + 1) |
|---|---|---|---|---|---|
| Example 30-1 | 5-[(1S,3R)-3-Carboxy-1-(3'-chloro-biphenyl-4-ylmethyl)-butylcarbamoyl]-1H-pyrazole-3-carboxylic acid | | Aq. NaOH, EtOH, RT | 1.13 min. (C) | 456.3 |
| Example 30-2 | 5-[(1S,3R)-3-Carboxy-1-(3'-chloro-biphenyl-4-ylmethyl)-butylcarbamoyl]-furan-2-carboxylic acid | | Aq. NaOH, EtOH, RT | 1.00 min. (C) | 456.1 |

Example 31

Synthesis of (S)-2-[(S)-2-(3'-chloro-biphenyl-4-yl)-1-(1H-tetrazol-5-ylcarbamoyl)-ethylamino]-propionic acid ethyl ester

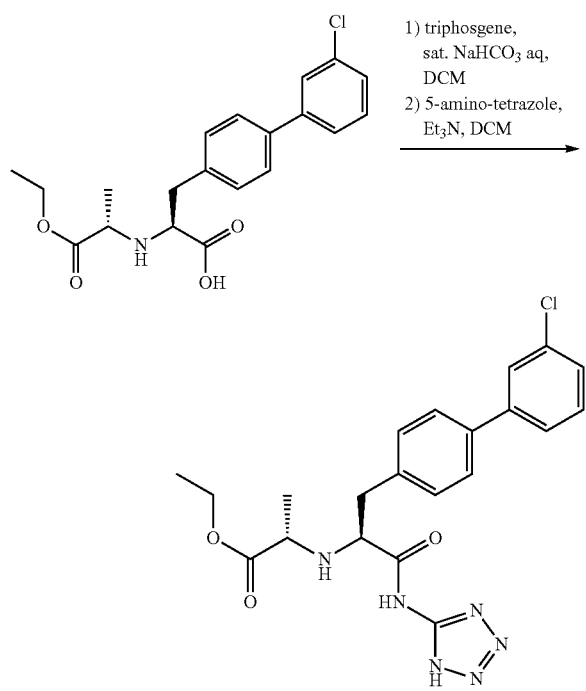

To a suspension of (S)-3-(3'-chloro-biphenyl-4-yl)-2-((S)-1-ethoxycarbonyl-ethylamino)-propionic acid (Intermediate 42: 4.0 g, 10.84 mmol) in dichloromethane (60 mL) and saturated aqueous $NaHCO_3$ (10 mL) was added triphosgene (1.90 g, 6.39 mmol). After vigorously stirred for 0.5 hour, the reaction mixture was diluted with EtOAc and partially concentrated under reduced pressure. Excess of triphosgene was quenched by adding saturated aqueous $NaHCO_3$ and stirred for 0.5 hour. The mixture was extracted with EtOAc and washed with brine. The organic layer was dried over $Na_2SO_4$ and concentrated under reduced pressure. The obtained residue was dissolved in dichloromethane (50 mL). To the mixture was added triethylamine (1.93 mL, 13.8 mmol) and 5-amino-1H-tetrazole (1.18 g, 13.84 mmol) at 0° C., and the reaction mixture was gradually warmed to room temperature.

After stirred for 2 hours, the reaction mixture was concentrated and purified by silica gel column chromatography (eluent: 10% MeOH in dichloromethane) to give a mixture of the desired trans isomer product and the cis isomer. The obtained material was re-crystallized from $CH_3CN$ three times to give (S)-2-[(S)-2-(3'-chloro-biphenyl-4-yl)-1-(1H-tetrazol-5-yl-carbamoyl)-ethylamino]-propionic acid ethyl ester. $^1$H NMR (400 MHz, DMSO-d6) δ 1.11 (t, 3H, J=7.1 Hz), 1.15 (d, 3H, J=6.8 Hz), 2.89 (dd, 1H, J=8.1, 13.7 Hz), 3.02 (dd, 1H, J=5.8, 14.0 Hz), 3.27-3.36 (m, 1H), 3.75-3.83 (m, 1H), 4.01 (dd, 2H, J=7.1, 14.1 Hz), 7.34 (d, 2H, J=8.3 Hz), 7.38-7.42 (m, 1H), 7.47 (dd, 1H, J=7.8, 7.8 Hz), 7.60-7.65 (m, 3H), 7.69 (dd, 1H, J=1.8, 1.8 Hz); MS: m/z (MH$^+$) 443; HRMS: calculated for $C_{22}H_{23}ClN_6O_3$ (M)$^+$442.1, found 442.1; EA: Calculated for C21H23ClN6O3: C, 56.95; H, 5.23; N, 18.97. Found: C, 56.88; H, 5.07; N, 19.1.

Chiral HPLC retention time=9.26 min. [condition: Daicel CHIRALCEL OJ-H 4.6×100 mm); flow rate=1 mL/min.; eluent: 20% EtOH (with 0.1% TFA) in heptane].

Following compounds were prepared using similar procedure as example 31 with appropriate intermediates:

| Example # | Product | Intermediates | HPLC-RT (condition) | MS (M + 1) |
|---|---|---|---|---|
| Example 31-1 | (S)-2-[(S)-2-(2',5'-Dichloro-biphenyl-4-yl)-1-(1H-tetrazol-5-ylcarbamoyl)-ethylamino]-propionic acid tert-butyl ester | (S)-2-((S)-1-tert-Butoxycarbonyl-ethylamino)-3-(2',5'-dichloro-biphenyl-4-yl)-propionic acid Intermediate 43 And 5-amino-1H-tetrazole | 1.38 min (C) | 505 |

-continued

| Example # | Product | Intermediates | HPLC-RT (condition) | MS (M + 1) |
|---|---|---|---|---|
| Example 31-2 | 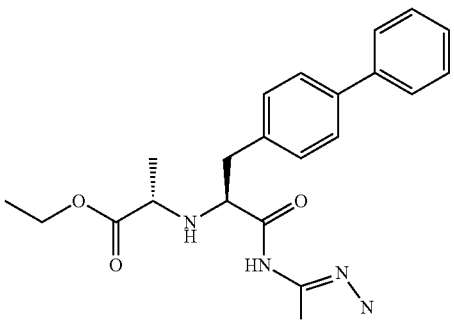<br>(S)-2-[(S)-2-Biphenyl-4-yl-1-(1H-tetrazol-5-ylcarbamoyl)-ethylamino]-propionic acid ethyl ester | 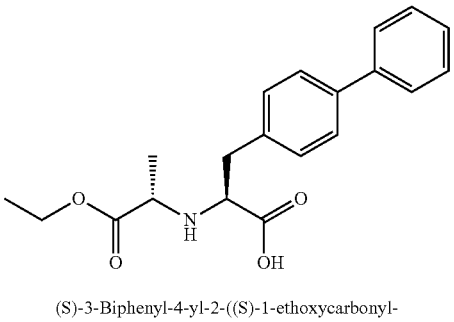<br>(S)-3-Biphenyl-4-yl-2-((S)-1-ethoxycarbonyl-ethylamino)-propionic acid<br>Intermediate 43-1<br>And<br>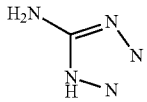<br>5-amino-1H-tetrazole | 1.55 min (I) | 409 |
| Example 31-3 | 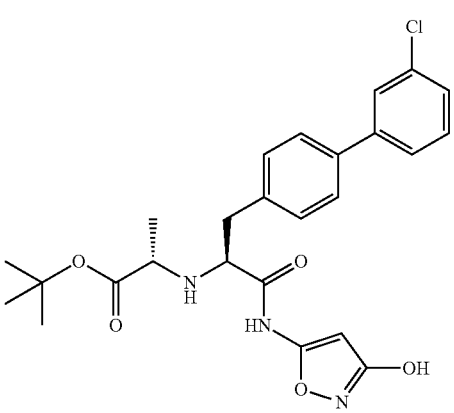 [SMILES: C[C@H](N[C@@H](Cc1ccc(-c2cccc(Cl)c2)cc1)C(=O)Nc1cc(O)no1)C(=O)OC(C)(C)C]<br>(S)-2-[(S)-2-(3'-Chloro-biphenyl-4-yl)-1-(3-hydroxy-isoxazol-5-ylcarbamoyl)-ethylamino]-propionic acid tert-butyl ester | 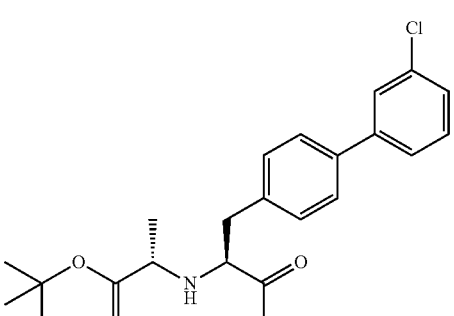<br>(S)-2-((S)-1-tert-Butoxycarbonyl-ethylamino)-3-(3'-chloro-biphenyl-4-yl)-propionic acid<br>And<br>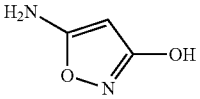<br>5-amino-isoxazol-3-ol | 1.48 min (J) | 486 |
| Example 31-4 | 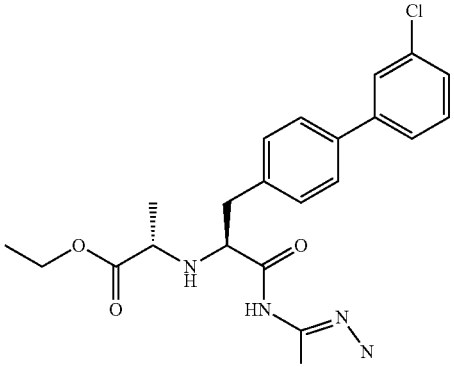 | 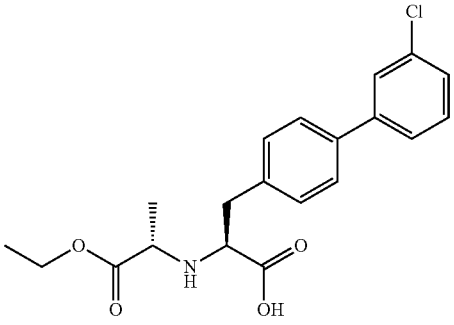 [SMILES: CCOC(=O)[C@H](C)N[C@@H](Cc1ccc(-c2cccc(Cl)c2)cc1)C(=O)O]<br>(S)-3-(3'-Chloro-biphenyl-4-yl)-2-((S)-1-ethoxycarbonyl-ethylamino)-propionic acid<br>Intermediate 42<br>And | 1.12 min (J) | 457 |

Example 31-7

(S)-2-{(S)-2-(3'-chloro-biphenyl-4-yl)-1-[methyl-(1H-tetrazol-5-yl)-carbamoyl]-ethylamino}-propionic acid ethyl ester

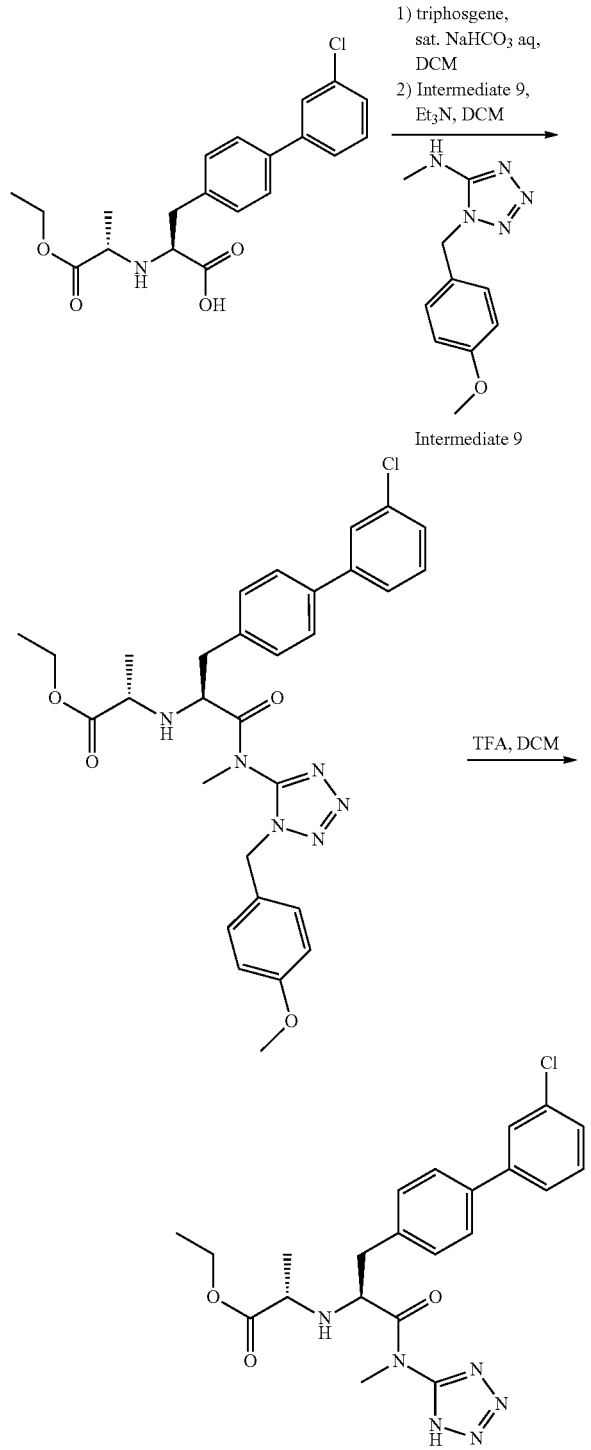

To a suspension of (S)-3-(3'-chloro-biphenyl-4-yl)-2-((S)-1-ethoxycarbonyl-ethylamino)-propionic acid (Intermediate 42: 225 mg, 0.599 mmol) in dichloromethane (4 mL) and saturated aqueous NaHCO$_3$ (1 mL) was added triphosgene (178 mg, 0.599 mmol). After vigorously stirred for 10 min, the reaction mixture was diluted with EtOAc and partially concentrated under reduced pressure. Excess of triphosgene was quenched by adding saturated aqueous NaHCO$_3$ and stirred for 0.5 hour. The mixture was extracted with EtOAc and washed with brine. The organic layer was dried over Na$_2$SO$_4$ and concentrated under reduced pressure. The obtained residue was dissolved in dichloromethane (5 mL). To the mixture were added triethylamine (0.167 mL, 1.197 mmol) and [1-(4-methoxy-benzyl)-1H-tetrazol-5-yl]-methyl-amine (197 mg, 0.898 mmol) and stirred at 45° C. overnight. Additional triethylamine (0.167 mL, 1.197 mmol) and [1-(4-methoxy-benzyl)-1H-tetrazol-5-yl]-methyl-amine (197 mg, 0.898 mmol) were added and stirred at 45° C. for 30 hours. The reaction mixture was concentrated under reduced pressure and purified by silica gel column chromatography (eluent: 10% MeOH in DCM) to give (S)-2-((S)-2-(3'-chloro-biphenyl-4-yl)-1-{[1-(4-methoxy-benzyl)-1H-tetrazol-5-yl]-methyl-carbamoyl}-methylamino)-propionic acid ethyl ester. MS: m/z (WO 577; HPLC retention time 1.36 min (HPLC condition J).

Next, (S)-2-(S)-2-(3'-chloro-biphenyl-4-yl)-1-{[1-(4-methoxy-benzyl)-1H-tetrazol-5-yl]-methyl-carbamoyl}-ethylamino)-propionic acid ethyl ester (260 mg, 0.451 mmol) was dissolved in TFA (5 mL) and DCM (5 mL) and stirred at 50° C. for 12 hours and at 75° C. for 5 hours. The reaction mixture was concentrated under reduced pressure to give (S)-2-{(S)-2-(3'-chloro-biphenyl-4-yl)-1-[methyl-(1H-tetrazol-5-yl)-carbamoyl]-ethylamino}-propionic acid ethyl ester. MS: m/z (MH$^+$) 457; HPLC retention time 0.95 min (HPLC condition J).

Following compounds were prepared using similar procedure as example 31 with appropriate intermediates:

| Example # | Product | Intermediates | HPLC-RT (condition) | MS (M + 1) |
|---|---|---|---|---|
| Example 31-8 | 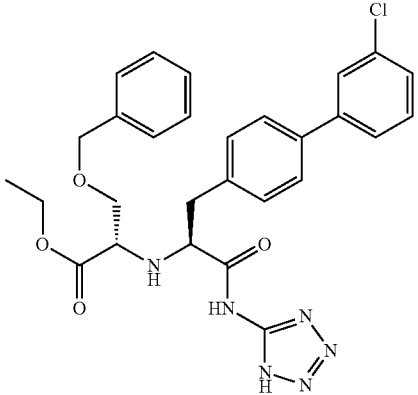 [SMILES: CCOC(=O)[C@H](COCc1ccccc1)N[C@@H](Cc1ccc(-c2cccc(Cl)c2)cc1)C(=O)Nc1nnn[nH]1]<br>(S)-3-benzyloxy-2-[(S)-2-(3'-chloro-biphenyl-4-yl)-1-(1H-tetrazol-5-ylcarbamoyl)-ethylamino]-propionic acid ethyl ester | 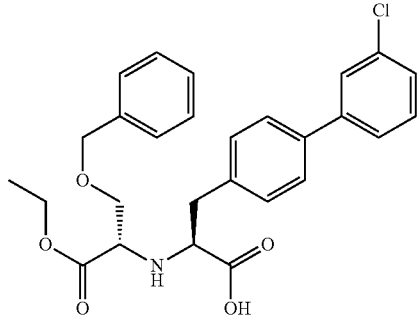 [SMILES: CCOC(=O)[C@H](COCc1ccccc1)N[C@@H](Cc1ccc(-c2cccc(Cl)c2)cc1)C(=O)O]<br>intermedaite 44-1<br>(S)-2-((S)-2-benzyloxy-1-ethoxycarbonyl-ethylamino)-3-(3'-chloro-biphenyl-4-yl)-propionic acid<br>And<br>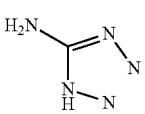<br>5-amino-1H-tetrazole | 1.31 min (J) | 549 |
| Example 31-9 | 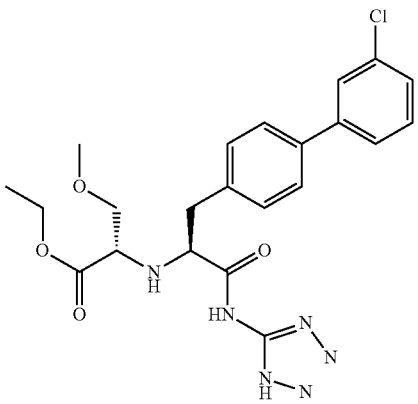 [SMILES: CCOC(=O)[C@H](COC)N[C@@H](Cc1ccc(-c2cccc(Cl)c2)cc1)C(=O)N/C(=N/N)NN]<br>(S)-2-[(S)-2-(3'-chloro-biphenyl-4-yl)-1-(1H-tetrazol-5-ylcarbamoyl)-ethylamino]-3-methoxy-propionic acid ethyl ester | 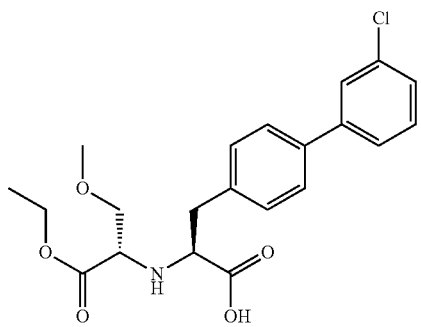 [SMILES: CCOC(=O)[C@H](COC)N[C@@H](Cc1ccc(-c2cccc(Cl)c2)cc1)C(=O)O]<br>Intermediate 44-2<br>(S)-3-(3'-chloro-biphenyl-4-yl)-2-((S)-1-ethoxycarbonyl-2-methoxy-ethylamino)-propionic acid<br>And<br>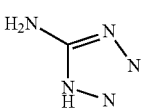<br>5-amino-1H-tetrazole | 1.29 min (I) | 471 |

Example 31-10

(S)-2-[(S)-2-(3'-chloro-biphenyl-4-yl)-1-(1H-tetrazol-5-ylcarbamoyl)-ethoxy]-propionic acid ethyl ester

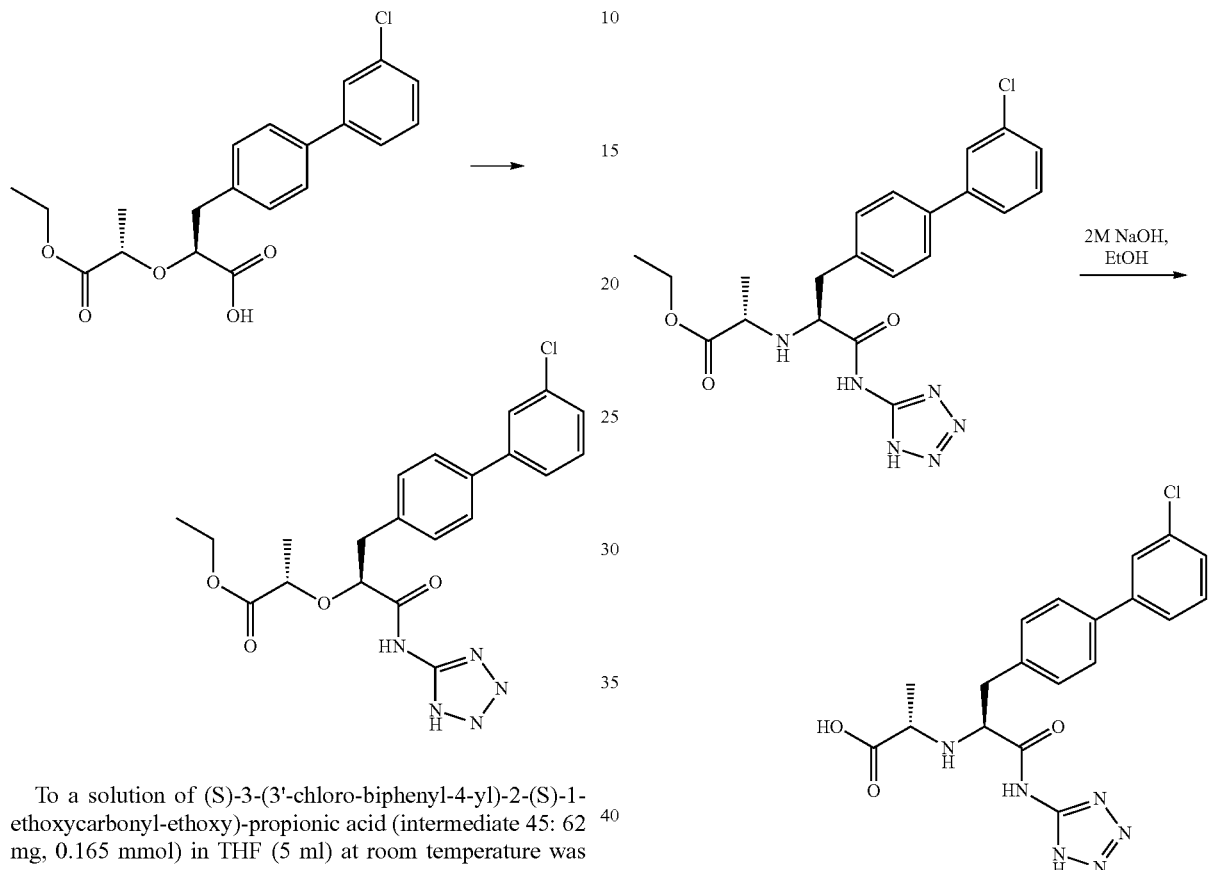

To a solution of (S)-3-(3'-chloro-biphenyl-4-yl)-2-(S)-1-ethoxycarbonyl-ethoxy)-propionic acid (intermediate 45: 62 mg, 0.165 mmol) in THF (5 ml) at room temperature was added 5-aminotetrazole (38.0 mg, 0.447 mmol), DIPEA (0.086 ml, 0.494 mmol) and followed by 1,3-diisopropylcarbodiimide (0.060 ml, 0.387 mmol). The reaction was stirred at room temperature for 3 hr. The reaction was quenched by brine and was extracted with EtOAc. The combined organic layer was washed with brine and dried over anhydrous sodium sulfate, filtered and concentrated. HPLC retention time=0.99 minutes (condition J); MS (m+1)=444.

Example 32-1

(S)-2-[(S)-2-(3'-chloro-biphenyl-4-yl)-1-(1H-tetrazol-5-ylcarbamoyl)-ethylamino]-propionic acid (S)-2-[(S)-2-(3'-chloro-biphenyl-4-yl)-1-(1H-tetrazol-5-ylcarbamoyl)-ethylamino]-propionic acid ethyl ester (Example 31: 100 mg, 0.226 mmol) was treated with 2M aqueous NaOH (2 mL) and EtOH (0.5 mL). After stirred at room temperature for 1 hour, the reaction mixture was acidified with 2M HCl to adjust pH 1. The resulted precipitate was collected by filtration. The obtained material was crystallized from EtOH to give (S)-2-[(S)-2-(3'-chloro-biphenyl-4-yl)-1-(1H-tetrazol-5-ylcarbamoyl)-ethylamino]-propionic acid.

1H NMR (400 MHz, DMSO-d6) δ 1.15 (d, 3H, J=7.1 Hz), 2.94 (dd, 1H, J=7.3, 13.7 Hz), 3.03 (dd, 1H, J=6.3, 13.6 Hz), 3.26 (dd, 1H, J=7.1, 13.9 Hz), 3.81 (dd, 1H, J=6.9, 6.9 Hz), 7.33 (d, 2H, J=8.3 Hz), 7.38-7.42 (m, 1H), 7.47 (dd, 1H, J=7.8, 7.8 Hz), 7.59-7.64 (m, 3H), 7.69 (dd, 1H, J=1.8, 1.8 Hz), 15.9 (bs, 1H); MS: m/z (MH$^+$) 415; HRMS: calculated for $C_{19}H_{19}ClN_6O_3$ (M)$^+$ 414.1. found 414.1

Chiral HPLC retention time=13.17 min. [condition: Daicel CHIRALPAK IA 4.6×100 mm); flow rate=1 ml/min.; eluent: 20% EtOH (with 0.1% TFA) in heptane].

Example 32-2

(S)-2-[(S)-2-(2',5'-dichloro-biphenyl-4-yl)-1-(1H-tetrazol-5-ylcarbamoyl)-ethylamino]propionic acid

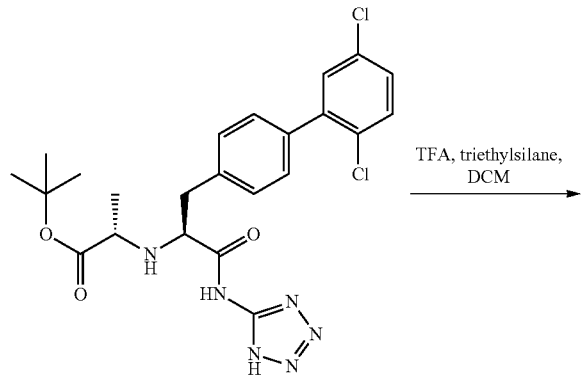

TFA, triethylsilane,
DCM
→

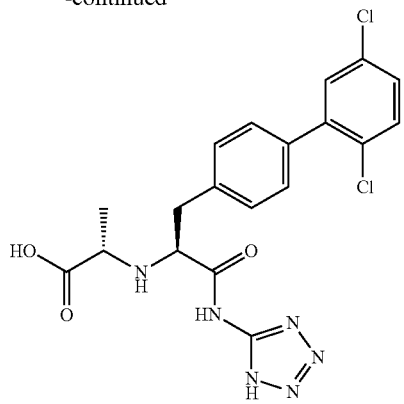

To a solution of (S)-2-[(S)-2-(2',5'-dichloro-biphenyl-4-yl)-1-(1H-tetrazol-5-ylcarbamoyl)-ethylamino]-propionic acid tert-butyl ester (Example 31-1: 103 mg, 0.204 mmol) in DCM (2 mL) were added TFA (1 mL) and triethylsilane (0.098 mL, 0.611 mmol). After stirred for 8 hours, the reaction mixture was concentrated under reduced pressure. The residue was purified by reverse phase HPLC (Sunfire C-18 column, eluent: 0.1% TFA in $H_2O$/CH3CN) to give (S)-2-[(S)-2-(2',5'-dichloro-biphenyl-4-yl)-1-(1H-tetrazol-5-ylcarbamoyl)-ethylamino]-propionic acid. 1H NMR (400 MHz, DMSO-d6+TFA-d) δ 1.49 (d, 3H, J=7.1 Hz), 3.29 (dd, 1H, J=7.6, 13.9 Hz), 3.42 (dd, 1H, J=7.1, 14.2 Hz), 4.13 (dd, 1H, J=7.1, 14.0 Hz), 4.62 (dd, 1H, J=7.3, 7.3 Hz), 7.37 (d, 1H, J=2.5 Hz), 7.37-7.43 (m, 2H), 7.40 (d, 2H, J=4.3 Hz), 7.48 (dd, 1H, J=2.5, 8.6 Hz), 7.59 (d, 1H, J=8.6 Hz), 14.89 (bs, 1H); HPLC Retention time 1.25 minutes (condition I); MS: m/z ($MH^+$) 449.

Following compounds were prepared using similar procedure as example 32-1 or 32-2 with appropriate starting material and conditions:

| Example # | Product | Starting Material | Hydrolysis Condition | HPLC-RT (condition) | MS (M+1) |
|---|---|---|---|---|---|
| Example 32-3 | (S)-2-[(S)-2-Biphenyl-4-yl-1-(1H-tetrazol-5-ylcarbamoyl)-ethylamino]-propionic acid | (S)-2-[(S)-2-Biphenyl-4-yl-1-(1H-tetrazol-5-ylcarbamoyl)-ethylamino]-propionic acid ethyl ester Example 31-2 | 1M LiOH, 2M NaOH aq, EtOH, RT | 1.28 min. (D) | 381 |

-continued

| Example # | Product | Starting Material | Hydrolysis Condition | HPLC-RT (condition) | MS (M + 1) |
|---|---|---|---|---|---|
| Example 32-4 | (S)-2-[(S)-2-(3'-Chloro-biphenyl-4-yl)-1-(3-hydroxy-isoxazol-5-ylcarbamoyl)-ethylamino]-propionic acid | (S)-2-[(S)-2-(3'-Chloro-biphenyl-4-yl)-1-(3-hydroxy-isoxazol-5-ylcarbamoyl)-ethylamino]-propionic acid tert-butyl ester. Example 31-3 | TFA, triethylsilane, DCM, RT | 1.30 min. (I) | 430 |
| Example 32-5 | (S)-2-[(S)-2-(3'-Chloro-biphenyl-4-yl)-1-(1-methyl-1H-tetrazol-5-ylcarbamoyl)-ethylamino]-propionic acid | (S)-2-[(S)-2-(3'-Chloro-biphenyl-4-yl)-1-(1-methyl-1H-tetrazol-5-ylcarbamoyl)-ethylamino]-propionic acid ethyl ester Example 31-4 | 2M NaOH aq, EtOH, RT | 1.38 min. (I) | 429 |
| Example 32-6 | (S)-2-[(S)-2-(3'-Chloro-biphenyl-4-yl)-1-(1H-tetrazol-5-ylcarbamoyl)-ethylamino]-4-phenyl-butyric acid | (S)-2-[(S)-2-(3'-Chloro-biphenyl-4-yl)-1-(1H-tetrazol-5-ylcarbamoyl)-ethylamino]-4-phenyl-butyric acid ethyl ester Example 31-5 | 2M NaOH aq, EtOH, RT | 0.82 min. (J) | 505 |

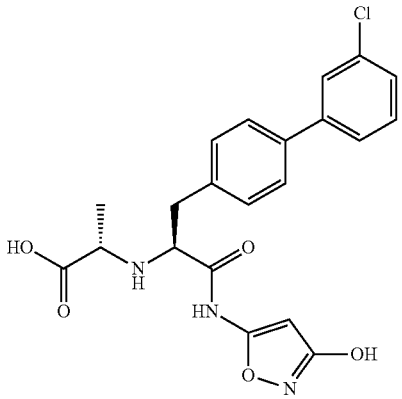 [SMILES: C[C@H](N[C@@H](Cc1ccc(-c2cccc(Cl)c2)cc1)C(=O)Nc1cc(O)no1)C(=O)O]
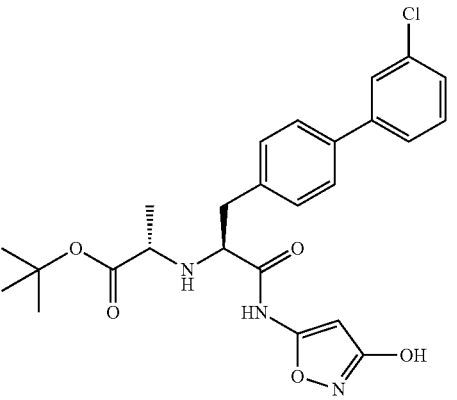 [SMILES: C[C@H](N[C@@H](Cc1ccc(-c2cccc(Cl)c2)cc1)C(=O)Nc1cc(O)no1)C(=O)OC(C)(C)C]
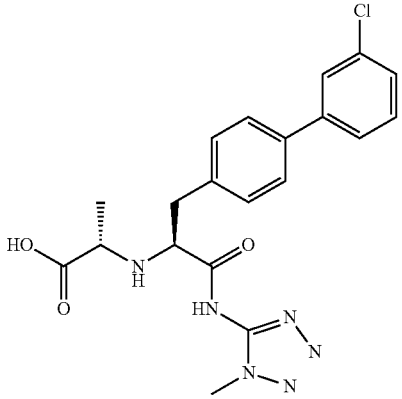 [SMILES: C[C@H](N[C@@H](Cc1ccc(-c2cccc(Cl)c2)cc1)C(=O)N/C(=N/N)N(C)N)C(=O)O]
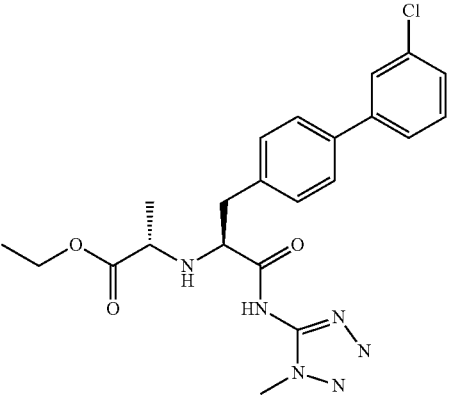 [SMILES: CCOC(=O)[C@H](C)N[C@@H](Cc1ccc(-c2cccc(Cl)c2)cc1)C(=O)N/C(=N/N)N(C)N]
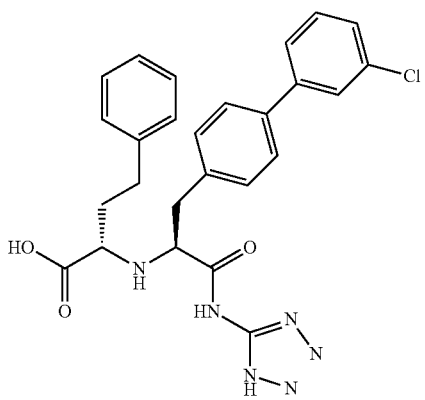 [SMILES: N/N=C(\NN)NC(=O)[C@H](Cc1ccc(-c2cccc(Cl)c2)cc1)N[C@@H](CCc1ccccc1)C(=O)O]
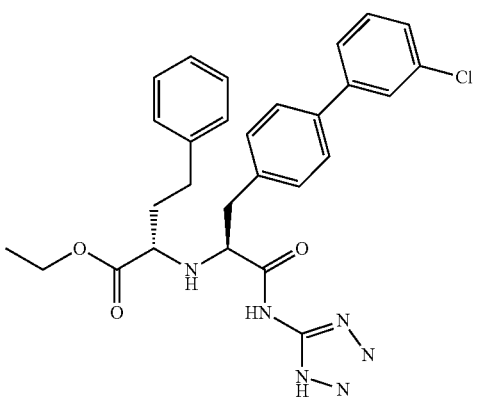 [SMILES: CCOC(=O)[C@H](CCc1ccccc1)N[C@@H](Cc1ccc(-c2cccc(Cl)c2)cc1)C(=O)N/C(=N/N)NN]

Example 32-3

¹H NMR (400 MHz, DMSO-d6) δ 1.37 (d, 3H, J=6.8 Hz), 3.20 (d, 2H, J=6.3 Hz), 3.73-3.87 (bs, 1H), 4.25-4.38 (bs, 1H), 7.33-7.38 (m, 1H), 7.36 (d, 2H, J=8.1 Hz), 7.45 (dd, 2H, J=7.4, 7.4 Hz), 7.60-7.66 (m, 4H).

Example 32-4

¹H NMR (400 MHz, DMSO-d6) δ 1.37 (bd, 3H, J=4.8 Hz), 3.09-3.26 (m, 2H), 3.67-3.90 (m, 1H), 4.10-4.37 (m, 1H), 5.83 (s, 1H), 7.34 (d, 2H, J=8.1 Hz), 7.40-7.45 (m, 1H), 7.48 (dd, 1H, J=7.8, 7.8 Hz), 7.61-7.66 (m, 1H), 7.66-7.73 (m, 3H).

Example 32-5

¹H NMR (400 MHz, DMSO-d6) δ 1.35-1.43 (m, 3H), 3.13-3.34 (m, 2H), 3.35-3.95 (m, 1H), 3.73 (s, 3H), 4.08-4.45 (m, 1H), 7.39-7.45 (m, 3H), 7.49 (dd, 1H, J=7.8, 7.8 Hz), 7.62-7.75 (m, 4H).

Example 32-6

¹H NMR (400 MHz, DMSO-$d_6$) δ ppm 1.67-1.90 (m, 2 H), 2.59 (t, J=7.7 Hz, 2 H), 2.96 (dd, J=13.6, 7.3 Hz, 1 H), 3.07 (dd, J=13.6, 7.1 Hz, 1 H), 3.11-3.17 (m, 1 H), 3.78 (t, J=7.1 Hz, 1 H), 7.07-7.18 (m, 5 H), 7.33 (d, J=8.3 Hz, 2 H), 7.37-7.42 (m, 1 H), 7.46 (t, J=8.0 Hz, 1 H), 7.61 (d, J=8.3 Hz, 3 H), 7.68 (t, J=1.8 Hz, 1 H), 12.02 (br. s., 1 H), 15.89 (br. s., 1 H).

Example 32-7

¹H NMR (400 MHz, DMSO-$d_6$) δ ppm 0.91 (t, J=7.5 Hz, 3 H), 1.67-1.80 (m, 2 H), 3.08-3.27 (m, 2 H), 3.56 (br. s., 3 H), 4.16 (br. s., 1 H), 7.34 (d, J=8.3 Hz, 2 H), 7.41 (ddd, J=7.8, 2.0, 1.0 Hz, 1 H), 7.47 (t, J=7.8 Hz, 1 H), 7.61 (dt, J=8.0, 1.5, 1.1 Hz, 1 H), 7.64 (d, J=8.3 Hz, 2 H), 7.68 (t, J=1.8 Hz, 1 H), 12.27 (br. s., 1 H), 16.09 (br. s., 1 H).

Example 32-8

1H NMR (400 MHz, DMSO-$d_6$) δ ppm 2.97 (dd, 1H, J=7.1, 13.6 Hz), 3.07 (dd, 1 H, J=6.3, 13.6 Hz), 3.47 (dd, 1H, J=5.1, 5.1 Hz), 3.58 (d, 2 H, J=5.1 Hz), 3.87 (dd, 1H, J=6.6 Hz), 4.41 (d, 1H, J=12.4 Hz), 4.46 (d, 1H, J=12.1 Hz), 7.22-7.36 (m, 7H), 7.38-7.42 (m, 1H), 7.47 (t, 1H, j=7.8 Hz), 7.58-7.64 (m, 3H), 7.68 (t, 1H, J=1.8 Hz).

Example 32-9

1H NMR (400 MHz, DMSO-$d_6$) d ppm 1.31 (d, J=6.6 Hz, 3 H), 3.05-3.18 (m, 2H), 4.03 (q, J=6.8 Hz, 1H), 4.58 (t, J=6.3 Hz, 1H), 7.35 (d, J=8.1 Hz, 2 H), 7.37-7.42 (m, 1H), 7.47 (t, J=7.8 Hz, 1 H), 7.55-7.65 (m, 3 H), 7.66-7.72 (m, 1 H), 12.13 (br. s., 1 H), 12.69 (br. s., 1 H), 15.96 (br. s., 1 H)

Example 32-10

(S)-2-[(S)-2-(3'-chloro-biphenyl-4-yl)-1-(1H-tetrazol-5-ylcarbamoyl)-ethylamino]-3-hydroxy-propionic acid

Example 32-11

(S)-2-[(S)-2-biphenyl-4-yl-1-(1H-tetrazol-5-ylcarbamoyl)-ethylamino]-3-hydroxy-propionic acid

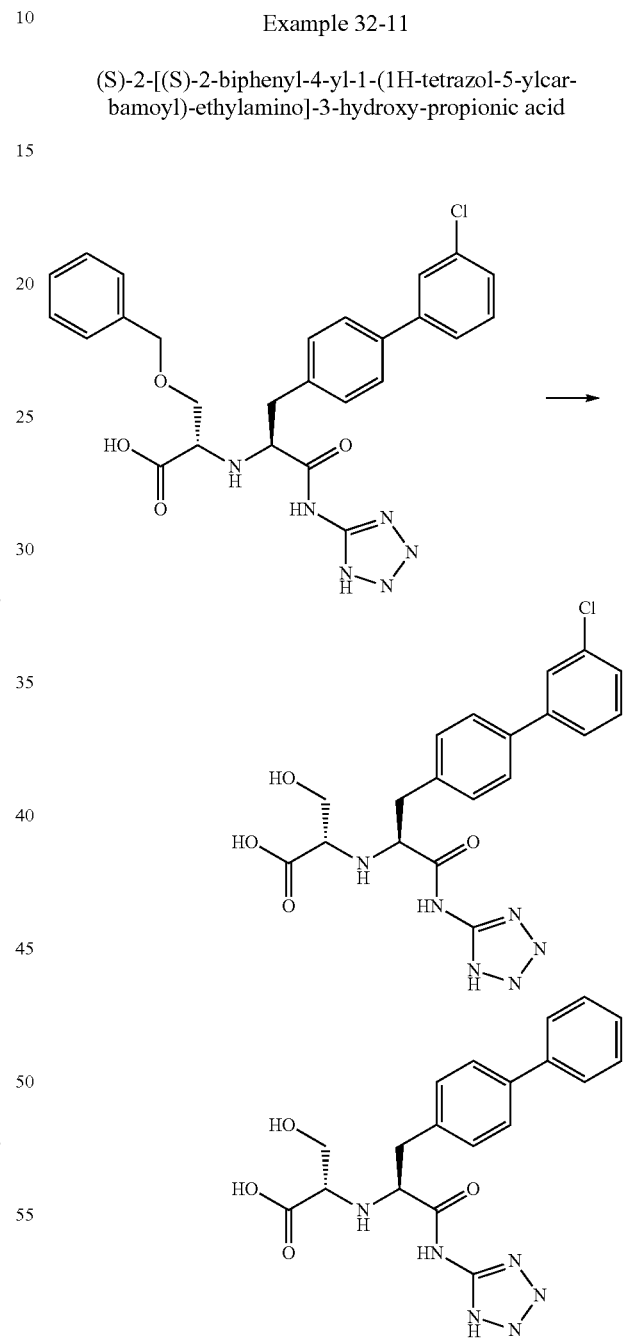

To a solution of (S)-3-benzyloxy-2-[(S)-2-(3'-chloro-biphenyl-4-yl)-1-(1H-tetrazol-5-ylcarbamoyl)-ethylamino]-propionic acid ethyl ester (Example 32-8: 47 mg, 0.090 mmol) in EtOAc (1 mL) and EtOH (1 mL) was added 5% Pd—C (9.6 mg, 0.0045 mmol). $H_2$ gas was loaded with a balloon and the reaction mixture was stirred at 50° C. for 6 hours. The reaction mixture was filtered through celite pad and the filtrate was concentrated. The residue was purified by reverse phase HPLC (Sunfire C-18 column, eluent: 0.1% TFA in H₂O/CH₃CN) to give (S)-2-[(S)-2-(3'-chloro-biphenyl-4-yl)-1-(1H-tetrazol-5-ylcarbamoyl)-ethylamino]-3-hydroxy-propionic acid and (S)-2-[(S)-2-biphenyl-4-yl-1-(1H-tetrazol-5-ylcarbamoyl): ethylamino]-3-hydroxy-propionic acid.

(S)-2-[(S)-2-(3'-chloro-biphenyl-4-yl)-1-(1H-tetrazol-5-ylcarbamoyl)-ethylamino]-3-hydroxy-propionic acid; NMR (400 MHz, DMSO-d6) δ ppm 2.99-3.14 (m, 2H), 3.50-3.67 (m, 3H), 3.86-3.98 (m, 1H), 7.34 (d, 2H, J=8.3 Hz), 7.38-7.42 (m, 1H), 7.47 (t, 2H, J=7.8 Hz), 7.58-7.70 (m, 4H)); HPLC Retention time 1.17 minutes (condition I); MS: m/z (MH+) 431.

(S)-2-[(S)-2-biphenyl-4-yl-1-(1H-tetrazol-5-ylcarbamoyl)-ethylamino]-3-hydroxy-propionic acid; NMR (400 MHz, DMSO-d6) δ ppm 3.18 (dd, 1H, J=7.6, 13.4 Hz), 3.24-3.36 (m, 1H), 3.66-3.87 (m, 3H), 4.17-4.37 (m, 1H), 7.32 (d, 2H, J=8.1 Hz), 7.32-7.38 (m, 1H), 7.44 (t, 2H, J=7.8 Hz), 7.56-7.67 (m, 4H)); HPLC Retention time 1.00 minutes (condition I); MS: m/z (MH+) 397.

Example 33-1

(S)-3-(3'-chloro-biphenyl-4-yl)-2-((S)-2-methanesulfonylamino-1-methyl-2-oxo-ethylamino)-N-(1H-tetrazol-5-yl)-propionamide

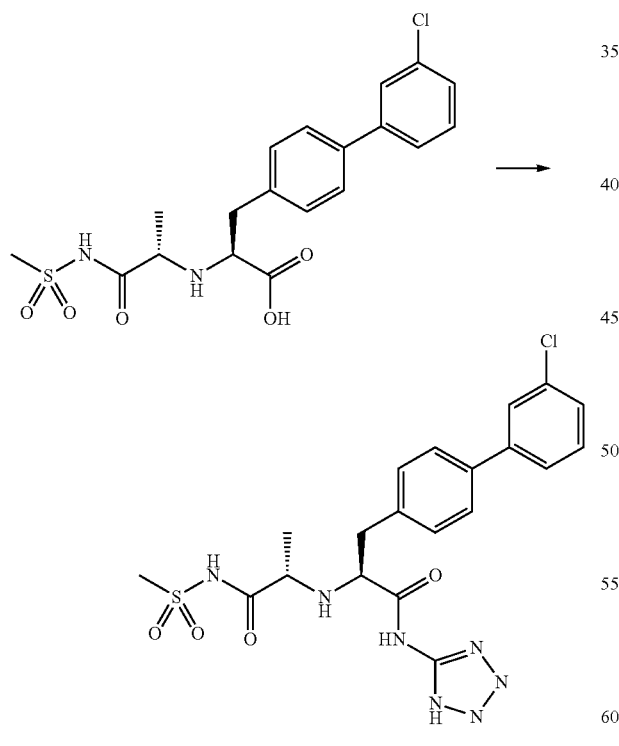

Example 33-1 was prepared using similar procedure as example 31 using Intermediate 46 as starting material. NMR (400 MHz, DMSO-d6+TFA-d) δ 1.21 (d, J=6.32 Hz, 3H), 2.92-3.05 (m, 1H), 3.05-3.14 (m, 1H), 3.17 (s, 3H), 3.34-3.46 (m, 1H), 3.82-3.95 (m, 1H), 7.35 (d, J=8.08 Hz, 2H), 7.39-7.43 (m, 1H), 7.47 (t, J=7.83 Hz), 7.60-7.66 (m, 3H), 7.68-7.22 (m, 1H)); HPLC Retention time 1.21 minutes (condition I); MS: m/z (MH+) 492.

Example 34

(2R,4S)-5-Biphenyl-4-yl-4-(3-carboxy-propionylamino)-2-methyl-pentanoic acid ethyl ester

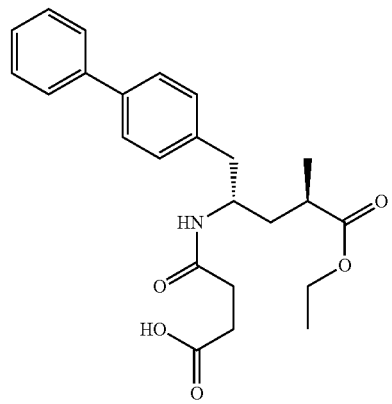 [SMILES: CCOC(=O)[C@H](C)C[C@@H](Cc1ccc(-c2ccccc2)cc1)NC(=O)CCC(=O)O]

This compound was prepared as described in U.S. Pat. No. 5,217,996.

Example 35

Synthesis of (2R,4S)-4-(3-carboxy-propionylamino)-5-(3'-chloro-biphenyl-4-yl)-2-methyl-pentanoic acid ethyl ester

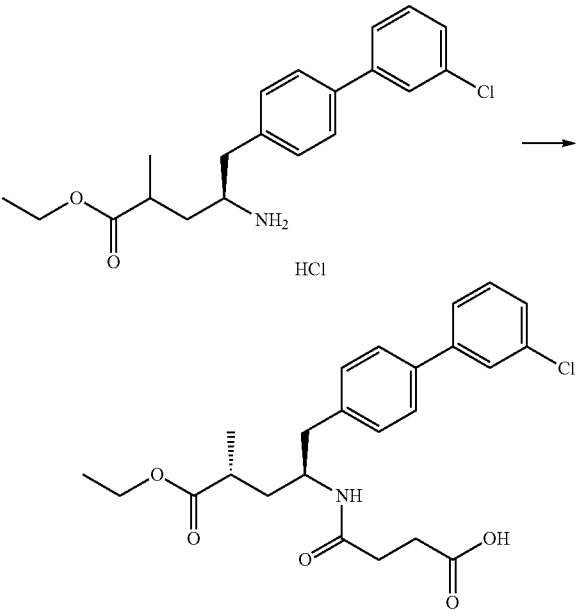

To a stirred solution of (S)-4-Amino-5-(3'-chloro-biphenyl-4-yl)-2-methyl-pentanoic acid ethyl ester hydrochloric acid salt (200 mg, 0.52 mmol) and dihydrofuran-2,5-dione (68 mg, 0.68 mmol) in 8 ml CH₂Cl₂ was added pyridine (0.17 ml, 2.1 mmol) and the solution was stirred for 2 hours. The reaction mixture was acidified to pH=3 with 1M HCl. Solvent was removed under reduced pressure and the residue was purified by preparatory HPLC (DAICEL CHIRALCEL OD-H 21×250 mm column, 18 ml/min, 90% heptane 10% EtOH+0.1% TFA), collected a peak at 3.9 minutes, to give 50 mg (2R,4S)-4-(3-carboxy-propionylamino)-5-(3'-chloro-biphenyl-4-yl)-2-methyl-pentanoic acid ethyl ester. MS m/z 446.3 (M+H), 444.3 (M–H). LC/MS (Condition A): 1.52 min. 1H NMR (400 MHz, DMSO-d6): 1.04-1.05 (d, J=7.07 Hz, 3H), 1.09-1.13 (t, J=7.07 Hz, 3H), 1.34-1.42 (m, 1H), 1.72-1.79 (m, 1H), 2.24-2.29 (m, 2H), 2.36-2.40 (m, 2H), 2.64-2.74 (m, 2H), 3.33 (s, 1H), 3.86-3.93 (m, 1H), 3.95-4.01 (q, J=7.33 Hz, 14.40 Hz, 2H), 7.25-7.27 (m, 2H), 7.39-7.41 (m, 1H), 7.46-7.50 (t, J=7.58 Hz, 1H), 7.61-7.64 (m, 3H), 7.70 (t, J=1.77 Hz, 1H), 7.75-7.77 (d, J=8.59 Hz, 1H), 12.08 (br s, 2H).

Example 36

Synthesis of (2R,4S)-4-(3-carboxy-propionylamino)-5-(3'-chloro-biphenyl-4-yl)-2-methyl-pentanoic acid

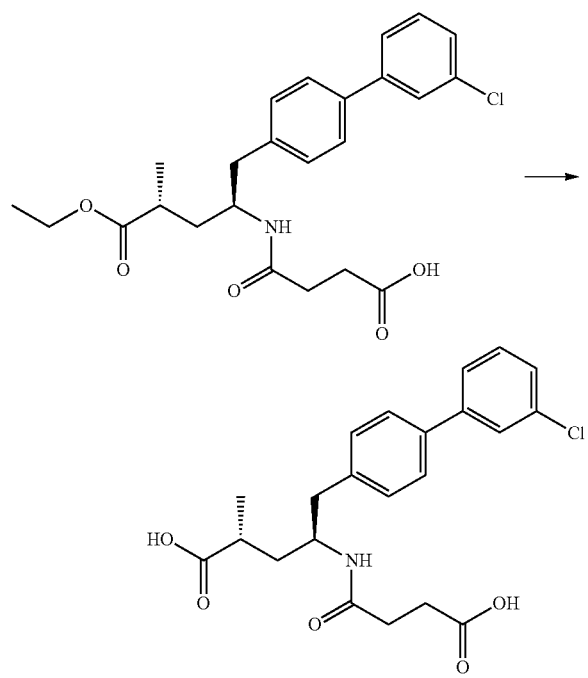

To a stirred solution of (2R,4S)-4-(3-carboxy-propionylamino)-5-(3'-chloro-biphenyl-4-yl)-2-methyl-pentanoic acid ethyl ester (20 mg, 0.045 mmol) in 2 ml EtOH was added 1 ml of aqueous 1M NaOH and the solution was stirred for an hour. The reaction mixture was acidified to pH=2 to 3 with aqueous 1M HCl. Solvent was removed under reduced pressure and the residue was purified by RP-HPLC to give 10 mg (2R,4S)-4-(3-carboxy-propionylamino)-5-(3'-chloro-biphenyl-4-yl)-2-methyl-pentanoic acid. LC/MS m/z 418.3 (M+H), 419.4 (M–H). LC/MS (Condition A): 1.21 min. 1H NMR (400 MHz, DMSO-d6): 1.04-1.05 (d, J=7.07 Hz, 3H), 1.30-1.37 (m, 1H), 1.73-1.80 (m, 1H), 2.24-2.39 (m, 5H), 2.66-2.73 (m, 2H), 3.90-3.98 (m, 1H), 7.25-7.27 (d, J=8.08 Hz, 2H), 7.39-7.41 (m, 1H), 7.45-7.49 (t, J=7.83 Hz, 1H), 7.60-7.64 (m, 3H), 7.70-7.71 (t, J=2.02 Hz, 1H), 7.75-7.77 (d, J=8.59 Hz, 1H), 12.04 (br s, 2H).

Example 37

Synthesis of (S)-4-(3-Carboxy-propionylamino)-5-(2'-methoxy-biphenyl-4-yl)-2-methyl-pentanoic acid ethyl ester

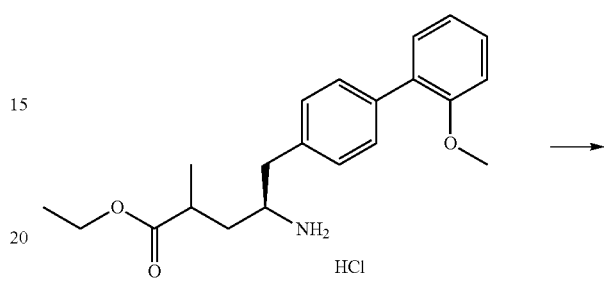

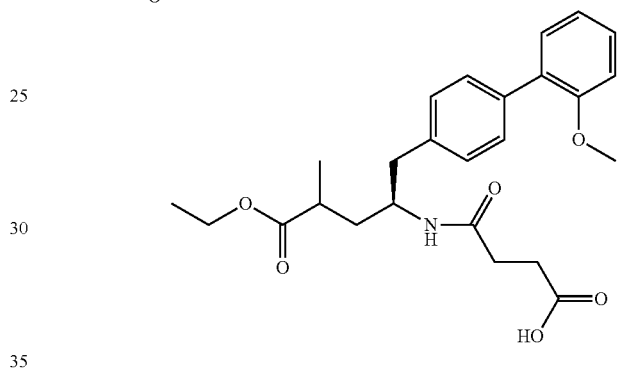

To a solution of (S)-4-amino-5-(2'-methoxy-biphenyl-4-yl)-2-methyl-pentanoic acid ethyl ester hydrochloric acid salt (240 mg, 0.703 mmol) in pyridine/DCM (1 ml/1 ml) was added succinic anhydride (84 mg, 0.843 mmol) and stirred at room temperature for 1 hour. Then, the mixture was concentrated under reduced pressure, and the residue was purified by RP-HPLC to give (S)-4-(3-Carboxy-propionylamino)-5-(2'-methoxy-biphenyl-4-yl)-2-methyl-pentanoic acid ethyl ester. HPLC Retention time 1.29 minutes (condition A): MS 442.4 (M+1)

Example 38

Synthesis of (S)-4-(3-Carboxy-propionylamino)-5-(2'-methoxy-biphenyl-4-yl)-2-methyl-pentanoic acid

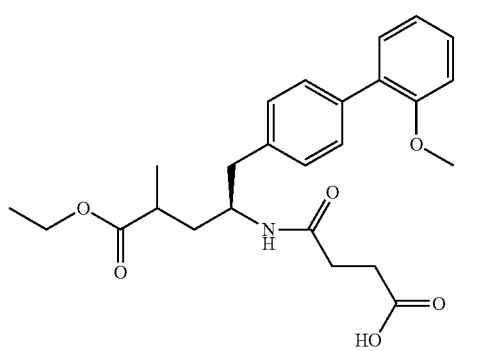

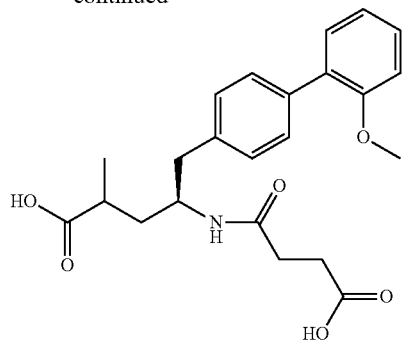

To (S)-4-(3-carboxy-propionylamino)-5-(2'-methoxy-biphenyl-4-yl)-2-methyl-pentanoic acid ethyl ester was added 1M NaOH (2 ml) and stirred at room temperature for 2 hours. Then, to the mixture was added 2 ml of 1M HCl and concentrated under reduced pressure. The obtained residue was purified by RP-HPLC (H2O (0.1% TFA)/CH$_3$CN) to afford 110 mg of white powder. HPLC Retention time 0.86 minutes (condition A): MS 414.1 (M+1) 1H NMR (400 MHz, DMSO-d6) δ ppm 0.99-1.06 (m, 3 H) 1.28-1.48 (m, 1 H) 1.66-1.84 (m, 1 H) 2.24-2.39 (m, 5 H) 2.63-2.75°(m, 2 H) 3.75-4.02 (m, 4 H) 6.97-7.04 (m, 1 H) 7.09 (d, J=7.58 Hz, 1 H) 7.16-7.22 (m, 2 H) 7.24-7.29 (m, 1 H) 7.29-7.35 (m, 1 H) 7.35-7.41 (m, 2 H) 7.77 (d, J=8.59 Hz, 1 H).

Starting materials or intermediates are prepared in following manner:

Intermediate 1

(R)-ethyl 4-(4-bromophenyl)-3-(4-methoxy-4-oxobutanamido)butanoate

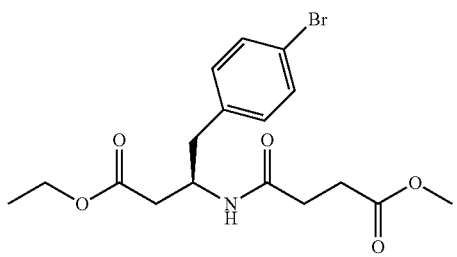 [SMILES: CCOC(=O)C[C@@H](Cc1ccc(Br)cc1)NC(=O)CCC(=O)OC]

To (R)-ethyl-4-(4-bromophenyl-4-yl)-3-(tert-butoxycarbonylamino)butanoate (2.02 g, 5.23 mmol) is added a solution of 4M HCl in 1,4-dioxane (13.1 mL, 52.3 mmol) at room temperature. After stirring for 1 hour, the reaction mixture is concentrated under reduced pressure to give (R)-3-amino-4-bromophenyl-4-yl-butyric acid ethyl ester hydrochloride. To a solution of (R)-3-amino-4-bromophenyl-4-yl-butyric acid ethyl ester hydrochloride is added succinic anhydride (0.707 g, 7.06 mmol) and DIPEA (2.06 mL, 11.8 mmol) in dichloromethane (20 mL) and allowed to stir for 4 hours. The reaction is quenched with 0.1 M aqueous HCl. The products are extracted with ethyl acetate and washed with brine. The organic layer is dried over Na$_2$SO$_4$, filtered, and concentrated under reduced pressure to give (R)-4-(1-(4-bromophenyl)-4-ethoxy-4-oxobutan-2-ylamino)-4-oxobutanoic acid (2.26 g). To a solution of the obtained residue (2.26 g) in toluene (25 mL) and MeOH (25 mL), TMSCHN$_2$ in hexanes (5.85 ml, 11.70 mmol) is added portionwise at room temperature under nitrogen. The reaction mixture is allowed to stir for 1.5 hour, then quenched with AcOH (0.5 mL; 8.78 mmol), and the solution is stirred for 10 minutes. The solution is concentrated, and the obtained residue is purified by flash column chromatography on 40 g silica gel (eluent: heptane/EtOAc=100:0 to 0:100) to give (R)-ethyl 4-(4-bromophenyl)-3-(4-methoxy-4-oxobutanamido)butanoate (1.92 g). HPLC retention time=1.04 minutes (condition B); MS (ES+)=400 (m+1), 402.0 (m+3; 100%); 1H NMR (400 MHz, CHLOROFORM-d) δ ppm 1.28 (t, J=7.2 Hz, 3 H) 2.40-2.53 (m, 4 H) 2.60-2.64 (m, 2 H) 2.79 (A of ABX, Jab=13.7 Hz, Jax=7.85 Hz, 1 H) 2.90 (B of ABX, Jab=13.7 Hz, Jbx=6.65 Hz, 1 H) 3.68 (s, 3 H) 4.10-4.22 (m, 2 H) 4.39-4.47 (m, 1 H) 6.29 (br d, J=8.6 Hz, 1 H) 7.06 (d, J=8.4 Hz, 2 H) 7.40-7.42 (m, 2 H).

Intermediate 2

(R)-ethyl 4-(biphenyl-4-yl)-3-(tert-butoxycarbonylamino)butanoate

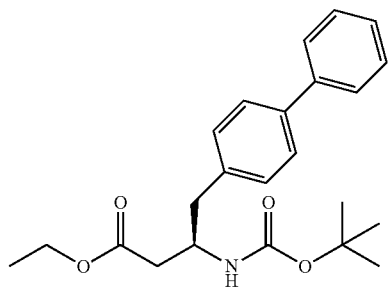 [SMILES: CCOC(=O)C[C@@H](Cc1ccc(-c2ccccc2)cc1)NC(=O)OC(C)(C)C]

A mixture of (R)-ethyl 4-(4-bromophenyl)-3-(tert-butoxycarbonylamino)butanoate (1.5 g, 3.88 mmol), phenylboronic acid (0.710 g, 5.82 mmol), Pd(Ph3P)4 (0.449 g, 0.388 mmol) and aqueous Na$_2$CO$_3$ (3.88 mL, 7.77 mmol) in toluene (25 mL) is allowed to stir at 95° C. under nitrogen for 14 hours. The reaction mixture is cooled to room temperature and quenched with brine. The mixture is extracted twice with ethylacetate, and the combined organic layer is washed with brine, dried over Na$_2$SO$_4$, filtered, and concentrated under reduced pressure. The obtained residue is purified by silica gel flash column chromatography (heptane/EtOAc=100:0 to 50:50) to give (R)-ethyl 4-(biphenyl-4-yl)-3-(tert-butoxycarbonylamino)butanoate (1.30 g); HPLC retention time=1.61 minutes (condition B); MS (ES+)=328.0 (m-tBu+2); 284.1 (m-Boc+2; 100%); 1H NMR (400 MHz, CHLOROFORM-d) δ ppm 1.28 (t, J=7.1 Hz, 3 H) 2.48 (A of ABX, Jab=16.1 Hz, Jax=5.9 Hz, 1 H) 2.53 (B of ABX, Jab=16.0 Hz, Jbx=5.3 Hz, 1 H) 2.83-3.00 (m, 2 H) 4.14-4.19 (m, 3 H) 5.06 (br s) 7.26-7.27 (m, 2 H) 7.31-7.35 (m, 2 H) 7.43 (t, J=7.6 Hz, 2 H) 7.52-7.58 (m, 4 H).

Following intermediates are prepared using similar procedure as described for intermediate 2:

| Intermediate # | Product | Condition | HPLC-RT (condition) | MS (ES+; 100%) |
|---|---|---|---|---|
| Intermediate 2-1 | (R)-ethyl 3-(tert-butoxycarbonylamino)-4-(5'-chloro-2'-fluorobiphenyl-4-yl)butanoate | Pd(PPh$_3$)$_4$, 5-chloro-2-fluorophenyl-boronic acid, aq. 2M Na2CO3, DME, 95° C. | 1.47 min. (B) | 336.1 (m-BOC + 2) |
| Intermediate 2-2 | (R)-ethyl 3-(tert-butoxycarbonylamino)-4-(5'-chloro-2'-methoxybiphenyl-4-yl)butanoate | PdCl2(dppf)•CH2Cl2 complex, 5-fluoro-2-methoxyphenyl-boronic acid, aq. 2M Na2CO3, toluene, 95° C. | 1.42 min. (B) | 332.2 (m-BOC + 2) |

Intermediate 3

(R)-4-(1-(biphenyl-4-yl)-4-tert-butoxy-4-oxobutan-2-ylamino)-4-oxobutanoic acid

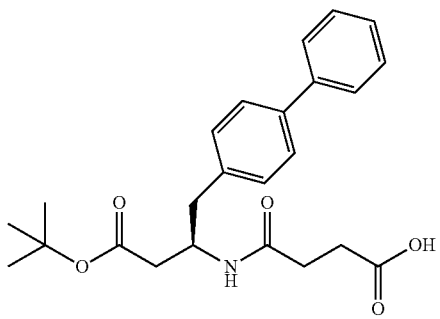 [SMILES: CC(C)(C)OC(=O)C[C@@H](Cc1ccc(-c2ccccc2)cc1)NC(=O)CCC(=O)O]

To (R)-tert-butyl 4-(biphenyl-4-yl)-3-(tert-butoxycarbonylamino)butanoate (26.4 mg, 0.064 mmol) is added 4M HCl in 1,4-dioxane (0.321 ml, 1.283 mmol) at room temperature. The reaction mixture is stirred for 45 minutes and concentrated under reduced pressure. To a solution of the obtained residue in dichloromethane (0.4 mL) is added succinic anhydride (7.70 mg, 0.077 mmol) and DIPEA (0.013 mL, 0.077 mmol). The reaction mixture is allowed to stir at room temperature for 14 hours and concentrated under reduced pressure. The obtained residue is purified by RP-HPLC (SunFire C-18, H$_2$O (0.1% TFA)/CH$_3$CN) to give (R)-4-(1-(biphenyl-4-yl)-4-tert-butoxy-4-oxobutan-2-ylamino)-4-oxobutanoic acid (9.5 mg). HPLC retention time=1.70 minutes (condition A); MS (ES+)=412.1 (m+1); 356.0 (m-tBu+2; 100%); 1H NMR (400 MHz, CHLOROFORM-d) δ ppm 1.48 (s, 9 H) 2.36-2.51 (m, 4 H) 2.64-2.67 (m, 2 H) 2.87 (A of ABX, Jab=13.5 Hz, Jax=5.7 Hz, 1 H), 2.97 (Jab=13.5 Hz, Jbx=6.2 Hz, 1 H) 7.24-7.26 (m, 2 H) 7.31-7.35 (m, 1 hp 7.43 (t, J=7.75 Hz, 2 H) 7.53 (d, J=8.0 Hz, 2 H) 7.57 (d, J=7.6 HZ, 2 H).

Following intermediates are prepared using similar procedure as described in intermediate 3:

| Intermediate # | Product | Starting Material | HPLC-RT (condition) | MS (M + 1) |
|---|---|---|---|---|
| Intermediate 3-1 | (R)-4-(4-Bromo-phenyl)-3-(3-carboxy-propionylamino)-butyric acid ethyl Ester Intermediate 1 | | 0.90 min. (B) | 385.9 |

Intermediate 4

(R)-ethyl 4-(4-bromophenyl)-3-(tert-butoxycarbonylamino)butanoate

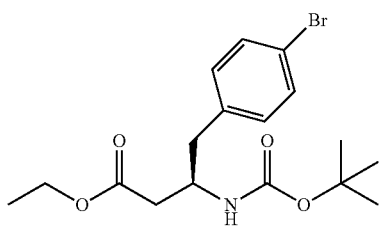 [SMILES: CCOC(=O)C[C@@H](Cc1ccc(Br)cc1)NC(=O)OC(C)(C)C]

To a suspension of (R)-4-(4-bromophenyl)-3-(tert-butoxycarbonylamino)butanoic acid (9.98 g, 27.9 mmol) and NaHCO$_3$ (4.68 g, 55.7 mmol) in DMF (45 mL) is added Ethyl iodide (6.75 mL, 84 mmol) at room temperature under nitrogen. After stirring for 71 hours, the reaction is quenched with H$_2$O (300 mL), and then precipitated solid is collected and washed with H$_2$O (500 mL) to give (R)-ethyl 4-(4-bromophenyl)-3-(tert-butoxycarbonylamino)butanoate (10.25 g, 94%). HPLC retention time=1.48 minutes (condition B); MS (ES+) =329.9 (m-tBu+2); 286.0 (m-Boc+2; 100%); 1H NMR (400 MHz, CHLOROFORM-d) δ ppm 1.27 (t, J=7.2 Hz, 3 H) 1.40 (s, 9 H), 2.43 (A of ABX, Jab=15.8 Hz, Jax=5.7 Hz, 1 H) 2.50 (B of ABX, Jab=15.8 Hz, Jbx=5.4 Hz, 1 H) 2.74-2.90 (m, 2 H) 4.11 (br s) 4.15 (q, J=7.1 Hz, 2 H) 5.04 (br d) 7.07 (d, J=8.3 Hz, 2 H) 7.40-7.43 (m, 2 H).

Following intermediates are prepared using similar procedure as described for intermediate 4:

| Intermediate # | Product | Condition | HPLC-RT (condition) | MS (ES+; 100%) |
|---|---|---|---|---|
| Intermediate 4-1 | (R)-4-(4-Bromo-phenyl)-3-tert-butoxycarbonyl-amino-butyric acid 5-methyl-2-oxo-[1,3]dioxol-4-ylmethyl ester | K$_2$CO$_3$, DMF, RT | 1.28 min. (B) | 470 (m + 1) |

| Intermediate # | Product | Condition | HPLC-RT (condition) | MS (ES+; 100%) |
|---|---|---|---|---|
| Intermediate 4-2 | (R)-4-(4-Bromo-phenyl)-3-tert-butoxycarbonyl-amino-butyric acid dimethylcarbamoyl methyl ester | K₂CO₃, DMF, RT | 1.65 min. (B) | 444 (m + 1) |
| Intermediate 4-3 | (R)-4-(4-Bromo-phenyl)-3-tert-butoxycarbonyl-amino-butyric acid 2-morpholin-4-yl-ethyl ester | K₂CO₃, DMF, RT | 1.19 min. (B) | 471 (m + 1) |

Intermediate 5

(R)-3-(biphenyl-4-ylmethyl)-4-(3-methoxy-3-oxo-propylamino)-4-oxobutanoic acid

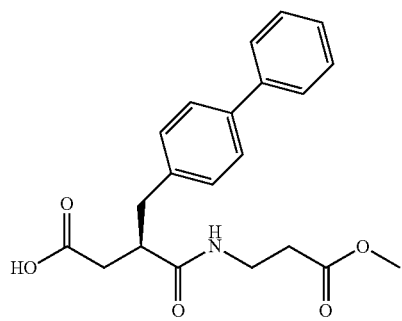 [SMILES: COC(=O)CCNC(=O)[C@@H](CC(=O)O)Cc1ccc(-c2ccccc2)cc1]

To a solution of (R)-tert-butyl 3-(biphenyl-4-ylmethyl)-4-(3-methoxy-3-oxopropylamino)-4-oxobutanoate (40 mg, 0.094 mmol) in DCM (0.5 mL), TFA (0.15 mL) is added at room temperature. The mixture is allowed to stir for 2 hours, and then concentrated under reduced pressure to give (R)-3-(biphenyl-4-ylmethyl)-4-(3-methoxy-3-oxopropylamino)-4-oxobutanoic acid (33.5 mg, 96%). HPLC retention time=1.20 minutes (condition A); MS (m+1)=370.1; 1H NMR (400 MHz, CHLOROFORM-d) δ ppm 2.21-2.29 (m, 1 H) 2.38-2.45 (m, 1 H) 2.62-2.66 (m, 1 H) 2.75-3.00 (m, 4 H) 3.29-3.37 (m, 1 H) 3.45-3.53 (m, 4 H) 6.12 (br s, 1 H) 7.23 (d, J=8 Hz, 2 H) 7.32-7.35 (m, 1 H) 7.41-7.45 (m, 2 H) 7.53 (d, J=8.1 Hz, 2 H) 7.56-7.59 (m, 2 H).

Intermediate 6

(R)-tert-butyl 3-(biphenyl-4-ylmethyl)-4-(3-methoxy-3-oxopropylamino)-4-oxobutanoate

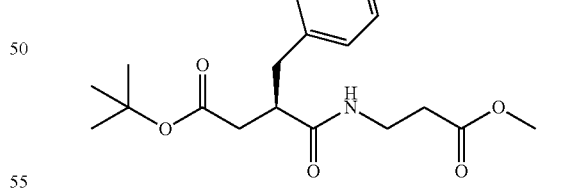

A solution of (R)-2-(biphenyl-4-ylmethyl)-4-tert-butoxy-4-oxobutanoic acid (142 mg, 0.417 mmol), 3-amino-propionic acid methyl ester hydrochloride (76 mg, 0.542 mmol), WSC hydrochloride (120 mg, 0.626 mmol), 1-hydroxy-7-azabenzotriazole (85 mg, 0.626 mmol) and DIPEA (0.219 ml, 1.251 mmol) in DMF (4 mL) is allowed to stir at room temperature under nitrogen for 13 hours. The reaction is quenched with H₂O. The products are extracted with ethyl acetate, washed with aqueous 1M HCl and then with brine, dried over Na₂SO₄, filtered, and concentrated under reduced pressure. The obtained residue is purified by flash column chromatography on 12 g of silica gel (heptane/EtOAc=70:30 to 0:100) to give (R)-tert-butyl 3-(biphenyl-4-ylmethyl)-4-(3-methoxy-3-oxopropylamino)-4-oxobutanoate (164 mg, 91%). HPLC retention time=1.59 minutes (condition A); MS (ES+)=425.4 (m); 369.4 (m-tBu+1; 100%); 1H NMR (400 MHz, CHLOROFORM-d) δ ppm 2.24-2.44 (m, 2 H) 2.67-2.79 (m, 3 H) 2.89-2.96 (m, 1 μl) 3.28-3.36 (m, 1 H) 3.45-3.53 (m, 1 H) 7.23 (d, J=5.8 Hz, 2 H) 7.33 (t, J=7.35 Hz, 1 H) 7.41-7.44 (m, 2 H) 7.51 (d, J=8.1 Hz, 2 H) 7.58 (d, J=7.4 Hz, 2 H).

Following intermediates are prepared using similar procedure as described in intermediate 6:

| Intermediate # | Product | Starting Material | Condition | HPLC-RT (condition) | MS (M + 1) |
|---|---|---|---|---|---|
| Intermediate 6-1 | (R)-3-Biphenyl-4-ylmethyl-N-tert-butoxycarbonylmethyl-succinamic acid tert-butyl ester | | WSC•HCl, HOAt, DIPEA, DMF, rt | 1.64 min. (B) | 454.1 |

Intermediate 7

(R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester

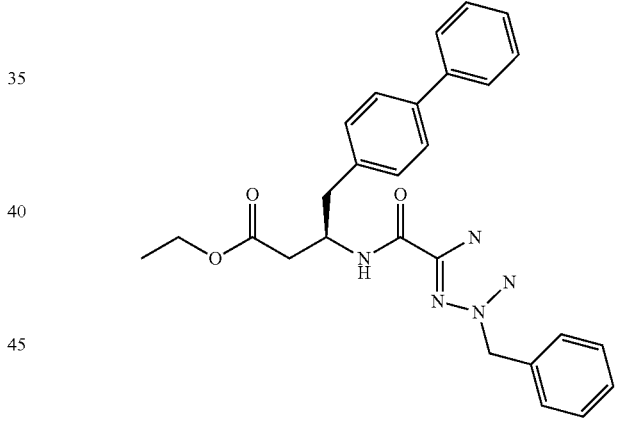

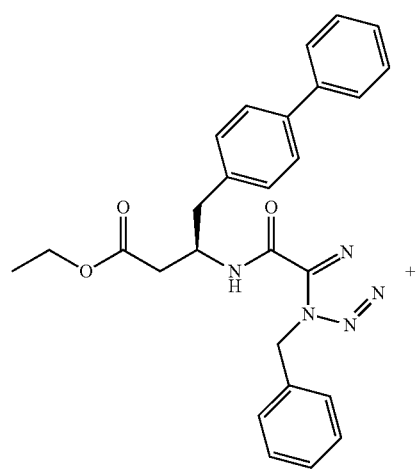

(R)-ethyl 4-(biphenyl-4-yl)-3-(tert-butoxycarbonylamino) butanoate (117 mg, 0.305 mmol) is treated with 4M HCl dioxane solution (2 mL). After stirring for 0.5 hour, the reaction mixture is concentrated under reduced pressure. To a solution of the obtained residue and Et$_3$N (0.106 mL, 0.763 mmol) in DCM (3 mL) is added benzyl-H-tetrazole-5-carbonyl chloride (mixture of 1 and 2-benzyl isomers, 82 mg, 0.366 mmol, prepared according to J. Med. Chem. 1986, 29, 538-549). After stirring for 10 minutes, Et$_3$N (0.106 mL, 0.763 mmol) and the acid chloride (82 mg, 0.366 mmol) are added. After stirring for 0.5 hour, the reaction mixture is diluted with ethyl acetate, washed with H$_2$O and brine, dried over Na$_2$SO$_4$, and concentrated under reduced pressure. The residue is purified by silica gel column chromatography to give (R)-3-[(1-benzyl-1H-tetrazole-5-carbonyl)-amino]-4-biphenyl-4-yl-butyric acid ethyl ester and (R)-3-[(2-benzyl-2H-tetrazole-5-carbonyl)-amino]-4-biphenyl-4-yl-butyric acid ethyl ester. HPLC retention time=1.51 minutes (condition D); MS=470.0

(m+1); 1H NMR (400 MHz, CDCl₃) δ ppm 1.27 (t, J=7.07, 7.07 Hz, 3H), 2.57-2.70 (m, 2H), 3.00 (dd, J=7.58, 13.77 Hz, 1H), 3.12 (dd, J=6.57, 13.77 Hz, 1H), 4.12-4.23 (m, 2H), 4.71-4.80 (m, 1H), 5.80 (s, 2H), 7.27-7.45 (m, 9H), 7.52 (d, J=8.34 Hz, 2H), 7.56 (d, J=8.46 Hz, 2H), 7.75 (d, J=7.33 Hz, 1H).

Intermediate 8-1

Synthesis of (R)-ethyl 3-amino-4-(3'-chlorobiphenyl-4-yl)butanoate hydrochloride

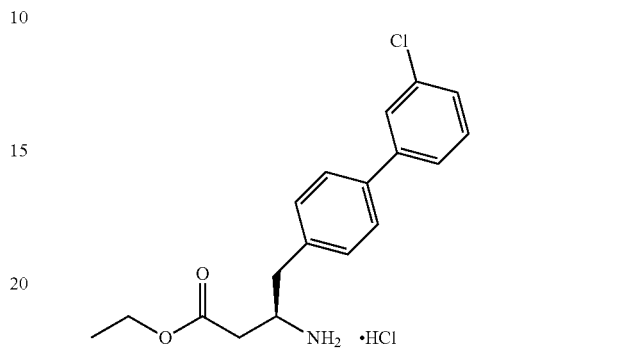

To (R)-ethyl 3-(tert-butoxycarbonylamino)-4-(3'-chlorobiphenyl-4-yl)butanoate (Intermediate 9-1: 3.33 g, 7.97 mmol) is added a solution of 4 M HCl in 1,4-dioxane (19.9 mL, 18.0 mmol) at room temperature. After stirring for 0.5 hours, the reaction mixture is concentrated under reduced pressure to give (R)-ethyl 3-amino-4-(3'-chlorobiphenyl-4-yl)butanoate hydrochloride (2.90 g). HPLC retention time=0.70 minutes (condition B); MS (m+1)=318.26; 1H NMR (400 MHz, CHLOROFORM-d) δ ppm 1.19-1.24 (m, 3 H) 2.73-2.78 (m, 1 H) 2.84-2.91 (m, 1 H) 3.05-3.11 (m, 1 H) 3.50-3.54 (m, 1 H) 3.92 (br s, 1 H) 4.14-4.17 (m, 2 H) 7.29-7.53 (m, 8 H) 8.73 (br. s., 3 H).

Following intermediates are prepared using similar procedure as described for intermediate 8-1:

| Intermediate # | Product | Starting Material | HPLC condition | RT (min) | MS (M+1) |
|---|---|---|---|---|---|
| Intermediate 8-2 | 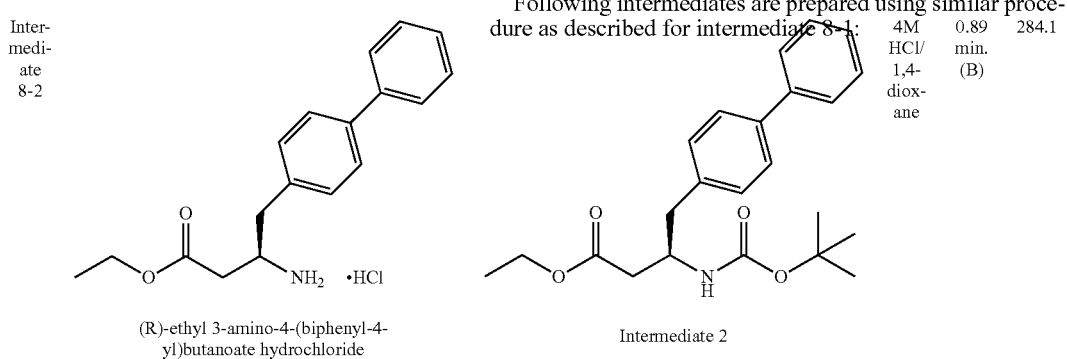 (R)-ethyl 3-amino-4-(biphenyl-4-yl)butanoate hydrochloride | Intermediate 2 | 4M HCl/1,4-dioxane | 0.89 min. (B) | 284.1 |
| Intermediate 8-3 | 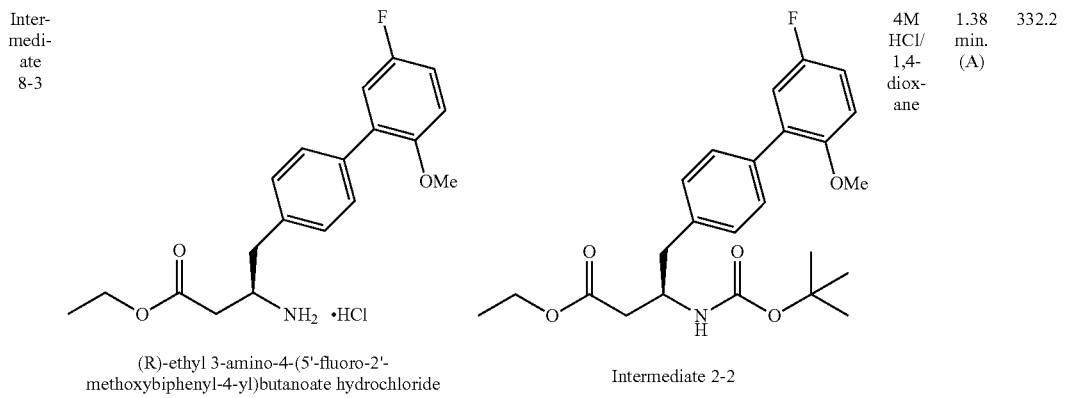 (R)-ethyl 3-amino-4-(5'-fluoro-2'-methoxybiphenyl-4-yl)butanoate hydrochloride | Intermediate 2-2 | 4M HCl/1,4-dioxane | 1.38 min. (A) | 332.2 |

| Intermediate # | Product | Starting Material | Condition | HPLC-RT (condition) | MS (M+1) |
|---|---|---|---|---|---|
| Intermediate 8-4 | (R)-benzyl 3-amino-4-(3'-chlorobiphenyl-4-yl)butanoate | Intermediate 9-2 | 4M HCl/1,4-dioxane | 1.20 min. (B) | 380.2 |
| Intermediate 8-5 | (R)-ethyl 3-amino-4-(5'-chloro-2'-fluorobiphenyl-4-yl)butanoate | Intermediate 2-1 | 4M HCl/1,4-dioxane | 0.88 min. (B) | 336.1 |

Intermediate 8-4

(R)-benzyl 3-amino-4-(3'-chlorobiphenyl-4-yl)butanoate hydrochloride

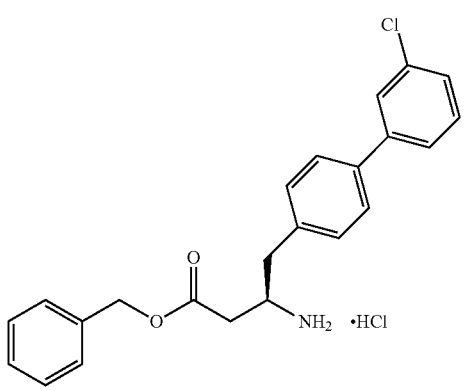 [SMILES: N[C@@H](CC(=O)OCc1ccccc1)Cc1ccc(-c2cccc(Cl)c2)cc1 ; Cl]

To (R)-benzyl 3-(tert-butoxycarbonylamino)-4-(3'-chlorobiphenyl-4-yl)butanoate (3.561 g, 7.42 mmol) is added a solution of 4 M HCl in 1,4-dioxane (18.55 mL, 74.2 mmol) at room temperature. After stirring for 4 hours, the reaction mixture is concentrated under reduced pressure to give (R)-benzyl 3-amino-4-(3'-chlorobiphenyl-4-yl)butanoate hydrochloride (3.11 g). HPLC retention time=1.07 minutes (condition B); MS (m+1)=380.1; 1H NMR (400 MHz, CHLOROFORM-d) δ ppm 2.81 (A of ABX, $J_{ab}$=17.4 Hz, $J_{ax}$=4.5 Hz, 1 H) 2.93 (B of ABX, $J_{ab}$=17.4 Hz, $J_{bx}$=7.6 Hz, 1 H) 3.03-3.09 (m, 1 H) 3.50 (dd, J=4.9 and 13.5 Hz, 1 H) 3.98 (br s, 1 H) 5.09 (s, 2 H) 7.24-7.22 (m, 9 H) 7.35-7.38 (m, 1 H) 7.42 (d, J=8.1 Hz, 2 H) 7.48-7.49 (m, 1 H) 8.78 (br s, 3 H).

Intermediate 9-1

Synthesis of (R)-ethyl 3-(tert-butoxycarbonylamino)-4-(3'-chlorobiphenyl-4-yl)butanoate

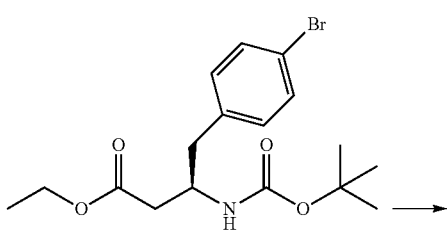

-continued

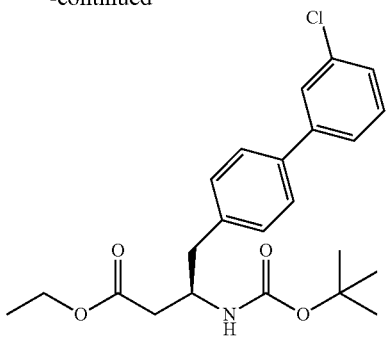

A mixture of (R)-ethyl 4-(4-bromophenyl)-3-(tert-butoxycarbonylamino)butanoate (4.89 g, 12.66 mmol), 3-chlorophenylboronic acid (2.97 g, 18.99 mmol), Pd(PPh$_3$)$_4$ (1.463 g, 1.266 mmol) and 2 M aqueous Na$_2$CO$_3$ (12.66 ml, 25.3 mmol) in 1,2-dimethoxyethane (100 ml) is allowed to stir at 95° C. under nitrogen for 3 hours. The reaction mixture is cooled to room temperature and quenched with brine. The two phases are separated. The mixture is extracted twice with ethyl acetate from the aqueous layer. The combined organic layer is washed with brine, dried over MgSO$_4$, filtered, and concentrated under reduced pressure. The obtained residue is purified by silica gel flash column chromatography (heptane/EtOAc=100:0 to 70:30) to give (R)-ethyl 3-(tert-butoxycarbonylamino)-4-(3'-chlorobiphenyl-4-yl)butanoate (3.33 g); HPLC retention time=1.44 minutes (condition B); MS (ES+) =318.26 (m-BOC+2; 100%); 1H NMR (400 MHz, CHLOROFORM-d) δ ppm 1.28 (t, J=7.2 Hz, 3 H) 1.41 (s, 9 H) 2.47 (A of ABX, J$_{ab}$=15.8 Hz, J$_{ax}$=5.9 Hz, 1 H) 2.52 (B of ABX, J$_{ab}$=15.8 Hz, J$_{bx}$=5.4 Hz, 1 H) 2.83-2.89 (m, 1 H) 2.95-3.00 (m, 1 H) 4.17 (q, J=7.2 Hz, 2 H) 4.18 (br s, 1 H) 5.07 (br s, 1 H) 7.26-7.37 (m, 4 H) 7.43-7.51 (m, 3 H) 7.55 (br t, J=1.8 Hz, 1 H).

Following intermediates are prepared using similar procedure as described for intermediate 9-1:

| Intermediate # | Product | Condition | HPLC-RT (condition) | MS (ES+; 100%) |
|---|---|---|---|---|
| Intermediate 9-2 | (R)-benzyl 3-(tert-butoxycarbonylamino)-4-(3'-chlorobiphenyl-4-yl)butanoate | Pd(PPh$_3$)$_4$, 3-chlorophenylboronic acid, aq. 2M Na2CO3, toluene, 95° C. | 1.74 min. (B) | 380.2 (m-BOC + 2) |

-continued

| Intermediate # | Product | Condition | HPLC-RT (condition) | MS (ES+; 100%) |
|---|---|---|---|---|
| Intermediate 9-3 | (R)-3-tert-Butoxycarbonylamino-4-(3'-chloro-biphenyl-4-yl)-butyric acid 5-methyl-2-oxo-[1,3]dioxol-4-ylmethyl ester | Pd(OAc)2, dicyclohexyl-(2',6'-dimethoxy-biphenyl-2-yl)-phosphane, 3-chlorophenyl-boronic acid, K3PO4, toluene, 95° C. | 1.53 min. (B) | 502 (m + 1) |
| Intermediate 9-4 | (R)-3-tert-Butoxycarbonylamino-4-(3'-chloro-biphenyl-4-yl)-butyric acid dimethylcarbamoyl methyl ester | Pd(PPh3)4, 3-chlorophenyl-boronic acid, K3PO4, DMF, 95° C. | 1.51 min. (B) | 475 (m + 1) |
| Intermediate 9-5 | (R)-3-tert-Butoxycarbonylamino-4-(3'-chloro-biphenyl-4-yl)-butyric acid 2-morpholin-4-yl-ethyl ester | Pd(PPh3)4, 3-chlorophenyl-boronic acid, K3PO4, DMF, 95° C. | 1.51 min. (B) | 503 (m + 1) |

Intermediate 9-2

(R)-benzyl 3-(tert-butoxycarbonylamino)-4-(3'-chlorobiphenyl-4-yl)butanoate

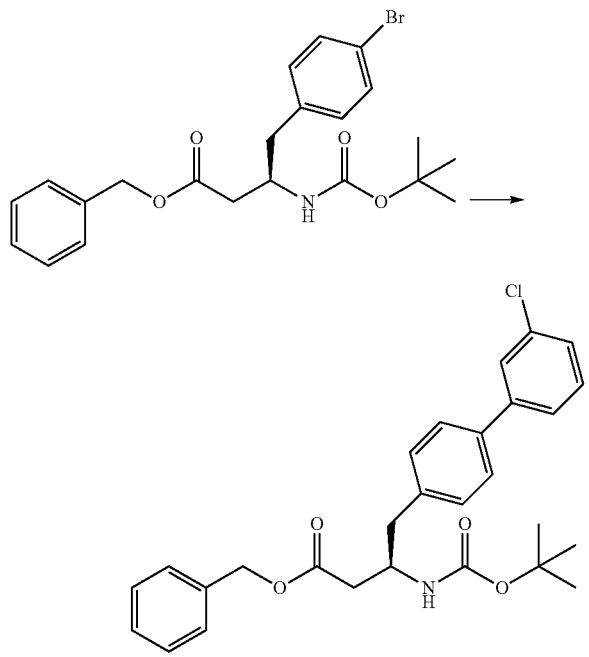

A suspension of give (R)-benzyl 4-(4-bromophenyl)-3-(tert-butoxycarbonylamino) butanoate (2.00 g, 4.46 mmol), 3-chlorophenylboronic acid (1.046 g, 6.69 mmol), Pd(PPh$_3$)$_4$ (0.515 g, 0.446 mmol) and Na2CO3aq (4.46 ml, 8.92 mmol) in Toluene (30 ml) is allowed to stir under nitrogen at 95° C. for 19 hr. The reaction mixture is cooled to ambient temperature, and diluted with brine and EtOAc. The products are extracted twice with EtOAc, washed with brine, dried over MgSO$_4$, filtered, and concentrated. The residue is purified by flash column chromatography on 90 g silica gel (eluent: heptane/EtOAc=100:0 to 65:35) to give (R)-benzyl 3-(tert-butoxycarbonylamino)-4-(3'-chlorobiphenyl-4-yl)butanoate (1.03 g); HPLC retention time=1.74 minutes (condition B); MS (ES+)=380.2 (m-BOC+2; 100%); 1H NMR (400 MHz, CHLOROFORM-d) δ ppm 1.40 (s, 9 H) 2.52 (A of ABX, J$_{ab}$=15.9 Hz, J$_{ax}$=5.8 Hz, 1 H) 2.58 (B of ABX, J$_{ab}$=15.9 Hz, J$_{bx}$=5.6 Hz, 1 H) 2.81-2.98 (m, 2 H) 4.19 (br s, 1 H) 5.07 (br d, 1 H) 5.12 (A of AB, J=12.3 Hz, 1 H) 5.17 (A of AB, J=12.3 Hz, 1 H) 7.20-7.22 (m, 2 H) 7.28-7.39 (m, 7 H) 7.42-7.47 (m, 3 H) 7.53-7.54 (m, 1 H).

Intermediate 10

Synthesis of (S)-benzyl 1-(2-tert-butoxy-2-oxoethyl)pyrrolidine-2-carboxylate

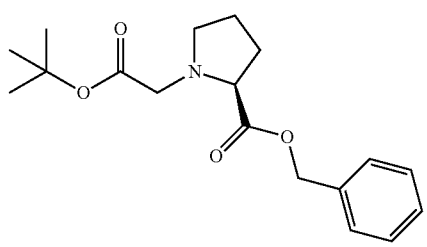 [SMILES: CC(C)(C)OC(=O)CN1CCC[C@H]1C(=O)OCc1ccccc1]

To a suspension of (S)-benzyl pyrrolidine-2-carboxylate hydrochloride (700 mg, 2.90 mmol) and K$_2$CO$_3$ (1201 mg, 8.69 mmol) in DMF (7 ml), t-butyl bromoacetate (0.535 ml, 3.62 mmol) is added. After stirring for 71 hours, aqueous K$_2$CO$_3$ (1.5 g of K$_2$CO$_3$/40 ml of H$_2$O) is added to the reaction mixture. The products are extracted with EtOAc. The organic layer is washed twice with water and once with brine, dried over K$_2$CO$_3$, filtered, and concentrated to give (S)-benzyl 1-(2-tert-butoxy-2-oxoethyl)pyrrolidine-2-carboxylate (458 mg); HPLC retention time=1.38 minutes (condition D); MS (m+1)=320.2; 1H NMR (400 MHz, CHLOROFORM-d) δ ppm 1.44 (s, 9 H) 1.81-2.03 (m, 3 H) 2.13-2.14 (m, 1 H) 2.82-2.88 (m, 1 H) 3.13-3.17 (m, 1 H) 3.46 (A of AB, J=17.3 Hz, 1 H) 3.49 (B of AB, J=17.3 Hz, 1 H) 3.73 (dd, J=8.8 and 4.8 Hz, 1 H) 5.15 (A of AB, J=12.4 Hz, 1 H) 5.17 (B of AB, J=12.4 Hz, 1 H) 7.29-7.38 (m, 5 H).

Intermediate 11

Synthesis of (R)-ethyl 3-(tert-butoxycarbonylamino)-4-(2',5'-dichlorobiphenyl-4-yl)butanoate

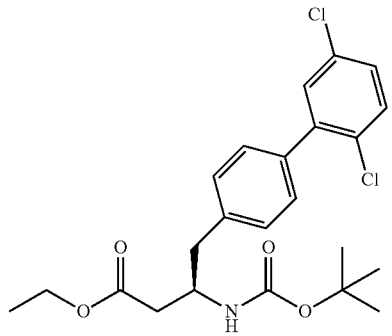 [SMILES: CCOC(=O)C[C@@H](Cc1ccc(-c2cc(Cl)ccc2Cl)cc1)NC(=O)OC(C)(C)C]

A mixture of (R)-ethyl 4-(4-bromophenyl)-3-(tert-butoxycarbonylamino)butanoate (1.005 g, 2.60 mmol), 2,5-dichlorophenylboronic acid (0.745 g, 3.90 mmol), Pd(PPh$_3$)$_4$ (0.301 g, 0.260 mmol) and 2 M aqueous Na$_2$CO$_3$ (2.60 ml, 5.20 mmol) in 1,2-dimethoxyethane (20 ml) is allowed to stir at 95° C. under nitrogen for 3 hours. The reaction mixture is cooled to room temperature and diluted with brine. The two phases are separated. The products are extracted twice with ethyl acetate (2×100 ml) from the aqueous layer. The combined organic layer is washed with brine, dried over MgSO$_4$, filtered, and concentrated under reduced pressure. The obtained residue is purified by silica gel flash column chromatography (heptane/EtOAc=100:0 to 70:30) to give (R)-ethyl 3-(tert-butoxycarbonylamino)-4-(2',5'-dichlorobiphenyl-4-yl)butanoate (1.09 g); HPLC retention time=1.50 minutes (condition B); MS (ES+)=352.00 (m-BOC+2; 100%); 1H NMR (400 MHz, CHLOROFORM-d) δ ppm 1.28 (t, J=7.1 Hz, 3 H) 1.41 (s, 9 H) 2.45-2.58 (m, 2 H) 2.85-3.00 (m, 2 H) 4.17 (t, J=7.1 Hz, 2 H) 4.20 (br s, 1 H) 5.06-5.08 (m, 1 H) 7.23-7.28 (m, 3 H) 7.31-7.40 (m, 4 H).

Intermediate 12

Synthesis of (R)-3-amino-4-(3'-chlorobiphenyl-4-yl)butanoic acid hydrochloride

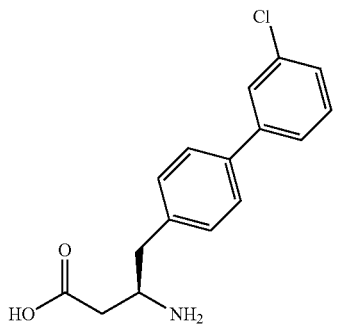 [SMILES: N[C@@H](CC(=O)O)Cc1ccc(-c2cccc(Cl)c2)cc1]

A solution of (R)-benzyl 3-(tert-butoxycarbonylamino)-4-(3'-chlorobiphenyl-4-yl)butanoate (152 mg, 0.317 mmol) and 1 M aqueous NaOH (1.583 ml, 1.583 mmol) in a mixed solvent of MeOH (0.3 ml) and THF (3 ml) is allowed to stir for 2 hours. The reaction is quenched with 1M aqueous HCl (2.5 ml). The products are extracted with EtOAc. The organic layer is dried over Na$_2$SO$_4$, filtered, and concentrated to give crude.

To the crude, a solution of 4 M HCl in 1,4-dioxane (1.583 ml, 6.33 mmol) is added. After stirring for 1 h, the precipitated solid is collected, and dried under reduced pressure to give (R)-3-amino-4-(3'-chlorobiphenyl-4-yl)butanoic acid hydrochloride (60.2 mg) as a white solid; HPLC retention time=0.52 minutes (condition B); MS (m+1)=290.22; 1H NMR (400 MHz, CD$_3$OD) δ ppm 2.58-2.74 (m, 2 H) 2.99-3.11 (m, 2 H) 3.80-3.85 (m, 1 H) 7.34-7.45 (m, 4 H) 7.54-7.57 (m, 1 H) 7.62-7.65 (m, 3 H).

Intermediate 13

(R)-tert-butyl 4-(1-(4-bromophenyl)-4-ethoxy-4-oxobutan-2-ylamino)-4-oxobutanoate

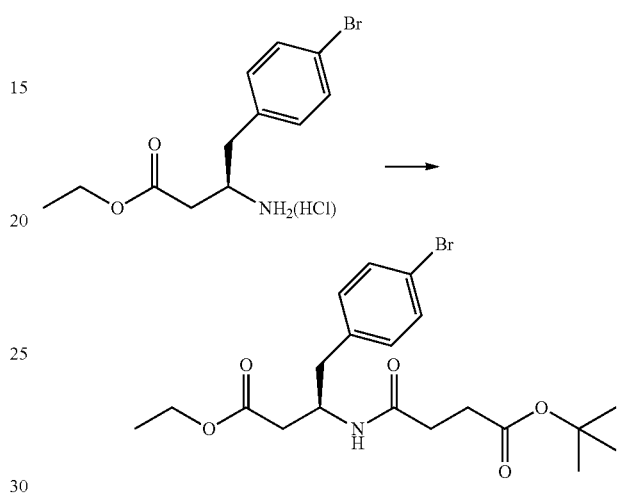

To a solution of 4-tert-butoxy-4-oxobutanoic acid (2.38 g, 13.64 mmol) in DMF (30 mL) and DCM (30 mL) is added (R)-ethyl 3-amino-4-(4-bromophenyl)butanoate hydrochloride (4 g, 12.4 mmol), HATU (5.19 g, 13.64 mmol), and TEA (6.91 mL, 49.6 mmol). After stirring at room temperature for 2 hours, the reaction is quenched with H$_2$O, and the crude is diluted with EtOAc, the organic layer is washed with brine, dried over Na$_2$SO$_4$, filtered, and concentrated under reduced pressure to give (R)-tert-butyl 4-(1-(4-bromophenyl)-4-ethoxy-4-oxobutan-2-ylamino)-4-oxobutanoate (4.0 g). HPLC retention time=1.70 minutes (condition A); MS (m+1)=444.1.

Intermediate 14

(R)-ethyl 4-(3'-chlorobiphenyl-4-yl)-3-(2-ethoxy-2-oxoacetamido)butanoate

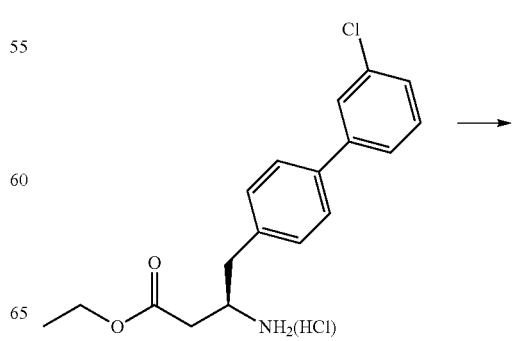

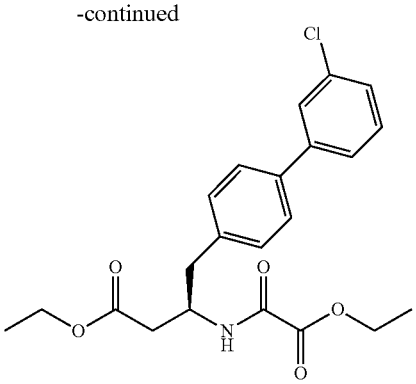

To a solution of (R)-ethyl 3-amino-4-(3'-chlorobiphenyl-4-yl)butanoate hydrochloride (500 mg, 1.57 mmol) in DMF (11 mL) is added TEA (0.23 mL, 1.65 mmol) and ethyl 2-chloro-2-oxoacetate (0.18 mL, 1.57 mmol) at room temperature. After stirring for 1 hour at room temperature, the reaction is quenched with H$_2$O, and the crude is diluted with EtOAc. The organic layer is washed with brine, dried over Na$_2$SO$_4$, filtered, and concentrated under reduced pressure. The obtained residue is purified by flash column chromatography on silica gel (eluent: heptane/EtOAc=70:30 to 50:50) to give (R)-ethyl 4-(3'-chlorobiphenyl-4-yl)-3-(2-ethoxy-2-oxoacetamido)butanoate (550 mg). HPLC retention time=1.88 minutes (condition A); MS (m+1)=418.3

Intermediate 15

(R)-ethyl 4-(3'-chlorobiphenyl-4-yl)-3-(2-hydrazinyl-2-oxoacetamido)butanoate

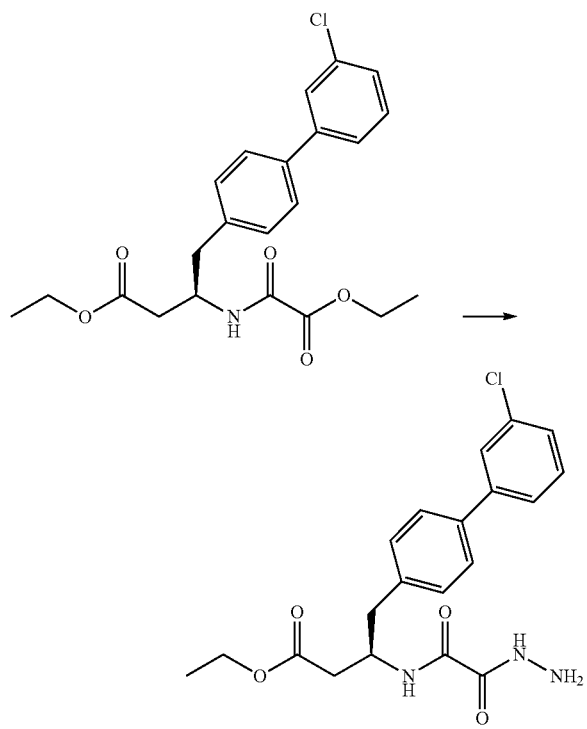

To a solution of (R)-ethyl 4-(3'-chlorobiphenyl-4-yl)-3-(2-ethoxy-2-oxoacetamido)butanoate (450 mg, 1.08 mmol) in MeOH (24 mL) is added a solution of 50% wt hydrazine (0.068 ml, 1.08 mmol) in MeOH (10 mL) at −20° C. After stirring for 18 hours at room temperature, the reaction mixture is concentrated under reduced pressure to give (R)-ethyl 4-(3'-chlorobiphenyl-4-yl)-3-(2-hydrazinyl-2-oxoacetamido)butanoate (412 mg). HPLC retention time=1.76 minutes (condition A); MS (m+1)=404.1

Intermediate 16

6-(methylsulfonamido)nicotinic acid

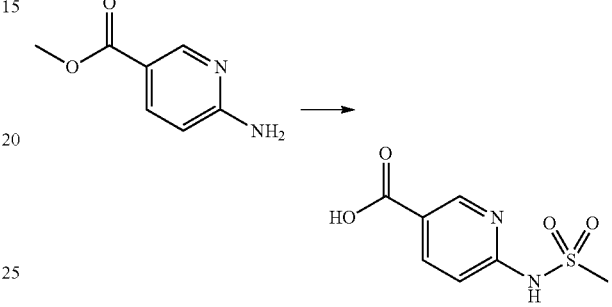

To a solution of methyl 6-aminonicotinate (1.0 g, 6.57 mmol) in CH$_2$Cl$_2$ (50 mL) with TEA (0.96 mL, 6.90 mmol) cooled in an ice bath is added MsCl (0.54 mL, 6.90 mmol) slowly. The crude is allowed to stir at room temperature for 2 hrs. The crude is then concentrated. The crude is dissolved in MeOH (20 mL) and to the crude is added 1 N NaOH (30 mL, 30 mmol). The crude is stirred at room temperature for 18 hrs. The crude is quenched with 1N HCl (32 mL, 32 mmol). The crude is concentrated to remove MeOH and some water is removed as well. The crude is diluted in CH$_2$Cl$_2$ and basified with 1 N NaOH (30 mL). The aq. layer is extracted with CH$_2$Cl$_2$. The aq. layer is acidified with concentrated HCl to bring the PH to 1 via PH paper indicator. The crude is diluted in EtOAc and the aq. layer is extracted with EtOAc. The combined organic layer is washed with brine, dried over MgSO$_4$, filtered, and concentrated to give 6-(methylsulfonamido)nicotinic acid (421 mg) as a yellow solid. HPLC retention time=0.40 minutes (condition D); MS (m+1)=217.2.

Intermediate 17 ethyl 2-ethyloxazole-5-carboxylate

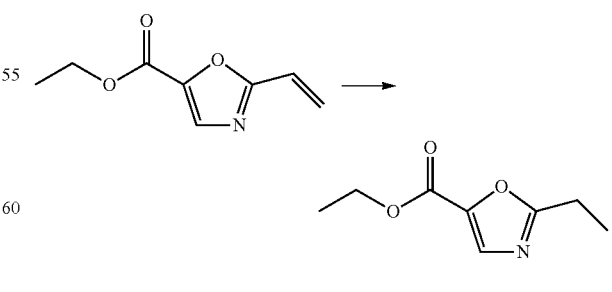

To a solution of ethyl 2-vinyloxazole-5-carboxylate (470 mg, 2.81 mmol) in MeOH (7 mL) is added 10% wt. Pd/C (100 mg, 0.094 mmol) at room temperature. After stirring at room temperature under a balloon of hydrogen for 1 hour, the crude is filtered to remove Pd/C. The filtrate is collected and concentrated to give ethyl 2-ethyloxazole-5-carboxylate (470 mg). HPLC retention time=1.09 minutes (condition A); MS (m+1)=170.3; 1H NMR (400 MHz, CD₃OD) δ ppm 1.35 (t, J=7.6 Hz, 3 H) 1.36 (t, J=7.2 Hz, 3 H) 2.87 (q, J=7.7 Hz, 2 H) 4.35 (q, J=7.2 Hz, 2 H) 7.71 (s, 1 H)

Intermediate 18

2-ethyloxazole-5-carboxylic acid

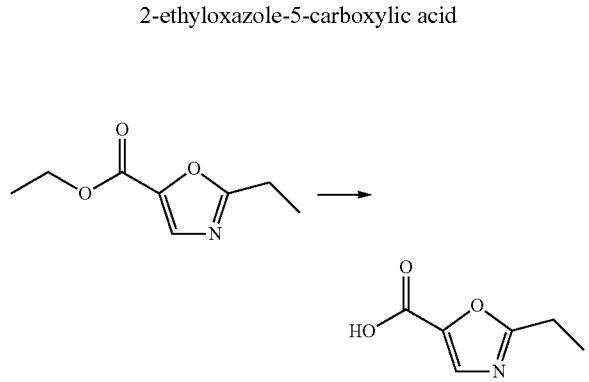

To a solution of 2-ethyloxazole-5-carboxylate (470 mg, 2.81 mmol) in MeOH (10 mL) is added 1N NaOH (6 mL, 6 mmol). After stirring at room temperature for 18 hours, the crude is concentrated under reduced pressure to remove MeOH and is diluted with EtOAc. The organic layer is washed with brine, dried over Na₂SO₄, filtered and concentrated under reduced pressure to give 2-ethyloxazole-5-carboxylic acid (244 mg). 1H NMR (400 MHz, CD₃OD) δ ppm 1.36 (t, J=7.7 Hz, 3 H) 2.89 (q, J=7.6 Hz, 2 H) 5.15 (br. s., 1 H) 7.69 (s, 1 H)

Intermediate 19

3-Hydroxy-isoxazole-5-carboxylic acid

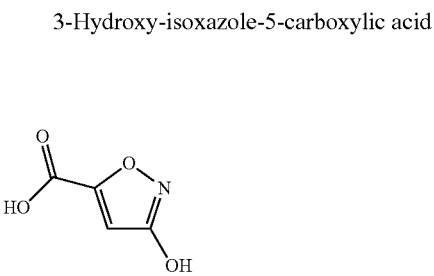

To a solution of 3-hydroxy-isoxazole-5-carboxylic acid methyl ester (286 mg, 2.0 mmol) in methanol (7 mL) is added 1N NaOH (4.0 mL, 4.0 mmol) and the mixture is stirred at room temperature for 18 hrs. The solvent is removed under reduced pressure and 4.0 mL of 1N HCl is added to the residue. The resulting solution is lyophilized to give the product which is used as is in subsequent reactions.

Intermediate 20

5-Methoxycarbonylmethyl-furan-2-carboxylic acid

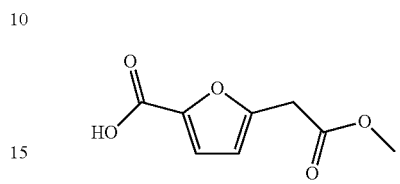

To a solution of 5-methoxycarbonylmethyl-furan-2-carboxylic acid methyl ester (250 mg, 1.26 mmol) in methanol (5 mL) is added 1N NaOH (2.78 mL, 2.78 mmol) and the mixture is stirred at room temperature for 18 hours. The solvent is removed under reduced pressure and 2.78 mL of 1N HCl is added to the residue. The resulting solution is lyophilized to give 5-carboxymethyl-furan-2-carboxylic acid.

Next, to a solution of the above diacid (220 mg, 1.29 mmol) in methanol (8 mL) is added Amberlyst-15 resin (50 mg) and the mixture is stirred at room temperature for 18 hours. The resin is filtered and the solvent is removed under reduced pressure to give the product which is used as is in subsequent reactions. 1H NMR (400 MHz, CHLOROFORM-d) δ ppm 3.75 (s, 3H), 3.82 (s, 2H), 6.45 (d, J=3.54 Hz, 1H), 7.29 (d, J=3.54 Hz, 1H), 10.17 (s, broad, 1H).

Intermediate 21

(R)-4-(3'-Chloro-biphenyl-4-yl)-3-isocyanato-butyric acid ethyl ester

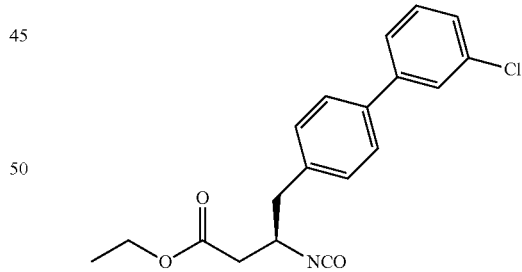

To a vigorously stirred mixture of 8% aqueous sodium bicarbonate (3 mL) and methylene chloride (3 mL) at 0° C. is added triphosgene (28.1 mg, 0.095 mmol) and the mixture is stirred at 0° C. for 5 minutes then Intermediate 17-1 (100 mg, 0.284 mmol) is added and stirring is continued for an additional 15 minutes. The organic layer is separated and dried over sodium sulfate. The solvent is removed under reduced pressure to give the title compound. This is used as is in subsequent reactions.

Intermediate 22

2-(4-Methoxy-benzyl)-2H-tetrazole-5-carbonyl chloride

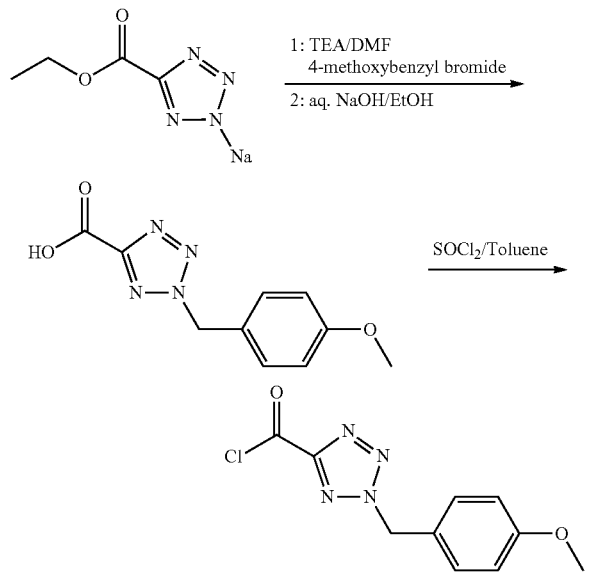

To a solution of 1H-tetrazole-5-carboxylic acid ethyl ester sodium salt (500 mg, 3.05 mmol) in DMF (5 ml) at room temperature is added 4-methoxybenzyl chloride (747 μl, 5.48 mmol) and TEA (1500 μl, 10.76 mmol). The reaction mixture is stirred at room temperature overnight. The reaction is added water and extracted with EtOAc. The combined organic layer is washed with brine and dried over anhydrous sodium sulfate, filtered and concentrated under reduced pressure. The residue is purified by column chromatography (10% to 30% EtOAc/Heptane). To a solution of the purified residue in EtOH (2 ml) at room temperature is added NaOH (2 ml, 2.000 mmol) and the mixture is stirred at room temperature. After stirring for 1 hour, the mixture is concentrated under reduced pressure to remove EtOH and extracted with EtOAC after being acidified to pH<5. The combined organic layer is washed with brine and dried over anhydrous sodium sulfate, filtered and concentrated under reduced pressure to give 2-(4-methoxy-benzyl)-2H-tetrazole-5-carboxylic acid.

Next, to a mixture of 2-(4-methoxy-benzyl)-2H-tetrazole-5-carboxylic acid in Toluene (15 ml) at room temperature is added SOCl$_2$ (1 ml, 13.70 mmol) and the mixture is heated at 80° C. for 3 hr. The reaction mixture is concentrated under reduced pressure to give the crude product, which is used without further purification.

Intermediate 23

(R)-3-Amino-4-(3'-chloro-biphenyl-4-yl)-butyric acid indan-5-yl ester

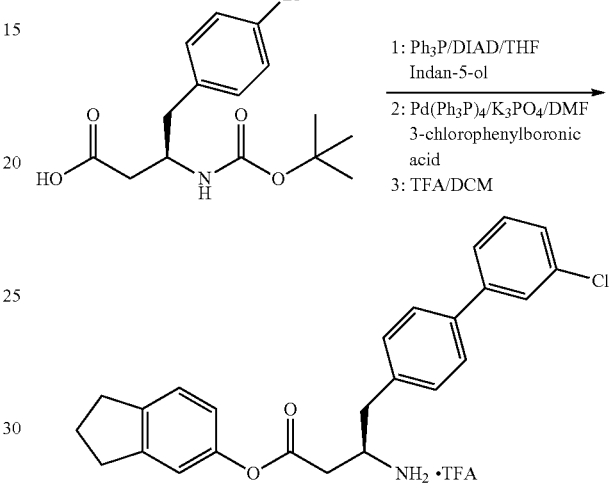

To a suspension of boc-(R)-3-amino-4-(4-bromo-phenyl)-butanoic acid (500 mg, 1.396 mmol) in THF (12 ml) at room temperature is added 5-indanol (187 mg, 1.396 mmol) and Ph$_3$P (403 mg, 1.535 mmol). To the mixture at ice bath is added DIAD (0.326 ml, 1.675 mmol) and the mixture is stirred from ice bath to room temperature overnight. The reaction is concentrated under reduced pressure and purified by column chromatography (5% to 20% EtOAc/Heptane) to give 450 mg of solid. To a solution of the obtained solid (200 mg, 0.422 mmol) in DMF (5 ml) at room temperature is added 3-chlorophenylboronic acid (79 mg, 0.506 mmol), tripotassium phosphate (134 mg, 0.632 mmol) and Pd(PPh$_3$)$_4$ (48.7 mg, 0.042 mmol). The reaction is stirred at 100° C. overnight. The reaction is quenched by brine and is extracted with EtOAc. The combined organic layer is washed with brine and dried over anhydrous sodium sulfate, filtered and concentrated under reduced pressure. The residue is purified by column chromatography (5% to 30% EtOAc/Heptane). To the obtained residue (143 mg, 0.283 mmol) in DCM (1 ml) at room temperature is added TFA (1 mL, 12.98 mmol) and the mixture is stirred at room temperature for 2 hours. The mixture is concentrated to give the crude salt which is used directly without further purification. HPLC retention time=1.27 minutes (condition B); MS (m+1)=406.

Intermediate 23-1

(R)-3-amino-4-(3'-chloro-biphenyl-4-yl)-2-hydroxy-butyric acid methyl ester hydrochloride

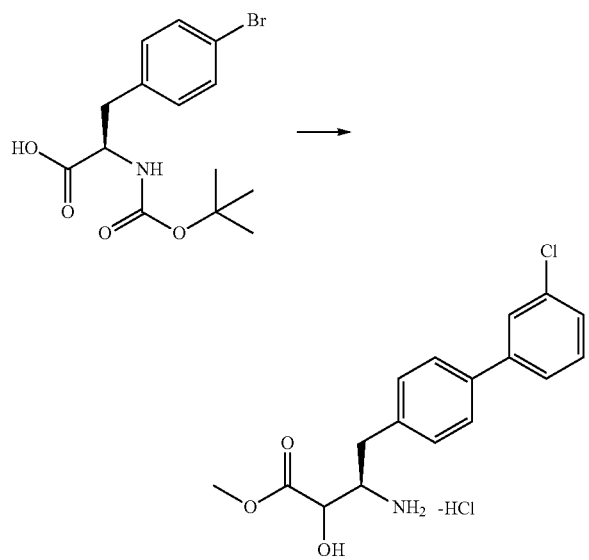

(R)-3-(4-Bromo-phenyl)-2-tert-butoxycarbonylamino-propionic acid (4.0 g, 11.6 mmol), 3-chlorophenylboronic acid (2.36 g, 15.11 mmol), Pd(PPh$_3$)$_4$ (0.067 g, 0.058 mmol) and 2M Na$_2$CO$_3$ aqueous solution (8.0 mL) are refluxed in 1,2-dimethoxyethane (70 mL) for 2.5 h under N$_2$ atmosphere. After cooling to room temperature, the reaction mixture is diluted with EtOAc and washed with 1M HCl and brine. The organic layer is dried over Na$_2$SO$_4$ and concentrated. The residue is purified by flash column chromatography (silica gel, DCM/10% MeOH in DCM=100:0 to 0:100) to give (R)-2-tert-butoxycarbonylamino-3-(3'-chloro-biphenyl-4-yl)-propionic acid (containing impurities). HPLC retention time=1.56 minutes (condition A): MS (m+1)=376.

This is dissolved in 1,2-dimethoxyethane (40 mL) and Et$_3$N (1.46 mL, 10.5 mmol) and ethyl chloroformate (1.00 mL, 10.5 mmol) are added. After being stirred at room temperature for 0.5 h, the resultant precipitate is removed by filtration. To the filtrate is slowly added NaBH$_4$ (0.44 g, 11.6 mmol) in H$_2$O (5 mL). After being stirred for 2 h, the reaction mixture is diluted with EtOAc and washed with H$_2$O and brine. The organic layer is dried over Na$_2$SO$_4$, concentrated and purified by flash column chromatography (silica gel, eluent; heptane/EtOAc=100:0 to 0:100) to give [(R)-2-(3'-chloro-biphenyl-4-yl)-1-hydroxymethyl-ethyl]-carbamic acid tert-butyl ester (2.8 g). HPLC retention time=1.26 minutes (condition A): MS (m+1-Boc)=262. 1H-NMR (400 MHz, DMSO-d6) ppm 1.43 (s, 9 H), 2.90 (d, 2 H, J=7.33 Hz), 3.60 (dd, 1 H, J=5.05, 10.86 Hz), 3.72 (dd, 1 H, J=3.79, 11.12 Hz), 3.91 (bs, 1 H), 4.75 (bs, 1 H), 7.29-7.34 (m, 3 H), 7.37 (t, 1 H, J=7.83 Hz), 7.44-7.48 (m, 1 H), 7.51 (d, 2 H, J=8.08 Hz), 7.57 (t, 1 H, J=1.77 Hz).

Next, to a solution of [(R)-2-(3'-chloro-biphenyl-4-yl)-1-hydroxymethyl-ethyl]-carbamic acid tert-butyl ester (2.0 g, 5.53 mmol) in DCM (30 mL) is added Dess-Martin periodinane (2.81 g, 6.63 mmol). After being stirred at room temperature for 2 h, the reaction mixture is diluted with EtOAc and washed with saturated NaHCO$_3$ aqueous solution and brine. The organic layer is dried over Na$_2$SO$_4$ and concentrated. The residue is purified by flash column chromatography (silica gel, eluent; heptane/EtOAc=100:0 to 0:100) to give [(R)-2-(3'-chloro-biphenyl-4-yl)-1-formyl-ethyl]-carbamic acid tert-butyl ester (1.05 g). HPLC retention time=1.27 minutes (condition A): MS (m+1)=360.

This is dissolved in MeOH (20 mL) and AcOH (0.199 mL, 3.47 mmol). To this solution KCN (0.226 g, 3.47 mmol) in H$_2$O (4 mL) is slowly added. After being stirred at room temperature overnight, the reaction mixture is diluted with EtOAc and washed with saturated NaHCO$_3$ aqueous solution, H$_2$O and brine. The organic layer is dried over Na$_2$SO$_4$ and concentrated. This is treated with 4M HCl in dioxane (20 mL) and MeOH (10 mL) at room temperature. After being stirred overnight, the reaction mixture is concentrated. The residue is dissolved in MeOH and treated with SOCl$_2$ (0.211 mL, 2.89 mmol). After being stirred at 50° C. for 5 h, the reaction mixture is concentrated to dryness. The residue is dissolved in THF (10 mL) and treated with saturated NaHCO$_3$ aqueous solution (5 mL) and Boc$_2$O (0.631 g, 2.89 mmol). After being stirred at room temperature for 2 h, the reaction mixture is diluted with EtOAc and washed with brine. The organic layer is dried over MgSO$_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-hydroxy-butyric acid methyl ester (0.61 g). HPLC retention time=1.01, 1.06 minutes (condition B): MS (m+1-Boc)=320. 1H-NMR (400 MHz, CDCl$_3$) δ ppm 1.40 (s, 9 H), 2.77-3.05 (m, 2 H), 3.63 (s, 0.7 H), 3.77 (s, 2.3 H), 4.11 (s, 0.8 H), 4.25-4.40 (m, 1.2 H), 4.78-4.95 (m, 1 H), 7.27-7.40 (m, 4 H), 7.42-7.58 (m, 4 H).

(R)-3-tert-butoxycarbonylamino-4-(3'-chloro-biphenyl-4-yl)-2-hydroxy-butyric acid methyl ester (113 mg, 0.269 mmol) is treated with 4M HCl in dioxane (2 mL). After being stirred at room temperature for 1 h, the reaction mixture is concentrated. The residue is used for a next step without further purification. HPLC retention time=1.22, 1.29 minutes (condition A): MS (m+1)=320.

Intermediate 24

(R)-3-amino-4-(3'-chloro-biphenyl-4-yl)-2-methoxy-butyric acid methyl ester hydrochloride

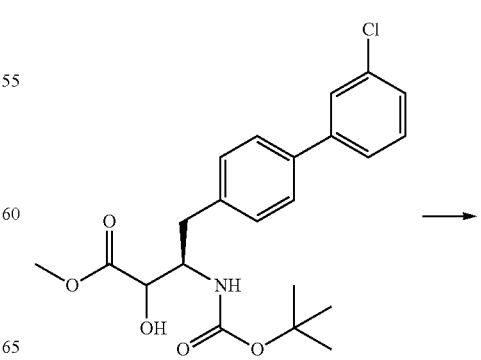

237
-continued

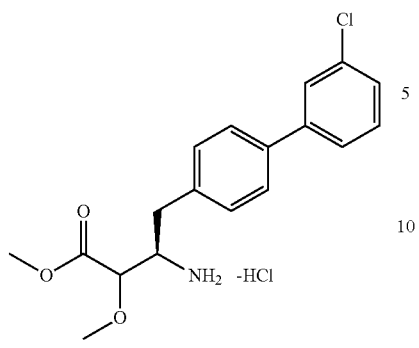

To a solution of (R)-3-tert-butoxycarbonylamino-4-(3'-chloro-biphenyl-4-yl)-2-hydroxy-butyric acid methyl ester (610 mg, 1.45 mmol) in CH$_3$CN (20 mL) are added iodomethane (0.545 mL, 8.72 mmol and silver oxide (1.35 g, 5.81 mmol). After being stirred at room temperature for 16 h, additional iodomethane (0.545 mL, 8.72 mmol) and silver oxide (1.35 g, 5.81 mmol) are added and stirred for 3 days. The reaction mixture is filtered through celite pad and the filtrate is washed with brine. The organic layer is dried over MgSO$_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-methoxy-butyric acid methyl ester (500 mg). HPLC retention time=1.20, 1.25 minutes (condition B): MS (m+1-Boc)=334. 1 H-NMR (400 MHz, CDCl$_3$) δ ppm 1.37, 1.41 (s, 9 H), 2.72-3.03 (m, 2 H), 3.43, 3.71 (s, 3H), 3.63-3.82 (m, 1 H), 4.27-4.41 (m, 1 H), 4.68-5.04 (m, 1 H), 7.28-7.40 (m, 4 H), 7.41-7.61 (m, 4 H).

(R)-3-tert-butoxycarbonylamino-4-(3'-chloro-biphenyl-4-yl)-2-methoxy-butyric acid methyl ester (200 mg, 0.461 mmol) is treated with 4M HCl in dioxane (3 mL). After being stirred at room temperature for 1 h, the reaction mixture is concentrated. The residue is used for a next step without further purification. HPLC retention time=1.26, 1.33 minutes (condition A): MS (m+1)=334.

Intermediate 25

(R)-3-Amino-4-(3'-chloro-biphenyl-4-yl)-2-fluoro-butyric acid methyl ester hydrochloride

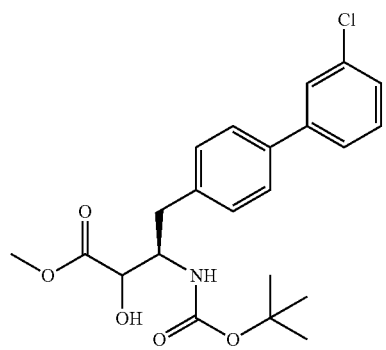

238
-continued

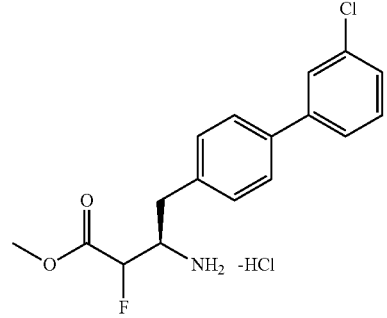

To a solution of (R)-3-tert-butoxycarbonylamino-4-(3'-chloro-biphenyl-4-yl)-2-hydroxy-butyric acid methyl ester (220 mg, 0.524 mmol) is added DAST (0.083 mL, 0.629 mmol) at 0° C. The reaction mixture is gradually warmed to room temperature and stirred for 1 h. Additional DAST (0.083 mL, 0.629 mmol) is added and stirred at room temperature for 2 h. The reaction mixture is diluted with EtOAc and washed with saturated NaHCO$_3$ aqueous solution and brine. The organic layer is dried over Na$_2$SO$_4$ and concentrated. The residue is purified by flash column chromatography (silica gel, eluent; heptane/EtOAc=100:0 to 0:100) to give (R)-3-tert-butoxycarbonylamino-4-(3'-chloro-biphenyl-4-yl)-2-fluoro-butyric acid methyl ester (63 mg). HPLC retention time=1.36 minutes (condition B): MS (m+1-Boc)=322. 1H-NMR (400 MHz, CDCl$_3$) δ ppm 1.39 (s, 9 H), 2.84-2.95 (m, 2 H), 3.06 (bs, 0.5 H), 3.69 (s, 3 H), 4.43-4.61 (m, 1 H), 4.72-4.80 (m, 0.5 H), 5.00 (s, 0.5 H), 5.12 (s, 0.5 H), 7.28-7.34 (m, 3 H), 7.37 (t, 1 H, J=7.58 Hz), 7.42-7.47 (m, 1 H), 7.48-7.53 (m, 1 H), 7.55 (t, 1 H, J=2.02 Hz). $^{19}$F-NMR (377 MHz, CDCl$_3$) δ ppm −204.18.

(R)-3-tert-butoxycarbonylamino-4-(3'-chloro-biphenyl-4-yl)-2-fluoro-butyric acid methyl ester (60 mg, 0.142 mmol) is treated with 4M HCl in dioxane (1.5 mL). After being stirred at room temperature for 1 h, the reaction mixture is concentrated. The residue is used for a next step without further purification. HPLC retention time=0.88 minutes (condition B): MS (m+1)=322.

Intermediate 26

[(R)-1-(3'-chloro-biphenyl-4-ylmethyl)-3-methanesulfonylamino-3-oxo-propyl]-carbamic acid tert-butyl ester

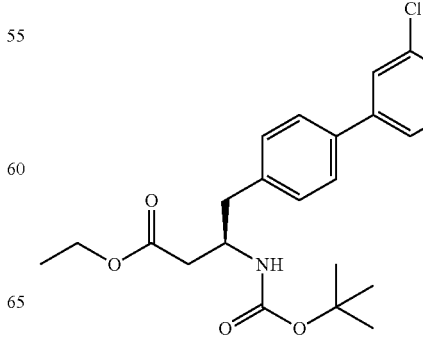

-continued

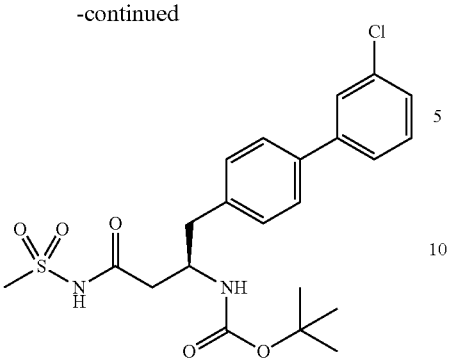

(R)-3-tert-butoxycarbonylamino-4-(3'-chloro-biphenyl-4-yl)-butyric acid ethyl ester (250 mg, 0.598 mmol) is treated with 2M NaOH aqueous solution (1 mL) in THF (1 mL) and EtOH (2 mL). After being stirred for 1 h, the reaction mixture is acidified with 1M HCl and extracted with EtOAc. The organic layer is washed with brine, dried over $Na_2SO_4$ and concentrated in vacuo. To a solution of this residue in DMF (2 mL) are added methylsulfonamide (85 mg, 0.897 mmol), EDC (172 mg, 0.897 mmol), HOAt (98 mg, 0.718 mmol), and $Et_3N$ (0.125 mL, 0.897 mmol). After being stirred at room temperature overnight, the reaction mixture is diluted with EtOAc, washed with 1M HCl and brine. The organic layer is dried over $Na_2SO_4$ and concentrated. The residue is purified by flash column chromatography (silica gel, eluent: DCM/ 10% MeOH in DCM=100:0 to 0:100) to give [(R)-1-(3'-chloro-biphenyl-4-ylmethyl)-3-methanesulfonylamino-3-oxo-propyl]-carbamic acid tert-butyl ester (244 mg). HPLC retentions time=1.30 minutes (condition B); MS (m+1)=467; 1H NMR (400 Mz, DMSO-d6) δ ppm 1.30 (s, 9 H), 2.41-2.48 (m, 2 H), 2.70-2.78 (m, 2 H), 3.18 (s, 3 H), 3.99-4.11 (m, 1 H), 7.28 (d, 2 H, J=8.34 Hz), 7.38-7.44 (m, 1 H), 7.48 (t, 1 H, J=7.83 Hz), 7.59-7.66 (m, 3 H), 7.69 (s, 1 H).

Intermediate 27-1

(R)-3-[2-(tert-butoxycarbonyl-ethoxycarbonylmethyl-amino)-propionylamino]-4-(3'-chloro-biphenyl-4-yl)-butyric acid ethyl ester

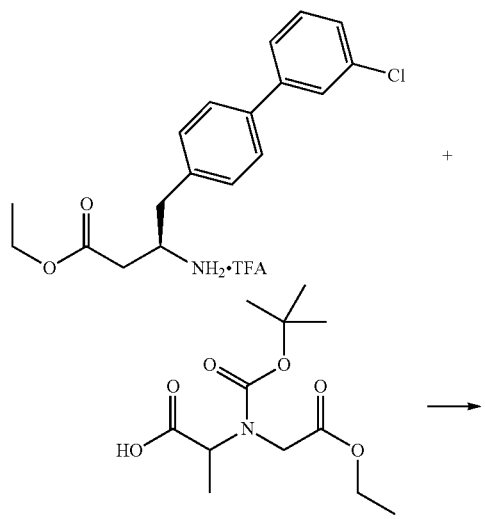

-continued

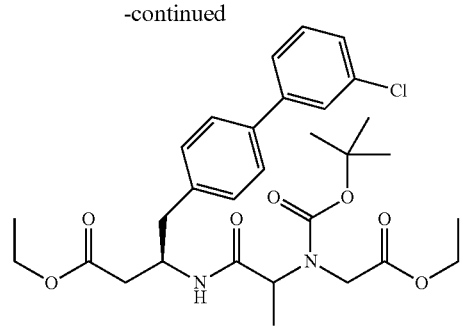

To a suspension of 2-(tert-butoxycarbonyl-ethoxycarbonylmethyl-amino)-propionic acid TFA salt (197 mg, 0.714 mmol) in THF (10 ml) at room temperature is added EDCl (219 mg, 1.142 mmol) and HOBT (164 mg, 1.071 mmol). The mixture is stirred at room temperature for 10 mins and then was added a solution of (R)-3-amino-4-(3'-chloro-biphenyl-4-yl)-butyric acid ethyl ester (202 mg, 0.571 mmol) in THF and TEA (0.199 ml, 1.428 mmol). The mixture is stirred at room temperature. Reverse phase HPLC [30 to 90% ACN—$H_2O$ (0.1% TFA) over 10 min by X-Bridge phenyl column] give the title compound (290 mg, 71% yield). LCMS (condition B): 575 (M+1); retention time=1.52 min.

Intermediate 27-2

2-(tert-Butoxycarbonyl-ethoxycarbonylmethyl-amino)-propionic acid

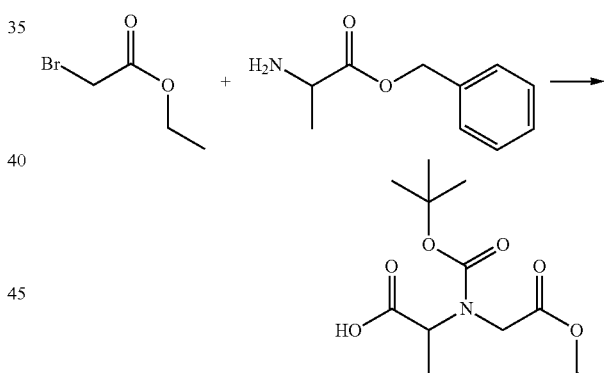

To a solution of H-DL-Ala-OBzl.p-tosylate (2.88 g, 8.20 mmol) in THF (80 ml) at room temperature was added TEA (3.43 ml, 24.60 mmol) and followed by ethyl bromoacetate (1.096 ml, 9.84 mmol). The reaction was stirred at room temperature over night. There were some white solid in the reaction. The reaction mixture was filtered off the white solid and concentrated for purification. Flash chromatography (silica gel, 2 to 4% EtOH/DCM) gave the title compound as an oil (1.7 g, 78% yield). LCMS (condition B): 266 (M+1); retention time=0.70 min.

Next, to a solution of 2-(ethoxycarbonylmethyl-amino)-propionic acid benzyl ester (1.7 g, 6.41 mmol) in DCM (80 ml) at 0° C. was added BOC-anhydride (2.232 ml, 9.61 mmol) and followed by TEA (2.68 ml, 19.22 mmol). The reaction mixture was slowly warmed up to room temperature and stirred over night. The reaction was quenched by brine and was extracted with DCM. The combined organic layer was washed with brine and dried over anhydrous sodium sulfate, filtered and concentrated to give the crude. Flash chromatography (silica gel, to 10% acetone/heptane) gave the title compound as an oil (1.66 g, 71% yield). LCMS (condition B): 366 (M+1); retention time=1.13 min.

Next, a solution of 2-(tert-butoxycarbonyl-ethoxycarbonylmethyl-amino)-propionic acid benzyl ester in EtOAc was hydrogenated under H₂ balloon by catalyst 10% Pd/C wet for 1 hr. The reaction was filtered off the catalyst and concentrated to give the crude for the next reaction.

Intermediate 28

(R)-3-Amino-4-(3'-chloro-biphenyl-4-yl)-2-methyl-butyric acid ethyl ester trifluoroacetate

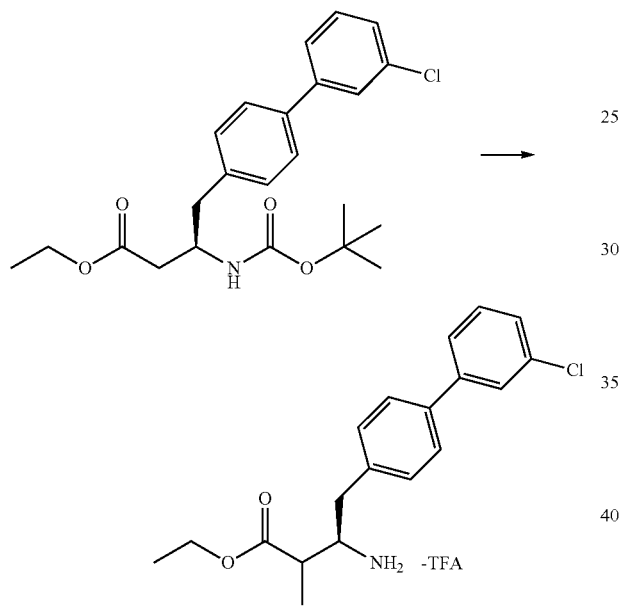

To a solution of (R)-3-tert-butoxycarbonylamino-4-(3'-chloro-biphenyl-4-yl)-butyric acid ethyl ester (300 mg, 0.718 mmol) in THF (10 ml) at −78° C. is added LiHMDS/THF (1M) (1.579 ml, 1.579 mmol). The reaction mixture is stirred at −78° C. for 50 min and then to this mixture is added methyl iodine (0.054 ml, 0.861 mmol) and the reaction is slowly warmed up to room temperature and stirred over night. The reaction is quenched by sat. NH₄Cl and is extracted with EtOAc. The combined organic layer is washed with brine and dried over anhydrous sodium sulfate, filtered and concentrated to give the crude. Reverse phase HPLC [20 to 90% ACN—H₂O (0.1% TFA) over 10 min by Sunfire C18] give (R)-3-tert-butoxycarbonylamino-4-(3'-chloro-biphenyl-4-yl)-2-methyl-butyric acid ethyl ester. LCMS (condition B): 432 (M+1); retention time=1.55 min. To a solution of (R)-3-tert-butoxycarbonylamino-4-(3'-chloro-biphenyl-4-yl)-2-methyl-butyric acid ethyl ester (240 mg, 0.556 mmol) in DCM (2 ml) at room temperature was added TFA (1.070 ml, 13.89 mmol) and the mixture is stirred at room temperature. 1 hr the reaction is done so the mixture is concentrated to give (R)-3-amino-4-(3'-chloro-biphenyl-4-yl)-2-methyl-butyric acid ethyl ester trifluoroacetate. LCMS (condition B): 332 (M+1); retention time=1.00 min.

Intermediate 29

(2R,4S)-4-amino-5-biphenyl-4-yl-2-methyl-pentanoic acid ethyl ester

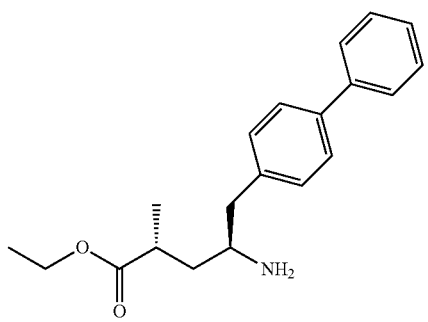 [SMILES: CCOC(=O)[C@H](C)C[C@H](N)Cc1ccc(-c2ccccc2)cc1]

Using the same procedure described in WO2008083967 or US005217996.

Intermediate 30

(2R,4S)-4-amino-5-biphenyl-4-yl-2-methyl-pentanoic acid benzyl ester hydrochloride

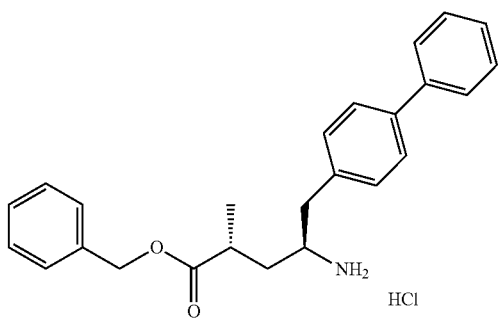 [SMILES: C[C@H](C[C@H](N)Cc1ccc(-c2ccccc2)cc1)C(=O)OCc1ccccc1 ; Cl]

To a solution of (2R,4S)-5-biphenyl-4-yl-4-tert-butoxycarbonylamino-2-methyl-pentanoic acid (prepared using the procedure described in WO 2008083967) (1.0 g, 2.61 mmol) and benzyl bromide (468 mg, 2.74 mmol) in DMF (15 mL) is added potassium carbonate (541 mg, 3.91 mmol) and the mixture is stirred at room temperature for 2 hours. Water is added and the mixture is extracted with ethyl acetate. The combined organic layers are washed with water and dried over magnesium sulfate. The solvent is removed under reduced pressure and the residual oil is purified by column chromatography using heptane/EtOAc (4:1) to furnish (2R, 4S)-5-biphenyl-4-yl-4-tert-butoxycarbonylamino-2-methyl-pentanoic acid benzyl ester.

Next, to a solution of (2R,4S)-5-biphenyl-4-yl-4-tert-butoxycarbonylamino-2-methyl-pentanoic acid benzyl ester in THF (5 mL) is added 4M HCl in dioxane (3 mL) and the solution is stirred at room temperature for 1 hour. The solvent is removed under reduced pressure to give the title compound. MS 374.4 (M+1).

Intermediate 31

(2R,4S)-4-[(1-Benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester

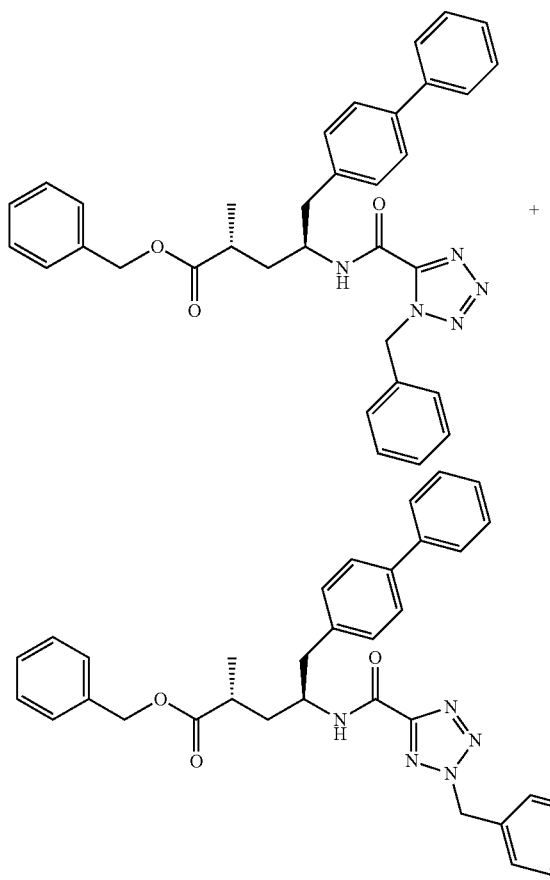

To a solution of (2R,4S)-benzyl 4-amino-5-(biphenyl-4-yl)-2-methylpentanoate (92 mg, 0.224 mmol) and Et$_3$N (0.078 mL, 0.561 mmol)) in DCM (2 mL) are added benzyl-H-tetrazole-5-carbonyl chloride (mixture of 1 and 2-benzyl isomers, 60 mg, 0.269 mmol, prepared according to *J. Med. Chem.* 1986, 29, 538-549). After stirring for 0.5 hour, Et$_3$N (0.078 mL, 0.561 mmol) and the acid chloride (60 mg, 0.269 mmol) are added. After stirring for 0.5 hour, the reaction mixture is diluted with ethyl acetate, washed with H$_2$O and brine, dried over Na$_2$SO$_4$, and concentrated. The residue is purified by silica gel column chromatography to give a mixture of (2R,4S)-4-[(1-benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester. HPLC Retention time 1.71 minutes (condition D); MS 560.0 (M+1); 1H NMR (400 MHz, CDCl$_3$) ppm 1.19 (d, J=7.07 Hz, 3H), 1.62-1.71 (m, 1H), 2.03-2.11 (m, 1H), 2.62-2.71 (m, 1H), 2.89-3.00 (m, H), 4.45-4.56 (m, 1H), 5.05 (d, J=12.38 Hz, 1H), 5.13 (d, J=12.38 Hz, 1H), 5.79 (s, 2H), 6.97 (d, J=9.09 Hz, 1H), 7.21 (d, J=8.08 Hz, 2H), 7.27-7.50 (m, 15H), 7.55 (d, J=7.07 Hz, 2H).

Intermediate 32

4-(2-methyl-benzothiazol-6-yl)-butyric acid

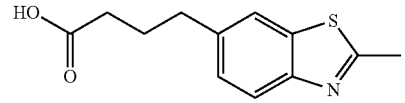 [SMILES: Cc1nc2ccc(CCCC(=O)O)cc2s1]

A mixture of 6-iodo-2-methylbenzo[d]thiazole (275 mg, 1 mmol), but-3-enoic acid methyl ester (100 mg, 1.2 mmol), diacetoxypalladium (22 mg, 0.1 mmol) and triethylamine (304 mg, 3 mmol) MeCN (8 mL) is heated in a microwave apparatus at 130° C. for 30 minutes. The solvent is removed under reduce pressure and the residue is purified by flash chromatography (heptane:EtOAc, 2:1) to give (E)-4-(2-methyl-benzothiazol-6-yl)-but-3-enoic acid methyl ester. MS 248.3 (M+1).

Next, a solution of (E)-4-(2-methyl-benzothiazol-6-yl)-but-3-enoic acid methyl ester in THF (10 mL) is hydrogenated over 10% Pd/C (22 mg, 10% wet) at 1 atm for 48 hours. The catalyst is filtered through Celite and the solvent is removed under reduced pressure. The residue is purified by flash chromatography (heptane:EtOAc, 2:1) to give 4-(2-methyl-benzothiazol-6-yl)-butyric acid methyl ester. MS 250.4 (M+1).

Next, to a solution of 4-(2-methyl-benzothiazol-6-yl)-butyric acid methyl ester in EtOH (4 mL) is added aqueous 1M NaOH (4 mL) and the mixture is stirred at room temperature for 2 hours. The solution is acidified to pH 2 with aqueous 1M HCl and is extracted with ethyl acetate. The organic layer is washed with water, brine, dried over magnesium sulfate and filtered. The solvent is removed under reduced pressure to give 4-(2-methyl-benzothiazol-6-yl)-butyric acid. MS 236.3 (M+1).

Intermediate 33

2-methyl-succinic acid 1-tert-butyl ester

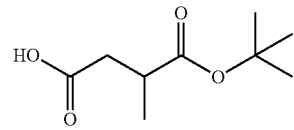

Succinic acid mono-tert-butyl ester is prepared according to the procedure described in J. Org. Chem. 59, 4862 (1994).

To a stirred solution of LDA (6.3 mmol, 2M in hexane) in THF (5 mL) at −78° C. is added a solution of succinic acid mono-tert-butyl ester (523 mg, 3 mmol) in THF (2 mL) dropwise. After the addition, the mixture is warmed to −20° C. slowly and stirred at −20° C. for 30 minutes. The solution is re-cooled to −78° C. and MeI (511 mg, 3.6 mmol) is added dropwise. The mixture is warmed to room temperature and stirred for 18 hours. The mixture is quenched with water and extracted with ethyl acetate. The organic layer is washed with water, brine, dried over MgSO$_4$ and filtered. The solvent is removed under reduced pressure to give 2-methyl-succinic acid 1-tert-butyl ester.

Intermediate 34

1-carboxymethyl-cyclopentanecarboxylic acid benzyl ester'

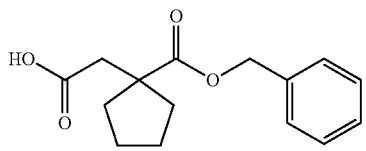 [SMILES: O=C(O)CC1(C(=O)OCc2ccccc2)CCCC1]

To a stirred solution of cyclopentanecarboxylic acid (1.14 g, 10 mmol) in DMF (15 mL) is added K$_2$CO$_3$ (2.07 g, 15 mmol) and benzyl bromide (1.71 g, 10 mmol). The suspension is stirred at room temperature for 18 hours. The mixture is quenched with water and extracted with ethyl acetate. The organic layer is washed with water, brine, dried over MgSO$_4$ and filtered. The solvent is removed under reduced pressure and the residue is purified by flash chromatography (heptane:EtOAc, 10:1) to give cyclopentanecarboxylic acid benzyl ester. Next, to a stirred solution of LDA (4 mmol, 2M in Hexane) in THF (8 mL) at −78° C. is added a solution of cyclopentanecarboxylic acid benzyl ester (817 mg, 4 mmol) in THF (3 mL) dropwise. After the addition, the mixture is stirred at −78° C. for 5 hours then allyl bromide (726 mg, 6 mmol) is added dropwise. The mixture is warmed to room temperature during 4 hours then the reaction mixture is quenched with saturated NaHCO$_3$. Magnesium sulfate (2 g) is added and stirred until all the MgSO$_4$ is dissolved. The mixture is extracted with ethyl acetate and the organic layer is washed with water, brine, dried over MgSO$_4$ and filtered. The solvent is removed under reduced pressure and the residue is purified by flash chromatography (hep:EtOAc, 10:1) to give 1-allyl-cyclopentanecarboxylic acid benzyl ester. Next, Ozone is bubbled through a solution of 1-allyl-cyclopentanecarboxylic acid benzyl ester in methylene chloride (15 mL) for 30 min then PS-triphenolphosphine (300 mg) is added and the mixture is stirred at room temperature for 5 hours. The resin is filtered and solvent is removed under reduced pressure. The residue is purified by flash chromatography (heptane:EtOAc, 10:1) to give 1-(2-oxo-ethyl)-cyclopentanecarboxylic acid benzyl ester MS 247.3 (M+1).

Next, to a solution of 1-(2-oxo-ethyl)-cyclopentanecarboxylic acid benzyl ester (200 mg, 0.81 mmol) in THF (5 mL) is added silver(II) oxide (201 mg, 1.62 mmol) and aqueous 1M NaOH (0.81 mL of 1.0 N, 0.81 mmol) and the suspension is stirred at room temperature for 18 hours. The mixture is acidified to pH 3 with aqueous 1M HCl and is extracted with ethyl acetate. The organic layer is washed with water, brine, dried over MgSO$_4$ and filtered. The solvent is removed under reduced pressure to furnish 1-carboxymethyl-cyclopentanecarboxylic acid benzyl ester MS 263.3 (M+1).

Intermediate 35

3-Hydroxy-isoxazole-5-carboxylic acid

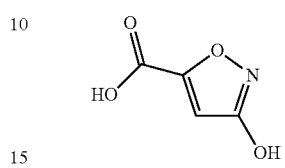

To a solution of 3-hydroxy-isoxazole-5-carboxylic acid methyl ester (286 mg, 2.0 mmol) in methanol (7 mL) is added 1N NaOH (4.0 mL, 4.0 mmol) and the mixture is stirred at room temperature for 18 hrs. The solvent is removed under reduced pressure and 4.0 mL of 1N HCl is added to the residue. The resulting solution is lyophilized to give the product which is used as is in subsequent reactions.

Intermediate 36

5-Carboxymethyl-furan-2-carboxylic acid

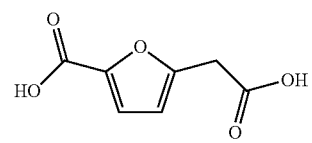

To a solution of 5-methoxycarbonylmethyl-furan-2-carboxylic acid methyl ester (250 mg, 1.26 mmol) in methanol (5 mL) is added 1N NaOH (2.78 mL, 2.78 mmol) and the mixture is stirred at room temperature for 18 hrs. The solvent is removed under reduced pressure and 2.78 mL of 1N HCl is added to the residue. The resulting solution is lyophilized to give the product which is used as is in subsequent reactions.

Intermediate 37

2-chloro-pyrimidine-4,6-dicarboxylic acid monomethyl ester

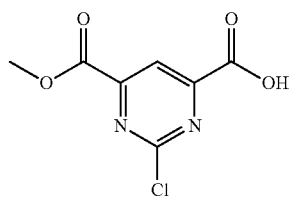

To a stirred solution of methyl 2-chloro-6-methylpyrimidine-4-carboxylate (3.73 g, 20 mmol.) in dioxane (20 mL) is added selenium dioxide (3.55 g, 32 mmol) and the mixture is heated at 105° C. for 12 hours. The suspension is filtered through Celite and washed well with dioxane. The solvent is removed under reduced pressure to give 2-chloro-pyrimidine-4,6-dicarboxylic acid monomethyl ester; HPLC Retention time 0.65 minutes (condition A); MS 217.2 (M+1).

Intermediate 38

1H-Imidazole-2,4-dicarboxylic acid 2-methyl ester

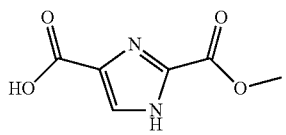

This intermediate is prepared according to the procedure described in patent application WO2005/040345.

Intermediate 39

(S)-4-Amino-5-(3'-chloro-biphenyl-4-yl)-2-methyl-pentanoic acid ethyl ester hydrochloride

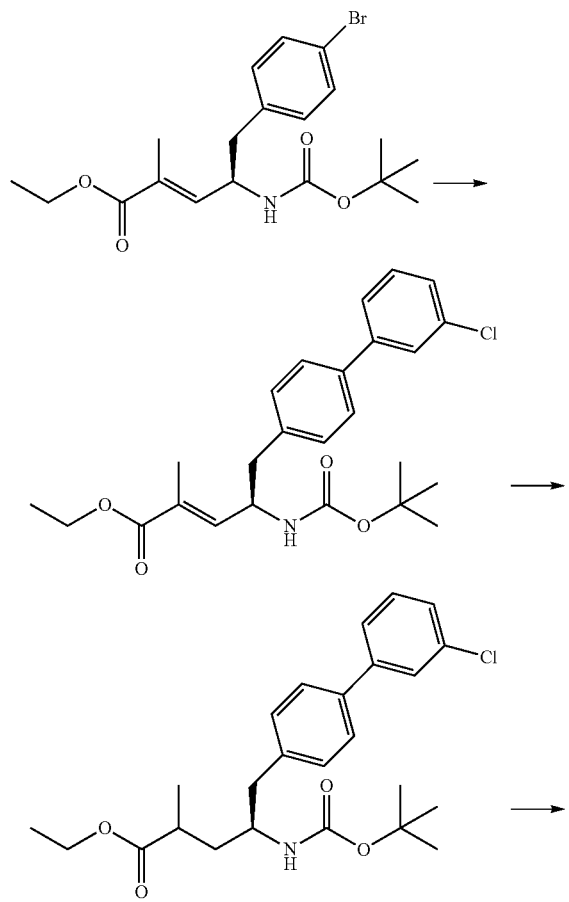

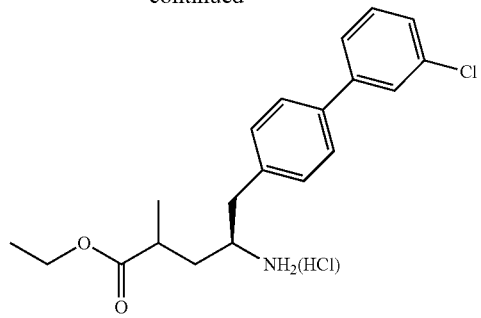

To a mixture of (R)-5-(4-bromo-phenyl)-4-tert-butoxycarbonylamino-2-methyl-pent-2-enoic acid ethyl ester (Intermediate 30) (2.6 g, 6.31 mmol), 3-chlorophenyl boronic acid (1.085 g, 6.94 mmol), $PdCl_2(dppf)\text{-}CH_2Cl_2$ (0.257 g, 0.315 mmol) in DMF (30 mL) is bubbled nitrogen for 10 minutes then $Na_2CO_3$ (6.3 mL of a 2N aqueous solution) is added. The resulting mixture is heated to 100° C. for 2 hours then is cooled to room temperature. A mixture of ice and water is added and the mixture is extracted with EtOAc. The combined organic phases were washed with water and brine, dried over $MgSO_4$, filtered and concentrated to give (E)-(R)-4-tert-butoxycarbonylamino-5-(3'-chloro-biphenyl-4-yl)-2-methyl-pent-2-enoic acid ethyl ester.

Next, to a solution of (E)-(R)-4-tert-butoxycarbonylamino-5-(3'-chloro-biphenyl-4-yl)-2-methyl-pent-2-enoic acid ethyl ester (2.5 g, 5.63 mmol) in ethanol (20 mL) is added PUC (250 mg) and the mixture is stirred overnight under an atmosphere of hydrogen ($H_2$ balloon). The catalyst is filtered through a Celite pad and, the filtrate is concentrated to give (S)-4-tert-butoxycarbonylamino-5-(3'-chloro-biphenyl-4-yl)-2-methyl-pentanoic acid ethyl ester.

Next, to a solution of (S)-4-tert-butoxycarbonylamino-5-(3'-chloro-biphenyl-4-yl)-2-methyl-pentanoic acid ethyl ester (2.47 g, 5.54 mmol) in DCM (15 mL) is added 5 mL of HCl (4N in dioxane) and the mixture is stirred at room temperature for 2 hours. The solvent is removed under reduced pressure to afford the title compound; HPLC Retention time 1.48 minutes (condition A): MS 346.2 (M+1).

Intermediate 40

(S)-1-Carboxymethyl-pyrrolidine-2-carboxylic acid methyl ester

To a solution of chloroacetic benzyl ester (1.8 g, 9.75 mmol) in DCM (50 mL) is added (S)-pyrrolidine-2-carboxylic acid methyl ester hydrochloride (1.51 g, 11.70 mmol), diisopropylethylamine (4.09 mL, 23.40 mmol) and tetrabutylammonium iodide (3.60 g, 9.75 mmol) and the resulting mixture is stirred at room temperature overnight. The solvent is removed under reduced pressure and the residue purified by column chromatography using a gradient of 2-45% EtOAc/ heptane to give (S)-1-benzyloxycarbonylmethyl-pyrrolidine-2-carboxylic acid methyl ester; 1H NMR (400 MHz, CHLOROFORM-d) δ ppm 1.81-2.05 (m, 3H), 2.13-2.24 (m, 1H), 2.78-2.84 (m, 1H), 3.15-3.20 (m, 1H), 3.57-3.69 (m, 3H), 3.70 (s, 3H), 5.15 (s, 2H), 7.36 (m, 5H).

Next, to the solution of (S)-1-benzyloxycarbonylmethyl-pyrrolidine-2-carboxylic acid methyl ester (2.50 g, 9.01 mmol) in methanol (30 mL)/ethyl acetate (30 mL) is added Pd/C (300 mg) and the mixture is stirred under an atmosphere of hydrogen ($H_2$ balloon) for 18 hours. The catalyst is filtered through a Celite pad and the filtrate is evaporated under reduced pressure to give the title compound; HPLC Retention time 0.94 minutes (condition A): MS 188.4 (M+1).

Intermediate 41

5-oxo-4,5-dihydro-1,2,4-oxadiazole-3-carboxylic acid

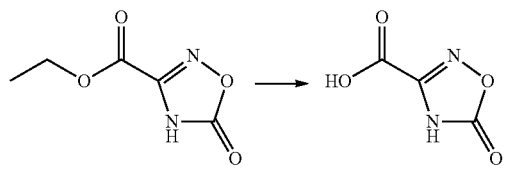

To a solution of crude ethyl 5-oxo-4,5-dihydro-1,2,4-oxadiazole-3-carboxylate (2.4 g, 15.14 mmol) in MeOH (2 mL) is added aqueous 1M NaOH (4 mL, 4 mmol) at room temperature. After stirring for 5 hours at room temperature the reaction was quenched with 1N HCl (5 mL, 5 mmol), the crude is concentrated under reduced pressure to remove MeOH. The crude is diluted with EtOAc, the organic layer is washed with brine, dried over $Na_2SO_4$, filtered and concentrated under reduced pressure to give 5-oxo-4,5-dihydro-1,2,4-oxadiazole-3-carboxylic acid (1.9 g).

Intermediate 42

(S)-3-(3'-Chloro-biphenyl-4-yl)-2-((S)-1-ethoxycarbonyl-ethylamino)-propionic acid

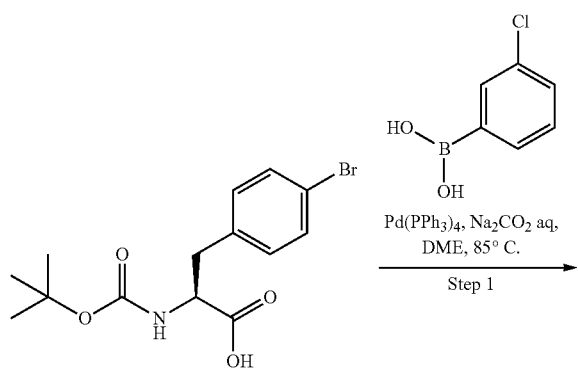

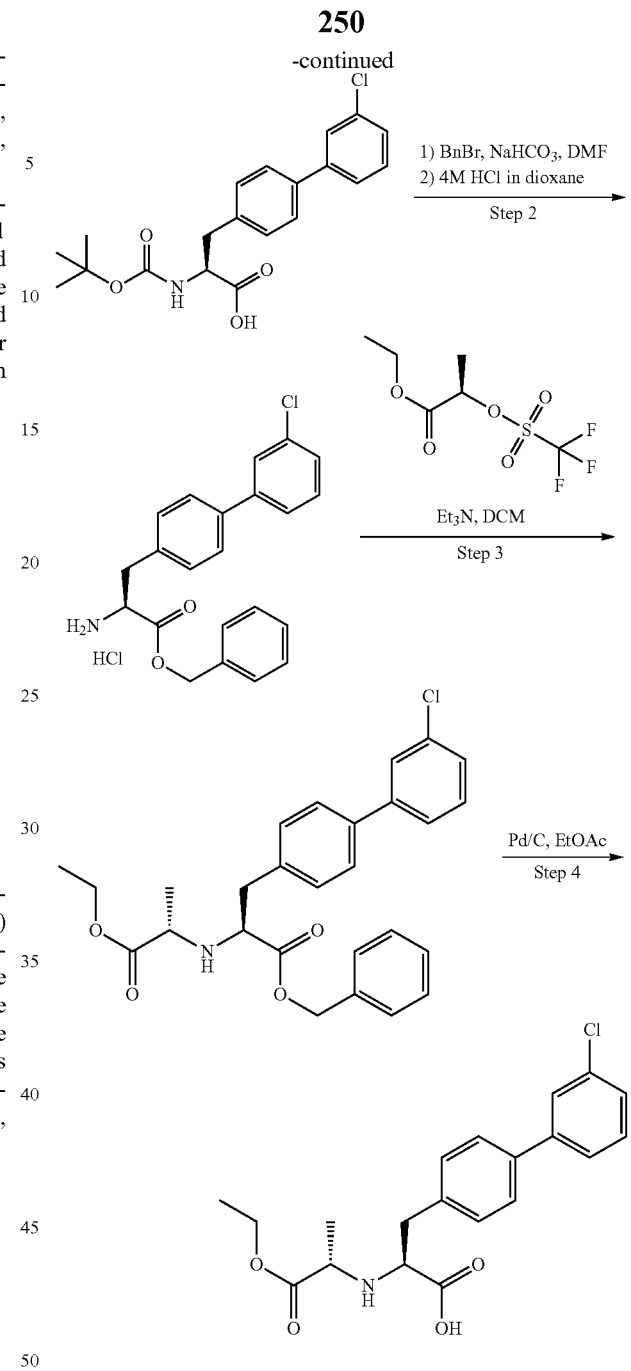

Step 1: To a solution of Boc-L-4-bromophenylalanine (15.0 g, 43.6 mmol), 3-chlorophenylboronic acid (8.52 g, 54.5 mmol), and tetrakis(triphenylphosphine)palladium(0) (1.51 g, 1.31 mmol) in 1,2-dimethoxyethane (180 mL) was added 2M solution of aqueous $NaCO_3$ (33 mL). The reaction mixture was heated to 85° C. After stirred for 2 hours, the reaction mixture was cooled to room temperature and diluted with EtOAc. The mixture was washed with 1M HCl and brine. The organic layer was dried over $Na_2SO_4$, concentrated under reduced pressure, and purified by silica gel column chromatography (eluent: 10% MeOH in dichloromethane) to give (S)-2-tert-butoxycarbonylamino-3-(3'-chloro-biphenyl-4-yl)-propionic acid. $^1$H NMR (400 MHz, $CDCl_3$) δ 1.43 (s, 9H), 3.08-3.17 (m, 1H), 3.21-3.31 (m, 1H), 4.65 (bs, 1H), 5.01 (bs, 1H), 7.23-7.32 (m, 3H), 7.45-7.50 (m, 2H), 7.52-7.60 (m, 1H), 7.63-7.70 (m, 2H); MS: m/z (MH$^+$) 376.

Step 2: To a solution of (S)-2-tert-butoxycarbonylamino-3-(3'-chloro-biphenyl-4-yl)-propionic acid (12.9 g, 34.3 mmol) in DMF (130 mL) were added benzyl bromide (8.16 mL, 68.6 mmol) and NaHCO$_3$ (5.77 g, 68.6 mmol). After stirred at room temperature overnight, the reaction mixture was diluted with EtOAc. The mixture was washed with H$_2$O and brine, dried over Na$_2$SO$_4$, and concentrated under reduced pressure. The obtained residue was treated with 4M HCl in dioxane (30 mL) and stirred for 2 hours. The reaction mixture was concentrated and the resulted residue was rinsed with iPr$_2$O to give (S)-2-amino-3-(3'-chloro-biphenyl-4-yl)-propionic acid benzyl ester. $^1$H NMR (400 MHz, DMSO-d6) δ 3.14 (dd, 1H, J=7.7, 12.0 Hz), 3.27 (dd, 1H, J=5.9, 12.0 Hz), 4.38 (dd, 1H, J=5.9, 7.7 Hz), 5.15 (s, 2H), 7.23-7.27 (m, 2H), 7.30-7.34 (m, 5H), 7.42-7.45 (m, 1H), 7.51 (dd, 1H, J=7.6, 7.6 Hz), 7.61-7.66 (m, 3H), 7.69 (dd, 1H, J=1.8, 1.8 Hz), 8.64 (bs, 2H); MS: m/z (MH$^+$) 366.

Step 3: To a solution of (S)-2-amino-3-(3'-chloro-biphenyl-4-yl)-propionic acid benzyl ester (10.0 g, 24.9 mmol) in dichloromethane (100 mL) was added triethylamine (10.4 mL, 74.6 mmol) at 0° C. After stirred for 10 min, ethyl (R)-2-(trifluoromethylsulfonyloxy)propionate (9.3 mL, 49.5 mmol) was added at room temperature and stirred for 1 hour. Additional triethylamine (10.4 mL, 74.6 mmol) and ethyl (R)-2-(trifluoromethylsulfonyloxy)propionate (9.3 mL, 49.5 mmol) were added at room temperature and stirred for additional 2 hours. The reaction mixture was washed with H$_2$O and the organic layer was concentrated under reduced pressure. The obtained residue was purified by silica gel column chromatography (EtOAc/heptane) to give (S)-3-(3'-chloro-biphenyl-4-yl)-2-(S)-1-ethoxycarbonyl-ethylamino)-propionic acid benzyl ester. $^1$H NMR (400 MHz, CDCl$_3$) δ 1.21 (t, 3H, J=7.3 Hz), 1.27 (d, 3H, J=6.8 Hz), 1.89 (bs, 1H), 2.95-3.07 (m, 2H), 3.38 (dd, 1H, J=6.8, 14.8 Hz), 3.69 (dd, 1H, J=7.1, 7.1 Hz), 4.06-4.17 (m, 2H), 5.06 (d, 1H, J=12.1 Hz), 5.12 (d, 1H, J=12.1 Hz), 7.20-7.25 (m, 4H), 7.28-7.34 (m, 4H), 7.35 (dd, 1H, J=7.6, 7.6 Hz), 7.41-7.46 (m, 3H), 7.53 (dd, 1H, J=1.5, 1.5 Hz); MS: m/z (MH$^+$) 466.

Step 4: A suspension of (S)-3-(3'-chloro-biphenyl-4-yl)-2-((S)-1-ethoxycarbonyl-ethylamino)-propionic acid benzyl ester (10.0 g, 21.5 mmol) and 5% Pd on carbon (0.914 g) in EtOAc (200 mL) was treated with H$_2$ (balloon) and stirred at 10-15° C. for 1.5 hour and at room temperature for 0.5 hour. The resulted precipitate was dissolved in methanol and filtered through celite pad. The filtrate was concentrated under reduced pressure and the obtained residue was re-crystallized from EtOAc to give (S)-3-(3'-chloro-biphenyl-4-yl)-2-(S)-1-ethoxycarbonyl-ethylamino)-propionic acid. The mother liquor was concentrated under reduced pressure and purified by silica gel column chromatography to give additional amount of (S)-3-(3'-chloro-biphenyl-4-yl)-2-((S)-1-ethoxycarbonyl-ethylamino)-propionic acid. $^1$H NMR (400 MHz, DMSO-d6) δ 1.13 (t, 3H, J=7.1 Hz), 1.15 (d, 3H, J=6.8 Hz), 2.85 (dd, 1H, J=7.1, 14.1 Hz), 2.93 (dd, 1H, J=6.3, 13.6 Hz), 3.30-3.37 (m, 1H), 3.48 (dd, 1H, J=6.5, 6.5 Hz), 4.03 (dd, 2H, J=7.1, 14.1 Hz), 7.32 (d, 2H, J=8.3 Hz), 7.38-7.43 (m, 1H), 7.48 (dd, 1H, J=7.8, 7.8 Hz), 7.59-7.65 (m, 3H), 7.70 (dd, 1H, J=2.0, 2.0 Hz); MS: m/z (MH$^+$) 376.

Intermediate 43

(S)-2-(S)-1-tert-Butoxycarbonyl-ethylamino)-3-(2',5'-dichloro-biphenyl-4-yl)-propionic acid

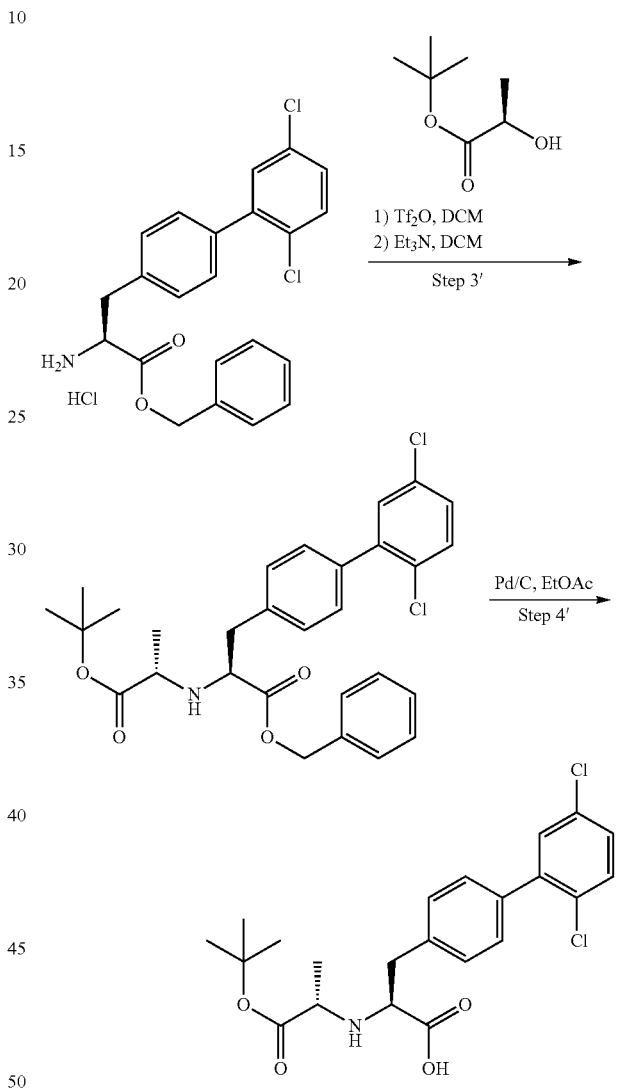

Same procedures described in step 1 (2,5-dichlorophenylboronic acid was used instead of 3-chlorophenylboronic acid) and step 2 for the preparation of intermediate 1 were used to prepare ((S)-2-amino-3-(2',5'-dichloro-biphenyl-4-yl)-propionic acid benzyl ester hydrochloride.

Step 3': t-Butyl (R)-2-(trifluoromethylsulfonyloxy)propionate was prepared from (R)-2-hydroxy-propionic acid tert-butyl ester (602 mg, 4.12 mmol), triflic anhydride (0.696 mL, 4.12 mmol) and 2,6-lutidine (0.480 mL, 4.12 mmol) in DCM (5 mL). To a suspension of ((S)-2-amino-3-(2',5'-dichloro-biphenyl-4-yl)-propionic acid benzyl ester hydrochloride (600 mg, 1.38 mmol) in dichloromethane (10 mL) was added triethylamine (0.574 mL, 4.12 mmol) at 0° C. After stirred for 10 min, a half amount of the freshly prepared t-butyl (R)-2-(trifluoromethylsulfonyloxy)propionate was added at room temperature and stirred for 1 hour. Additional triethylamine (0.574 mL, 4.12 mmol) and the rest of t-butyl (R)-2-(trifluoromethylsulfonyloxy)propionate were added at room temperature and stirred for additional 2 hours. The reaction mixture was washed with H$_2$O and the organic layer was concentrated under reduced pressure. The obtained residue was purified by silica gel column chromatography (EtOAc/heptane) to give (S)-2-(S)-1-tert-butoxycarbonyl-ethylamino)-3-(2',5'-dichloro-biphenyl-4-yl)-propionic acid benzyl ester. $^1$H NMR (400 MHz, CDCl$_3$) δ 1.24 (t, 3H, J=6.8 Hz), 1.41 (s, 9H), 3.00-3.07 (m, 2H), 3.26 (dd, 1H, J=7.1, 13.9 Hz), 3.70 (dd, 1H, J=7.1, 7.1 Hz), 5.09 (s, 2H), 7.20-7.42 (m, 12H); MS: m/z (MH$^+$) 528.

was concentrated under reduced pressure and the obtained residue was re-crystallized from EtOAc to give (S)-2-((S)-1-tert-butoxycarbonyl-ethylamino)-3-(2',5'-dichloro-biphenyl-4-yl)-propionic acid. $^1$H NMR (400 MHz, DMSO-d6) δ 1.12 (d, 3H, J=7.1 Hz), 1.35 (s, 9H), 2.84 (dd, 2H, J=7.3, 13.6 Hz), 2.95 (dd, 2H, J=6.1, 13.6 Hz), 3.20 (dd, 1H, J=6.8, 13.6 Hz), 3.48 (dd, 1H, J=6.1, 7.3 Hz), 7.33 (d, 2H, J=8.6 Hz), 7.37 (d, 2H, J=8.3 Hz), 7.42-7.49 (m, 2H), 7.60 (d, 2H, J=8.6 Hz); MS: m/z (MH$^+$) 438.

Following intermediates were prepared using similar procedure as intermediate 42 or intermediate 43 with appropriate reagent:

| Intermediate # | Intermediate | Reagent | HPLC-RT (condition) | MS (M + 1) |
|---|---|---|---|---|
| Intermediate 43-1 | (S)-3-Biphenyl-4-yl-2-((S)-1-ethoxy carbonyl-ethylamino)-propionic acid | phenylboronic acid was used instead of 3-chlorophenylboronic acid in step 1 | 0.71 min (J) | 342 |
| Intermediate 43-2 | (S)-2-[(S)-1-carboxy-2-(3'-chloro-biphenyl-4-yl)-ethylamino]-4-phenyl-butyric acid ethyl ester | (R)-2-Hydroxy-4-phenyl-butyric acid ethyl ester was used instead of (R)-2-hydroxy-propionic acid tert-butyl ester in Step 3' | 1.39 min (J) | 466 |
| Intermediate 43-3 | (S)-2-[(S)-1-Carboxy-2-(3'-chloro-biphenyl-4-yl)-ethylamino]-butyric acid tert-butyl ester | (R)-2-Hydroxy-butyric acid tert-butyl ester was used instead of (R)-2-hydroxy-propionic acid tert-butyl ester in Step 3' | 1.15 min (J) | 418 |

Step 4': A suspension of (S)-2-(S)-1-tert-Butoxycarbonyl-ethylamino)-3-(2',5'-dichloro-biphenyl-4-yl)-propionic acid benzyl ester (580 mg, 1.10 mmol) and 5% Pd on carbon (0.146 g) in EtOAc (10 mL) was treated with H$_2$ (balloon) and stirred at it for 1.5 hour. The resulted precipitate was dissolved in methanol and filtered through celite pad. The filtrate

Intermediate 44

[1-(4-Methoxy-benzyl)-1H-tetrazol-5-yl]-methyl-amine

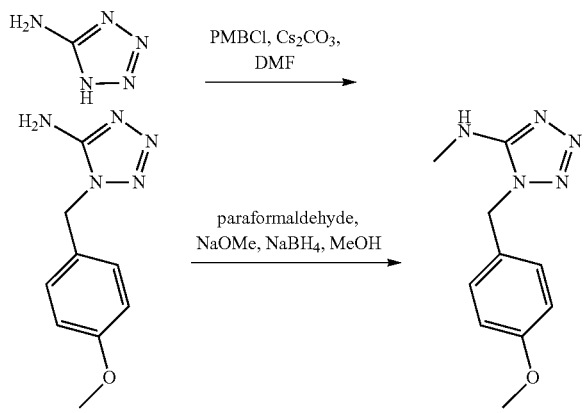

To a suspension of 5-amino-1H-tetrazole (1.50 g, 17.6 mmol) in DMF (30 mL) were added $Cs_2CO_3$ (8.62 g, 26.4 mmol) and PMBCl (2.90 g, 18.5 mmol). After stirred at 60° C. for 3 hours, the reaction mixture was cooled to room temperature and diluted with EtOAc. The mixture was washed with $H_2O$ and brine, dried over $Na_2SO_4$, and concentrated under reduced pressure. The residue was diluted with DCM and the resulted precipitate was collected by filtration to give 1-(4-methoxy-benzyl)-1H-tetrazol-5-ylamine. $^1H$ NMR (400 MHz, DMSO-d6) δ 3.73 (s, 3H), 5.27 (s, 2H), 6.78 (s, 2H), 6.92 (d, 2H, J=8.8 Hz), 7.21 (d, 2H, J=8.8 Hz).

Next, to a suspension of 1-(4-methoxy-benzyl)-1H-tetrazol-5-ylamine (600 mg, 2.92 mmol) in MeOH (10 mL) were added paraformaldehyde (132 mg, 4.39 mmol) and sodium methoxide (632 mg, 25 wt % in MeOH). The mixture was refluxed for 30 min until the suspension turned into a clear solution. The mixture was cooled to room temperature and sodium borohydride (332 mg, 8.77 mmol) was added portionwise. The reaction mixture was refluxed again for 15 min. After cooled to room temperature, the reaction was quenched with $H_2O$. The mixture was diluted with EtOAc, partially concentrated, and washed with brine. The organic layer was dried over $Na_2SO_4$ and concentrated under reduced pressure. The residue was purified by silica gel column chromatography (eluent: 10% MeOH in DCM) to give [1-(4-methoxy-benzyl)-1H-tetrazol-5-yl]-methyl-amine. $^1H$ NMR (400 MHz, $CDCl_3$) δ 3.00 (d, 3H, J=5.3 Hz), 3.61 (bs, 1H), 3.82 (s, 3H), 5.25 (s, 2H), 6.91 (d, 2H, J=8.8 Hz), 7.16 (d, 2H, J=8.8 Hz); MS: m/z ($MH^+$) 220.

Following intermediates were prepared using similar procedure as intermediate 42 or intermediate 43 with appropriate reagent:

| Intermediate # | Intermediate | Reagent | HPLC-RT (condition) | MS (M + 1) |
|---|---|---|---|---|
| Intermediate 44-1 | (S)-2-((S)-2-benzyloxy-1-ethoxycarbonyl-ethylamino)-3-(3'-chloro-biphenyl-4-yl)-propionic acid | (R)-3-Benzyloxy-2-hydroxy-propionic acid ethyl ester was used instead of (R)-2-hydroxy-propionic acid ethyl ester in Step 3 | 1.41 min (J) | 482 |
| Intermediate 44-2 | (S)-3-(3'-chloro-biphenyl-4-yl)-2-((S)-1-ethoxycarbonyl-2-methoxy-ethylamino)-propionic acid | (R)-2-Hydroxy-3-methoxy-propionic acid ethyl ester was used instead of (R)-2-hydroxy-propionic acid ethyl ester in Step 3 | 0.56 min (J) | 496 |

Intermediate 45

(S)-3-(3'-chloro-biphenyl-4-yl)-2-((S)-1-ethoxycarbonyl-ethoxy)-propionic acid

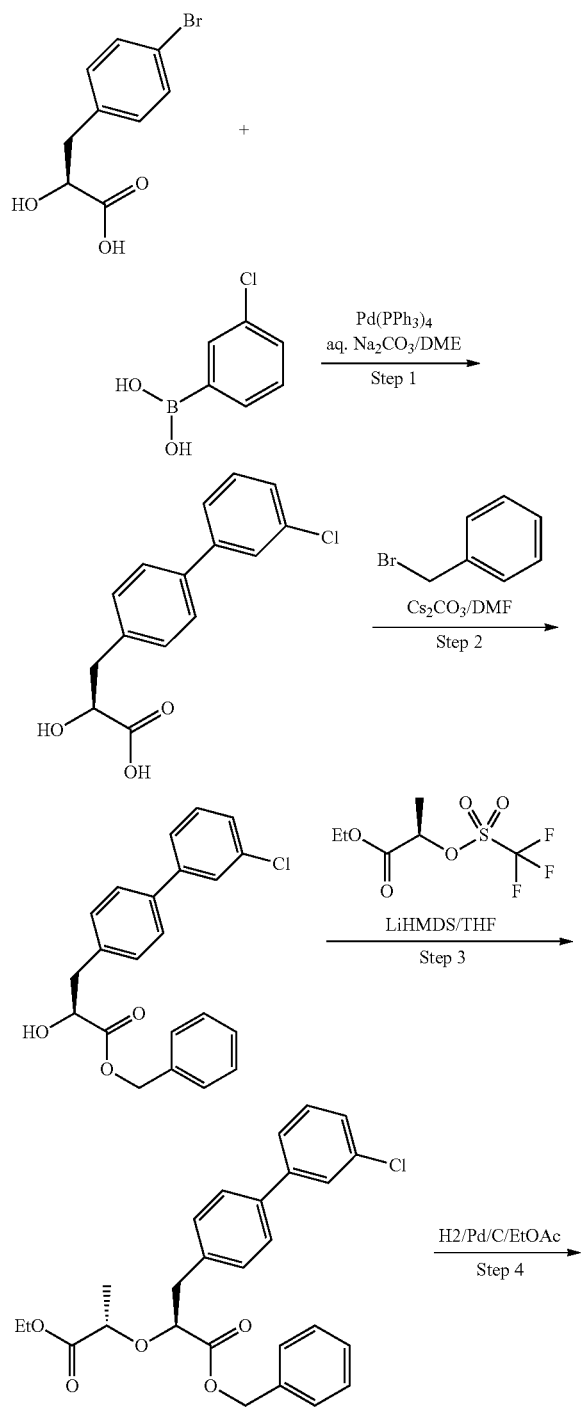

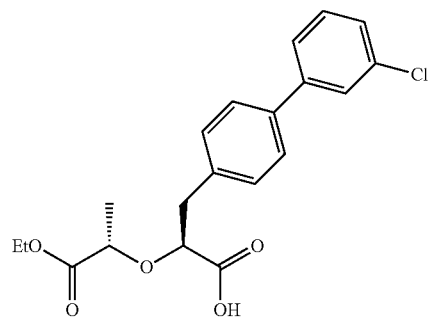

Step 1: To a mixture of 4-bromo-L-phenylalanine (2.5 g, 10.24 mmol) and the solvent of acetic acid (20 ml) and water (75 ml) in an ice bath was added dropwise a solution of sodium nitrite (2.120 g, 30.7 mmol) in water (20.00 ml). The mixture was slowly warmed up to room temperature and stirred overnight. To the suspension was added methylamine in THF (20.48 ml, 41.0 mmol) dropwise slowly and the mixture turned to clear and stirred at room temperature for 1 hr. The mixture was concentrated to remove THF and extracted with EtOAc. The combined organic layer was washed with brine and dried over anhydrous sodium sulfate, filtered and concentrated to give the crude as off white solid: 1.7 g (yield: 43%). HPLC retention time=0.83 minutes (condition I); MS (m+2)=246.

Step 2: To a solution of (S)-3-(4-bromo-phenyl)-2-hydroxy-propionic acid (1.5 g, 6.12 mmol) in DME (60 ml) at room temperature was added 3-chlorobenzeneboronic acid (1.436 g, 9.18 mmol) and followed by aq. $Na_2CO_3$ (6.12 ml, 12.24 mmol) and $Pd(Ph_3P)_4$ (0.212 g, 0.184 mmol). The mixture was stirred at 85° C. overnight. The reaction was added more EtOAc and acidified by 1N HCl to PH~5. The combined organic layer was washed with brine and dried over anhydrous sodium sulfate, filtered and concentrated. The residue was purified by HPLC (20 to 80% ACN—$H_2O$ (0.1% TFA)) to give the white solid: 550 mg (yield: 32%). HPLC retention time=1.23 minutes (condition I); MS (m−1)=275.

Step 3: To a solution of (S)-3-(3'-chloro-biphenyl-4-yl)-2-hydroxy-propionic acid benzyl ester (282 mg, 0.769 mmol) in THF (6 ml) at −78° C. was added LiHMDS/THF (1.999 ml, 1.999 mmol) and the resulting yellow mixture was stirred at −78° C. for 25 mins then was added (R)-ethyl 2-(trifluoromethylsulfonyloxy)propanoate (0.860 ml, 4.61 mmol) at −20° C. 1 hr the reaction was almost complete. The reaction was quenched by sat. $NH_4Cl$ and was extracted with EtOAc. The combined organic layer was washed with brine, filtered and concentrated. The residue was purified by HPLC (75 to 100% ACN—$H_2O$ (0.1% TFA)) to give the product: 140 mg (yield: 39%). HPLC retention time=1.57 minutes (condition J); MS (m+1)=467.

Step 4: A mixture of (S)-3-(3'-chloro-biphenyl-4-yl)-2-(S)-1-ethoxycarbonyl-ethoxy)-propionic acid benzyl ester and 10% Pd/C wet in EtOAc was hydrogenated under $H_2$ balloon for 30 mins. The reaction was filtered off the catalyst and concentrated. The residue was purified by HPLC (15 to 70% ACN—H₂O (0.1% TFA)) to give oil: 128 mg. HPLC retention time=1.07 minutes (condition J); MS (m−1)=375.

Intermediate 46

(S)-3-(3'-chloro-biphenyl-4-yl)-2-((S)-2-methanesulfonylamino-1-methyl-2-oxo-ethylamino)-propionic acid

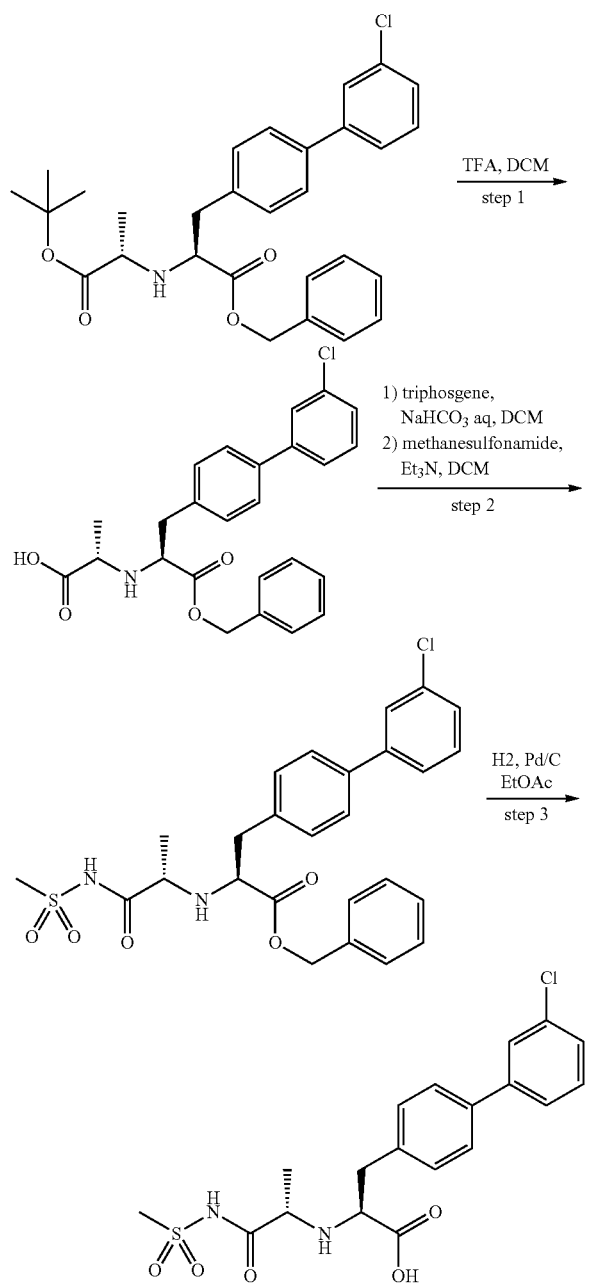

Step 1: To a solution of (S)-2-(S)-1-tert-butoxycarbonyl-ethylamino)-3-(3'-chloro-biphenyl-4-yl)-propionic acid benzyl ester (1.12 g, 2.27 mmol) in DCM (5 mL) was added TFA (5 mL). After being stirred for 3 hours, the reaction mixture was concentrated and purified by silica gel column chromatography (eluent: 10% MeOH in DCM) to give (S)-2-(S)-1-carboxy-ethylamino)-3-(3'-chloro-biphenyl-4-yl)-propionic acid benzyl ester. MS: m/z (MH⁺) 438; HPLC retention time 0.73 min (HPLC condition J).

Step 2: To a solution of (S)-2-(S)-1-carboxy-ethylamino)-3-(3'-chloro-biphenyl-4-yl)-propionic acid benzyl ester (600 mg, 1.37 mmol) in DCM (7 mL) and saturated aqueous NaHCO₃ solution (2 mL) was added triphosgene (407 mg, 1.37 mmol). After being stirred for 0.5 hours, the reaction mixture was diluted with EtOAc and stirred for additional 0.5 hours until generation of gas was completed. The organic layer was separated, washed with brine and concentrated. This was dissolved in DCM (7 mL) and methanesulfonamide (195 mg, 2.06 mmol) was added. After being stirred at rt for 1 hour, the reaction mixture was diluted with EtOAc and washed with brine. The organic layer was dried over Na₂SO₄, concentrated and purified by silica gel column chromatography (eluent: 10% MeOH in DCM) to give (S)-3-(3'-chloro-biphenyl-4-yl)-2-((S)-2-methanesulfonylamino-1-methyl-2-oxo-ethylamino)-propionic acid benzyl ester. MS: m/z (MH⁺) 515; HPLC retention time 1.58 min (HPLC condition I).

Step 3: This was dissolved in EtOAc. 5% Pd—C (146 mg) was added and hydrogenated with H₂ balloon at rt for 1 hour. The reaction mixture was filtered through celite pad and the filtrate was concentrated. The resultant solid was re-crystallized from MeOH to give (S)-3-(3'-chloro-biphenyl-4-yl)-2-((S)-2-methanesulfonylamino-1-methyl-2-oxo-ethylamino)-propionic acid. MS: m/z (MH⁺) 425; HPLC retention time 1.14 min (HPLC condition I).

Intermediate 46-1

(S)-2-((S)-1-tert-butoxycarbonyl-ethylamino)-3-(3'-chloro-biphenyl-4-yl)-propionic acid benzyl ester

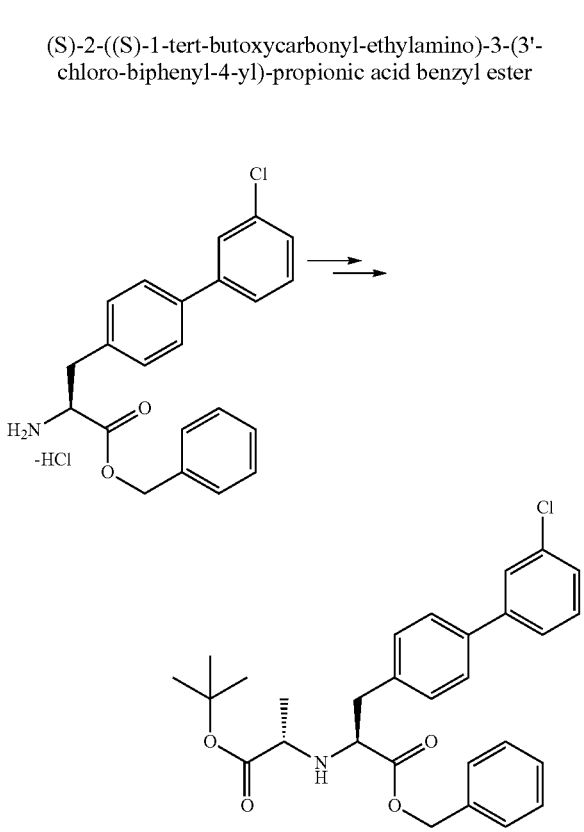

Intermediate 46-1 was prepared using similar procedure as intermediate 42 and intermediate 43 with appropriate reagent. MS: m/z (MH$^+$) 494; HPLC retention time 1.50 min (HPLC condition J).

Intermediate 47

Synthesis of (S)-4-Amino-5-(2'-methoxy-biphenyl-4-yl)-2-methyl-pentanoic acid ethyl ester hydrochloric acid salt

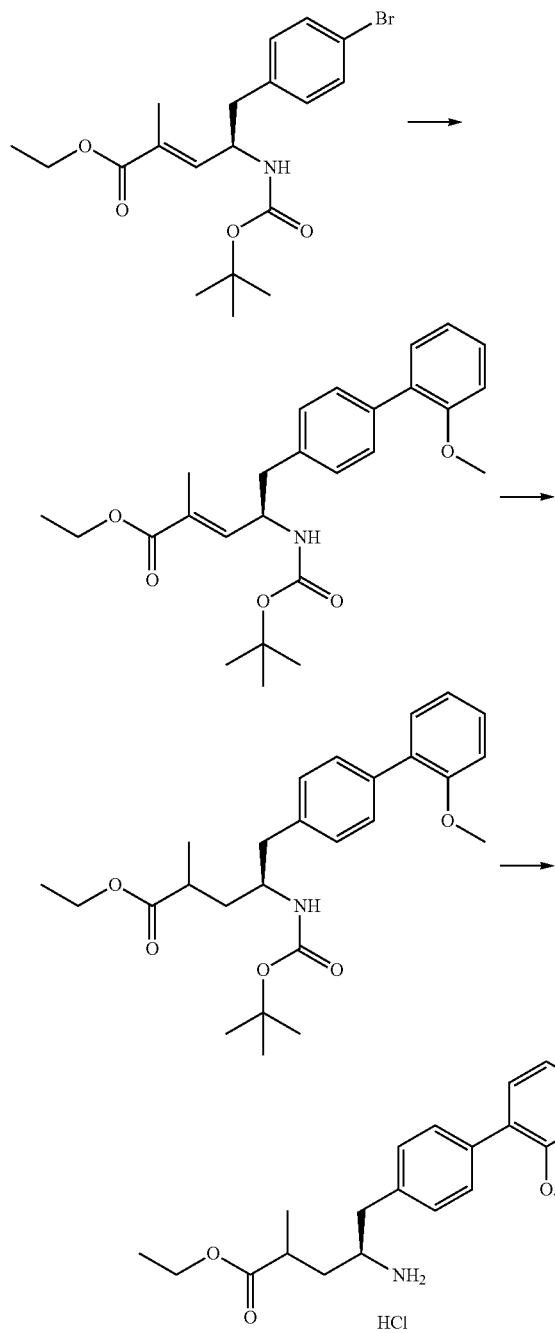

The mixture of (R)-5-(4-bromo-phenyl)-4-tert-butoxycarbonylamino-2-methyl-pent-2-enoic acid ethyl ester (600 mg, 1.455 mmol), 2-methoxyphenylboronic acid (243 mg, 1.601 mmol) and 1.1'-[Bis(diphenylphosphino)-ferrocene]dichloropalladium(II), complex with dichloromethane (59.4 mg, 0.073 mmol) in toluene (15 ml) was bubble with nitrogen for 10 minutes, then the solution of sodium carbonate (2M, 1.455 ml) was added. The resulting mixture was heated to 100° C. for 2 hours. After cooling down to room temperature, the mixture was diluted with ice-water and extracted with ethyl acetate. The combined organic phase was washed with brine, dried over magnesium sulfate, filtered, and concentrated under reduced pressure. The obtained residue was purified by column chromatography to afford 600 mg pale brown oil. HPLC Retention time 1.49 minutes (condition A): MS 457.4 (M+18)

Next, to a solution of (R)-4-tert-butoxycarbonylamino-5-(2'-methoxy-biphenyl-4-yl)-2-methyl-pent-2-enoic acid ethyl ester (500 mg, 1.138 mmol) in ethanol (15 ml) was added Pt/C (10%, 50 mg) and stirred at room temperature overnight under hydrogen. Then, the mixture was filtered through a pad of celite and washed with ethanol. The filtrate was concentrated to afford 471 mg colorless oil. The obtained material was used for next step without further purification. HPLC Retention time 1.53 minutes (condition A): MS 459.5 (M+18)

Next, to a solution of (S)-4-tert-butoxycarbonylamino-5-(2'-methoxy-biphenyl-4-yl)-2-methyl-pentanoic acid ethyl ester (473 mg, 1.017 mmol) in DCM (5 ml) was added HCl in dioxane (4M, 1 ml), and the resulting mixture was stirred at room temperature for 2 hours. Then, the mixture was concentrated on under reduced pressure. The obtained residue was used for next step without further purification. HPLC Retention time 1.28 minutes (condition A): MS 342.4 (M+1).

Intermediate 47-1

Synthesis of (S)-4-Amino-5-(3'-chloro-biphenyl-4-yl)-2-methyl-pentanoic acid ethyl ester hydrochloric acid salt

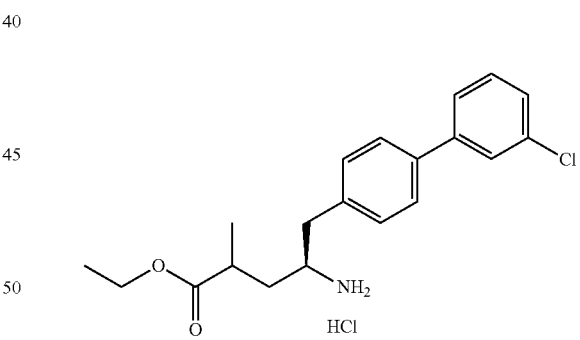

Intermediate 2 was prepared using same procedure as described for intermediate 1. For intermediate 2,3-chlorophenylboronic acid was used instead of 2-methoxyphenylboronic acid described in intermediate 1. HPLC Retention time 1.59 minutes (condition A): MS 346.2 (M+1).

The following are further embodiments of the invention:

Embodiment 1 A neutral endopeptidase EC. 3.4. 24.11. inhibitor, for use in the treatment, amelioration or prevention of contrast-induced nephropathy.

Embodiment 2 A neutral endopeptidase EC. 3.4. 24.11. inhibitor according to embodiment 1 which is selected from the group consisting of Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester.

Embodiment 3 A neutral endopeptidase inhibitor according to embodiment 1 which is a compound of Formula I:

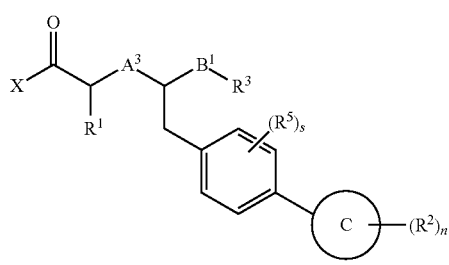

or a pharmaceutically acceptable salt thereof, wherein:
$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy, $C_{3-7}$cycloalkyl or $C_{1-6}$ alkoxy;
$R^2$ for each occurrence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^bR^c$, $C_{6-10}$aryl, heteroaryl or heterocyclyl;
$R^3$ is $A^1$-C(O)$X^1$ or $A^2$-$R^4$;
$R^4$ is $C_{6-10}$aryl, $C_{3-7}$cycloalkyl, or a heteroaryl, which can be monocyclic or bicyclic, each of which can be optionally substituted with one or more substituents independently selected from the group consisting of hydroxy, hydroxy$C_{1-7}$alkyl, nitro, —$NR^bR^c$, —C(O)$C_{1-7}$alkyl, C(O)—O—$C_{1-7}$alkyl, $C_{1-7}$alkoxy, halo, $C_{1-7}$alkyl, halo-$C_{1-7}$alkyl, $C_{2-7}$alkenyl, $C_{6-10}$aryl, heteroaryl, —NHSO$_2$—$C_{1-7}$alkyl, S(O)$_2$—$C_{1-7}$alkyl, C(O)—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl;
$R^5$ is H, halo, hydroxy, $C_{1-7}$alkoxy, halo, $C_{1-7}$alkyl or halo-$C_{1-7}$alkyl; and
X and $X^1$ are independently OH, —O—$C_{1-7}$alkyl, —$NR^bR^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of $C_{6-10}$aryl, heteroaryl, heterocyclyl, C(O)NH$_2$, C(O)NH—$C_{1-6}$alkyl, and C(O)N($C_{1-6}$alkyl)$_2$;
$B^1$ is —C(O)$NR^d$— or —$NR^d$C(O)—;
$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or
$A^1$ is a linear or branched $C_{1-7}$alkenylene; or
$A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, —C(O)—O—$C_{1-7}$alkyl or —CH$_2$C(O)OH; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^bR^c$, —OCH$_2$CO$_2$H, and —OCH$_2$C(O)NH$_2$; or
$A^1$ is a $C_{3-7}$cycloalkyl or heterocyclyl;
$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and
$A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl;
$A^3$ is CH$_2$, O, $NR^e$ or is absent; and when $A^3$ is O or $NR^e$ then $B^1$ is C(O)$NR^d$;
$R^b$ and $R^c$ for each occurrence are independently H, $C_{6-10}$aryl or $C_{1-7}$alkyl;
$R^d$ and $R^e$ are independently H or $C_{1-7}$alkyl;
Ring C is a phenyl or a monocyclic heteroaryl;
n is 0, 1, 2, 3, 4 or 5;
s is 0, 1, 2, 3 or 4; and
when $B^1$ is C(O)$NR^d$ and $R^3$ is $A^2$-$R^4$, then $R^d$ and $A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, CO$_2$H and CO$_2C_{1-6}$alkyl;
wherein each heteroaryl is a monocyclic or bicyclic aromatic ring comprising 5-10 ring atoms selected from carbon atoms and 1 to 5 heteroatoms unless otherwise specified, and
each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

Embodiment 4 A neutral endopeptidase inhibitor according to embodiment 1 or 3, which is a compound of Formula II:

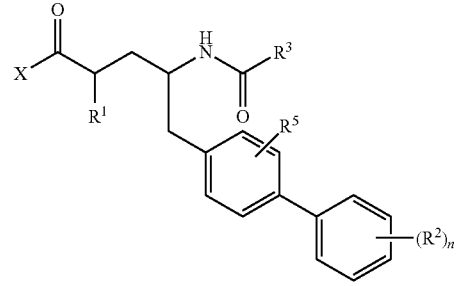

Formula II or a pharmaceutically acceptable salt thereof, wherein:
$R^1$ is $C_{1-7}$alkyl;
for each occurrence, $R^2$ is independently $C_{1-7}$alkyl, NO$_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl; wherein $R^b$ and $R^c$ for each occurrence, are independently H or $C_{1-7}$alkyl;
$R^3$ is $A^1$C(O)$X^1$ or $A^2$-$R^4$;
$R^4$ is $C_{6-10}$aryl or a heteroaryl, which can be monocyclic or bicyclic and which can be optionally substituted with one or more substituents independently selected from hydroxy, hydroxy-$C_{1-7}$alkyl, $NR^bR^c$, nitro, $C_{1-7}$alkoxy, halo, $C_{1-7}$alkyl, halo-$C_{1-7}$alkyl, $C_{2-7}$alkenyl, $C_{6-10}$aryl, heteroaryl, —C(O)$C_{1-7}$alkyl, —NHS(O)$_2$—$C_{1-7}$alkyl, —SO$_2$$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, —NR$^b$R$^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of aryl, heteroaryl, heterocyclyl, —C(O)NH$_2$, —C(O)NH—$C_{1-6}$alkyl, and —C(O)N($C_{1-6}$alkyl)$_2$;

$A^1$ is a bond or a linear $C_{1-4}$alkylene substituted with one or more substituents independently selected from the group consisting of halo, O-acetate, $C_{1-7}$ alkyl and $C_{3-7}$cycloalkyl; in which two geminal alkyl can optionally combine to form a $C_{3-7}$cycloalkyl; or $A^1$ is a linear or branched $C_{2-6}$alkenylene; or $A^1$ is a linear $C_{1-4}$ alkylene wherein one or more carbon atom(s) is/are replaced with an heteroatom selected from O, NR$^a$; and $A^1$ is optionally substituted with one or more substituents independently selected from the group consisting of halo and $C_{1-7}$alkyl; in which R$^a$ for each occurrence, is independently H, $C_{1-7}$alkyl or CH$_2$C(O)OH; or $A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, hydroxy, $C_{1-7}$alkoxy, halo, NR$^b$R$^c$, OCH$_2$CO$_2$H, and OCH$_2$C(O)NH$_2$; or $A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

Embodiment 5 A neutral endopeptidase inhibitor according to embodiment 4, which is a compound of Formula:

Formula II-A

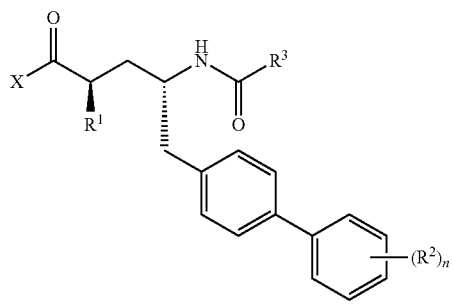

Formula II-B

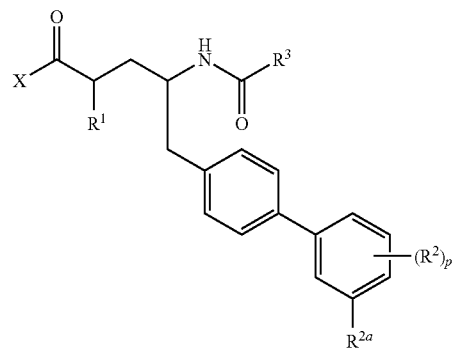

Formula II-C

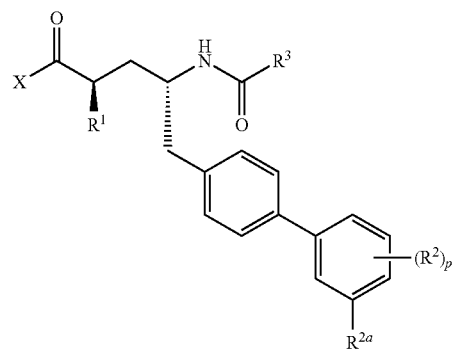

Formula II-D

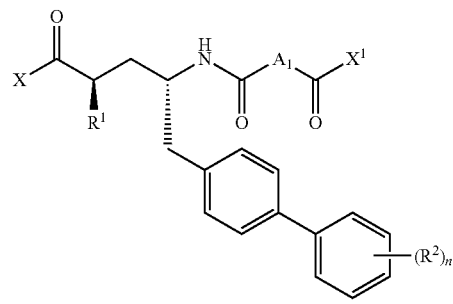

Formula II-E

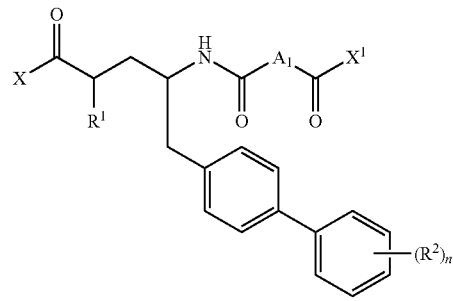

Formula II-F
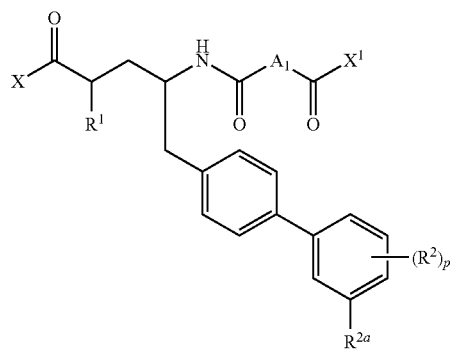
Formula II-G
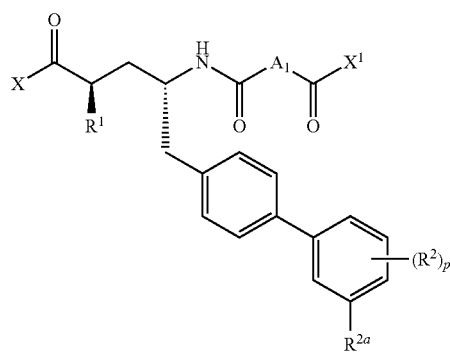
Formula II-H
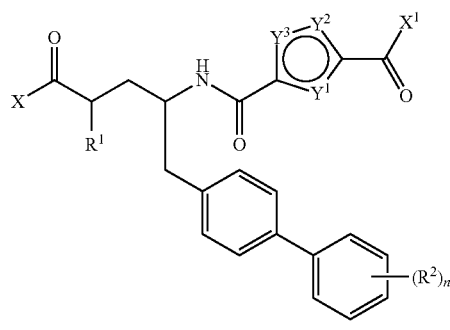
Formula II-I
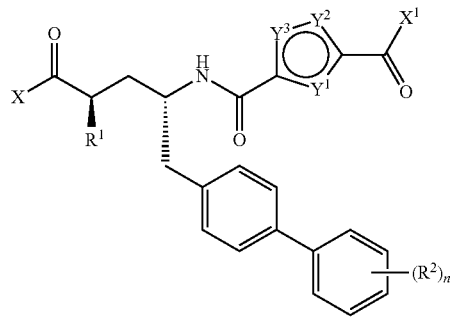
Formula II-J
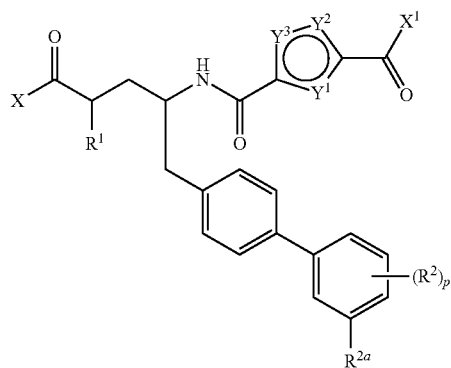
Formula II-K
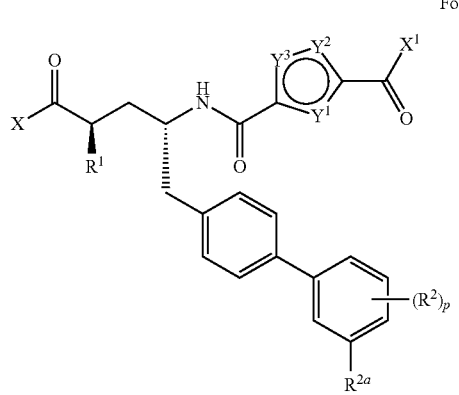
Formula II-L
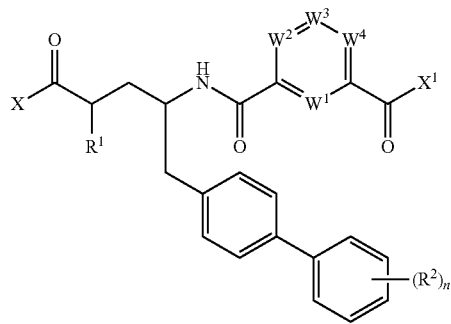
Formula II-M
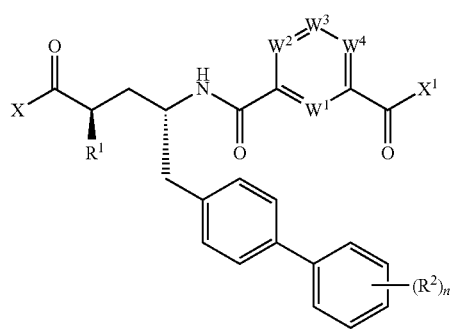

Formula II-N

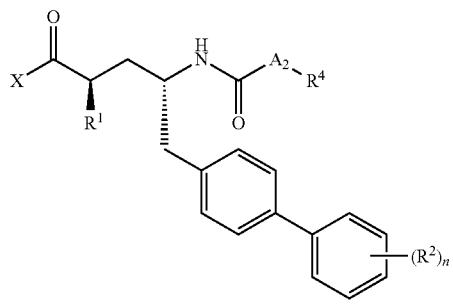

Formula II-O

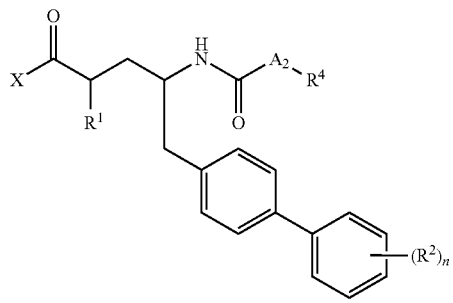

Formula II-P

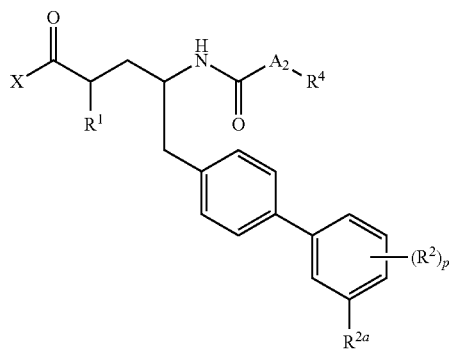

Formula II-Q

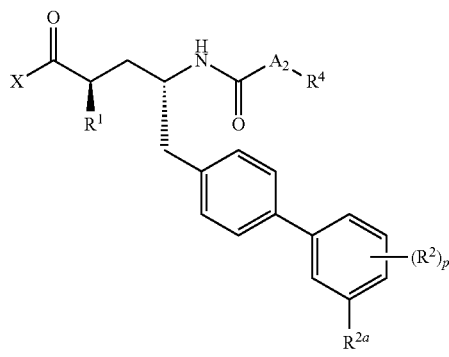

Formula II-R

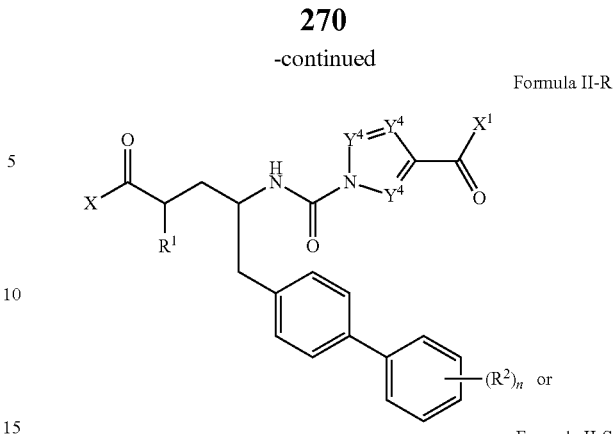

Formula II-S

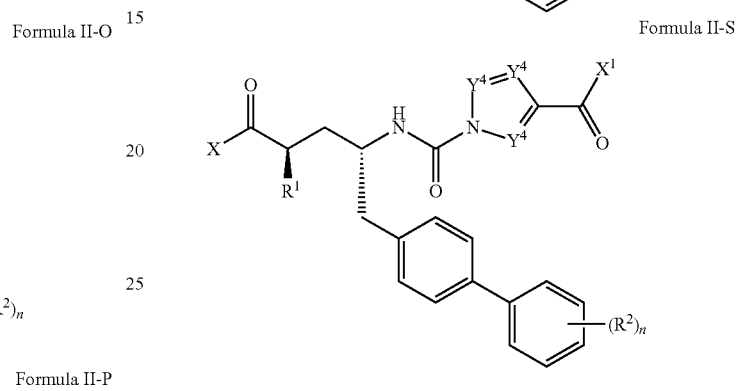

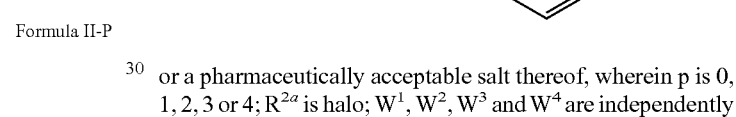

or a pharmaceutically acceptable salt thereof, wherein p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; $R^b$ and $R^c$ for each occurrence, are independently H or $C_{1-7}$alkyl;

and $Y^1$, $Y^2$ and $Y^3$ are independently N, NH, S, O or CH and form together with the ring atoms to which they are attached a 5-membered heteroaryl ring, and each $Y^4$ is independently N, S, O or CH.

Embodiment 6 A neutral endopeptidase inhibitor according to embodiment 1 or 3, which is a compound of Formula III:

Formula III

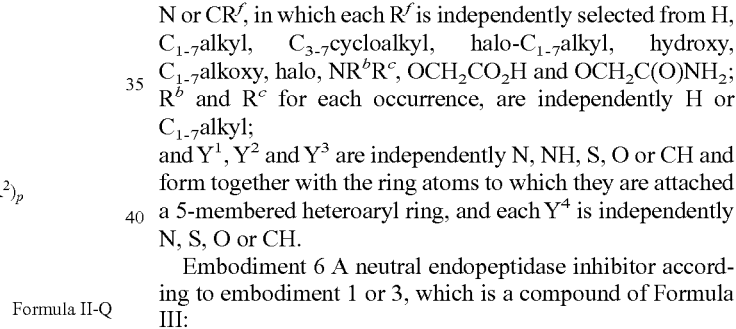

or a pharmaceutically acceptable salt thereof, wherein:
$R^1$ is H, $C_{1-7}$alkyl, hydroxy, $C_{1-7}$alkoxy, halogen, —SH, —S—$C_{1-7}$alkyl or $NR^bR^c$;
$R^2$ for each occurrence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^bR^c$, $C_{6-10}$aryl, heteroaryl or heterocyclyl; wherein $R^b$ and $R^c$ for each occurrence are independently H or $C_{1-7}$alkyl;

$R^3$ is $A^1$-C(O)$X^1$ or $A^2$-$R^4$;

$R^4$ is $C_{6-10}$aryl or a heteroaryl, which can be monocyclic or bicyclic, and which can be optionally substituted with one or more substituents independently selected from the group consisting of hydroxy, hydroxy$C_{1-7}$alkyl, nitro, —NR$^b$R$^c$, —C(O)$C_{1-7}$alkyl, C(O)—O—$C_{1-7}$alkyl, $C_{1-7}$alkoxy, halo, $C_{1-7}$alkyl, halo-$C_{1-7}$alkyl, $C_{2-7}$alkenyl, $C_{6-10}$aryl, heteroaryl, —NHSO$_2$—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$alkyl, $C_{6-10}$aryl, heteroaryl, —NHSO$_2$—$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, —NR$^b$R$^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of $C_{6-10}$aryl, heteroaryl, heterocyclyl, C(O)NH$_2$, C(O)NH—$C_{1-6}$alkyl, and C(O)N($C_{1-6}$alkyl)$_2$;

$B^1$ is —C(O)NH— or —NHC(O)—;

$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a linear or branched $C_{1-7}$alkenylene; or $A^1$ is a linear $C_{1-4}$ alkylene wherein one or more carbon atom(s) is/are replaced with an heteroatom selected from O, NR$^a$; and $A^1$ is optionally substituted with one or more substituents independently selected from the group consisting of halo and $C_{1-7}$alkyl; in which $R^a$ for each occurrence, is independently H, $C_{1-7}$alkyl, —C(O)—O—$C_{1-7}$alkyl or —CH$_2$C(O)OH; or $A^1$ is a phenyl or a heteroaryl; each of which is optionally substituted with one or more substituents independently selected from the group consisting of $C_{1-7}$alkyl, $C_{3-7}$cycloalkyl, hydroxy, $C_{1-7}$alkoxy, halo, —NR$^b$R$^c$, —OCH$_2$CO$_2$H, and —OCH$_2$C(O)NH$_2$; or $A^1$ is a $C_{3-7}$cycloalkyl;

$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$ alkylene; which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5. heteroatoms, wherein each heteroatom of a heteroaryl or a heterocyclyl is independently selected from O, N and S.

Embodiment 7 A neutral endopeptidase inhibitor according to embodiment 6, which is a compound of Formula:

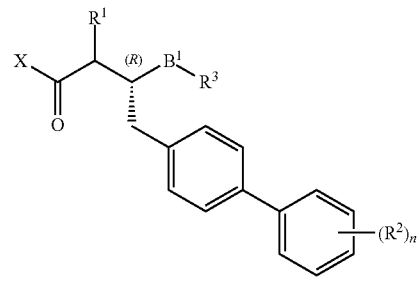

Formula III-A

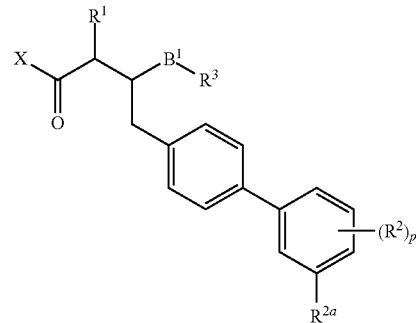

Formula III-B

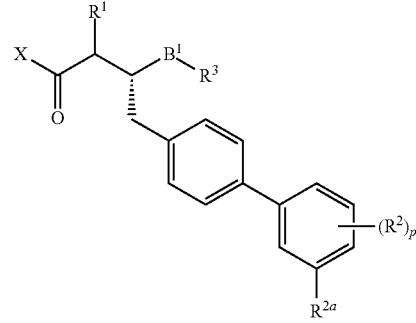

Formula III-C

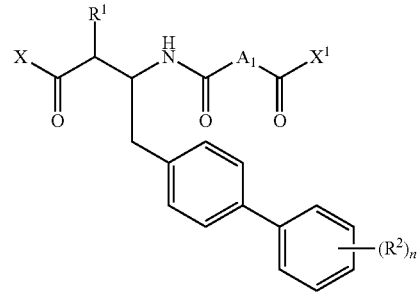

Formula III-D

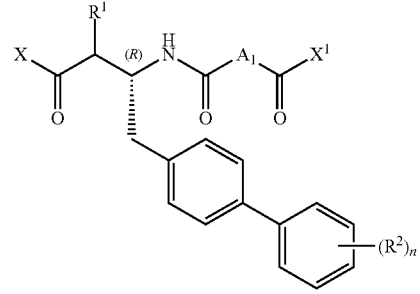

Formula III-E

Formula III-F
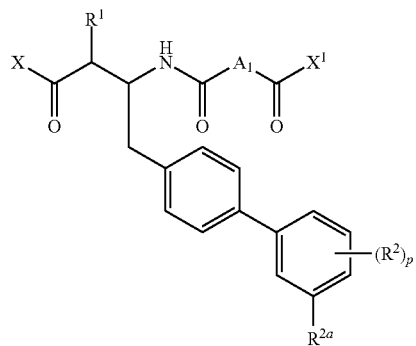
Formula III-G
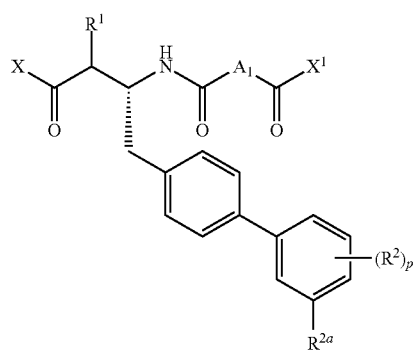
Formula III-H
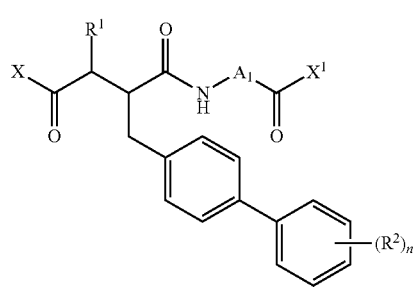
Formula III-I
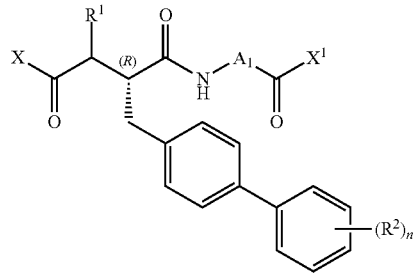
Formula III-J
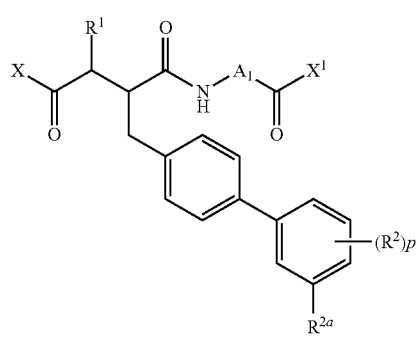
Formula III-K
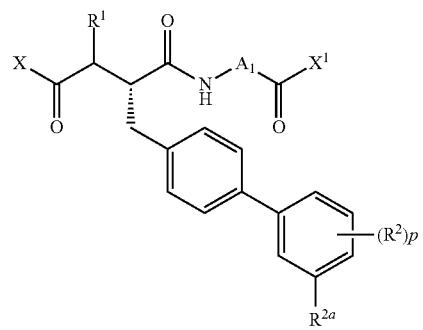
Formula III-L
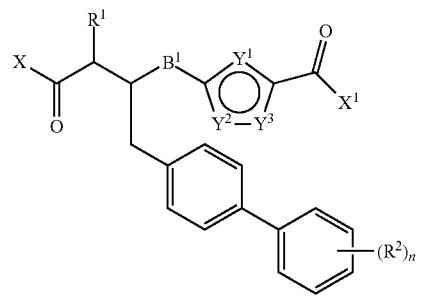
Formula III-M
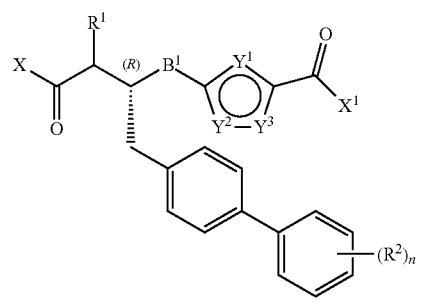
Formula III-N
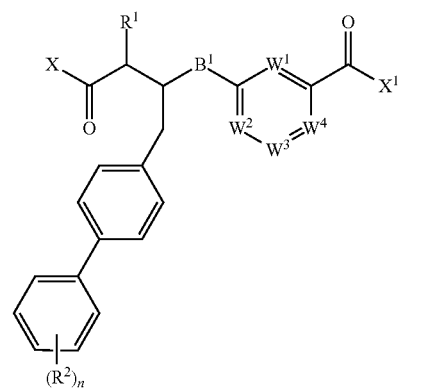

Formula III-O
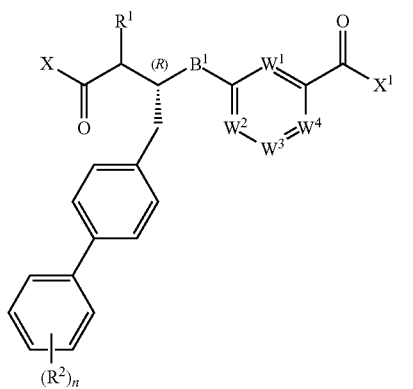

Formula III-P
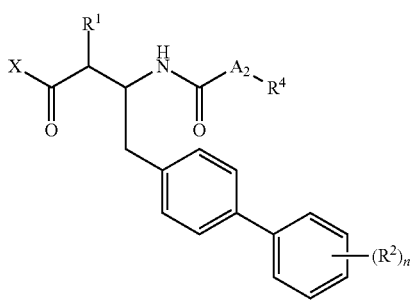

Formula III-Q
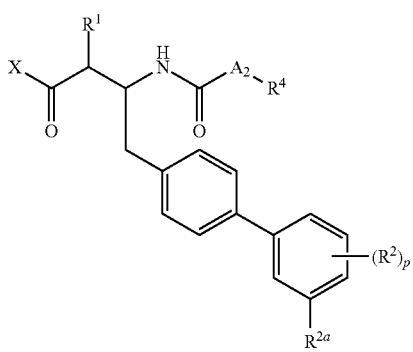

Formula III-R
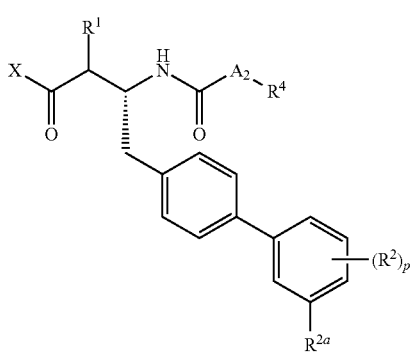

Formula III-S
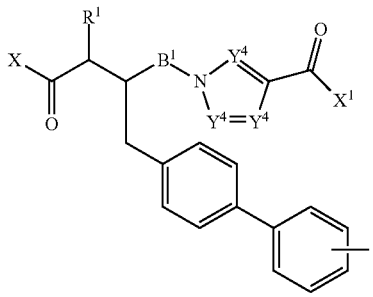

or

Formula III-T
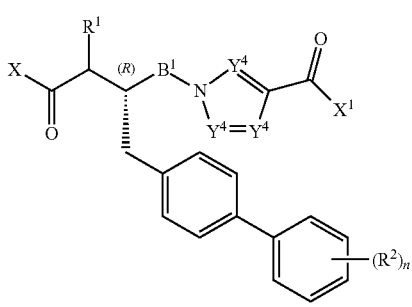

or a pharmaceutically acceptable salt thereof, wherein p is 0, 1, 2, 3 or 4; $R^{2a}$ is halo; $W^1$, $W^2$, $W^3$ and $W^4$ are independently N or $CR^f$, in which each $R^f$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$; $R^b$ and $R^c$ for each occurrence are independently H or $C_{1-7}$alkyl; and $Y^1$, $Y^2$ and $Y^3$ are independently N, NH, S, O or CH and form together with the ring atoms to which they are attached a 5-membered heteroaryl ring, and each $Y^4$ is independently N, S, O or CH.

Embodiment 8 A neutral endopeptidase inhibitor according to embodiment 7, which is a compound of Formula III-F or III-G, wherein $A^1$ is —$CH_2$—, —$CH_2CH_2$—, —$CH_2CH_2CH_2$—, or a pharmaceutically acceptable salt thereof.

Embodiment 9 A neutral endopeptidase inhibitor according to embodiment 8 wherein $R^1$ is H, p is 0; X and $X^1$ are independently OH or —O—$C_{1-7}$alkyl, $R^{2a}$ is chloro; or a pharmaceutically acceptable salt thereof.

Embodiment 10 A neutral endopeptidase inhibitor according to embodiment 1 or 3, which is a compound of Formula IV:

IV
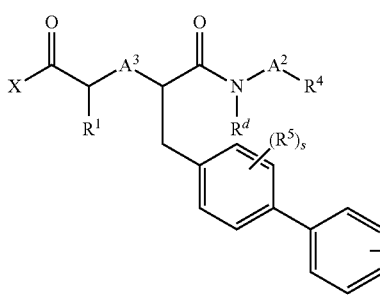

wherein:
X is OH, —O—$C_{1-7}$alkyl, —$NR^bR^c$, —$NHS(O)_2$—$C_{1-7}$alkyl or —$NHS(O)_2$-benzyl; wherein $R^b$ and $R^c$ for each occurrence are independently H or $C_{1-7}$alkyl;

$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy or $C_{1-6}$ alkoxy;

for each occurrence, $R^2$ is independently $C_{1-6}$-alkoxy, hydroxy, halo, $C_{1-6}$-alkyl, cyano or trifluoromethyl;

$A^3$ is O or $NR^e$;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$alkyl or halo-$C_{1-7}$alkyl; or $R^d$, $A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

Embodiment 11 A neutral endopeptidase inhibitor according to embodiment 10, which is a compound of Formula IV-A:

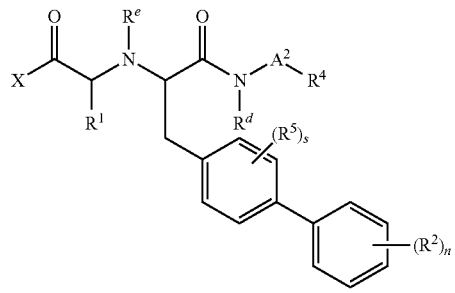

IV-A wherein:

X represent OH or O—$C_{1-6}$-alkyl;

$R^1$ is H, $C_{1-6}$ alkyl or $C_{6-10}$-aryl-$C_{1-6}$ alkyl; for each occurrence, $R^2$ is independently $C_{1-6}$-alkoxy, hydroxy, halo, $C_{1-6}$-alkyl, cyano or trifluoromethyl;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo-$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$alkyl or halo-$C_{1-7}$alkyl; or $R^d$, $A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

Embodiment 12 A neutral endopeptidase inhibitor according to embodiment 10 or 11, which is a compound of Formula

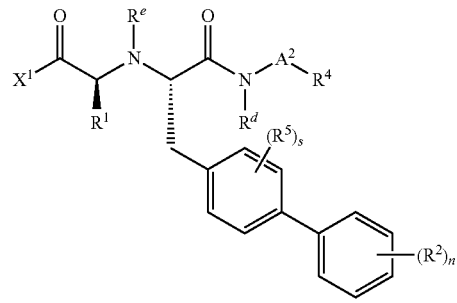

Formula IV-B

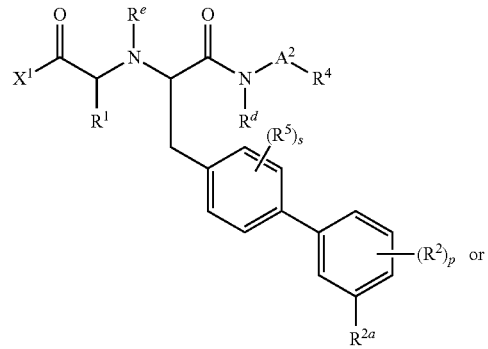

Formula IV-C

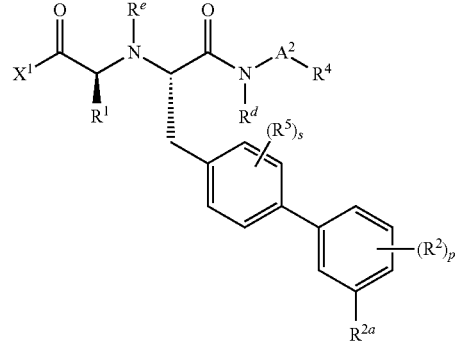

Formula IV-D or a pharmaceutically acceptable salt thereof, wherein p is 0, 1, 2, 3 or 4 and $R^{2a}$ is halo.

Embodiment 13 A neutral endopeptidase inhibitor according to embodiment 1 to 12, in combination with at least one other therapeutic agent as a combined preparation for simultaneous, separate or sequential use in therapy.

Embodiment 14 A neutral endopeptidase inhibitor according to embodiment 13, wherein the other therapeutic agent is selected from adenosine-receptor antagonist, a calcium channel blocker, an anti-apoptotic agent, an antioxidant, a MAP kinase inhibitor, a prostacyclin or prostacyclin analogue, endothelin antagonist, an ion chelator and a dopamine receptor agonist or a pharmaceutically acceptable salt thereof.

It can be seen that the compounds of the invention are useful as inhibitors of Neutral endopeptidase (EC 3.4.24.11) activity and therefore useful in the treatment of diseases and conditions associated with Neutral endopeptidase (EC 3.4.24.11) activity such as the diseases disclosed herein.

It will be understood that the invention has been described by way of example only and modifications may be made whilst remaining within the scope and spirit of the invention.

What is claimed is:

1. A method of treating or ameliorating contrast-induced nephropathy in a subject in need thereof comprising administering to the subject a therapeutically effective amount of a compound of Formula I:

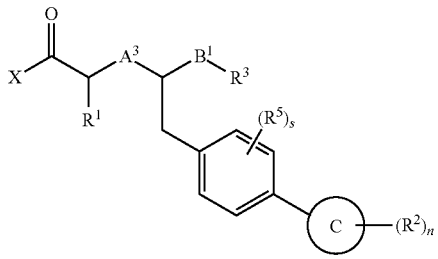

or a pharmaceutically acceptable salt thereof, wherein:

$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy, $C_{3-7}$cycloalkyl or $C_{1-6}$ alkoxy;

$R^2$ for each occurence, is independently $C_{1-7}$alkyl, halo, $NO_2$, CN, $C_{1-7}$alkanoylamino, $C_{3-7}$cycloalkyl, hydroxy, $C_{1-7}$alkoxy, halo$C_{1-7}$alkyl, —$NR^bR^c$, $C_{6-10}$aryl, heteroaryl or heterocyclyl;

$R^3$ is $A^1$-C(O)$X^1$ or $A^2$-$R^4$;

$R^4$ is $C_{6-10}$aryl, $C_{3-7}$cycloalkyl, or a heteroaryl, which can be monocyclic or bicyclic, each of which can be optionally substituted with one or more substituents independently selected from the group consisting of hydroxy, hydroxy$C_{1-7}$alkyl, nitro, —$NR^bR^c$, —C(O)$C_{1-7}$alkyl, C(O)—O—$C_{1-7}$alkyl, $C_{1-7}$alkoxy, halo, $C_{1-7}$alkyl, halo-$C_{1-7}$alkyl, $C_{2-7}$alkenyl, $C_{6-10}$aryl, heteroaryl, —$NHSO_2$—$C_{1-7}$alkyl, $S(O)_2$—$C_{1-7}$alkyl, C(O)—$C_{1-7}$alkyl and benzyl; or $R^4$ is a heterocyclyl which can be optionally substituted with one or more substituents independently selected from the group consisting of oxo, hydroxy, hydroxy$C_{1-7}$alkyl, amino, C(O)—O—$C_{1-7}$alkyl, $C_{1-7}$alkoxy, halo, $C_{1-7}$alkyl, halo-$C_{1-7}$akyl, $C_{6-10}$aryl, heteroaryl, —$NHSO_2$—$C_{1-7}$alky and benzyl;

$R^5$ is H, halo, hydroxy, $C_{1-7}$alkoxy, halo, $C_{1-7}$alkyl or halo-$C_{1-7}$akyl; and X and $X^1$ are independently OH, —O—$C_{1-7}$alkyl, —$NR^bR^c$, —$NHS(O)_2$—$C_{1-7}$alkyl, —$NHS(O)_2$-benzyl or —O—$C_{6-10}$aryl; wherein alkyl is optionally substituted with one or more substituents independently selected from the group consisting of $C_{6-10}$aryl, heteroaryl, heterocyclyl, $C(O)NH_2$, $C(O)NH$—$C_{1-6}$alkyl, and $C(O)N(C_{1-6}$alkyl$)_2$;

$B^1$ is —C(O)$NR^d$— or —$NR^d$C(O)—;

$A^1$ is a bond or a linear or branched $C_{1-7}$alkylene; which is optionally substituted with one or more substituents independently selected from the group consisting of halo, $C_{3-7}$cycloalkyl, $C_{1-7}$alkoxy, hydroxy and O-acetate; in which two geminal alkyl can optionally combine to form a $C_{3-7}$cycloalkyl; or $A^1$ is a linear or branched $C_{1-7}$alkenylene; or $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, $C_{1-7}$alkyl, —C(O)—O—$C_{1-7}$alkyl or —$CH_2C(O)OH$; or $A^1$ is a phenyl or a heteroaryl; each of which is optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, —$NR^bR^c$, —$OCH_2CO_2H$, and —$OCH_2C(O)NH_2$; or $A^1$ is a $C_{3-7}$cycloalkyl or heterocyclyl;

$A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$alkylene; which is optionally substituted with one or more substituents independently selected from the group consisting of halo, $C_{1-7}$alkoxy, hydroxy, O-Acetate and $C_{3-7}$cycloalkyl;

$A^3$ is $CH_2$, O, $NR^e$ or is absent; and when $A^3$ is O or $NR^e$ then $B^1$ is C(O)$NR^d$;

$R^b$ and $R^c$ for each occurrence are independently H, $C_{6-10}$aryl or $C_{1-7}$alkyl;

$R^d$ and $R^e$ are independently H or $C_{1-7}$alkyl;

Ring C is a phenyl or a monocyclic heteroaryl;

n is 0, 1, 2, 3, 4 or 5;

s is 0, 1, 2, 3 or 4; and when $B^1$ is C(O)$NR^d$ and $R^3$ is $A^2$-$R^4$, then $R^d$ and $A^2$-$R^4$, together with the nitrogen to which $R^d$ and $A^2$-$R^4$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

wherein each heteroaryl is a monocyclic or bicyclic aromatic ring comprising 5-10 ring atoms selected from carbon atoms and 1 to 5 heteroatoms unless otherwise specified, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

2. The method of treating or ameliorating contrast-induced nephropathy in a subject in need thereof, according to claim 1, comprising administering to the subject a therapeutically effective amount of a compound of Formula IV:

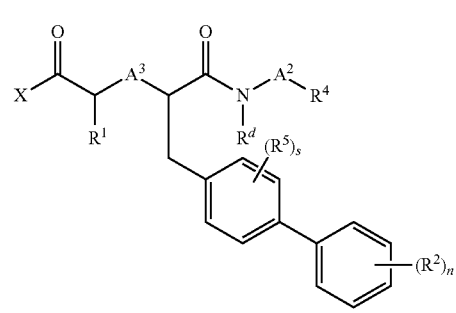

wherein:

X is OH, —O—$C_{1-7}$alkyl, —$NR^bR^c$, —$NHS(O)_2$—$C_{1-7}$alkyl or —$NHS(O)_2$-benzyl; wherein $R^b$ and $R^c$ for each occurrence are independently H or $C_{1-7}$alkyl;

$R^1$ is H, $C_{1-7}$alkyl, hydroxy, $C_{1-7}$alkoxy, halogen, —SH, —S—$C_{1-7}$alkyl or $NR^bR^c$; wherein alkyl is optionally substituted with $C_{6-10}$-aryl, benzyloxy, hydroxy or $C_{1-6}$ alkoxy;

for each occurence, $R^2$ is independently $C_{1-6}$-alkoxy, hydroxy, halo, $C_{1-6}$-alkyl, cyano or trifluoromethyl;

$A^3$ is O or $NR^e$;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$alkyl or halo-$C_{1-7}$akyl; or $R^d$, $A^2$-$R^4$, together with the nitrogen to which $R^d$ and $A^2$-$R^4$ are attached, form a 4- to 7-membered heterocyclyl or a 5- to 6- membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

3. The method of claim 2 wherein the compound is of Formula IV-A:

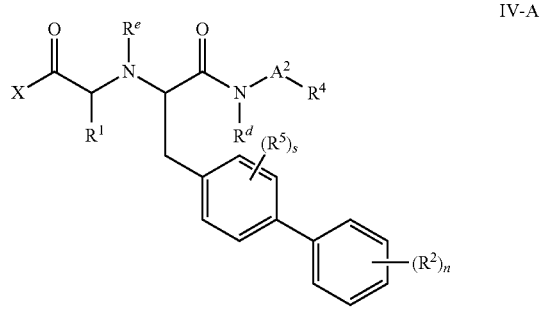

IV-A

Wherein:

X represent OH or O—$C_{1-6}$-alkyl;

$R^1$ is H, $C_{1-6}$ alkyl or $C_{6-10}$-aryl-$C_{1-6}$ alkyl;

for each occurence, $R^2$ is independently $C_{1-6}$-alkoxy, hydroxy, halo, $C_{1-6}$-alkyl, cyano or trifluoromethyl;

$R^d$ and $R^e$ are independently H or $C_{1-6}$ alkyl;

$A^2$ is a bond or $C_{1-3}$alkylene chain;

$R^4$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo-$C_{1-6}$alkyl, $C_{1-6}$alkoxy, hydroxy, $CO_2H$ and $CO_2C_{1-6}$alkyl;

$R^5$ for each occurrence is independently halo, hydroxy, $C_{1-7}$alkoxy, halo, $C_{1-7}$alkyl or halo-$C_{1-7}$akyl; or $R^d$, $A^2$-$R^4$, together with the nitrogen to which $R^d$ and $A^2$-$R^4$ are attached, form a 4- to 7-membered heterocyclyl or a 5- to 6- membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl; and n is 0 or an integer from 1 to 5;

s is 0 or an integer from 1 to 4; or a pharmaceutically acceptable salt thereof.

4. The method of claim 2 wherein the compound is of Formula:

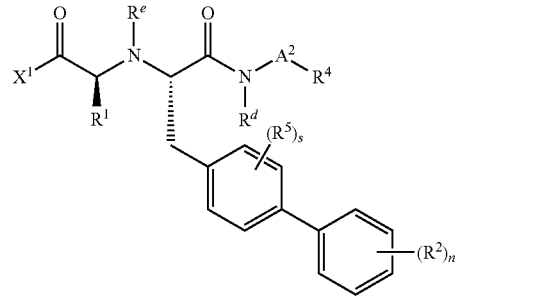

Formula IV-B

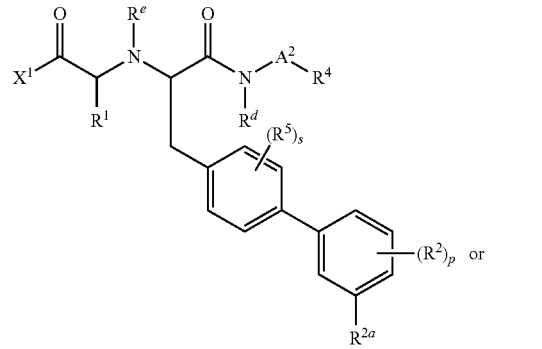

Formula IV-C

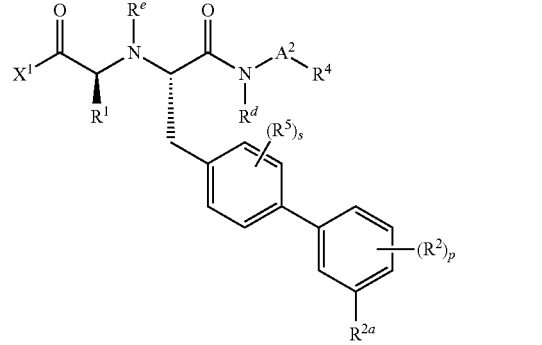

Formula IV-D or a pharmaceutically acceptable salt therof, wherein p is 0, 1, 2, 3 or 4 and $R^{2a}$ is halo.

5. The method of claim 4 wherein the compound is selected from:

(S)-2-[(S)-2-(3'-chloro-biphenyl-4-yl)-1-(1H-tetrazol-5-ylcarbamoyl)-ethylamino]-propionic acid ethyl ester;

(S)-2-[(S)-2-(3'-chloro-biphenyl-4-yl)-1-(1H-tetrazol-5-ylcarbamoyl)-ethylamino]-propionic acid;

(S)-2-[(S)-2-(3'-chloro-biphenyl-4-yl)-1-(1H-tetrazol-5-ylcarbamoyl)-ethoxy]-propionic acid ethyl ester; and (S)-2-[(S)-2-(3'-Chloro-biphenyl-4-yl)-1-(1H-tetrazol-5-ylcarbamoyl)-ethylamino]-4-phenyl-butyric acid ethyl ester; or a pharmaceutically acceptable salt thereof.

* * * * *